United States Patent
Tashiro et al.

(10) Patent No.: US 12,234,247 B2
(45) Date of Patent: Feb. 25, 2025

(54) HETEROCYCLIC COMPOUND AND HARMFUL ARTHROPOD-CONTROLLING COMPOSITION CONTAINING SAME

(71) Applicant: SUMITOMO CHEMICAL COMPANY, LIMITED, Chuo-ku (JP)

(72) Inventors: Masayuki Tashiro, Takarazuka (JP); Ayaka Tanaka, Chuo-ku (JP); Yuji Nakajima, Takarazuka (JP)

(73) Assignee: SUMITOMO CHEMICAL COMPANY, LIMITED, Chuo-ku (JP)

( * ) Notice: Subject to any disclaimer, the term of this patent is extended or adjusted under 35 U.S.C. 154(b) by 774 days.

(21) Appl. No.: 17/431,950

(22) PCT Filed: Feb. 18, 2020

(86) PCT No.: PCT/JP2020/006331
§ 371 (c)(1),
(2) Date: Aug. 18, 2021

(87) PCT Pub. No.: WO2020/171077
PCT Pub. Date: Aug. 27, 2020

(65) Prior Publication Data
US 2021/0380610 A1    Dec. 9, 2021

(30) Foreign Application Priority Data

Feb. 19, 2019  (JP) ................. 2019-027139
Jun. 25, 2019  (JP) ................. 2019-117010

(51) Int. Cl.
C07D 519/00     (2006.01)
A01C 1/06       (2006.01)
A01N 43/90      (2006.01)

(52) U.S. Cl.
CPC ......... *C07D 519/00* (2013.01); *A01C 1/06* (2013.01); *A01N 43/90* (2013.01)

(58) Field of Classification Search
None
See application file for complete search history.

(56) References Cited

U.S. PATENT DOCUMENTS

| | | | |
|---|---|---|---|
| 2018/0022760 A1 | 1/2018 | Kudo et al. | |
| 2019/0375765 A1 | 12/2019 | Kudo et al. | |
| 2021/0059255 A1 | 3/2021 | Tanaka et al. | |

FOREIGN PATENT DOCUMENTS

| | | |
|---|---|---|
| CN | 103037694 A | 4/2013 |
| CN | 107207506 A | 9/2017 |
| JP | 2018-177759 A | 11/2018 |
| WO | WO 2016/129684 A1 | 8/2016 |
| WO | WO 2017/061497 A1 | 4/2017 |
| WO | WO 2018/033455 A1 | 2/2018 |
| WO | WO 2018/052136 A1 | 3/2018 |
| WO | WO 2019/131575 A1 | 7/2019 |

OTHER PUBLICATIONS

Combined Chinese Office Action and Search Report issued Feb. 14, 2022 in Patent Application No. 202080029490.1 (with English language translation), 16 pages.
Office Action issued on Feb. 27, 2023 in Indian Patent Application No. 202147040283, 6 pages.
Extended European Search Report issued on Sep. 23, 2022 in European Patent Application No. 20759467.2, 7 pages.
Office Action issued Oct. 3, 2023, in corresponding Japanese Patent Application No. 2021-502037 (with English Translation), 7 pages.
(Continued)

*Primary Examiner* — Brian J Davis
(74) *Attorney, Agent, or Firm* — Oblon, McClelland, Maier & Neustadt, L.L.P.

(57) ABSTRACT

A compound represented by formula (I) or its N-oxide, having a controlling effect on a harmful arthropod,

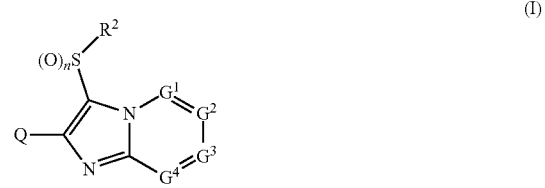

Q is a group Q1 or Q2;

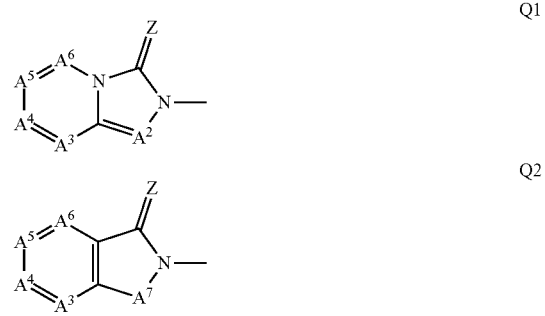

Z is an oxygen atom; $A^2$, $A^3$, and $A^6$ each a nitrogen atom; $A^4$ is $CR^{1a}$; $A^5$ is a nitrogen atom; $A^7$ is $NR^{6g}$; $G^1$ to $G^4$ each is a nitrogen atom; $R^{1a}$ is a C1-C6 chain hydrocarbon group substituted with a cyano group and/or a halogen atom; $R^2$ is a C1-C6 alkyl group optionally substituted with one or more halogen atoms; n is 0, 1, or 2. A composition and method for controlling a harmful arthropod by applying the compound or its N-oxide are also presented.

15 Claims, No Drawings

(56) References Cited

OTHER PUBLICATIONS

Japanese Decision of Rejection issued Jan. 30, 2024 in Japanese Patent Application No. 2021-502037 (with unedited computer-generated English Translation), 6 pages.
International Search Report issued Apr. 21, 2020 in PCT/JP2020/006331 issued Feb. 12, 2020, 3 pages.
International Preliminary Report on Patentability and Written Opinion issued Aug. 10, 2021 in PCT/JP2020/006331, 7 pages.
Tohru Koyanagi, et al., "Bioisosterism in Agrochemicals," ACS Symposium Series, vol. 584, Chap. 2, 1995, 11 pages.

HETEROCYCLIC COMPOUND AND HARMFUL ARTHROPOD-CONTROLLING COMPOSITION CONTAINING SAME

CROSS-REFERENCE TO RELATED APPLICATIONS

This application is a national stage application of PCT/JP2020/006331, filed Feb. 18, 2020, which claims priority to Japanese application 2019-027139, filed Feb. 19, 2019, and Japanese application 2019-117010, filed Jun. 25, 2019. The contents of all three applications are incorporated by reference herein in their entireties.

TECHNICAL FIELD

This patent application claims the priorities to and the benefits under the Paris convention of Japanese Patent Application No. 2019-027139 filed on Feb. 19, 2019 and Japanese Patent Application No. 2019-117010 filed on Jun. 25, 2019, the entire contents of which are incorporated herein by reference.

The present invention relates to heterocyclic compounds and compositions for controlling harmful arthropods comprising the same.

BACKGROUND ART

To date, various compounds have been studied in order to control harmful arthropods. For example, Patent Document 1 discloses that certain kinds of compounds have control effects on pests.

CITATION LIST

Patent Document

Patent Document 1: WO 2016/129684 pamphlet

SUMMARY OF THE INVENTION

Problems to be Solved by Invention

An object of the present invention is to provide compounds having excellent control efficacy against harmful arthropods.

Means to Solve Problems

The present inventors have studied to find out a compound having excellent control efficacy against harmful arthropods, and as a result found out that a compound represented by following formula (I) and the like have excellent control efficacy against harmful arthropods.

Namely, the present invention provides the followings.

[1] A compound represented by formula (I):

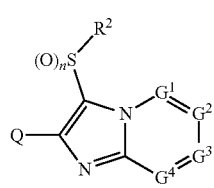

[wherein:
$R^2$ represents a C1-C6 alkyl group optionally substituted with one or more halogen atom(s), a cyclopropyl group, or a cyclopropylmethyl group;
n represents 0, 1, or 2;
$G^1$ represents a nitrogen atom or $CR^{3a}$;
$G^2$ represents a nitrogen atom or $CR^{3b}$;
$G^3$ represents a nitrogen atom or $CR^{3c}$;
$G^4$ represents a nitrogen atom or $CR^{3d}$;
$R^{3a}$, $R^{3b}$, $R^{3c}$, and $R^{3d}$ are identical to or different from each other, and each represent a C1-C6 chain hydrocarbon group optionally substituted with one or more substituent(s) selected from Group B, a C3-C7 cycloalkyl group optionally substituted with one or more substituent(s) selected from Group E, a phenyl group optionally substituted with one or more substituent(s) selected from Group H, a 5 or 6 membered aromatic heterocyclic group optionally substituted with one or more substituent(s) selected from Group H, $OR^{12}$, $NR^{11}R^{12}$, $NR^{11a}R^{12a}$, $NR^{24}NR^{11}R^{12}$, $NR^{24}OR^{11}$, $NR^{11}C(O)R^{13}$, $NR^{24}NR^{11}C(O)R^{13}$, $NR^{11}C(O)OR^{14}$, $NR^{24}NR^{11}C(O)OR^{14}$, $NR^{11}C(O)NR^{31}R^{32}$, $NR^{24}NR^{11}C(O)NR^{31}R^{32}$, $N=CHNR^{31}R^{32}$, $N=S(O)_pR^{15}R^{16}$, $C(O)R^{13}$, $C(O)OR^{17}$, $C(O)NR^{31}R^{32}$, $C(O)NR^{11}S(O)_2R^{23}$, $CR^{30}=NOR^{17}$, $NR^{11}CR^{24}=NOR^{17}$, $S(O)_mR^{23}$, a cyano group, a nitro group, a hydrogen atom, or a halogen atom;
p represents 0 or 1;
m represents 0, 1, or 2;
$R^{30}$ represents a C1-C6 chain hydrocarbon group optionally substituted with one or more halogen atom(s), a halogen atom, $OR^{35}$, $NR^{36}R^{37}$, or a hydrogen atom;
$R^{35}$ represents a C1-C6 chain hydrocarbon group optionally substituted with one or more halogen atom(s);
$R^{17}$ represents a C1-C6 chain hydrocarbon group optionally substituted with one or more halogen atom(s), a phenyl group optionally substituted with one or more substituent(s) selected from Group D, or a hydrogen atom;
$R^{11}$, $R^{24}$, $R^{36}$, and $R^{37}$ are identical to or different from each other, and each represent a C1-C6 chain hydrocarbon group optionally substituted with one or more halogen atom(s), or a hydrogen atom;
$R^{12}$ represents a C1-C6 chain hydrocarbon group optionally substituted with one or more substituent(s) selected from Group F, a C3-C7 cycloalkyl group optionally substituted with one or more substituent(s) selected from Group J, a C3-C7 cycloalkenyl group optionally substituted with one or more substituent(s) selected from Group J, a phenyl group optionally substituted with one or more substituent(s) selected from Group D, a 6 membered aromatic heterocyclic group optionally substituted with one or more substituent(s) selected from Group D, a hydrogen atom, or $S(O)_2R^{23}$;
$R^{23}$ represents a C1-C6 chain hydrocarbon group optionally substituted with one or more halogen atom(s), or a phenyl group optionally substituted with one or more substituent(s) selected from Group D;
$R^{11a}$ and $R^{12a}$ are combined with the nitrogen atom to which they are attached to form a 3-7 membered nonaromatic heterocyclic group optionally substituted with one or more substituent(s) selected from Group E;

$R^{13}$ represents a C1-C6 chain hydrocarbon group optionally substituted with one or more halogen atom(s), a C3-C7 cycloalkyl group optionally substituted with one or more halogen atom(s), a (C3-C6 cycloalkyl) C1-C3 alkyl group optionally substituted with one or more halogen atom(s), a phenyl group optionally substituted with one or more substituent(s) selected from Group D, a 5 or 6 membered aromatic heterocyclic group optionally substituted with one or more substituent(s) selected from Group D, or a hydrogen atom;

$R^{14}$ represents a C1-C6 chain hydrocarbon group optionally substituted with one or more halogen atom(s), a C3-C7 cycloalkyl group optionally substituted with one or more halogen atom(s), a (C3-C6 cycloalkyl) C1-C3 alkyl group optionally substituted with one or more halogen atom(s), or a phenyl C1-C3 alkyl group {wherein the phenyl moiety in said phenyl C1-C3 alkyl group is optionally substituted with one or more substituent(s) selected from Group D};

$R^{15}$ and $R^{16}$ are identical to or different from each other, and each represent a C1-C6 alkyl group optionally substituted with one or more halogen atom(s);

$R^{31}$ represents a C1-C6 alkyl group optionally substituted with one or more halogen atom(s), or a hydrogen atom;

$R^{32}$ represents a C1-C6 chain hydrocarbon group optionally substituted with one or more substituent(s) selected from Group F, a C3-C7 cycloalkyl group optionally substituted with one or more substituent(s) selected from Group J, $S(O)_2R^{23}$, or a hydrogen atom;

Q represents a group represented by Q1 or a group represented by Q2;

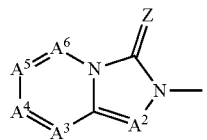

Q1

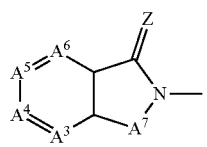

Q2

Z represents an oxygen atom or a sulfur atom;
$A^2$ represents a nitrogen atom or $CR^{6b}$;
$A^3$ represents a nitrogen atom or $CR^{6c}$;
$A^6$ represents a nitrogen atom or $CR^{6f}$;
$A^7$ represents $NR^{6g}$, $CR^{6h}R^{6i}$, or an oxygen atom;
the combination of $A^4$ and $A^5$ represents:
a combination wherein $A^4$ represents $CR^{1a}$, and $A^5$ represents a nitrogen atom or $CR^{6c}$; or
a combination wherein $A^4$ represents a nitrogen atom or $CR^{6d}$, and $A^5$ represents $CR^{1b}$;
$R^{1a}$ and $R^{1b}$ are identical to or different from each other, and each represent a C1-C6 chain hydrocarbon group substituted with one or more substituent(s) selected from the group consisting of a cyano group and a halogen atom, a C3-C4 cycloalkyl group optionally substituted with one or more substituent(s) selected from the group consisting of a cyano group and a halogen atom, $SR^8$, $S(O)R^8$, $S(O)_2R^8$, $OR^8$, or $OS(O)_2R^8$;

$R^8$ represents a C1-C6 chain hydrocarbon group substituted with one or more substituent(s) selected from the group consisting of a cyano group and a halogen atom, or a C3-C4 cycloalkyl group optionally substituted with one or more substituent(s) selected from the group consisting of a cyano group and a halogen atom;

$R^{6b}$, $R^{6h}$, and $R^{6i}$ are identical to or different from each other, and each represent a C1-C6 chain hydrocarbon group optionally substituted with one or more halogen atom(s), a C3-C7 cycloalkyl group optionally substituted with one or more halogen atom(s), a halogen atom, or a hydrogen atom;

$R^{6c}$, $R^{6d}$, $R^{6e}$, and $R^{6f}$ are identical to or different from each other, and each represent a C1-C6 chain hydrocarbon group optionally substituted with one or more halogen atom(s), a C3-C7 cycloalkyl group optionally substituted with one or more halogen atom(s), a C1-C6 alkoxy group optionally substituted with one or more halogen atom(s), $NR^{25}R^{26}$, $C(O)R^7$, $C(O)OR^7$, $C(O)NR^{19}R^{20}$, $NR^{25}C(O)R^{18}$, $NR^{2b}C(O)OR^{18}$, $NR^{2b}C(O)NR^{19}R^{20}$, a cyano group, a halogen atom, or a hydrogen atom;

$R^{6g}$ represents a C1-C6 chain hydrocarbon group optionally substituted with one or more halogen atom(s), or a hydrogen atom;

$R^{19}$ and $R^{25}$ are identical to or different from each other, and each represent a C1-C6 chain hydrocarbon group optionally substituted with one or more halogen atom(s), or a hydrogen atom;

$R^{26}$ represents a C1-C6 chain hydrocarbon group optionally substituted with one or more substituent(s) selected from Group L, a C3-C7 cycloalkyl group optionally substituted with one or more substituent(s) selected from Group M, a C3-C7 cycloalkenyl group optionally substituted with one or more substituent(s) selected from Group M, a phenyl group optionally substituted with one or more substituent(s) selected from Group K, a 6 membered aromatic heterocyclic group optionally substituted with one or more substituent(s) selected from Group K, a hydrogen atom, or $S(O)_2R^{27}$;

$R^{27}$ represents a C1-C6 chain hydrocarbon group optionally substituted with one or more halogen atom(s), a C3-C7 cycloalkyl group optionally substituted with one or more halogen atom(s), or a phenyl group optionally substituted with one or more substituent(s) selected from Group K; and $R^7$, $R^{18}$, and $R^{20}$ are identical to or different from each other, and each represent a C1-C6 chain hydrocarbon group optionally substituted with one or more substituent(s) selected from Group L, a C3-C7 cycloalkyl group optionally substituted with one or more substituent(s) selected from Group M, or a hydrogen atom;

Group B: a group consisting of a C1-C6 alkoxy group optionally substituted with one or more halogen atom(s), a C3-C6 alkenyloxy group optionally substituted with one or more halogen atom(s), a C3-C6 alkynyloxy group optionally substituted with one or more halogen atom(s), a C1-C6 alkylsulfanyl group optionally substituted with one or more halogen atom(s), a C1-C6 alkylsulfinyl group optionally substituted with one or more halogen atom(s), a C1-C6 alkylsulfonyl group optionally substituted with one or more halogen atom(s), a C3-C6 cycloalkyl group optionally substituted with one or more halogen atom(s), a cyano group, a hydroxy group, and a halogen atom;

Group C: a group consisting of a C1-C6 chain hydrocarbon group optionally substituted with one or more halogen atom(s), a C1-C6 alkoxy group optionally substituted with one or more halogen atom(s), a C3-C6 alkenyloxy group optionally substituted with one or more halogen atom(s), a C3-C6 alkynyloxy group optionally substituted with one or more halogen atom(s), and a halogen atom;

Group D: a group consisting of a C1-C6 chain hydrocarbon group optionally substituted with one or more halogen atom(s), a hydroxy group, a C1-C6 alkoxy group optionally substituted with one or more halogen atom(s), a C3-C6 alkenyloxy group optionally substituted with one or more halogen atom(s), a C3-C6 alkynyloxy group optionally substituted with one or more halogen atom(s), a sulfanyl group, a C1-C6 alkylsulfanyl group optionally substituted with one or more halogen atom(s), a C1-C6 alkylsulfinyl group optionally substituted with one or more halogen atom(s), a C1-C6 alkylsulfonyl group optionally substituted with one or more halogen atom(s), an amino group, $NHR^{21}$, $NR^{21}R^{22}$, $C(O)R^{21}$, $OC(O)R^{21}$, $C(O)OR^{21}$, a cyano group, a nitro group, and a halogen atom;

$R^{21}$ and $R^{22}$ are identical to or different from each other, and each represent a C1-C6 alkyl group optionally substituted with one or more halogen atom(s);

Group E: a group consisting of a C1-C6 chain hydrocarbon group optionally substituted with one or more halogen atom(s), a C1-C6 alkoxy group optionally substituted with one or more halogen atom(s), a C3-C6 alkenyloxy group optionally substituted with one or more halogen atom(s), a C3-C6 alkynyloxy group optionally substituted with one or more halogen atom(s), a halogen atom, an oxo group, a hydroxy group, a cyano group, and a nitro group;

Group F: a group consisting of a C1-C6 alkoxy group optionally substituted with one or more halogen atom(s), a phenyl group optionally substituted with one or more substituent(s) selected from Group D, a 5 or 6 membered aromatic heterocyclic group optionally substituted with one or more substituent(s) selected from Group D, a C3-C7 cycloalkyl group optionally substituted with one or more halogen atom(s), a 3-7 membered nonaromatic heterocyclic group optionally substituted with one or more substituent(s) selected from Group C, an amino group, $NHR^{21}$, $NR^{21}R^{22}$, a halogen atom, and a cyano group;

Group H: a group consisting of a C1-C6 alkyl group optionally substituted with one or more halogen atom(s), a 5 or 6 membered aromatic heterocyclic group optionally substituted with one or more substituent(s) selected from Group D, $OR^{10}$, $NR^9R^{10}$, $C(O)R^{10}$, $C(O)NR^9R^{10}$, $OC(O)R^9$, $OC(O)OR^9$, $NR^{10}C(O)R^9$, $NR^{10}C(O)OR^9$, $C(O)OR^{10}$, a halogen atom, a nitro group, a cyano group, and an amino group;

$R^9$ represents a C1-C6 alkyl group optionally substituted with one or more halogen atom(s), or a C3-C6 cycloalkyl group optionally substituted with one or more halogen atom(s);

$R^{10}$ represents a C1-C6 alkyl group optionally substituted with one or more halogen atom(s), a C3-C6 cycloalkyl group optionally substituted with one or more halogen atom(s), or a hydrogen atom;

Group J: a group consisting of a C1-C6 alkyl group optionally substituted with one or more halogen atom(s), a halogen atom, and a cyano group;

Group K: a group consisting of a C1-C6 chain hydrocarbon group optionally substituted with one or more halogen atom(s), a C1-C6 alkoxy group optionally substituted with one or more halogen atom(s), a C3-C6 alkenyloxy group optionally substituted with one or more halogen atom(s), a C3-C6 alkynyloxy group optionally substituted with one or more halogen atom(s), a C1-C6 alkylsulfanyl group optionally substituted with one or more halogen atom(s), a C1-C6 alkylsulfinyl group optionally substituted with one or more halogen atom(s), a C1-C6 alkylsulfonyl group optionally substituted with one or more halogen atom(s), a C3-C6 cycloalkyl group optionally substituted with one or more halogen atom(s), a (C1-C6 alkyl optionally substituted with one or more halogen atom(s))amino group, a di(C1-C4 alkyl)amino group optionally substituted with one or more halogen atom(s), a C2-C6 alkylcarbonyl group optionally substituted with one or more halogen atom(s), a C2-C6 alkoxycarbonyl group optionally substituted with one or more halogen atom(s), a C2-C6 alkoxycarbonyloxy group optionally substituted with one or more halogen atom(s), an aminocarbonyl group, a (C1-C6 alkyl optionally substituted with one or more halogen atom(s))aminocarbonyl group, a [di(C1-C4 alkyl)amino optionally substituted with one or more halogen atom(s)]carbonyl group, a (C2-C6 alkoxycarbonyl optionally substituted with one or more halogen atom(s))amino group, a (C2-C6 alkoxycarbonyl)(C1-C6 alkyl)amino group optionally substituted with one or more halogen atom(s), a cyano group, an amino group, a nitro group, a hydroxy group, and a halogen atom;

Group L: a group consisting of a C3-C6 cycloalkyl group optionally substituted with one or more halogen atom(s), a phenyl group optionally substituted with one or more substituent(s) selected from Group K, a 5 or 6 membered aromatic heterocyclic group optionally substituted with one or more substituent(s) selected from Group K, a C1-C6 alkoxy group optionally substituted with one or more halogen atom(s), a (C1-C6 alkyl optionally substituted with one or more halogen atom(s))amino group, a di(C1-C4 alkyl)amino group optionally substituted with one or more halogen atom(s), a cyano group, an amino group, a nitro group, a hydroxy group, and a halogen atom;

Group M: a group consisting of a C1-C6 alkyl group optionally substituted with one or more halogen atom(s), a C1-C6 alkoxy group optionally substituted with one or more halogen atom(s), a C2-C6 alkoxycarbonyl group optionally substituted with one or more halogen atom(s), an amino group, a cyano group, and a halogen atom]

(hereinafter referred to as "Present compound N" or "Compound N of the present invention") or an N-oxide thereof (hereinafter the compound represented by formula (I) or an N-oxide thereof is referred to as "Present compound" or "Compound of the present invention").

[2] The compound or an N-oxide thereof according to [1], wherein Q represents the group represented by Q1.

[3] The compound or an N-oxide thereof according to [1], wherein Q represents the group represented by Q2.

[4] The compound or an N-oxide thereof according to any one of [1] to [3], wherein
$R^{3a}$, $R^{3b}$, $R^{3c}$, and $R^{3d}$ are identical to or different from each other, and each represent a C1-C6 alkyl group, a C2-C6 alkenyl group, a C3-C7 cycloalkyl group {wherein said C1-C6 alkyl group, said C2-C6 alkenyl group, and said C3-C7 cycloalkyl group are optionally substituted with one or more substituent(s) selected from the group consisting of a halogen atom and a cyano group}, a phenyl group, a pyridyl group, a pyrimidinyl group {wherein said phenyl group, said pyridyl group, and said pyrimidinyl group are optionally substituted with one or more substituent(s) selected from Group J}, $OR^{12}$, $CR^{30}$=$NOR^{17}$, a hydrogen atom, or a halogen atom.

[5] The compound or an N-oxide thereof according to any one of [1] to [4], wherein
$G^1$ represents a nitrogen atom or CH;
$G^2$ represents $CR^{3b}$;
$G^3$ represents $CR^{3c}$;
$G^4$ represents a nitrogen atom or CH; and
$R^{3b}$ and $R^{3c}$ are identical to or different from each other, and each represent a C1-C6 alkyl group, a C2-C6 alkenyl group, a C3-C7 cycloalkyl group {wherein said C1-C6 alkyl group, said C2-C6 alkenyl group, and said C3-C7 cycloalkyl group are optionally substituted with one or more substituent(s) selected from the group consisting of a halogen atom and a cyano group}, $OR^{12}$, a hydrogen atom, or a halogen atom.

[6] The compound or an N-oxide thereof according to any one of [1] to [5], wherein
$G^1$ represents CH;
$G^2$ represents $CR^{3b}$;
$G^3$ represents $CR^{3c}$;
$G^4$ represents CH; and
$R^{3b}$ and $R^{3c}$ are identical to or different from each other, and each represent a C1-C6 alkyl group optionally substituted with one or more halogen atom(s), or a hydrogen atom.

[7] The compound or an N-oxide thereof according to any one of [1] to [6], wherein
$R^{1a}$ and $R^{1b}$ are identical to or different from each other, and each represent a C1-C6 alkyl group substituted with one or more substituent(s) selected from the group consisting of a cyano group and a halogen atom; or a cyclopropyl group optionally substituted with one or more substituent(s) selected from the group consisting of a cyano group and a halogen atom.

[8] The compound or an N-oxide thereof according to any one of [1] to [7], wherein $R^2$ represents an ethyl group.

[9] The compound or an N-oxide thereof according to any one of [1] to [8], wherein Z represents an oxygen atom.

[10] A composition for controlling a harmful arthropod comprising the compound or an N-oxide thereof according to any one of [1] to [9].

[11] A composition comprising one or more ingredient(s) selected from the group consisting of Group (a), Group (b), Group (c), and Group (d), and the compound or an N-oxide thereof according to any one of [1] to [9] (hereinafter referred to as "Present composition" or "Composition of the present invention"):
Group (a): a group consisting of insecticidal active ingredients, miticidal active ingredients, and nematicidal active ingredients;
Group (b): fungicidal active ingredients;
Group (c): plant growth regulatory ingredients;
Group (d): repellent ingredients.

[12] A method for controlling a harmful arthropod which comprises applying an effective amount of the compound or an N-oxide thereof according to any one of [1] to [9] or an effective amount of the composition according to [11] to a harmful arthropod or a habitat where a harmful arthropod lives.

[13] A seed or a vegetative reproduction organ holding an effective amount of the compound or an N-oxide thereof according to any one of [1] to [9] or an effective amount of the composition according to [11].

Effect of Invention

According to the present invention, harmful arthropods can be controlled.

MODE FOR CARRYING OUT THE INVENTION

The substituents in the present invention are explained as follows.

The term of "halogen atom" represents a fluorine atom, a chlorine atom, a bromine atom, or an iodine atom.

When a substituent is substituted with two or more halogen atoms or substituents, these halogen atoms or substituents may be identical to or different from each other.

The expression of "CX-CY" as described herein means that the number of carbon atom is X to Y. For example, the expression of "C1-C6" means that the number of carbon atom is 1 to 6.

The term of "chain hydrocarbon group" represents an alkyl group, an alkenyl group, or an alkynyl group.

Examples of the term of "alkyl group" include a methyl group, an ethyl group, a propyl group, an isopropyl group, a 1,1-dimethylpropyl group, a 1,2-dimethylpropyl group, a 1-ethylpropyl group, a butyl group, a sec-butyl group, a tert-butyl group, a pentyl group, and a hexyl group.

Examples of the term of "alkenyl group" include a vinyl group, a 1-propenyl group, a 2-propenyl group, a 1-methyl-1-propenyl group, a 1-methyl-2-propenyl group, a 1,2-dimethyl-1-propenyl group, a 1-ethyl-2-propenyl group, a 3-butenyl group, a 4-pentenyl group, and a 5-hexenyl group.

Examples of the term of "alkynyl group" include an ethynyl group, a 1-propynyl group, a 2-propynyl group, a 1-methyl-2-propynyl group, a 1, 1-dimethyl-2-propynyl group, a 1-ethyl-2-propynyl group, a 2-butynyl group, a 4-pentynyl group, and a 5-hexynyl group.

Examples of the term of "alkoxy group" include a methoxy group, an ethoxy group, a propoxy group, an isopropoxy group, a butoxy group, a tert-butoxy group, a pentyloxy group, and a hexyloxy group.

Examples of the term of "alkenyloxy group" include a 2-propenyloxy group, a 2-butenyloxy group, and a 5-hexenyloxy group.

Examples of the term of "alkynyloxy group" include a 2-propynyloxy group, a 2-butynyloxy group, and a 5-hexynyloxy group.

Examples of the term of "fluoroalkyl group" include a trifluoromethyl group, a 2,2,2-trifluoroethyl group, a pentafluoroethyl group, a 2,2,3,3,3-pentafluoropropyl group, a 1,1,1-trifluoropropan-2-yl group, and a heptafluoropropyl group.

Examples of the term of "cycloalkyl group" include a cyclopropyl group, a cyclobutyl group, a cyclopentyl group, a cyclohexyl group, and a cycloheptyl group.

Examples of the term of "cycloalkenyl group" include a cyclopropenyl group, a cyclobutenyl group, a cyclopentenyl group, a cyclohexenyl group, and a cycloheptenyl group.

The term of "3-7 membered nonaromatic heterocyclic group" represents an aziridine ring, an azetidine ring, a pyrrolidine ring, an imidazoline ring, an imidazolidine ring, a piperidine ring, a tetrahydropyrimidine ring, a hexahydropyrimidine ring, a piperazine ring, an azepane ring, an oxazolidine ring, an isoxazolidine ring, a 1,3-oxazinane ring, a morpholine ring, a 1,4-oxazepane ring, a thiazolidine ring, an isothiazolidine ring, a 1,3-thiazinane ring, a thiomorpholine ring, or a 1,4-thiazepane ring.

Examples of the term of "3-7 membered nonaromatic heterocyclic group optionally substituted with one or more substituent(s) selected from Group E" include the following groups.

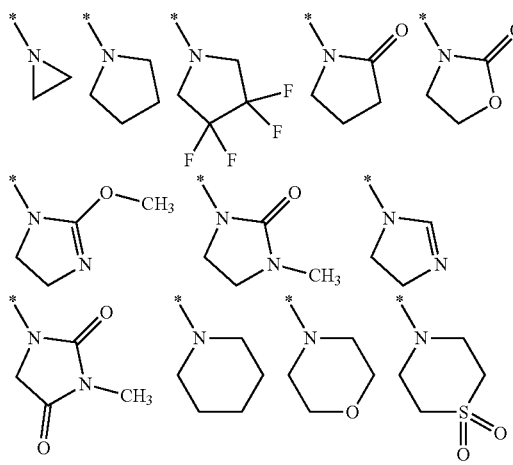

The term of "5 or 6 membered aromatic heterocyclic group" represents a 5 membered aromatic heterocyclic group or a 6 membered aromatic heterocyclic group. The term of "5 membered aromatic heterocyclic group" represents a pyrrolyl group, a furyl group, a thienyl group, a pyrazolyl group, an imidazolyl group, a triazolyl group, a tetrazolyl group, an oxazolyl group, an isoxazolyl group, a thiazolyl group, an isothiazolyl group, an oxadiazolyl group, or a thiadiazolyl group. The term of "6 membered aromatic heterocyclic group" represents a pyridyl group, a pyridazinyl group, a pyrimidinyl group, a pyrazinyl group, a triazinyl group, or a tetrazinyl group.

Examples of the term of "(C3-C6 cycloalkyl) C1-C3 alkyl group optionally substituted with one or more halogen atom(s)" include a cyclopropylmethyl group, a (2-fluorocyclopropyl)methyl group, a cyclopropyl(fluoro)methyl group, and a (2-fluorocyclopropyl)(fluoro)methyl group.

Examples of the term of "phenyl C1-C3 alkyl group {wherein the phenyl moiety in said phenyl C1-C3 alkyl group is optionally substituted with one or more substituent(s) selected from Group D}" include a benzyl group, a 2-fluorobenzyl group, a 4-chlorobenzyl group, a 4-(trifluoromethyl)benzyl group, and a 2-[4-(trifluoromethyl)phenyl]ethyl group.

The terms of "alkylsulfanyl group", "alkylsulfinyl group", and "alkylsulfonyl group" represent alkyl groups having a moiety represented by $S(O)_z$.

Examples of the term of "alkylsulfanyl group" wherein z represents 0 include a methylsulfanyl group, an ethylsulfanyl group, a propylsulfanyl group, and an isopropylsulfanyl group.

Examples of the term of "alkylsulfinyl group" wherein z represents 1 include a methylsulfinyl group, an ethylsulfinyl group, a propylsulfinyl group, and an isopropylsulfinyl group.

Examples of the term of "alkylsulfonyl group" wherein z represents 2 include a methylsulfonyl group, an ethylsulfonyl group, a propylsulfonyl group, and an isopropylsulfonyl group.

Examples of N-oxide of the compound represented by formula (I) include the compounds represented by the following formulae.

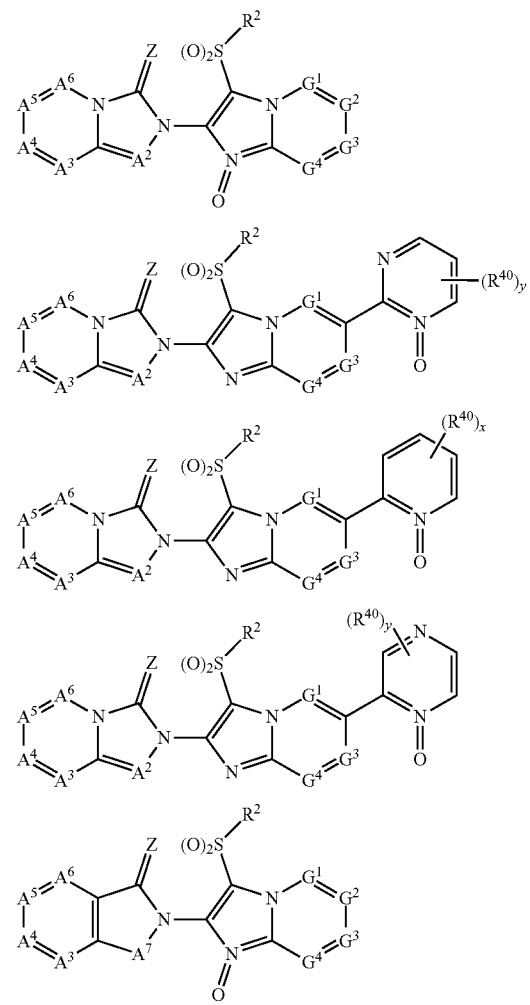

-continued

[wherein R$^{40}$ represents any one substituent selected from Group H; x represents 0, 1, 2, 3, or 4; y represents 0, 1, 2, or 3; and the other symbols are the same as defined above.]

The Present compound may optionally have one or more stereoisomer(s). Examples of the stereoisomer(s) include enantiomers, diastereomers, and geometric isomers. The Present compound encompasses each stereoisomer and mixtures of stereoisomers at any ratio.

The Present compound may optionally form an acid addition salt. Examples of the acid to form the acid addition salt include inorganic acids such as hydrogen chloride, phosphoric acid, and sulfuric acid; and organic acids such as acetic acid, trifluoroacetic acid, benzoic acid, and p-toluenesulfonic acid. Such acid addition salt may be prepared by mixing the Present compound with an acid.

Embodiments of the Present Compound N Include the Following Compounds.

[Aspect 1] The Present compound N, wherein
R$^{3a}$, R$^{3b}$, R$^{3c}$, and R$^{3d}$ are identical to or different from each other, and each represent a C1-C6 alkyl group, a C2-C6 alkenyl group, a C3-C7 cycloalkyl group {wherein said C1-C6 alkyl group, said C2-C6 alkenyl group, and said C3-C7 cycloalkyl group are optionally substituted with one or more substituent(s) selected from the group consisting of a halogen atom and a cyano group}, a phenyl group, a pyridyl group, a pyrimidinyl group {wherein said phenyl group, said pyridyl group, and said pyrimidinyl group are optionally substituted with one or more substituent(s) selected from Group J}, OR$^{12}$, CR$^{30}$=NOR$^{17}$, a hydrogen atom, or a halogen atom.

[Aspect 2] The Present compound N, wherein
R$^{3a}$, R$^{3b}$, R$^{3c}$, and R$^{3d}$ are identical to or different from each other, and each represent a C1-C6 alkyl group, a C2-C6 alkenyl group, a C3-C7 cycloalkyl group {wherein said C1-C6 alkyl group, said C2-C6 alkenyl group, and said C3-C7 cycloalkyl group are optionally substituted with one or more halogen atom(s)}, a hydrogen atom, or a halogen atom.

[Aspect 3] The compound according to the Aspect 2, wherein
G$^1$ represents a nitrogen atom or CH;
G$^2$ represents CR$^{3b}$;
G$^3$ represents CR$^{3c}$; and
G$^4$ represents a nitrogen atom or CH.

[Aspect 4] The compound according to the Aspect 2, wherein
G$^1$ represents CH;
G$^2$ represents CR$^{3b}$;
G$^3$ represents CR$^{3c}$; and
G$^4$ represents CH.

[Aspect 5] The Present compound N, wherein
G$^1$ represents CH;
G$^2$ represents CR$^{3b}$;
G$^3$ represents CR$^{3c}$;
G$^4$ represents CH; and
R$^{3b}$ and R$^{3c}$ are identical to or different from each other, and each represent a C1-C6 alkyl group optionally substituted with one or more halogen atom(s), or a hydrogen atom.

[Aspect 6] The Present compound N, wherein
G$^1$, G$^3$, and G$^4$ each represent CH; and
G$^2$ represents CCF$_3$.

[Aspect 7] The compound according to the Aspect 2, wherein
G$^1$ represents a nitrogen atom;
G$^2$ represents CR$^{3b}$;
G$^3$ represents CR$^{3c}$; and
G$^4$ represents CH.

[Aspect 8] The compound according to the Aspect 2, wherein
G$^1$ represents CH;
G$^2$ represents CR$^{3b}$;
G$^3$ represents CR$^{3c}$; and
G$^4$ represents a nitrogen atom.

[Aspect 9] The Present compound N, wherein R$^2$ represents a C1-C6 alkyl group.

[Aspect 10] The Present compound N, wherein R$^2$ represents an ethyl group.

[Aspect 11] The compound according to the Aspect 1, wherein R$^2$ represents a C1-C6 alkyl group.

[Aspect 12] The compound according to the Aspect 2, wherein R$^2$ represents a C1-C6 alkyl group.

[Aspect 13] The compound according to the Aspect 3, wherein R$^2$ represents a C1-C6 alkyl group.

[Aspect 14] The compound according to the Aspect 4, wherein R$^2$ represents a C1-C6 alkyl group.

[Aspect 15] The compound according to the Aspect 5, wherein R$^2$ represents a C1-C6 alkyl group.

[Aspect 16] The compound according to the Aspect 6, wherein R$^2$ represents a C1-C6 alkyl group.

[Aspect 17] The compound according to the Aspect 7, wherein R$^2$ represents a C1-C6 alkyl group.

[Aspect 18] The compound according to the Aspect 8, wherein R$^2$ represents a C1-C6 alkyl group.

[Aspect 19] The compound according to the Aspect 1, wherein R$^2$ represents an ethyl group.

[Aspect 20] The compound according to the Aspect 2, wherein R$^2$ represents an ethyl group.

[Aspect 21] The compound according to the Aspect 3, wherein R$^2$ represents an ethyl group.

[Aspect 22] The compound according to the Aspect 4, wherein R$^2$ represents an ethyl group.

[Aspect 23] The compound according to the Aspect 5, wherein R$^2$ represents an ethyl group.

[Aspect 24] The compound according to the Aspect 6, wherein $R^2$ represents an ethyl group.
[Aspect 25] The compound according to the Aspect 7, wherein $R^2$ represents an ethyl group.
[Aspect 26] The compound according to the Aspect 8, wherein $R^2$ represents an ethyl group.
[Aspect 27] The Present compound N, wherein Q represents the group represented by Q1.
[Aspect 28] The Present compound N, wherein Q represents the group represented by Q2.
[Aspect 29] The compound according to the Aspect 1, wherein Q represents the group represented by Q1.
[Aspect 30] The compound according to the Aspect 2, wherein Q represents the group represented by Q1.
[Aspect 31] The compound according to the Aspect 3, wherein Q represents the group represented by Q1.
[Aspect 32] The compound according to the Aspect 4, wherein Q represents the group represented by Q1.
[Aspect 33] The compound according to the Aspect 5, wherein Q represents the group represented by Q1.
[Aspect 34] The compound according to the Aspect 6, wherein Q represents the group represented by Q1.
[Aspect 35] The compound according to the Aspect 7, wherein Q represents the group represented by Q1.
[Aspect 36] The compound according to the Aspect 8, wherein Q represents the group represented by Q1.
[Aspect 37] The compound according to the Aspect 9, wherein Q represents the group represented by Q1.
[Aspect 38] The compound according to the Aspect 10, wherein Q represents the group represented by Q1.
[Aspect 39] The compound according to the Aspect 11, wherein Q represents the group represented by Q1.
[Aspect 40] The compound according to the Aspect 12, wherein Q represents the group represented by Q1.
[Aspect 41] The compound according to the Aspect 13, wherein Q represents the group represented by Q1.
[Aspect 42] The compound according to the Aspect 14, wherein Q represents the group represented by Q1.
[Aspect 43] The compound according to the Aspect 15, wherein Q represents the group represented by Q1.
[Aspect 44] The compound according to the Aspect 16, wherein Q represents the group represented by Q1.
[Aspect 45] The compound according to the Aspect 17, wherein Q represents the group represented by Q1.
[Aspect 46] The compound according to the Aspect 18, wherein Q represents the group represented by Q1.
[Aspect 47] The compound according to the Aspect 19, wherein Q represents the group represented by Q1.
[Aspect 48] The compound according to the Aspect 20, wherein Q represents the group represented by Q1.
[Aspect 49] The compound according to the Aspect 21, wherein Q represents the group represented by Q1.
[Aspect 50] The compound according to the Aspect 22, wherein Q represents the group represented by Q1.
[Aspect 51] The compound according to the Aspect 23, wherein Q represents the group represented by Q1.
[Aspect 52] The compound according to the Aspect 24, wherein Q represents the group represented by Q1.
[Aspect 53] The compound according to the Aspect 25, wherein Q represents the group represented by Q1.
[Aspect 54] The compound according to the Aspect 26, wherein Q represents the group represented by Q1.
[Aspect 55] The compound according to the Aspect 1, wherein Q represents the group represented by Q2.
[Aspect 56] The compound according to the Aspect 2, wherein Q represents the group represented by Q2.
[Aspect 57] The compound according to the Aspect 3, wherein Q represents the group represented by Q2.
[Aspect 58] The compound according to the Aspect 4, wherein Q represents the group represented by Q2.
[Aspect 59] The compound according to the Aspect 5, wherein Q represents the group represented by Q2.
[Aspect 60] The compound according to the Aspect 6, wherein Q represents the group represented by Q2.
[Aspect 61] The compound according to the Aspect 7, wherein Q represents the group represented by Q2.
[Aspect 62] The compound according to the Aspect 8, wherein Q represents the group represented by Q2.
[Aspect 63] The compound according to the Aspect 9, wherein Q represents the group represented by Q1.
[Aspect 64] The compound according to the Aspect 10, wherein Q represents the group represented by Q2.
[Aspect 65] The compound according to the Aspect 11, wherein Q represents the group represented by Q2.
[Aspect 66] The compound according to the Aspect 12, wherein Q represents the group represented by Q2.
[Aspect 67] The compound according to the Aspect 13, wherein Q represents the group represented by Q2.
[Aspect 68] The compound according to the Aspect 14, wherein Q represents the group represented by Q2.
[Aspect 69] The compound according to the Aspect 15, wherein Q represents the group represented by Q2.
[Aspect 70] The compound according to the Aspect 16, wherein Q represents the group represented by Q2.
[Aspect 71] The compound according to the Aspect 17, wherein Q represents the group represented by Q2.
[Aspect 72] The compound according to the Aspect 18, wherein Q represents the group represented by Q2.
[Aspect 73] The compound according to the Aspect 19, wherein Q represents the group represented by Q2.
[Aspect 74] The compound according to the Aspect 20, wherein Q represents the group represented by Q2.
[Aspect 75] The compound according to the Aspect 21, wherein Q represents the group represented by Q2.
[Aspect 76] The compound according to the Aspect 22, wherein Q represents the group represented by Q2.
[Aspect 77] The compound according to the Aspect 23, wherein Q represents the group represented by Q2.
[Aspect 78] The compound according to the Aspect 24, wherein Q represents the group represented by Q2.
[Aspect 79] The compound according to the Aspect 25, wherein Q represents the group represented by Q2.
[Aspect 80] The compound according to the Aspect 26, wherein Q represents the group represented by Q2.
[Aspect 81] The compound according to any one of the Aspects 1 to 80 or the Present compound N, wherein
$R^{1a}$ and $R^{1b}$ are identical to or different from each other, and each represent a C1-C6 alkyl group substituted with one or more substituent(s) selected from the group consisting of a halogen atom and a cyano group; or a cyclopropyl group optionally substituted with one or more substituent(s) selected from the group consisting of a cyano group and a halogen atom;
$A^2$ represents a nitrogen atom or CH;
$A^7$ represents $NR^{6g}$; and
$R^{6c}$, $R^{6d}$, $R^{6e}$, and $R^{6f}$ are identical to or different from each other, and each represent a halogen atom or a hydrogen atom.

[Aspect 82] The compound according to the Aspect 81, wherein $R^{6g}$ represents a methyl group.

[Aspect 83] The compound according to the Aspect 81, wherein
$A^4$ represents a nitrogen atom or $CR^{6d}$;
$A^b$ represents $CR^{1b}$; and
$A^6$ represents $CR^{6f}$.

[Aspect 84] The compound according to the Aspect 82, wherein
$A^4$ represents a nitrogen atom or $CR^{6d}$;
$A^5$ represents $CR^{1b}$; and
$A^6$ represents $CR^{6f}$.

[Aspect 85] The compound according to any one of the Aspects 1 to 80 or the Present compound N, wherein
$R^{1a}$ and $R^{1b}$ are identical to or different from each other, and each represent a C1-C6 alkyl group substituted with one or more substituent(s) selected from the group consisting of a halogen atom and a cyano group; or a cyclopropyl group optionally substituted with one or more substituent(s) selected from the group consisting of a cyano group and a halogen atom;
$A^2$ represents a nitrogen atom;
$A^7$ represents $NR^{6g}$; and
$R^{6c}$, $R^{6d}$, $R^{6e}$, and $R^{6f}$ are identical to or different from each other, and each represent a halogen atom or a hydrogen atom.

[Aspect 86] The compound according to the Aspect 85, wherein $R^{6g}$ represents a methyl group.

[Aspect 87] The compound according to any one of the Aspects 1 to 80 or the Present compound N, wherein
$R^{1a}$ and $R^{1b}$ are identical to or different from each other, and each represent a C1-C3 fluoroalkyl group;
$A^2$ represents a nitrogen atom or CH;
$A^7$ represents $NR^{6g}$;
$R^{6c}$, $R^{6d}$, $R^{6e}$, and $R^{6f}$ each represent a hydrogen atom; and
Z represents an oxygen atom.

[Aspect 88] The compound according to the Aspect 87, wherein $R^{6g}$ represents a methyl group.

[Aspect 89] The compound according to the Aspect 87, wherein
$A^4$ represents a nitrogen atom or $CR^{6d}$;
$A^5$ represents $CR^{1b}$; and
$A^6$ represents $CR^{6f}$.

[Aspect 90] The compound according to the Aspect 88, wherein
$A^4$ represents a nitrogen atom or $CR^{6d}$;
$A^5$ represents $CR^{1b}$; and
$A^6$ represents $CR^{6f}$.

[Aspect 91] The compound according to any one of the Aspects 1 to 80 or the Present compound N, wherein
$R^{1a}$ and $R^{1b}$ are identical to or different from each other, and each represent a C1-C3 fluoroalkyl group;
$A^2$ represents a nitrogen atom or CH;
$A^4$ represents a nitrogen atom or $CR^{6d}$;
$A^3$ represents $CR^{1b}$;
$A^6$ represents $CR^{6f}$;
$A^7$ represents $NR^{6g}$;
$R^{6c}$, $R^{6d}$, $R^{6e}$, and $R^{6d}$ each represent a hydrogen atom; and
Z represents an oxygen atom.

[Aspect 92] The compound according to the Aspect 91, wherein $R^{6g}$ represents a methyl group.

[Aspect 93] The compound according to any one of the Aspects 1 to 80 or the Present compound N, wherein
$R^{1a}$ and $R^{1b}$ are identical to or different from each other, and each represent a C1-C3 fluoroalkyl group;
$A^2$ represents a nitrogen atom;
$A^7$ represents $NCH_3$;
$R^{6c}$, $R^{6d}$, $R^{6e}$, and $R^{6f}$ each represent a hydrogen atom; and
Z represents an oxygen atom.

[Aspect 94] The compound according to the Aspect 93, wherein
$A^3$ and $A^4$ each represent a nitrogen atom;
$A^5$ represents $CR^{1b}$; and
$A^6$ represents CH.

[Aspect 95] The compound according to the Aspect 93, wherein
$A^3$ represents a nitrogen atom;
$A^5$ represents $CR^{1b}$; and
$A^4$ and $A^6$ each represent CH.

[Aspect 96] The compound according to the Aspect 93, wherein
$A^4$ represents a nitrogen atom;
$A^5$ represents $CR^{1b}$; and
$A^3$ and $A^6$ each represent CH.

[Aspect 97] The compound according to the Aspect 93, wherein
$A^5$ represents $CR^{1b}$; and
$A^3$, $A^4$, and $A^6$ each represent CH.

[Aspect A1] The Present compound N, wherein
$R^2$ represents an ethyl group;
$G^1$ and $G^4$ each represent CH;
$G^2$ represents $CR^{3b}$;
$G^3$ represents $CR^{3c}$;
$R^{3b}$ and $R^{3c}$ are identical to or different from each other, and each represent a C1-C3 chain hydrocarbon group optionally substituted with one or more halogen atom(s), a cyclopropyl group, a phenyl group optionally substituted with one or more halogen atom(s), $OR^{12}$, a halogen atom, or a hydrogen atom;
$R^{12}$ represents a C1-C3 alkyl group optionally substituted with one or more halogen atom(s), or a hydrogen atom;
Z represents an oxygen atom;
$A^6$ represents CH;
$R^{1a}$ and $R^{1b}$ are identical to or different from each other, and each represent a C1-C3 alkyl group substituted with one or more halogen atom(s), or $SR^8$; and
$R^8$ represents a C1-C3 alkyl group substituted with one or more halogen atom(s).

[Aspect A2] The compound according to the Aspect A1, wherein
n represents 2; and
Q represents the group represented by Q1.

[Aspect A3] The compound according to the Aspect A1, wherein
n represents 2; and
Q represents the group represented by Q2.

[Aspect A4] The compound according to the Aspect A2, wherein
$A^2$ represents a nitrogen atom; and
$A^3$ and $A^6$ each represent CH.

[Aspect A5] The compound according to the Aspect A4, wherein
$A^4$ represents a nitrogen atom or CH; and
$A^5$ represents $CR^{1b}$.

[Aspect A6] The compound according to any one of the Aspects A1 to A5, wherein $R^{1a}$, $R^{1b}$, and $R^8$ each represent a trifluoromethyl group.

[Aspect A7] The compound according to any one of the Aspects A1 to A5, wherein $R^{12}$ represents a C1-C3 alkyl group.

[Aspect A8] The compound according to the Aspect A7, wherein $R^{1a}$, $R^{1b}$, and $R^8$ each represent a trifluoromethyl group.

[Aspect A9] The compound according to the Aspect A3, wherein
  $A^3$ represents a nitrogen atom;
  $A^7$ represents $NCH_3$;
  $A^4$ represents CH; and
  $A^5$ represents $CR^{1b}$.

[Aspect A10] The compound according to the Aspect A9, wherein $R^{1b}$ represents a trifluoromethyl group.

[Aspect A11] The compound according to the Aspect A10, wherein $R^{12}$ represents a C1-C3 alkyl group.

Next, production methods for the Present compounds are described.

Production Method 1

A compound represented by formula (I-b) (hereinafter referred to as "Compound (I-b)") or a compound represented by formula (I-c) (hereinafter referred to as "Compound (I-c)") may be prepared by reacting a compound represented by formula (I-a) (hereinafter referred to as "Compound (I-a)") with an oxidizing agent.

[Structural scheme showing (I-a) → (I-b) → (I-c)]

[wherein the symbols are the same as defined above.]

First, a method for producing the Compound (I-b) from the Compound (I-a) is described.

The reaction is usually carried out in a solvent. Examples of the solvent include halogenated hydrocarbons such as dichloromethane and chloroform (hereinafter collectively referred to as "halogenated hydrocarbons"); nitriles such as acetonitrile (hereinafter collectively referred to as "nitriles"); alcohols such as methanol and ethanol (hereinafter collectively referred to as "alcohols"); acetic acid; water; and mixtures of two or more of them.

Examples of the oxidizing agent include sodium periodate, m-chloroperbenzoic acid (hereinafter referred to as "mCPBA"), and hydrogen peroxide.

When hydrogen peroxide is used as the oxidizing agent, a base or a catalyst may be used as needed.

Examples of the base include sodium carbonate. When a base is used in the reaction, the base is usually used at a ratio of 0.01 to 1 mol relative to 1 mol of the Compound (I-a).

Examples of the catalyst include tungstic acid and sodium tungstate. When a catalyst is used in the reaction, the catalyst is usually used at a ratio of 0.01 to 0.5 mol relative to 1 mol of the Compound (I-a).

In the reaction, the oxidizing agent is usually used at a ratio of 1 to 1.2 mol relative to 1 mol of the Compound (I-a).

The reaction temperature is usually within the range of −20 to 80° C. The reaction time is usually within the range of 0.1 to 12 hour(s).

When the reaction is completed, to the reaction mixture is added water, the resulting mixture is subjected to extraction with organic solvent(s), and the resulting organic layer is washed with an aqueous solution of a reducing agent (for example, sodium sulfite or sodium thiosulfate) and an aqueous solution of a base (for example, sodium hydrogen carbonate) as needed. The resulting organic layer is dried and/or concentrated to give the Compound (I-b).

Next, a method for producing the Compound (I-c) from the Compound (I-b) is described.

The reaction is usually carried out in a solvent. Examples of the solvent include halogenated hydrocarbons, nitriles, alcohols, acetic acid, water, and mixtures of two or more of them.

Examples of the oxidizing agent include mCPBA and hydrogen peroxide.

When hydrogen peroxide is used as the oxidizing agent, a base or a catalyst may be used as needed.

Examples of the base include sodium carbonate. When a base is used in the reaction, the base is usually used at a ratio of 0.01 to 1 mol relative to 1 mol of the Compound (I-b).

Examples of the catalyst include sodium tungstate. When a catalyst is used in the reaction, the catalyst is usually used at a ratio of 0.01 to 0.5 mol relative to 1 mol of the Compound (I-b).

In the reaction, the oxidizing agent is usually used at a ratio of 1 to 2 mol relative to 1 mol of the Compound (I-b).

The reaction temperature is usually within the range of −20 to 120° C. The reaction time is usually within the range of 0.1 to 12 hour(s).

When the reaction is completed, to the reaction mixture is added water, the resulting mixture is subjected to extraction with organic solvent(s), and the resulting organic layer is washed with an aqueous solution of a reducing agent (for example, sodium sulfite or sodium thiosulfate) and an aqueous solution of a base (for example, sodium hydrogen carbonate) as needed. The resulting organic layer is dried and/or concentrated to give the Compound (I-c).

Also, the Compound (I-c) may be prepared in one step reaction (one-pot) by reacting the Compound (I-a) with an oxidizing agent.

The reaction may be carried out according to the method for producing the Compound (I-c) from the Compound (I-b) by usually using the oxidizing agent at a ratio of 2 to 5 mol relative to 1 mol of the Compound (I-a).

Production Method 2

A compound represented by formula (II-1S) (hereinafter referred to as "Compound (II-1S)") may be prepared by reacting a compound represented by formula (II-1O) (hereinafter referred to as "Compound (II-1O)") with a sulfating agent.

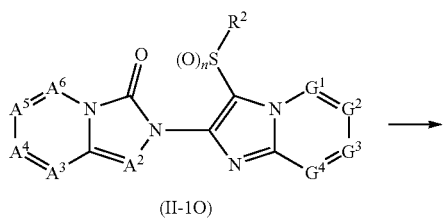

(II-1O)

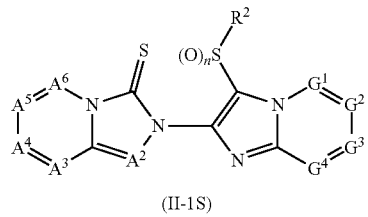

(II-1S)

[wherein the symbols are the same as defined above.]

The reaction is carried out in a solvent or in the absence of a solvent. Examples of the solvent include ethers such as tetrahydrofuran and methyl tert-butyl ether (hereinafter collectively referred to as "ethers"); halogenated hydrocarbons; aromatic hydrocarbons such as toluene and xylene (hereinafter collectively referred to as "aromatic hydrocarbons"); nitriles; nitrogen-containing aromatic compounds such as pyridine, picoline, lutidine, and quinoline; and mixtures of two or more of them.

Examples of the sulfating agent include phosphorus pentasulfide and Lawesson's reagent (2,4-bis(4-methoxyphenyl)-1,3-dithia-2,4-diphosphetane-2,4-disulfide).

In the reaction, the sulfating agent is usually used at a ratio of 1 to 3 mol relative to 1 mol of the Compound (II-1O).

The reaction temperature is usually within the range of 0° C. to 200° C. The reaction time is usually within the range of 1 to 24 hour(s).

When the reaction is completed, the reaction mixture may be subjected to a work-up such as adding water to the reaction mixture, subjecting the resulting mixture to extraction with organic solvent(s), and drying and/or concentrating the resulting organic layer to give the Compound (II-1S).

Production Method 3

A compound represented by formula (II-2S) (hereinafter referred to as "Compound (II-2S)") may be prepared by reacting a compound represented by formula (II-2O) (hereinafter referred to as "Compound (II-2O)") with a sulfating agent.

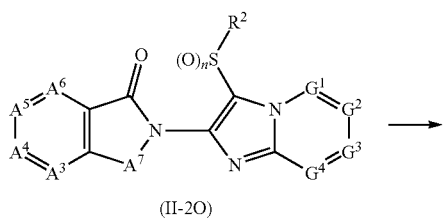

(II-2O)

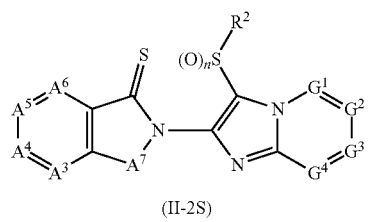

(II-2S)

[wherein the symbols are the same as defined above.]

The reaction may be carried out according to the Production method 2.

Production Method 4

The Compound (II-1O) may be prepared by reacting a compound represented by formula (M-1) (hereinafter referred to as "Compound (M-1)") with a compound represented by formula (M-2) (hereinafter referred to as "Compound (M-2)") in the presence of a base.

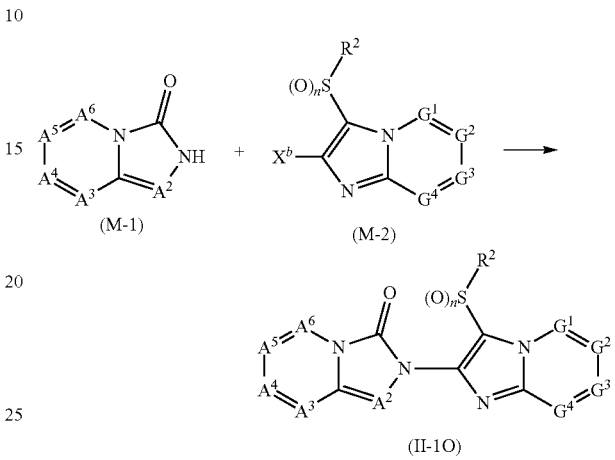

[wherein $X^b$ represents a leaving group such as a fluorine atom, a chlorine atom, a bromine atom, and an iodine atom; and the other symbols are the same as defined above.]

The reaction is usually carried out in a solvent. Examples of the solvent include ethers; aromatic hydrocarbons; nitriles; aprotic polar solvents such as dimethylformamide (hereinafter referred to as "DMF"), N-methylpyrrolidone (hereinafter referred to as "NMP"), and dimethyl sulfoxide (hereinafter referred to as "DMSO") (hereinafter collectively referred to as "aprotic polar solvents"); and mixtures of two or more of them.

Examples of the base include organic bases such as triethylamine, diisopropylethylamine, pyridine, and 4-(dimethylamino)pyridine (hereinafter collectively referred to as "organic bases"); alkali metal carbonates such as sodium carbonate and potassium carbonate (hereinafter collectively referred to as "alkali metal carbonates"); and alkali metal hydrides such as sodium hydride (hereinafter collectively referred to as "alkali metal hydrides").

The reaction may also be carried out by using a metal catalyst as needed. Examples of the metal catalyst include copper catalysts such as copper(I) iodide, copper (I) bromide, copper (I) chloride, copper(I) oxide, copper (I) trifluoromethanesulfonate benzene complex, tetrakis(acetonitrile)copper(I) hexafluorophosphate, and copper(I) 2-thiophenecarboxylate; nickel catalysts such as bis(cyclooctadiene)nickel(0) and nickel(II) chloride; and palladium catalysts such as palladium(II) acetate, tetrakis(triphenylphosphine)palladium(0), and tris(dibenzylideneacetone)dipalladium(II). When a metal catalyst is used in the reaction, the metal catalyst is usually used at a ratio of 0.01 to 0.5 mol relative to 1 mol of the Compound (M-1).

The reaction may also be carried out by using a ligand as needed. Examples of the ligand include triphenylphosphine, 4,5-bis(diphenylphosphino)-9,9-dimethylxanthene (hereinafter referred to as "Xantphos"), 2,2'-bis(diphenylphosphino)-1,1'-binaphthyl, 1,1'-bis(diphenylphosphino)ferrocene, 2-dicyclohexylphosphino-2',4',6'- triisopropylbiphenyl, 2-dicyclohexylphosphino-2',6'-dimethoxybiphenyl, 1,2-bis(diphenylphosphino)ethane, 2,2'-bipyridine, 2-aminoethanol, 8-hydroxyquinoline, 1,10-phenanthroline, trans-1,2-cyclohexanediamine, trans-N,N'-dimethylcyclohexane-1,2-diamine, and N,N'-dimethylethylenediamine. When a ligand is used in the reaction, the ligand is usually used at a ratio of 0.01 to 0.5 mol relative to 1 mol of the Compound (M-1).

In the reaction, the Compound (M-2) is usually used at a ratio of 0.8 to 1.2 mol, and the base is usually used at a ratio of 1 to 3 mol, relative to 1 mol of the Compound (M-1).

The reaction temperature is usually within the range of −20° C. to 150° C. The reaction time is usually within the range of 0.5 to 24 hour(s).

When the reaction is completed, the reaction mixture may be subjected to a work-up such as adding water to the reaction mixture, subjecting the resulting mixture to extraction with organic solvent(s), and drying and/or concentrating the resulting organic layer to give the Compound (II-1O).

Production Method 5

The Compound (II-2O) may be prepared by reacting a compound represented by formula (M-3) (hereinafter referred to as "Compound (M-3)") with the Compound (M-2) in the presence of a base.

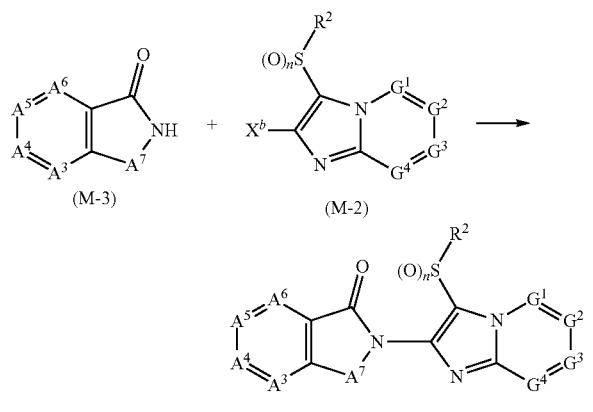

[wherein the symbols are the same as defined above.]

The reaction may be carried out according to the Production method 4 by using the Compound (M-3) instead of the Compound (M-1).

Production Method 6

The Compound (II-1O) may be prepared by reacting a compound represented by formula (M-4) (hereinafter referred to as "Compound (M-4)") with a carbonylating agent.

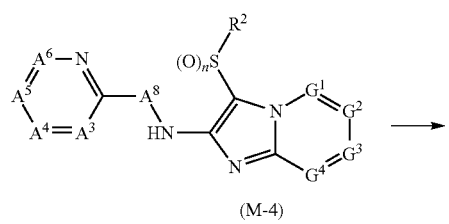

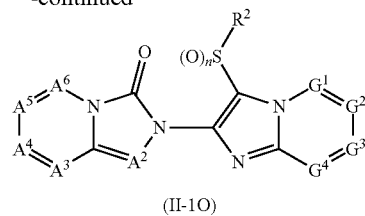

[wherein $A^8$ represents NH or $CHR^{6b}$; and the other symbols are the same as defined above.]

The reaction is usually carried out in a solvent or in the absence of a solvent. Examples of the solvent include ethers; aromatic hydrocarbons; halogenated hydrocarbons; esters such as ethyl acetate (hereinafter collectively referred to as "esters"); nitriles; aprotic polar solvents; water; and mixtures of two or more of them.

Examples of the carbonylating agent include 1,1'-carbonyldiimidazole and 1,1'-carbonyldi(1,2,4-triazole).

In the reaction, the carbonylating agent is usually used at a ratio of 1 to 3 mol relative to 1 mol of the Compound (M-4).

The reaction temperature is usually within the range of 0 to 150° C. The reaction time is usually within the range of 0.1 to 24 hour(s).

When the reaction is completed, the reaction mixture may be subjected to a work-up such as adding water to the reaction mixture, subjecting the resulting mixture to extraction with organic solvent(s), and drying and/or concentrating the resulting organic layer to give the Compound (II-1O).

Production Method 7

A compound represented by formula (II-3O) (hereinafter referred to as "Compound (II-3O)") may be prepared by reacting a compound represented by formula (M-5) (hereinafter referred to as "Compound (M-5)") with a compound represented by formula (M-6) (hereinafter referred to as "Compound (M-6)") in the presence of a base.

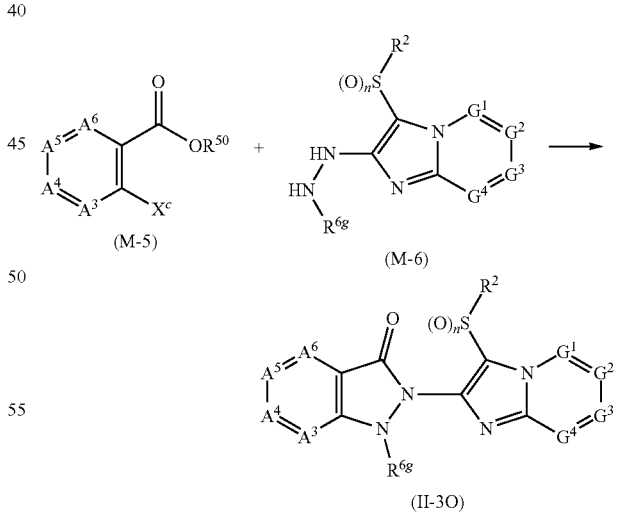

[wherein $R^{50}$ represents a C1-C6 alkyl group; $X^c$ represents a fluorine atom, a chlorine atom, or a bromine atom; and the other symbols are the same as defined above.]

The reaction is usually carried out in a solvent. Examples of the solvent include ethers, aromatic hydrocarbons, halogenated hydrocarbons, esters, nitriles, aprotic polar solvents, alcohols, water, and mixtures of two or more of them.

Examples of the base include organic bases, alkali metal carbonates, and alkali metal hydrides.

In the reaction, the Compound (M-6) is usually used at a ratio of 1 to 2 mol, and the base is usually used at a ratio of 1 to 5 mol, relative to 1 mol of the Compound (M-5).

The reaction temperature is usually within the range of 0 to 150° C. The reaction time is usually within the range of 0.1 to 24 hour(s).

When the reaction is completed, the reaction mixture may be subjected to a work-up such as adding water to the reaction mixture, subjecting the resulting mixture to extraction with organic solvent(s), and drying and/or concentrating the resulting organic layer to give the Compound (II-3O).

The Compound (M-5) is a commercially available compound or may be prepared by using known method(s).

Production Method 8

A compound represented by formula (II-4O) (hereinafter referred to as "Compound (II-4O)") may be prepared by reacting a compound represented by formula (M-7) (hereinafter referred to as "Compound (M-7)") with a condensing agent.

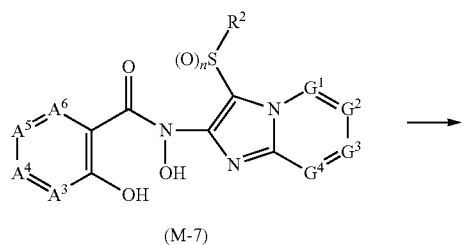

(M-7)

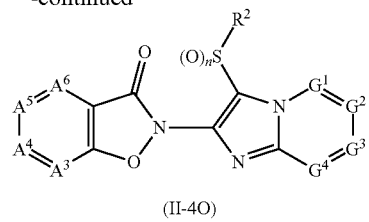

(II-4O)

[wherein the symbols are the same as defined above.]

The reaction is usually carried out in a solvent or in the absence of a solvent. Examples of the solvent include ethers, aromatic hydrocarbons, halogenated hydrocarbons, esters, nitriles, aprotic polar solvents, and mixtures of two or more of them.

Examples of the condensing agent include a mixture of two or more of triphenylphosphine and an azodiester such as diethyl azodicarboxylate.

In the reaction, triphenylphosphine is usually used at a ratio of 1 to 5 mol, and the azodiester is usually used at a ratio of 1 to 5 mol, relative to 1 mol of the Compound (M-7).

The reaction temperature is usually within the range of 0 to 150° C. The reaction time is usually within the range of 0.1 to 24 hour(s).

When the reaction is completed, the reaction mixture may be subjected to a work-up such as adding water to the reaction mixture, subjecting the resulting mixture to extraction with organic solvent(s), and drying and/or concentrating the resulting organic layer to give the Compound (II-4O).

Production Method 9

A compound represented by formula (II-1n0) (hereinafter referred to as "Compound (II-1n0)") may be prepared according to the following scheme.

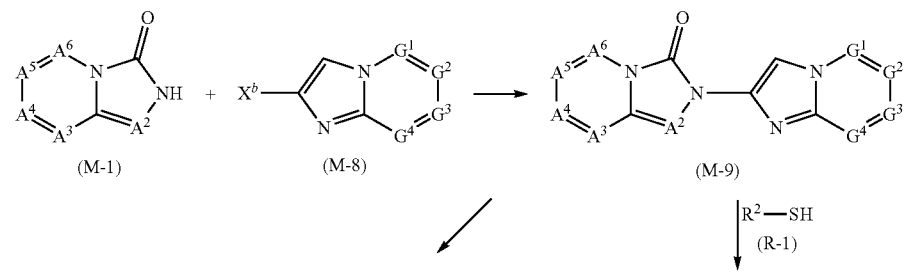

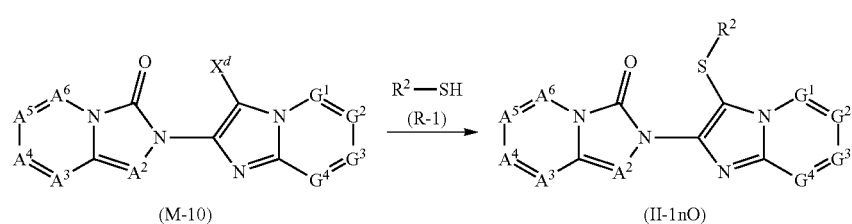

[wherein X$^d$ represents a chlorine atom, a bromine atom, or an iodine atom; and the other symbols are the same as defined above.]

First, a method for producing a compound represented by formula (M-9) (hereinafter referred to as "Compound (M-9)") is described.

The Compound (M-9) may be prepared according to the Production method 4 by using a compound represented by formula (M-8) (hereinafter referred to as "Compound (M-8)") instead of the Compound (M-2).

Next, a method for producing a compound represented by formula (M-10) (hereinafter referred to as "Compound (M-10)") is described.

The Compound (M-10) may be prepared by reacting the Compound (M-9) with a halogenating agent.

The reaction is usually carried out in a solvent. Examples of the solvent include alcohols, nitriles, ethers, aromatic hydrocarbons, aprotic polar solvents, halogenated hydrocarbons, water, and mixtures of two or more of them.

Examples of the halogenating agent include chlorine, bromine, iodine, N-chlorosuccinimide, N-bromosuccinimide, and N-iodosuccinimide.

In the reaction, the halogenating agent is usually used at a ratio of 1 to 20 mol relative to 1 mol of the Compound (M-9).

The reaction temperature is usually within the range of −20° C. to 200° C. The reaction time is usually within the range of 0.1 to 72 hour(s).

When the reaction is completed, the reaction mixture may be subjected to a work-up such as adding water to the reaction mixture, subjecting the resulting mixture to extraction with organic solvent(s), and drying and/or concentrating the resulting organic layer to give the Compound (M-10).

Next, a method for producing the Compound (II-1n0) from the Compound (M-9) is described.

The Compound (II-1n0) may be prepared by reacting the Compound (M-9), a compound represented by formula (R-1) (hereinafter referred to as "Compound (R-1)"), and a halogenating agent.

The reaction is usually carried out in a solvent. Examples of the solvent include alcohols, nitriles, ethers, aromatic hydrocarbons, aprotic polar solvents, halogenated hydrocarbons, water, and mixtures of two or more of them.

Examples of the halogenating agent include chlorine, bromine, iodine, N-chlorosuccinimide, N-bromosuccinimide, and N-iodosuccinimide.

In the reaction, the Compound (R-1) is usually used at a ratio of 1 to 20 mol, and the halogenating agent is usually used at a ratio of 1 to 20 mol, relative to 1 mol of the Compound (M-9).

The reaction temperature is usually within the range of −20° C. to 200° C. The reaction time is usually within the range of 0.1 to 72 hour(s).

When the reaction is completed, the reaction mixture may be subjected to a work-up such as adding water to the reaction mixture, subjecting the resulting mixture to extraction with organic solvent(s), and drying and/or concentrating the resulting organic layer to give the Compound (II-1n0).

The Compound (R-1) is a commercially available compound or may be prepared by using known method(s).

Next, a method for producing the Compound (II-1n0) from the Compound (M-10) is described.

The Compound (II-1n0) may also be prepared by reacting the Compound (M-10) and the Compound (R-1) in the presence of a metal catalyst and a base.

The reaction is usually carried out in a solvent. Examples of the solvent include alcohols, nitriles, ethers, aromatic hydrocarbons, aprotic polar solvents, water, and mixtures of two or more of them.

Examples of the metal catalyst include palladium catalysts such as tetrakis(triphenylphosphine)palladium(0), [1,1'-bis(diphenylphosphino)ferrocene]palladium(II) dichloride, tris(dibenzylideneacetone)dipalladium(0), and palladium(II) acetate; nickel catalysts such as bis(cyclooctadiene)nickel(0) and nickel(II) chloride; and copper catalysts such as copper(I) iodide and copper(I) chloride.

Examples of the base include alkali metal hydrides, alkali metal carbonates, and organic bases.

In the reaction, a ligand may also be used. Examples of the ligand include triphenylphosphine, Xantphos, 2,2'-bis(diphenylphosphino)-1,1'-binaphthyl, 1,1'-bis(diphenylphosphino)ferrocene, 2-dicyclohexylphosphino-2',4',6'-tri isopropylbiphenyl, 2-dicyclohexylphosphino-2',6'-dimethoxybiphenyl, 1,2-bis(diphenylphosphino)ethane, 2,2'-bipyridine, 2-aminoethanol, 8-hydroxyquinoline, and 1,10-phenanthroline. When a ligand is used in the reaction, the ligand is usually used at a ratio of 0.01 to 1 mol relative to 1 mol of the Compound (M-10).

In the reaction, the Compound (R-1) is usually used at a ratio of 1 to 20 mol, the metal catalyst is usually used at a ratio of 0.01 to 0.5 mol, and the base is usually used at a ratio of 0.1 to 5 mol, relative to 1 mol of the Compound (M-10).

The reaction temperature is usually within the range of −20° C. to 200° C. The reaction time is usually within the range of 0.1 to 72 hour(s).

When the reaction is completed, the reaction mixture may be subjected to a work-up such as adding water to the reaction mixture, subjecting the resulting mixture to extraction with organic solvent(s), and drying and/or concentrating the resulting organic layer to give the Compound (II-1n0).

Production Method 10

A compound represented by formula (II-2n0) (hereinafter referred to as "Compound (II-2n0)") may be prepared according to the following scheme.

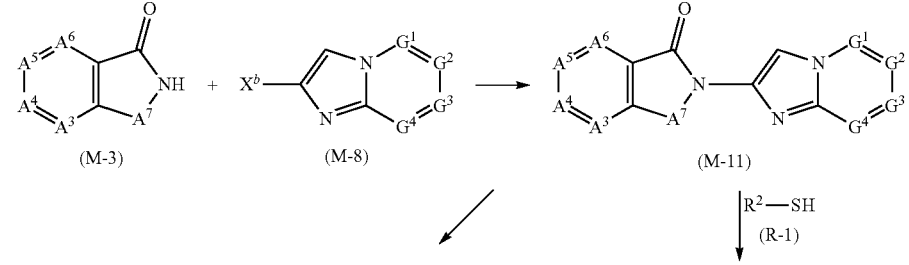

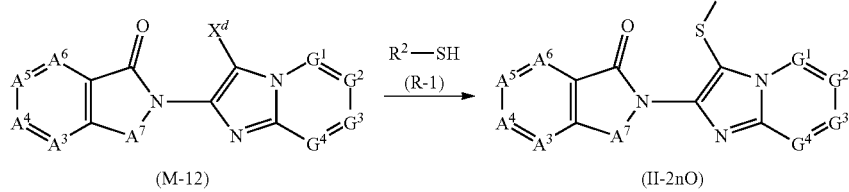

[wherein the symbols are the same as defined above.]

A compound represented by formula (M-11) (hereinafter referred to as "Compound (M-11)") may be prepared according to the Production method 4 by using the Compound (M-3) instead of the Compound (M-1), and using the Compound (M-8) instead of the Compound (M-2).

A compound represented by formula (M-12) (hereinafter referred to as "Compound (M-12)") may be prepared according to the method for producing the Compound (M-10) from the Compound (M-9) in the Production method 9 by using the Compound (M-11) instead of the Compound (M-9).

The Compound (II-2n0) may be prepared according to the method for producing the Compound (II-1n0) from the Compound (M-9) in the Production method 9 by using the Compound (M-11) instead of the Compound (M-9).

Also, the Compound (II-2n0) may also be prepared according to the method for producing the Compound (II-1n0) from the Compound (M-10) in the Production method 9 by using the Compound (M-12) instead of the Compound (M-10).

Production Method 11

An N-oxide of the compound represented by formula (I) may be prepared by reacting the compound represented by formula (I) with an oxidizing agent. The reaction may be carried out according to the method described in, for example, the Production method 1, US Patent Application Publication No. 2018/0009778, or WO 2016/121970 pamphlet.

Hereinafter, production methods for the production intermediate compounds are described.

Reference Production Method 1

A compound represented by formula (M-1A) (hereinafter referred to as "Compound (M-1A)") and a compound represented by formula (M-1B) (hereinafter referred to as "Compound (M-1B)") may be prepared according to the following scheme.

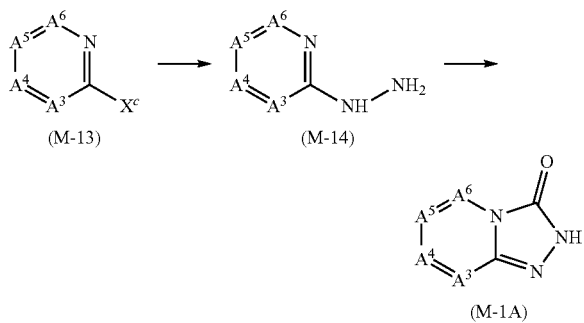

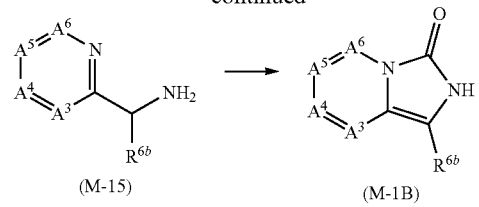

[wherein the symbols are the same as defined above.]

A compound represented by formula (M-14) (hereinafter referred to as "Compound (M-14)") may be prepared by reacting a compound represented by formula (M-13) (hereinafter referred to as "Compound (M-13)") with hydrazine.

The reaction is usually carried out in a solvent. Examples of the solvent include ethers, aromatic hydrocarbons, nitriles, aprotic polar solvents, alcohols, water, and mixtures of two or more of them.

In the reaction, a base may also be used as needed. Examples of the base include alkali metal carbonates, alkali metal hydrides, and organic bases. When a base is used in the reaction, the base is usually used at a ratio of 1 to 3 mol relative to 1 mol of the Compound (M-13).

In the reaction, hydrazine is usually used at a ratio of 1 to 3 mol relative to 1 mol of the Compound (M-13).

The reaction temperature is usually within the range of 0° C. to 150° C. The reaction time is usually within the range of 0.5 to 24 hour(s).

When the reaction is completed, the reaction mixture may be subjected to a work-up such as adding water to the reaction mixture, subjecting the resulting mixture to extraction with organic solvent(s), and drying and/or concentrating the resulting organic layer to give the Compound (M-14).

The Compound (M-1A) may be prepared according to the Production method 6 by using the Compound (M-14) instead of the Compound (M-4).

The Compound (M-1B) may be prepared according to the Production method 6 by using the Compound (M-15) instead of the Compound (M-4).

The Compound (M-13) and the Compound (M-15) are commercially available compounds or may be prepared by using known methods.

Reference Production Method 2

A compound represented by formula (M-3A) (hereinafter referred to as "Compound (M-3A)") may be prepared by reacting a compound represented by formula (M-16) (hereinafter referred to as "Compound (M-16)") with a compound represented by formula (R-2) (hereinafter referred to as "Compound (R-2)").

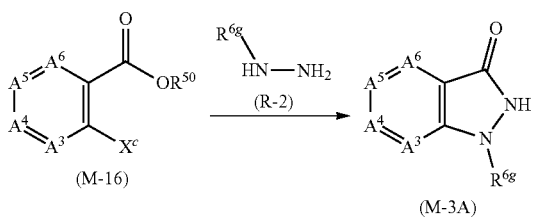

[wherein the symbols are the same as defined above.]

The reaction is usually carried out in a solvent. Examples of the solvent include ethers, aromatic hydrocarbons, nitriles, aprotic polar solvents, alcohols, water, and mixtures of two or more of them.

In the reaction, a base may also be used as needed. Examples of the base include alkali metal carbonates, alkali metal hydrides, and organic bases. When a base is used in the reaction, the base is usually used at a ratio of 1 to 3 mol relative to 1 mol of the Compound (M-16).

In the reaction, the Compound (R-2) is usually used at a ratio of 1 to 3 mol relative to 1 mol of the Compound (M-16).

The reaction temperature is usually within the range of 0° C. to 150° C. The reaction time is usually within the range of 0.5 to 24 hour(s).

When the reaction is completed, the reaction mixture may be subjected to a work-up such as adding water to the reaction mixture, subjecting the resulting mixture to extraction with organic solvent(s), and drying and/or concentrating the resulting organic layer to give the Compound (M-3A).

The Compound (M-16) and the Compound (R-2) are commercially available compounds or may be prepared by using known methods.

Reference Production Method 3

A compound represented by formula (M-3B) (hereinafter referred to as "Compound (M-3B)") may be prepared by subjecting a compound represented by formula (M-17) (hereinafter referred to as "Compound (M-17)") to intramolecular condensation.

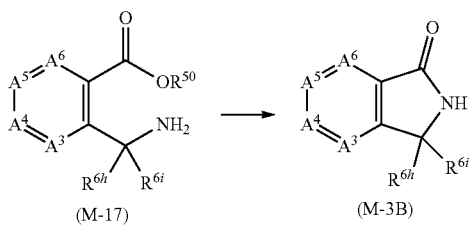

[wherein the symbols are the same as defined above.]

The reaction is usually carried out in a solvent. Examples of the solvent include ethers, aromatic hydrocarbons, halogenated hydrocarbons, esters, nitriles, aprotic polar solvents, water, and mixtures of two or more of them.

In the reaction, an acid or a base may be used. Examples of the acid include sulfonic acids such as p-toluenesulfonic acid; carboxylic acids such as acetic acid; and polyphosphoric acid. Examples of the base include organic bases, alkali metal carbonates, and alkali metal hydrides. In the reaction, when an acid is used, the acid is usually used at a ratio of 0.1 to 2 mol, and when a base is used, the base is usually used at a ratio of 1 to 5 mol, relative to 1 mol of the Compound (M-17).

The reaction temperature is usually within the range of 0 to 150° C. The reaction time is usually within the range of 0.1 to 24 hour(s).

When the reaction is completed, the reaction mixture may be subjected to a work-up such as adding water to the reaction mixture, subjecting the resulting mixture to extraction with organic solvent(s), and drying and/or concentrating the resulting organic layer to give the Compound (M-3B).

The Compound (M-17) is a commercially available compound or may be prepared by using known method(s).

Reference Production Method 4

The Compound (M-4) may be prepared by reacting a compound represented by formula (M-18) (hereinafter referred to as "Compound (M-18)") with the Compound (M-2).

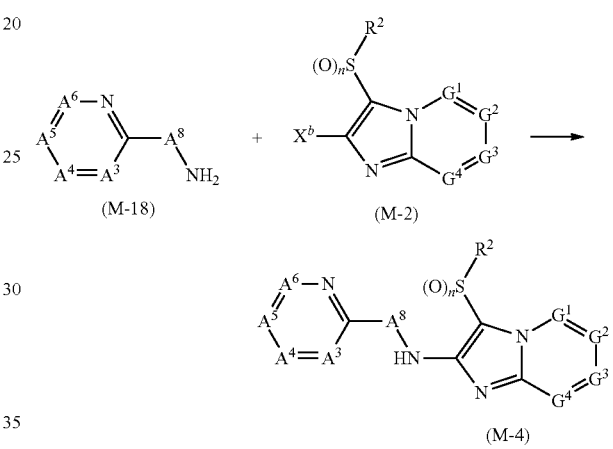

[wherein the symbols are the same as defined above.]

The reaction is usually carried out in a solvent. Examples of the solvent include ethers, aromatic hydrocarbons, nitriles, aprotic polar solvents, alcohols, water, and mixtures of two or more of them.

In the reaction, a base may also be used as needed. Examples of the base include alkali metal carbonates, alkali metal hydrides, and organic bases. When a base is used in the reaction, the base is usually used at a ratio of 1 to 3 mol relative to 1 mol of the Compound (M-18).

In the reaction, the Compound (M-2) is usually used at a ratio of 0.8 to 1.2 mol relative to 1 mol of the Compound (M-18).

The reaction temperature is usually within the range of 0° C. to 150° C. The reaction time is usually within the range of 0.5 to 24 hour(s).

When the reaction is completed, the reaction mixture may be subjected to a work-up such as adding water to the reaction mixture, subjecting the resulting mixture to extraction with organic solvent(s), and drying and/or concentrating the resulting organic layer to give the Compound (M-4).

The Compound (M-18) is a commercially available compound or may be prepared by using known method(s).

Reference Production Method 5

The Compound (M-6) may be prepared by reacting the Compound (M-2) with the Compound (R-2).

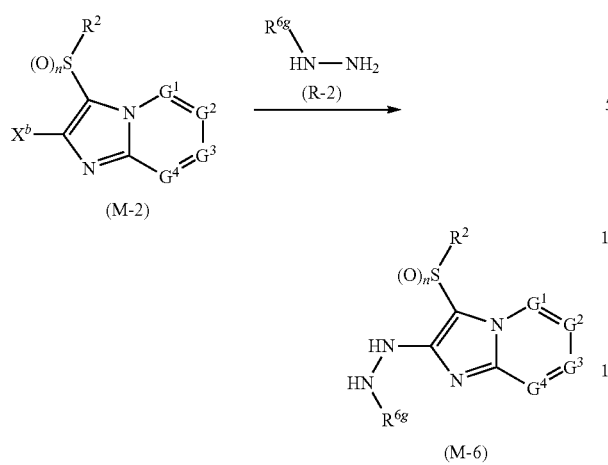

(M-2)

(M-6)

[wherein the symbols are the same as defined above.]

The reaction is usually carried out in a solvent. Examples of the solvent include ethers, aromatic hydrocarbons, nitriles, aprotic polar solvents, alcohols, water, and mixtures of two or more of them.

In the reaction, a base may also be used as needed. Examples of the base include alkali metal carbonates, alkali metal hydrides, and organic bases. When a base is used in the reaction, the base is usually used at a ratio of 1 to 5 mol relative to 1 mol of the Compound (M-2).

In the reaction, the Compound (R-2) is usually used at a ratio of 1 to 5 mol relative to 1 mol of the Compound (M-2).

The reaction temperature is usually within the range of 0° C. to 150° C. The reaction time is usually within the range of 0.5 to 24 hour(s).

When the reaction is completed, the reaction mixture may be subjected to a work-up such as adding water to the reaction mixture, subjecting the resulting mixture to extraction with organic solvent(s), and drying and/or concentrating the resulting organic layer to give the Compound (M-6).

Reference Production Method 6

The Compound (M-7) may be prepared by reacting a compound represented by formula (M-19) (hereinafter referred to as "Compound (M-19)") with a compound represented by formula (M-20) (hereinafter referred to as "Compound (M-20)").

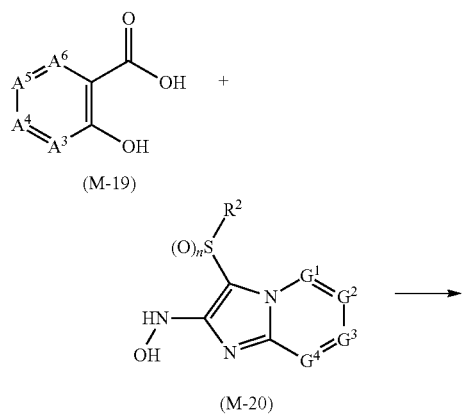

(M-19)

(M-20)

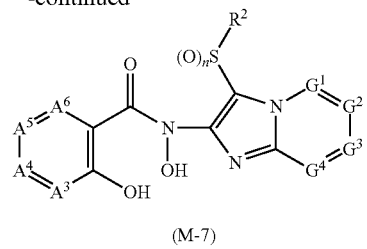

(M-7)

[wherein the symbols are the same as defined above.]

The reaction may be carried out according to the method described in, for example, Tetrahedron Letters, 41, 2295, 2000.

The Compound (M-19) is a commercially available compound or may be prepared by using known method(s).

Reference Production Method 7

The Compound (M-20) may be prepared by reacting the Compound (M-2) with hydroxylamine.

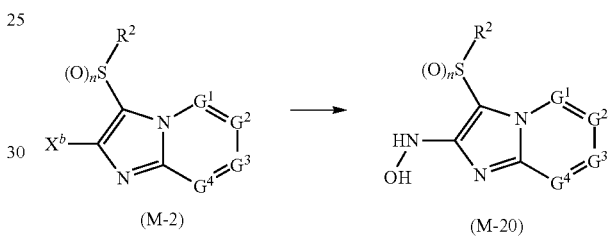

(M-2)  (M-20)

[wherein the symbols are the same as defined above.]

The reaction is usually carried out in a solvent. Examples of the solvent include ethers, aromatic hydrocarbons, nitriles, aprotic polar solvents, alcohols, water, and mixtures of two or more of them.

In the reaction, a base may also be used as needed. Examples of the base include alkali metal carbonates, alkali metal hydrides, and organic bases. When a base is used in the reaction, the base is usually used at a ratio of 1 to 5 mol relative to 1 mol of the Compound (M-2).

In the reaction, hydroxylamine is usually used at a ratio of 1 to 5 mol relative to 1 mol of the Compound (M-2).

The reaction temperature is usually within the range of 0° C. to 150° C. The reaction time is usually within the range of 0.5 to 24 hour(s).

When the reaction is completed, the reaction mixture may be subjected to a work-up such as adding water to the reaction mixture, subjecting the resulting mixture to extraction with organic solvent(s), and drying and/or concentrating the resulting organic layer to give the Compound (M-20).

Reference Production Method 8

A compound represented by formula (M-2-b) or a compound represented by formula (M-2-c) may be prepared by reacting a compound represented by formula (M-2-a) with an oxidizing agent, and a compound represented by formula (M-2-c) may also be prepared by reacting a compound represented by formula (M-2-b) with an oxidizing agent.

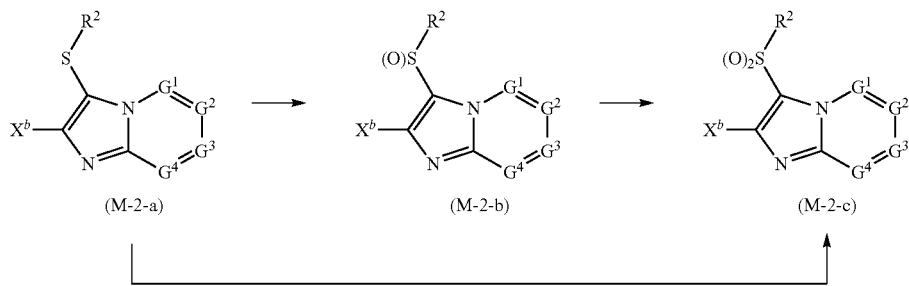

(M-2-a) → (M-2-b) → (M-2-c)

[wherein the symbols are the same as defined above.]

These reactions may be carried out according to the Production method 1.

Reference Production Method 9

A compound represented by formula (M-2-d) (hereinafter referred to as "Compound (M-2-d)") may be prepared according to the following scheme.

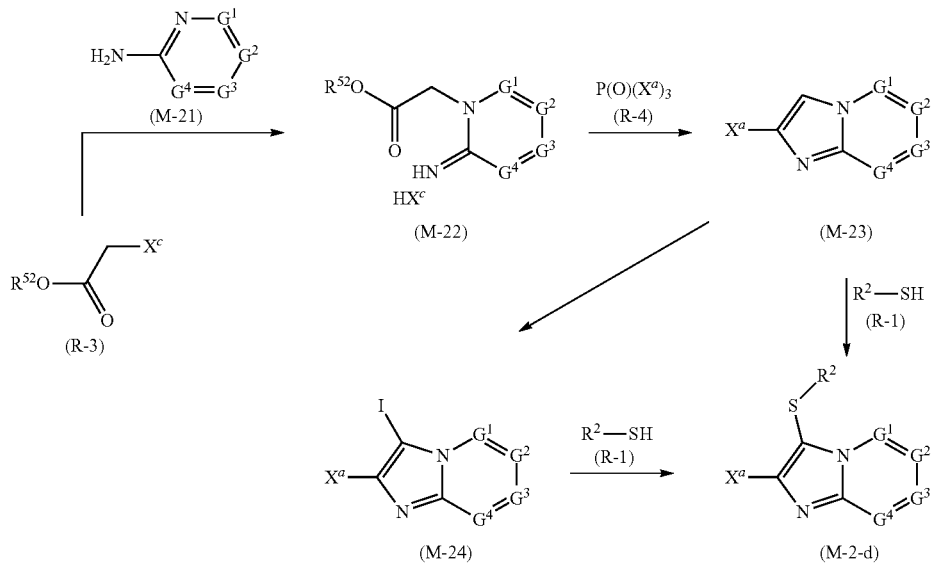

[wherein $R^{52}$ represents a hydrogen atom, a methyl group, or an ethyl group; $X^a$ represents a chlorine atom or a bromine atom; and the other symbols are the same as defined above.]

A compound represented by formula (M-22) (hereinafter referred to as "Compound (M-22)") may be prepared by reacting a compound represented by formula (M-21) (hereinafter referred to as "Compound (M-21)") with a compound represented by formula (R-3) (hereinafter referred to as "Compound (R-3)").

The reaction is usually carried out in a solvent. Examples of the solvent include aromatic hydrocarbons, alcohols, nitriles, and mixtures of two or more of them.

In the reaction, the Compound (M-21) is usually used at a ratio of 1 to 10 mol relative to 1 mol of the Compound (R-3).

The reaction temperature is usually within the range of 0° C. to 200° C. The reaction time is usually within the range of 0.1 to 48 hour(s).

When the reaction is completed, the reaction mixture may be subjected to a conventional work-up to give the Compound (M-22).

The Compound (R-3) and the Compound (M-21) are commercially available compounds or may be prepared by using known methods.

A compound represented by formula (M-23) (hereinafter referred to as "Compound (M-23)") may be prepared by reacting the Compound (M-22) with a compound represented by formula (R-4) (hereinafter referred to as "Compound (R-4)").

The reaction is usually carried out in a solvent. Examples of the solvent include aromatic hydrocarbons, nitriles, and mixtures of two or more of them.

In the reaction, the Compound (R-4) is usually used at a ratio of 1 to 10 mol relative to 1 mol of the Compound (M-22).

The reaction temperature is usually within the range of 60° C. to 120° C. The reaction time is usually within the range of 0.1 to 48 hour(s).

When the reaction is completed, the reaction mixture may be subjected to a conventional work-up to give the Compound (M-23).

The Compound (R-4) is a commercially available compound or may be prepared by using known method(s).

A compound represented by formula (M-24) (hereinafter referred to as "Compound (M-24)") may be prepared by reacting the Compound (M-23) with N-iodosuccinimide. The reaction may be carried out according to the method for producing the Compound (M-10) from the Compound (M-9) in the Production method 9.

The Compound (M-2-d) may be prepared by reacting the Compound (M-23) or the Compound (M-24) with the Compound (R-1). These reactions may be carried out according to the method for producing the Compound (II-1n0) from the Compound (M-9) or the Compound (M-10) in the Production method 9.

Reference Production Method 10

A compound represented by formula (M-2-f) may be prepared by reacting a compound represented by formula (M-2-e) (hereinafter referred to as "Compound (M-2-e)") with silver fluoride in the presence of a metal catalyst.

[wherein the symbols are the same as defined above.]

The reaction may be carried out according to the method described in, for example, Journal of the American Chemical Society, 2014, 136, 3792.

Reference Production Method 11

A compound represented by formula (M-2-g) may be prepared by reacting the Compound (M-2-e) with sodium iodide in the presence of a metal catalyst.

[wherein the symbols are the same as defined above.]

The reaction may be carried out according to the method described in, for example, Journal of the American Chemical Society, 2002, 124, 14844.

The Present compound may be mixed with or used in combination with one or more ingredient(s) selected from the group consisting of the following Group (a), Group (b), Group (c), and Group (d) (hereinafter referred to as "Present ingredient").

When the Present compound is mixed with or used in combination with the Present ingredient, they are used simultaneously, separately, or at time intervals with each other.

When the Present compound is used simultaneously with the Present ingredient, the Present compound and the Present ingredient may be contained in separate formulations with each other or contained in one formulation.

One aspect of the present invention provides a composition comprising one or more ingredient(s) selected from the group consisting of Group (a), Group (b), Group (c), and Group (d), and the Present compound (hereinafter referred to as "Composition A").

Group (a) is a group consisting of acetylcholinesterase inhibitors (for example, carbamate insecticides and organophosphate insecticides), GABA-gated chloride channel blockers (for example, phenylpyrazole insecticides), sodium channel modulators (for example, pyrethroid insecticides), nicotinic acetylcholine receptor competitive modulators (for example, neonicotinoid insecticides), nicotinic acetylcholine receptor allosteric modulators, glutamate-gated chloride channel allosteric modulators (for example, macrolide insecticides), juvenile hormone mimics, multisite inhibitors, chordotonal organ TRPV channel modulators, mite growth inhibitors, microbial disruptors of insect midgut membranes, inhibitors of mitochondrial ATP synthase, uncouplers of oxidative phosphorylation, nicotinic acetylcholine receptor channel blockers (for example, nereistoxin insecticides), inhibitors of chitin biosynthesis, moulting disruptors, ecdysone receptor agonists, octopamine receptor agonists, mitochondrial complexes I, II, III, and IV electron transport inhibitors, voltage-dependent sodium channel blockers, inhibitors of acetyl CoA carboxylase, ryanodine receptor modulators (for example, diamide insecticides), chordotonal organ modulators, and microbial insecticides, and other insecticidal active ingredients, miticidal active ingredients, and nematicidal active ingredients. These ingredients are described in the classification on the basis of action mechanism by IRAC.

Group (b) is a group consisting of nucleic acids synthesis inhibitors (for example, phenylamide fungicides and acylamino acid fungicides), cell division and cytoskeleton inhibitors (for example, MBC fungicides), respiration inhibitors (for example, QoI fungicides and QiI fungicides), amino acids synthesis and protein synthesis inhibitors (for example, anilino-pyridine fungicides), signal transduction inhibitors, lipid synthesis and membrane synthesis inhibitors, sterol biosynthesis inhibitors (for example, DMI fungicides such as triazole fungicides), cell wall biosynthesis inhibitors, melanin synthesis inhibitors, plant defense inducers, fungicides with multi-site contact activity, microbial fungicides, and other fungicidal active ingredients. These ingredients are described in the classification on the basis of action mechanism by FRAC.

Group (c) is a group of plant growth regulatory ingredients (including mycorrhizal fungi and root nodule bacteria).

Group (d) is a group of repellent ingredients.

Hereinafter, examples of the combination of the Present ingredient and the Present compound are described. For example, "alanycarb+SX" indicates a combination of alanycarb and SX.

The abbreviation of "SX" indicates any one of the Present compound selected from the Compound groups SX1 to SX1630 described in Examples. Also, all of the following Present ingredient are known ingredients, and may be obtained from commercially available formulations, or may be prepared by known methods. When the Present ingredient is a microorganism, it may also be available from a bacterial authority depository. Further, the number in parentheses represents the CAS RN (registered trademark).

Combinations of the Present ingredient in the above Group (a) and the Present compound:
  abamectin+SX, acephate+SX, acequinocyl+SX, acetamiprid+SX, acetoprole+SX, acrinathrin+SX, acynonapyr+SX, afidopyropen+SX, afoxolaner+SX, alanycarb+SX, aldicarb+SX, allethrin+SX, alpha-cypermethrin+SX, alpha-endosulfan+SX, aluminium phosphide+SX, amitraz+SX, azadirachtin+SX, azamethiphos+SX, azinphos-ethyl+SX, azinphos-methyl+SX, azocyclotin+SX, bark of *Celastrus angulatus*+SX, bendiocarb+SX, benfluthrin+SX, benfuracarb+SX, bensultap+SX, benzoximate+SX, benzpyrimoxan+SX, beta-cyfluthrin+SX, beta-cypermethrin+SX, bifenazate+SX, bifenthrin+SX, bioallethrin+SX, bioresmethrin+SX, bistrifluron+SX, borax+SX, boric acid+SX, broflanilide+SX, bromopropylate+SX, buprofezin+SX, butocarboxim+SX, butoxycarboxim+SX, cadusafos+SX, calcium phosphide+SX, carbaryl+SX, carbofuran+SX, carbosulfan+SX, cartap hydrochloride+SX, cartap+SX, chinomethionat+SX, chlorantraniliprole+SX, chlordane+SX, chlorethoxyfos+SX, chlorfenapyr+SX, chlorfenvinphos+SX, chlorfluazuron+SX, chlormephos+SX, chloropicrin+SX, chlorpyrifos+SX, chlorpyrifos-methyl+SX, chromafenozide+SX, clofentezine+SX, clothianidin+SX, concanamycin A+SX, coumaphos+SX, cryolite+SX, cyanophos+SX, cyantraniliprole+SX, cyclaniliprole+SX, cycloprothrin+SX, cycloxaprid+SX, cyenopyrafen+SX, cyflumetofen+SX, cyfluthrin+SX, cyhalodiamide+SX, cyhalothrin+SX, cyhexatin+SX, cypermethrin+SX, cyphenothrin+SX, cyromazine+SX, dazomet+SX, deltamethrin+SX, demeton-S-methyl+SX, diafenthiuron+SX, diazinon+SX, dichlorvos+SX, dicloromezotiaz+SX, dicofol+SX, dicrotophos+SX, diflovidazin+SX, diflubenzuron+SX, dimefluthrin+SX, dimethoate+SX, dimethylvinphos+SX, dimpropyridaz+SX, dinotefuran+SX, disodium octaborate+SX, disulfoton+SX, DNOC (2-methyl-4,6-dinitrophenol)+SX, doramectin+SX, dried leaves of *Dryopteris filix*-mas+SX, emamectin-benzoate+SX, empenthrin+SX, endosulfan+SX, EPN (O-ethyl O-(4-nitrophenyl) phenylphosphonothioate)+SX, epsilon-metofluthrin+SX, epsilon-momfluorothrin+SX, esfenvalerate+SX, ethiofencarb+SX, ethion+SX, ethiprole+SX, ethoprophos+SX, etofenprox+SX, etoxazole+SX, extract of *Artemisia absinthium*+SX, extract of *Cassia nigricans*+SX, extract of *Clitoria ternatea*+SX, extract of *Symphytum officinale*+SX, extracts or simulated blend of *Chenopodium ambrosiodes*+SX, extract of *Tanacetum vulgare*+SX, extract of *Urtica dioica*+SX, extract of *Viscum album*+SX, famphur+SX, fenamiphos+SX, fenazaquin+SX, fenbutatin oxide+SX, fenitrothion+SX, fenobucarb+SX, fenoxycarb+SX, fenpropathrin+SX, fenpyroximate+SX, fenthion+SX, fenvalerate+SX, fipronil+SX, flometoquin+SX, flonicamid+SX, fluacrypyrim+SX, fluazaindolizine+SX, fluazuron+SX, flubendiamide+SX, flucycloxuron+SX, flucythrinate+SX, fluensulfone+SX, flufenoprox+SX, flufenoxuron+SX, flufiprole+SX, flumethrin+SX, flupyradifurone+SX, flupyrimin+SX, fluralaner+SX, fluvalinate+SX, fluxametamide+SX, formetanate+SX, fosthiazate+SX, furamethrin+SX, furathiocarb+SX, gamma-cyhalothrin+SX, GS-omega/kappa HXTX-Hvla peptide+SX, halfenprox+SX, halofenozide+SX, heptafluthrin+SX, heptenophos+SX, hexaflumuron+SX, hexythiazox+SX, potassium salt of hop beta acid+SX, hydramethylnon+SX, hydroprene+SX, imicyafos+SX, imidacloprid+SX, imidaclothiz+SX, imiprothrin+SX, indoxacarb+SX, isocycloseram+SX, isofenphos+SX, isoprocarb+SX, isopropyl-O-(methoxyaminothiophosphoryl) salicylate+SX, isoxathion+SX, ivermectin+SX, kadethrin+SX, kappa-tefluthrin+SX, kappa-bifenthrin+SX, kinoprene+SX, lambda-cyhalothrin+SX, lenoremycin+SX, lepimectin+SX, lime sulfur+SX, lotilaner+SX, lufenuron+SX, machine oil+SX, malathion+SX, mecarbam+SX, meperfluthrin+SX, metaflumizone+SX, metam+SX, methamidophos+SX, methidathion+SX, methiocarb+SX, methomyl+SX, methoprene+SX, methoxychlor+SX, methoxyfenozide+SX, methyl bromide+SX, metofluthrin+SX, metolcarb+SX, metoxadiazone+SX, mevinphos+SX, milbemectin+SX, milbemycin oxime+SX, momfluorothrin+SX, monocrotophos+SX, moxidectin+SX, naled+SX, neem oil+SX, nicotine+SX, nicotine-sulfate+SX, nitenpyram+SX, novaluron+SX, noviflumuron+SX, oil of the seeds of *Chenopodium anthelminticum*+SX, omethoate+SX, oxamyl+SX, oxazosulfyl+SX, oxydemeton-methyl+SX, parathion+SX, parathion-methyl+SX, permethrin+SX, phenothrin+SX, phenthoate+SX, phorate+SX, phosalone+SX, phosmet+SX, phosphamidon+SX, phosphine+SX, phoxim+SX, pirimicarb+SX, pirimiphos-methyl+SX, prallethrin+SX, profenofos+SX, profluthrin+SX, propargite+SX, propetamphos+SX, propoxur+SX, propylene glycol alginate+SX, prothiofos+SX, pyflubumide+SX, pymetrozine+SX, pyraclofos+SX, pyrethrins+SX, pyridaben+SX, pyridalyl+SX, pyridaphenthion+SX, pyrifluquinazone+SX, pyrimidifen+SX, pyriminostrobin+SX, pyriprole+SX, pyriproxyfen+SX, quinalphos+SX, resmethrin+SX, rotenone+SX, ryanodine+SX, sarolaner+SX, selamectin+SX, sigma-cypermethrin+SX, silafluofen+SX, sodium borate+SX, sodium metaborate+SX, spinetoram+SX, spinosad+SX, spirodiclofen+SX, spiromesifen+SX, spiropidion+SX, spirotetramat+SX, sulfluramid+SX, sulfotep+SX, sulfoxaflor+SX, sulfur+SX, sulfuryl fluoride+SX, tartar emetic+SX, tau-fluvalinate+SX, tebufenozide+SX, tebufenpyrad+SX, tebupirimfos+SX, teflubenzuron+SX, tefluthrin+SX, temephos+SX, terbufos+SX, terpene constituents of the extract of *Chenopodium ambrosioides* near *ambrosioides*+SX, tetrachlorantraniliprole+SX, tetrachlorvinphos+SX, tetradifon+SX, tetramethrin+SX, tetramethylfluthrin+SX, tetraniliprole+SX, theta-cypermethrin+SX, thiacloprid+SX, thiamethoxam+SX, thiocyclam+SX, thiodicarb+SX, thiofanox+SX, thiometon+SX, thiosultap-disodium+SX, thiosultap-monosodium+SX, tioxazafen+SX, tolfenpyrad+SX, tralomethrin+SX, transfluthrin+SX, triazamate+SX, triazophos+SX, trichlorfon+SX, triflumezopyrim+SX, triflumuron+SX, trimethacarb+SX, tyclopyrazoflor+SX, vamidothion+SX, wood extract of *Quassia amara*+SX, XMC (3,5-dimethylphenyl N-methylcarbamate)+SX, xylylcarb+SX, zeta-cypermethrin+SX, zinc phosphide+SX, N-[3-chloro-1-(pyridin-3-yl)-1H-pyrazol-4-yl]-N-ethyl-3-(3,3,3-trifluoropropanesulfinyl)propanamide (1477923-37-7)+SX, 4-[5-(3,5-dichlorophenyl)-5-(trifluoromethyl)-4,5-dihydro-1,2-oxazol-3-yl]-2-methyl-N-(1-oxothietan-3-yl)benzamide (1241050-20-3)+SX, 3-methoxy-N-(5-{5-(trifluoromethyl)-5-[3-(trifluoromethyl)phenyl]-4,5-dihydro-1,2-oxazol-3-yl}indan-1-yl)propanamide (1118626-57-5)+SX, N-[2-bromo-6-chloro-4-(1,1,1,2,3,3,3-heptafluoropropan-2-yl)phenyl]-3-{ethyl[(pyridin-4-yl)carbonyl]amino}-2-methoxybenzamide (1429513-53-0)+SX, N-[2-bromo-6-chloro-4-(1,1,1,2,3,3,3-heptafluoropropan-2-yl)phenyl]-3-[ethyl(4-cyanobenzoyl)amino]-2-methoxybenzamide (1609007-65-9)+SX, N-[2-bromo-6-(difluoromethoxy)-4-(1,1,1,2,3,3,3-heptafluoropropan-2-yl)phenyl]-3-{methyl[(pyridin-4-yl)carbonyl]amino}-2-methoxybenzamide (1630969-78-6)+SX, 1-{2-fluoro-4-methyl-5-[(2,2,2-trifluoroethyl)sulfanyl]phenyl}-3-(trifluoromethyl)-1H-1,2,4-triazol-5-amine (885026-50-6)+SX, BT crop protein Cry1Ab+SX, BT crop protein Cry1Ac+SX, BT crop protein Cry1Fa+SX, BT crop protein Cry1A.105+ SX, BT crop protein Cry2Ab+SX, BT crop protein Vip3A+SX, BT crop protein Cry3A+SX, BT crop protein Cry3Ab+SX, BT crop protein Cry3Bb+SX, BT crop protein Cry34Ab1/Cry35Ab1+SX, *Adoxophyes orana* granulosis virus strain BV-0001+SX, *Anticarsia gemmatalis* mNPV+SX, *Autographa californica* mNPV+SX, *Cydia pomonella* GV strain V15+SX, *Cydia pomonella* GV strain V22+SX, *Cryptophlebia leucotreta* GV+SX, *Dendrolimus punctatus* cypovirus+SX, *Helicoverpa armigera* NPV strain BV-0003+SX, *Helicoverpa zea* NPV+SX, *Lymantria dispar* NPV+SX, *Mamestra brassicae* NPV+SX, *Mamestra configurata* NPV+SX, *Neodiprion abietis* NPV+SX, *Neodiprion lecontei* NPV+SX, *Neodiprion sertifer* NPV+SX, *Nosema locustae*+SX, *Orgyia pseudotsugata* NPV+SX, *Pieris rapae* GV+SX, *Plodia interpunctella* GV+SX, *Spodoptera exigua* mNPV+SX, *Spodoptera littoralis* mNPV+SX, *Spodoptera litura* NPV+SX, *Arthrobotrys dactyloides*+SX, *Bacillus firmus* strain GB-126+SX, *Bacillus firmus* strain 1-1582+SX, *Bacillus megaterium*+SX, *Bacillus* sp. strain AQ175+SX, *Bacillus* sp. strain AQ177+SX, *Bacillus* sp. strain AQ178+SX, *Bacillus sphaericus* strain 2362+SX, *Bacillus sphaericus* strain ABTS1743+SX, *Bacillus sphaericus* Serotype strain H5a5b+SX, *Bacillus thuringiensis* strain AQ52+SX, *Bacillus thuringiensis* strain BD #32+SX, *Bacillus thuringiensis* strain CR-371+SX, *Bacillus thuringiensis* subsp. *Aizawai* strain ABTS-1857+SX, *Bacillus thuringiensis* subsp. *Aizawai* strain AM65-52+SX, *Bacillus thuringiensis* subsp. *Aizawai* strain GC-91+SX, *Bacillus thuringiensis* subsp. *Aizawai* Serotype strain H-7+SX, *Bacillus thuringiensis* subsp. *kurstaki* strain ABTS351+SX, *Bacillus thuringiensis* subsp. *kurstaki* strain BMP123+SX, *Bacillus thuringiensis* subsp. *kurstaki* strain EG234+SX, *Bacillus thuringiensis* subsp. *kurstaki* strain EG7841+SX, *Bacillus thuringiensis* subsp. *kurstaki* strain EVB113-19+SX, *Bacillus thuringiensis* subsp. *kurstaki* strain F810+SX, *Bacillus thuringiensis* subsp. *kurstaki* strain HD-1+SX, *Bacillus thuringiensis* subsp. *kurstaki* strain PB54+SX, *Bacillus thuringiensis* subsp. *kurstaki* strain SA-11+SX, *Bacillus thuringiensis* subsp. *kurstaki* strain SA-12+SX, *Bacillus thuringiensis* subsp. *tenebriosis* strain NB176+SX, *Bacillus thuringiensis* subsp. *thuringiensis* strain MPPL002+SX, *Bacillus thuringiensis* subsp. *morrisoni*+SX, *Bacillus thuringiensis* var. *coimeri*+SX, *Bacillus thuringiensis* var. *darmstadiensis* strain 24-91+SX, *Bacillus thuringiensis* var. *dendrolimus*+SX, *Bacillus thuringiensis* var. *galleriae*+SX, *Bacillus thuringiensis* var. *israelensis* strain BMP144+SX, *Bacillus thuringiensis* var. *israelensis* serotype strain H-14+SX, *Bacillus thuringiensis* var. *japonensis* strain buibui+SX, *Bacillus thuringiensis* var. *san diego* strain M-7+SX, *Bacillus thuringiensis* var. 7216+SX, *Bacillus thuringiensis* var. *aegypti*+SX, *Bacillus thuringiensis* var. T36+SX, *Beauveria bassiana* strain ANT-03+SX, *Beauveria bassiana* strain ATCC74040+SX, *Beauveria bassiana* strain GHA+SX, *Beauveria brongniartii*+SX, *Burkholderia rinojensis* strain A396+SX, *Chromobacterium subtsugae* strain PRAA4-1T+SX, *Dactyllela ellipsospora*+SX, *Dectylaria thaumasia*+SX, *Hirsutella minnesotensis*+SX, *Hirsutella rhossiliensis*+SX, *Hirsutella thompsonii*+SX, *Lagenidium giganteum*+SX, *Lecanicillium lecanii* strain KV01+SX, *Lecanicillium lecanii* conidia of strain DAOM198499+SX, *Lecanicillium lecanii* conidia of strain DAOM216596+SX, *Lecanicillium muscarium* strain Ve6+SX, *Metarhizium anisopliae* strain F52+SX, *Metarhizium anisopliae* var. *acridum*+SX, *Metarhizium anisopliae* var. *anisopliae* BIPESCO 5/F52+SX, *Metarhizium flavoviride*+SX, *Monacrosporium phymatopagum*+SX, *Paecilomyces fumosoroseus* Apopka strain 97+SX, *Paecilomyces lilacinus* strain 251+SX, *Paecilomyces tenuipes* strain T1+SX, *Paenibacillus popilliae*+SX, *Pasteuria nishizawae* strain Pn1+SX, *Pasteuria penetrans*+SX, *Pasteuria usgae*+SX, *Pasteuria thoynei*+SX, *Serratia entomophila*+SX, *Verticillium chlamydosporium*+SX, *Verticillium lecani* strain NCIM1312+SX.

Combinations of the Present ingredient in the above Group (b) and the Present compound:

acibenzolar-S-methyl+SX, aldimorph+SX, ametoctradin+SX, aminopyrifen+SX, amisulbrom+SX, anilazine+SX, azaconazole+SX, azoxystrobin+SX, basic copper sulfate+SX, benalaxyl+SX, benalaxyl-M+SX, benodanil+SX, benomyl+SX, benthiavalicarb+SX, benthiavalicarb-isopropyl+SX, benzovindiflupyr+SX, binapacryl+SX, biphenyl+SX, bitertanol+SX, bixafen+SX, blasticidin-S+SX, Bordeaux mixture+SX, boscalid+SX, bromothalonil+SX, bromuconazole+SX, bupirimate+SX, captafol+SX, captan+SX, carbendazim+SX, carboxin+SX, carpropamid+SX, chinomethionat+SX, chitin+SX, chloroneb+SX, chlorothalonil+SX, chlozolinate+SX, colletochlorin B+SX, copper(II) acetate+SX, copper(II) hydroxide+SX, copper oxychloride+SX, copper(II) sulfate+SX, coumoxystrobin+SX, cyazofamid+SX, cyflufenamid+SX, cymoxanil+SX, cyproconazole+SX, cyprodinil+SX, dichlobentiazox+SX, dichlofluanid+SX, diclocymet+SX, diclomezine+SX, dicloran+SX, diethofencarb+SX, difenoconazole+SX, diflumetorim+SX, dimethachlone+SX, dimethirimol+SX, dimethomorph+SX, dimoxystrobin+SX, diniconazole+SX, diniconazole-M+SX, dinocap+SX, dipotassium hydrogenphosphite+SX, dipymetitrone+SX, dithianon+SX, dodecylbenzenesulphonic acid bisethylenediamine copper(II) salt+SX, dodemorph+SX, dodine+SX, edifenphos+SX, enoxastrobin+SX, epoxiconazole+SX, etaconazole+SX, ethaboxam+SX, ethirimol+SX, etridiazole+SX, extract from *Melaleuca alternifolia*+SX, extract from *Reynoutria sachalinensis*+SX, extract from the cotyledons of lupine plantlets (“BLAD”)+SX, extract of *Allium sativum*+SX, extract of *Equisetum arvense*+SX, extract of *Tropaeolum majus*+SX, famoxadone+SX, fenamidone+SX, fenaminstrobin+SX, fenarimol+SX, fenbuconazole+SX, fenfuram+SX, fenhexamid+SX, fenoxanil+SX, fenpiclonil+SX, fenpicoxamid+SX, fenpropidin+SX, fenpropimorph+SX, fenpyrazamine+SX, fentin acetate+SX, fentin chloride+SX, fentin hydroxide+SX, ferbam+SX, ferimzone+SX, florylpicoxamid+SX, fluazinam+SX, fludioxonil+SX, flufenoxystrobin+SX, fluindapyr+SX, flumorph+SX, fluopicolide+SX, fluopyram+SX, fluopimomide+SX, fluoroimide+SX, fluoxapiprolin+SX, fluoxastrobin+SX, fluquinconazole+SX, flusilazole+SX, flusulfamide+SX, flutianil+SX, flutolanil+SX, flutriafol+SX, fluxapyroxad+SX, folpet+SX, fosetyl+SX, fosetyl-aluminium+SX, fuberidazole+SX, furalaxyl+SX, furametpyr+SX, guazatine+SX, hexaconazole+SX, hymexazole+SX, imazalil+SX, imibenconazole+SX, iminoctadine+SX, iminoctadine triacetate+SX, inpyrfluxam+SX, iodocarb+SX, ipconazole+SX, ipfentrifluconazole+SX, ipflufenoquin+SX, iprobenfos+SX, iprodione+SX, iprovalicarb+SX, isofetamid+SX, isoflucypram+SX, isoprothiolane+SX, isopyrazam+SX, isotianil+SX, kasugamycin+SX, kresoxim-methyl+SX, laminarin+SX, leaves and bark of *Quercus*+SX, mancozeb+SX, mandestrobin+SX, mandipropamid+SX, maneb+SX, mefentrifluconazole+SX, mepanipyrim+SX, mepronil+SX, meptyldinocap+SX, metalaxyl+SX, metalaxyl-M+SX, metconazole+SX, methasulfocarb+SX, metiram+SX, metominostrobin+SX, metrafenone+SX, metyltetraprole+SX, mineral oils+SX, myclobutanil+SX, naftifine+SX, nuarimol+SX, octhilinone+SX, ofurace+SX, orysastrobin+SX, oxadixyl+SX, oxathiapiprolin+SX, oxine-copper+SX, oxolinic acid+SX, oxpoconazole+SX, oxpoconazole fumarate+SX, oxycarboxin+SX, oxytetracycline+SX, pefurazoate+SX, penconazole+SX, pencycuron+SX, penflufen+SX, penthiopyrad+SX, phenamacril+SX, phosphorous acid+SX, phthalide+SX, picarbutrazox+SX, picoxystrobin+SX, piperalin+SX, polyoxins+SX, potassium hydrogencarbonate+SX, potassium dihydrogenphosphite+SX, probenazole+SX, prochloraz+SX, procymidone+SX, propamidine+SX, propamocarb+SX, propiconazole+SX, propineb+SX, proquinazid+SX, prothiocarb+SX, prothioconazole+SX, pydiflumetofen+SX, pyraclostrobin+SX, pyrametostrobin+SX, pyraoxystrobin+SX, pyrapropoyne+SX, pyraziflumid+SX, pyrazophos+SX, pyribencarb+SX, pyributicarb+SX, pyridachlometyl+SX, pyrifenox+SX, pyrimethanil+SX, pyrimorph+SX, pyriofenone+SX, pyrisoxazole+SX, pyroquilon+SX, *Quillaja* extract+SX, quinconazole+SX, quinofumelin+SX, quinoxyfen+SX, quintozene+SX, Saponins of *Chenopodium quinoa*+SX, sedaxane+SX, silthiofam+SX, simeconazole+SX, sodium hydrogencarbonate+SX, spiroxamine+SX, streptomycin+SX, sulfur+SX, tebuconazole+SX, tebufloquin+SX, teclofthalam+SX, tecnazene+SX, terbinafine+SX, tetraconazole+SX, thiabendazole+SX, thifluzamide+SX, thiophanate+SX, thiophanate-methyl+SX, thiram+SX, thymol+SX, tiadinil+SX, tolclofos-methyl+SX, tolfenpyrad+SX, tolprocarb+SX, tolylfluanid+SX, triadimefon+SX, triadimenol+SX, triazoxide+SX, triclopyricarb+SX, tricyclazole+SX, tridemorph+SX, trifloxystrobin+SX, triflumizole+SX, triforine+SX, triticonazole+SX, validamycin+SX, valifenalate+SX, vinclozolin+SX, yellow mustard powder+SX, zinc thiazole+SX, zineb+SX, ziram+SX, zoxamide+SX, N'-[4-({3-[(4-chlorophenyl)methyl]-1,2,4-thiadiazol-5-yl}oxy)-2,5-dimethylphenyl]-N-ethyl-N-methylmethanimidamide (1202781-91-6)+SX, 4-(2-bromo-4-fluorophenyl)-N-(2-chloro-6-fluorophenyl)-1,3-dimethyl-1H-pyrazol-5-amine (1362477-26-6)+SX, 2-[6-(3-fluoro-4-methoxyphenyl)-5-methylpyridin-2-yl]quinazoline (1257056-97-5)+SX, 5-fluoro-2-[(4-methylphenyl)methoxy]pyrimidin-4-amine (1174376-25-0)+SX, 5-fluoro-4-imino-3-methyl-1-tosyl-3,4-dihydropyrimidin-2(1H)-one (1616664-98-2)+SX, N'-(2,5-dimethyl-4-phenoxyphenyl)-N-ethyl-N-methylmethanimidamide (1052688-31-9)+SX, N'-{4-[(4,5-dichlorothiazol-2-yl)oxy]-2,5-dimethylphenyl}-N-ethyl-N-methylmethanimidamide (929908-57-6)+SX, ethyl (2Z)-3-amino-2-cyano-3-phenylacrylate (39491-78-6)+SX, N-[(2-chlorothiazol-5-yl)methyl]-N-ethyl-6-methoxy-3-nitropyridin-2-amine (1446247-98-8)+SX, 5-(4-chlorobenzyl)-2-(chloromethyl)-2-methyl-1-(1H-1,2,4-triazol-1-ylmethyl)cyclopentan-1-ol (1394057-11-4)+SX, (1R, 2S, 5S)-5-(4-chlorobenzyl)-2-(chloromethyl)-2-methyl-1-(1H-1,2,4-triazol-1-ylmethyl)cyclopentan-1-ol (1801930-06-2)+SX, (1S, 2R, 5R)-5-(4-chlorobenzyl)-2-(chloromethyl)-2-methyl-1-(1H-1,2,4-triazol-1-ylmethyl)cyclopentan-1-ol (1801930-07-3)+SX, 2-(chloromethyl)-5-(4-fluorobenzyl)-2-methyl-1-(1H-1,2,4-triazol-1-ylmethyl)cyclopentan-1-ol (1394057-13-6)+SX, (1R, 2S, 5S)-2-(chloromethyl)-5-(4-fluorobenzyl)-2-methyl-1-(1H-1,2,4-triazol-1-ylmethyl)cyclopentan-1-ol (1801930-08-4)+SX, (1S, 2R, 5R)-2-(chloromethyl)-5-(4-fluorobenzyl)-2-methyl-1-(1H-1,2,4-triazol-1-ylmethyl)cyclopentan-1-ol (1801930-09-5)+SX, methyl 3-[(4-chlorophenyl)methyl]-2-hydroxy-1-methyl-2-(1H-1,2,4-triazol-1-ylmethyl)cyclopentan-1-carboxylate (1791398-02-1)+SX, methyl ({2-methyl-5-[1-(4-methoxy-2-methylphenyl)-1H-pyrazol-3-yl]phenyl}methyl)carbamate (1605879-98-8)+SX, 2-(difluoromethyl)-N-[1,1,3-trimethyl-2,3-dihydro-1H-inden-4-yl]pyridine-3-carboxamide (1616239-21-4)+SX, 2-(difluoromethyl)-N-[3-ethyl-1,1-dimethyl-2,3-dihydro-1H-inden-4-yl]pyridine-3-carboxamide (1847460-02-9)+SX, 2-(difluoromethyl)-N-[3-propyl-1,1-dimethyl-2,3-dihydro-1H-inden-4-yl]pyridine-3-carboxamide (1847460-05-2)+SX, (2E,3Z)-5-{[1-(4-chlorophenyl)-1H-pyrazol-3-yl]oxy}-2-(methoxyimino)-N,3-dimethylpent-3-enamide (1445331-27-0)+SX, *Agrobacterium radiobactor* strain K1026+SX, *Agrobacterium radiobactor* strain K84+SX, *Bacillus amyloliquefaciens* (Aveo (trademark) EZ Nematicide)+SX, *Bacillus amyloliquefaciens* strain AT332+SX, *Bacillus amyloliquefaciens* strain B3+SX, *Bacillus amyloliquefaciens* strain D747+SX, *Bacillus amyloliquefaciens* strain DB101+SX, *Bacillus amyloliquefaciens* strain DB102+SX, *Bacillus amyloliquefaciens* strain GB03+SX, *Bacillus amyloliquefaciens* strain FZB24+SX, *Bacillus amyloliquefaciens* strain FZB42+SX, *Bacillus amyloliquefaciens* strain IN937a+SX, *Bacillus amyloliquefaciens* strain MB1600+SX, *Bacillus amyloliquefaciens* strain QST713+SX, *Bacillus amyloliquefaciens* isolate strain B246+SX, *Bacillus amyloliquefaciens* strain F727+SX, *Bacillus amyloliquefaciens* subsp. *plantarum* strain D747+SX, *Bacillus licheniformis* strain HB-2+SX, *Bacillus licheniformis* strain SB3086+SX, *Bacillus pumilus* strain AQ717+SX, *Bacillus pumilus* strain BUF-33+SX, *Bacillus pumilus* strain GB34+SX, *Bacillus pumilus* strain QST2808+SX, *Bacillus simplex* strain CGF2856+SX, *Bacillus subtilis* strain AQ153+SX, *Bacillus subtilis* strain AQ743+SX, *Bacillus subtilis* strain BU1814+SX, *Bacillus subtilis* strain D747+SX, *Bacillus subtilis* strain DB101+SX, *Bacillus subtilis* strain FZB24+SX, *Bacillus subtilis* strain GB03+SX, *Bacillus subtilis* strain HAI0404+SX, *Bacillus subtilis* strain IAB/BS03+SX, *Bacillus subtilis* strain MBI600+SX, *Bacillus subtilis* strain QST30002/AQ30002+SX, *Bacillus subtilis* strain QST30004/AQ30004+SX, *Bacillus subtilis* strain QST713+SX, *Bacillus subtilis* strain QST714+SX, *Bacillus subtilis* var. *Amyloliquefaciens* strain FZB24+SX, *Bacillus subtilis* strain Y1336+SX, *Burkholderia cepacia*+SX, *Burkholderia cepacia* type Wisconsin strain J82+SX, *Burkholderia cepacia* type Wisconsin strain M54+SX, *Candida oleophila* strain O+SX, *Candida saitoana*+SX, *Chaetomium cupreum*+SX, *Clonostachys rosea*+SX, *Coniothyrium minitans* strain CGMCC8325+SX, *Coniothyrium minitans* strain CON/M/91-8+SX, *Cryptococcus albidus*+SX, *Erwinia carotovora* subsp. *carotovora* strain CGE234M403+SX, *Fusarium oxysporum* strain Fo47+SX, *Gliocladium catenulatum* strain J1446+SX, *Paenibacillus polymyxa* strain AC-1+SX, *Paenibacillus polymyxa* strain BS-0105+SX, *Pantoea agglomerans* strain E325+SX, *Phlebiopsis gigantea* strain VRA1992+SX, *Pseudomonas aureofaciens* strain TX-1+SX, *Pseudomonas chlororaphis* strain 63-28+SX, *Pseudomonas chlororaphis* strain AFS009+SX, *Pseudomonas chlororaphis* strain MA342+SX, *Pseudomonas fluorescens* strain 1629RS+SX, *Pseudomonas fluorescens* strain A506+SX, *Pseudomonas fluorescens* strain CL145A+SX, *Pseudomonas fluorescens* strain G7090+SX, *Pseudomonas* sp. strain CAB-02+SX, *Pseudomonas syringae* strain 742RS+SX, *Pseudomonas syringae* strain MA-4+SX, *Pseudozyma flocculosa* strain PF-A22UL+SX, *Pseudomonas rhodesiae* strain HAI-0804+SX, *Pythium oligandrum* strain DV74+SX, *Pythium oligandrum* strain M1+SX, *Streptomyces griseoviridis* strain K61+SX, *Streptomyces lydicus* strain WYCD108US+SX, *Streptomyces lydicus* strain WYEC108+SX, *Talaromyces flavus* strain SAY-Y-94-01+SX, *Talaromyces flavus* strain V117b+SX, *Trichoderma asperellum* strain ICC012+SX, *Trichoderma asperellum* SKT-1+SX, *Trichoderma asperellum* strain T25+SX, *Trichoderma asperellum* strain T34+SX, *Trichoderma asperellum* strain TV1+SX, *Trichoderma atroviride* strain CNCM 1-1237+SX, *Trichoderma atroviride* strain LC52+SX, *Trichoderma atroviride* strain IMI 206040+SX, *Trichoderma atroviride* strain SC1+SX, *Trichoderma atroviride* strain SKT-1+SX, *Trichoderma atroviride* strain T11+SX, *Trichoderma gamsii* strain ICC080+SX, *Trichoderma harzianum* strain 21+SX, *Trichoderma harzianum* strain DB104+SX, *Trichoderma harzianum* strain DSM 14944+SX, *Trichoderma harzianum* strain ESALQ-1303+SX, *Trichoderma harzianum* strain ESALQ-1306+SX, *Trichoderma harzianum* strain IIHR-Th-2+SX, *Trichoderma harzianum* strain ITEM908+SX, *Trichoderma harzianum* strain kd+SX, *Trichoderma harzianum* strain MO1+SX, *Trichoderma harzianum* strain SF+SX, *Trichoderma harzianum* strain T22+SX, *Trichoderma harzianum* strain T39+SX, *Trichoderma harzianum* strain T78+SX, *Trichoderma harzianum* strain TH35+SX, *Trichoderma polysporum* strain IMI1206039+SX, *Trichoderma stromaticum*+SX, *Trichoderma virens* strain G-41+SX, *Trichoderma virens* strain GL-21+SX, *Trichoderma viride*+SX, *Variovorax paradoxus* strain CGF4526+SX, Harpin protein+SX.

Combinations of the Present ingredient in the above Group (c) and the Present compound:

1-methylcyclopropene+SX, 1,3-diphenylurea+SX, 2,3,5-triiodobenzoic acid+SX, IAA ((1H-indol-3-yl)acetic acid)+SX, IBA (4-(1H-indol-3-yl)butyric acid)+SX, MCPA (2-(4-chloro-2-methylphenoxy)acetic acid)+SX, MCPB (4-(4-chloro-2-methylphenoxy)butyric acid)+SX, 4-CPA (4-chlorophenoxyacetic acid)+SX, 5-aminolevulinic acid hydrochloride+SX, 6-benzylaminopurine+SX, abscisic acid+SX, AVG (aminoethoxyvinylglycine)+SX, ancymidol+SX, butralin+SX, calcium carbonate+SX, calcium chloride+SX, calcium formate+SX, calcium peroxide+SX, calcium polysulfide+SX, calcium sulfate+SX, chlormequat-chloride+SX, chlorpropham+SX, choline chloride+SX, cloprop+SX, cyanamide+SX, cyanilide+SX, daminozide+SX, decan-1-ol+SX, dichlorprop+SX, dikegulac+SX, dimethipin+SX, diquat+SX, ethephon+SX, ethychlozate+SX, flumetralin+SX, flurprimidol+SX, forchlorfenuron+SX, formononetin+SX, Gibberellin A+SX, Gibberellin A3+SX, inabenfide+SX, Kinetin+SX, lipochitooligosaccharide SP104+SX, maleic hydrazide+SX, mefluidide+SX, mepiquat-chloride+SX, oxidized giutathione+SX, pacrobutrazol+SX, pendimethalin+SX, prohexandione-calcium+SX, prohydrojasmon+SX, pyraflufen-ethyl+SX, sintofen+SX, sodium 1-naphthaleneacetate+SX, sodium cyanate+SX, streptmycin+SX, thidiazuron+SX, triapenthenol+SX, Tribufos+SX, trinexapac-ethyl+SX, uniconazole-P+SX, 2-(naphthalen-1-yl)acetamide+SX, [4-oxo-4-(2-phenylethyl)amino]butyric acid+SX, methyl 5-(trifluoromethyl)benzo[b]thiophene-2-carboxylate+SX, 3-[(6-chloro-4-phenylquinazolin-2-yl)amino]-1-propanol+SX, *Claroideoglomus etunicatum*+SX, *Claroideoglomus claroideum*+SX, *Funneliformis mosseae*+SX, *Gigaspora margarita*+SX, *Gigaspora rosea*+SX, *Glomus aggregatum*+SX, *Glomus deserticola*+SX, *Glomus monosporum*+SX, *Paraglomus brasillianum*+SX, *Rhizophagus clarus*+SX, *Rhizophagus intraradices* RTI-801+SX, *Rhizophagus irregularis* DAOM 197198+SX, *Azorhizobium caulinodans*+SX, *Azospirillum amazonense*+SX, *Azospirillum brasilense* XOH+SX, *Azospirillum brasilense* Ab-V5+SX, *Azospirillum brasilense* Ab-V6+SX, *Azospirillum caulinodans*+SX, *Azospirillum halopraeferens*+SX, *Azospirillum irakense*+SX, *Azospirillum lipoferum*+SX, *Bradyrhizobium elkanii* SEMIA 587+SX, *Bradyrhizobium elkanii* SEMIA 5019+SX, *Bradyrhizobium japonicum* TA-11+SX, *Bradyrhizobium japonicum* USDA 110+SX, *Bradyrhizobium liaoningense*+SX, *Bradyrhizobium lupini*+SX, *Delftia acidovorans* RAY209+SX, *Mesorhizobium ciceri*+SX, *Mesorhizobium huakii*+SX, *Mesorhizobium loti*+SX, *Rhizobium etli*+SX, *Rhizobium galegae*+SX, *Rhizobium leguminosarum* bv. *Phaseoli*+SX, *Rhizobium leguminosarum* bv. *Trifolii*+SX, *Rhizobium leguminosarum* bv. *Viciae*+SX, *Rhizobium trifolii*+SX, *Rhizobium tropici*+SX, *Sinorhizobium fredii*+SX, *Sinorhizobium meliloti*+SX, Zucchini Yellow Mosaik Virus weak strain+SX.

Combinations of the Present ingredient in the above Group (d) and the Present compound:

anthraquinone+SX, deet+SX, icaridin+SX.

Examples of the ratio of the Present compound and the Present ingredient include, but are not limited to, 1000:1 to 1:1000, 500:1 to 1:500, 100:1 to 1:100, 50:1, 20:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:20, and 1:50, in the ratio by weight (Present compound: Present ingredient).

The Present compound has control effects on harmful arthropods such as harmful insects and harmful mites, harmful nematodes, and harmful mollusks. Examples of the harmful arthropods, harmful nematodes, and harmful mollusks include the followings.

Hemiptera:

from the family Delphacidae, small brown planthopper (*Laodelphax striatellus*), brown planthopper (*Nilaparvata lugens*), white-backed planthopper (*Sogatella furcifera*), corn planthopper (*Peregrinus maidis*), cereal leafhopper (*Javesella pellucida*), sugarcane leafhopper (*Perkinsiella saccharicida*), *Tagosodes orizicolus*, and the like;

from the family Cicadellidae, green rice leafhopper (*Nephotettix cincticeps*), green paddy leafhopper (*Nephotettix virescens*), rice leafhopper (*Nephotettix* nigropictus), zigzag-striped leafhopper (*Recilia dorsalis*), tea green leafhopper (*Empoasca onukii*), potato leafhopper (*Empoasca fabae*), corn leafhopper (*Dalbulus maidis*), rice leafhopper (*Cofana spectra*), and the like;

from the family Cercopidae, *Mahanarva posticata*, *Mahanarva fimbriolata*, and the like;

from the family Aphididae, bean aphid (*Aphis fabae*), soybean aphid (*Aphis glycines*), cotton aphid (*Aphis gossypii*), green apple aphid (*Aphis pomi*), apple aphid (*Aphis spiraecola*), green peach aphid (*Myzus persicae*), leaf-curling plum aphid (*Brachycaudus helichrysi*), cabbage aphid (*Brevicoryne brassicae*), rosy apple aphid (*Dysaphis plantaginea*), false cabbage aphid (*Lipaphis erysimi*), potato aphid (*Macrosiphum euphorbiae*), foxglove aphid (*Aulacorthum solani*), lettuce aphid (*Nasonovia ribisnigri*), grain aphid (*Rhopalosiphum padi*), corn aphid (*Rhopalosiphum maidis*), brown citrus aphid (*Toxoptera citricida*), mealy plum aphid (*Hyalopterus pruni*), cane aphid (*Melanaphis sacchari*), black rice root aphid (*Tetraneura nigriabdominalis*), sugarcane cottony aphid (*Ceratovacuna lanigera*), apple woolly aphid (*Eriosoma lanigerum*), and the like;

from the family Phylloxeridae, grapevine phylloxera (*Daktulosphaira vitifoliae*), Pecan *phylloxera* (*Phylloxera devastatrix*), Pecan leaf *phylloxera* (*Phylloxera notabilis*), Southern pecan leaf *phylloxera* (*Phylloxera russellae*), and the like;

from the family Adelgidae, hemlock woolly aphid (*Adelges tsugae*), *Adelges piceae*, *Aphrastasia pectinatae*, and the like;

from the family Pentatomidae, black rice bug (*Scotinophara lurida*), Malayan rice black bug (*Scotinophara coarctata*), common green stink bug (*Nezara antennata*), white-spotted spined bug (*Eysarcoris aeneus*), lewis spined bug (*Eysarcoris lewisi*), white-spotted bug (*Eysarcoris ventralis*), *Eysarcoris annamita*, brown marmorated stink bug (*Halyomorpha halys*), green plant bug (*Nezara viridula*), Brown stink bug (*Euschistus heros*), Red banded stink bug (*Piezodorus guildinii*), *Oebalus pugnax*, *Dichelops melacanthus*, and the like;

from the family Cydnidae, Burrower brown bug (*Scaptocoris castanea*), and the like;

from the family Alydidae, bean bug (*Riptortus pedestris*), corbett rice bug (*Leptocorisa chinensis*), rice bug (*Leptocorisa acuta*), and the like;

from the family Coreidae, *Cletus punctiger*, Australian leaf-footed bug (*Leptoglossus australis*), and the like;

from the family Lygaeidae, oriental chinch bug (*Caverelius saccharivorus*), seed bug (*Togo hemipterus*), chinch bug (*Blissus leucopterus*), and the like;

from the family Miridae, rice leaf bug (*Trigonotylus caelestialium*), sorghum plant bug (*Stenotus rubrovittatus*), wheat leaf bug (*Stenodema calcarata*), American tarnished plant bug (*Lygus lineolaris*), and the like;

from the family Aleyrodidae, greenhouse whitefly (*Trialeurodes vaporariorum*), tobacco whitefly (*Bemisia tabaci*), citrus whitefly (*Dialeurodes citri*), citrus spiny whitefly (*Aleurocanthus spiniferus*), tea spiny whitefly (*Aleurocanthus camelliae*), *Pealius euryae*, and the like;

from the family Diaspididae, *Abgrallaspis cyanophylli*, red scale (*Aonidiella aurantii*), San José scale (*Diaspidiotus perniciosus*), white peach scale (*Pseudaulacaspis pentagona*), arrowhead scale (*Unaspis yanonensis*), citrus snow scale (*Unaspis citri*), and the like;

from the family Coccidae, pink wax scale (*Ceroplastes rubens*), and the like;

from the family Margarodidae, fluted scale (*Icerya purchasi*), seychelles fluted scale (*Icerya seychellarum*), and the like;

from the family Pseudococcidae, *solanum* mealybug (*Phenacoccus solani*), cotton mealybug (*Phenacoccus solenopsis*), Japanese mealybug (*Planococcus kraunhiae*), white peach scale (*Pseudococcus comstocki*), citrus mealybug (*Planococcus citri*), currant mealybug (*Pseudococcus calceolariae*), long-tailed mealybug (*Pseudococcus longispinus*), tuttle mealybug (*Brevennia rehi*), and the like;

from the family Psyllidae, citrus psylla (*Diaphorina citri*), two-spotted citrus psyllid (*Trioza erytreae*), pear sucker (*Cacopsylla pyrisuga*), *Cacopsylla chinensis*, potato psyllid (*Bactericera cockerelli*), Pear psylla (*Cacopsylla pyricola*), and the like;

from the family Tingidae, sycamore lace bug (*Corythucha ciliata*), aster tingid (*Corythucha marmorata*), Japanese pear lace bug (*Stephanitis nashi*), azalea lace bug (*Stephanitis pyrioides*), and the like;

from the family Cimicidae, common bed bug (*Cimex lectularius*), tropical bed bug (*Cimex lectularius*), and the like;

from the family Cicadidae, Giant Cicada (*Quesada gigas*), and the like;

from the family Reduviidae, *Triatoma infestans*, *Rhodnius prolixus*, and the like, *Triatoma* spp.;

and the others.

Lepidoptera:

from the family Crambidae, rice stem borer (*Chilo suppressalis*), Dark-headed stem borer (*Chilo polychrysus*), white stem borer (*Scirpophaga innotata*), yellow paddy borer (*Scirpophaga incertulas*), *Rupela albina*, rice leaf roller (*Cnaphalocrocis medinalis*), *Marasmia patnalis*, rice leaf roller (*Marasmia exigua*), cotton leaf roller (*Notarcha derogata*), corn borer (*Ostrinia furnacalis*), European corn borer (*Ostrinia nubilalis*), cabbage webworm (*Hellula undalis*), grape leafroller (*Herpetogramma luctuosale*), bluegrass webworm (*Pediasia teterrellus*), rice case-worm (*Nymphula depunctalis*), Sugarcane borer (*Diatraea saccharalis*), and the like;

from the family Pyralidae, lesser cornstalk borer (*Elasmopalpus lignosellus*), mealworm moth (*Plodia interpunctella*), persimmon bark borer (*Euzophera batangensis*), fig moth (*Cadra cautella*), and the like;

from the family Noctuidae, cotton worm (*Spodoptera litura*), beet armyworm (*Spodoptera exigua*), rice armyworm (*Mythimna separata*), cabbage moth (*Mamestra brassicae*), pink borer (*Sesamia inferens*), grass armyworm (*Spodoptera mauritia*), green rice caterpillar (*Naranga aenescens*), *Spodoptera frugiperda*, true armyworm (*Spodoptera exempta*), black cutworm (*Agrotis ipsilon*), beet worm (*Autographa nigrisigna*), rice looper (*Plusia festucae*), soybean looper (*Chrysodeixis includens*), *Trichoplusia* spp., *Heliothis* spp. (such as tobacco budworm (*Heliothis virescens*)), *Helicoverpa* spp. (such as tobacco budworm (*Helicoverpa armigera*) and corn earworm (*Helicoverpa zea*)), Velvetbean caterpillar (*Anticarsia gemmatalis*), Cotton leafworm (*Alabama argillacea*), Hop vine borer (*Hydraecia immanis*), and the like;

from the family Pieridae, common cabbage worm (*Pieris rapae*), and the like;

from the family Tortricidae, oriental fruit moth (*Grapholita molesta*), *Grapholita dimorpha*, soybean moth (*Leguminivora glycinivorella*), *Matsumuraeses azukivora*, summer fruit *tortrix* (*Adoxophyes orana fasciata*), smaller tea *tortrix* (*Adoxophyes honmai*), Japanese tea *tortrix* (*Homona magnanima*), apple *tortrix* (*Archips fuscocupreanus*), codling moth (*Cydia pomonella*), sugarcane shoot borer (*Tetramoera schistaceana*), Bean Shoot Borer (*Epinotia aporema*), Citrus fruit borer (*Ecdytolopha aurantiana*), and the like;

from the family Gracillariidae, tea leaf roller (*Caloptilia theivora*), Asiatic apple leaf miner (*Phyllonorycter ringoniella*), and the like;

from the family Carposinidae, peach fruit moth (*Carposina sasakii*), and the like;

from the family Lyonetiidae, Coffee Leaf miner (*Leucoptera coffeella*), peach leaf miner (*Lyonetia clerkella*), *Lyonetia prunifoliella*, and the like;

from the family Lymantriidae, *Lymantria* spp. (such as gypsy moth (*Lymantria dispar*)), *Euproctis* spp. (such as tea lymantriid (*Euproctis pseudoconspersa*)), and the like;

from the family Plutellidae, diamondback moth (*Plutella xylostella*), and the like;

from the family Gelechiidae, peach worm (*Anarsia lineatella*), sweetpotato leaf folder (*Helcystogramma triannulella*), pink bollworm (*Pectinophora gossypiella*), potato moth (*Phthorimaea operculella*), *Tuta absoluta*, and the like;

from the family Arctiidae, American white moth (*Hyphantria cunea*), and the like;

from the family Castniidae, Giant Sugarcane borer (*Telchin licus*), and the like;

from the family Cossidae, *Cossus insularis*, and the like;

from the family Geometridae, Ascotis selenaria, and the like;

from the family Limacodidae, blue-striped nettle grub (*Parasa lepida*), and the like;

from the family Stathmopodidae, persimmon fruit moth (*Stathmopoda masinissa*), and the like;

from the family Sphingidae, tobacco hornworm (*Acherontia lachesis*), and the like;

from the family Sesiidae, *Nokona feralis*, cherry borer (*Synanthedon hector*), *Synanthedon tenuis*, and the like:

from the family Hesperiidae, rice skipper (*Parnara guttata*), and the like;

from the family Tineidae, casemaking clothes moth (*Tinea translucens*), common clothes moth (*Tineola bisselliella*), and the like;

and the others.

Thysanoptera:

from the family Thripidae, western flower *thrips* (*Frankliniella occidentalis*), oriental *thrips* (*Thrips palmi*) yellow tea *thrips* (*Scirtothrips dorsalis*), onion *thrips* (*Thrips tabaci*), eastern flower *thrips* (*Frankliniella intonsa*), rice *thrips* (Stenchaetothrips *biformis*), *Echinothrips americanus*, and the like;

from the family Phlaeothripidae, aculeated rice *thrips* (*Haplothrips aculeatus*), and the like;

and the others.

Diptera:

from the family Anthomyiidae, seedcorn maggot (*Delia platura*), onion maggot (*Delia antiqua*), beet leaf miner (*Pegomya cunicularia*), and the like;

from the family Ulidiidae, sugarbeet root maggot (*Tetanops myopaeformis*), and the like;

from the family Agromyzidae, rice leaf miner (*Agromyza oryzae*), tomato leaf miner (*Liriomyza sativae*), chrysanthemum leaf miner (*Liriomyza trifolii*), pea leafminer (*Chromatomyia horticola*), and the like;

from the family Chloropidae, rice stem maggot (*Chlorops oryzae*), and the like;

from the family Tephritidae, melon fly (*Bactrocera cucurbitae*), oriental fruit fly (*Bactrocera dorsalis*), Malaysian fruit fly (*Bactrocera latifrons*), olive fruit fly (*Bactrocera oleae*), Queensland fruit fly (*Bactrocera tryoni*) Mediterranean fruit fly (*Ceratitis capitata*), apple maggot (*Rhagoletis pomonella*), Japanese cherry fruit fly (*Rhacochlaena japonica*), and the like;

from the family Ephydridae, smaller rice leaf miner (*Hydrellia griseola*), whorl maggot (*Hydrellia philippina*), paddy stem maggot (*Hydrellia sasakii*), and the like;

from the family Drosophilidae, cherry *drosophila* (*Drosophila suzukii*), and the like;

from the family Phoridae, *Megaselia spiracularis*, and the like;

from the family Psychodidae, *Clogmia albipunctata*, and the like;

from the family Sciaridae, *Bradysia difformis*, and the like;

from the family Cecidomyiidae, Hessian fly (*Mayetiola destructor*), paddy gall fly (*Orseolia oryzae*), and the like;

from the family Diopsidae, *Diopsis macrophthalma*, and the like;

from the family Tipulidae, rice crane fly (*Tipula aino*), Common cranefly (*Tipula oleracea*), European cranefly (*Tipula paludosa*), and the like;

from the family Culicidae, southern house mosquito (*Culex pipiens pallens*), *Culex tritaeniorhynchus*, *Culex pipiens* f. *molestus*, brown house mosquito (*Culex quinquefasciatus*), northern house mosquito (*Culex pipiens pipiens*), *Culex vishnui*, Asian tiger mosquito (*Aedes albopictus*), dengue mosquito (*Aedes aegypti*), Chinese malaria mosquito (*Anopheles sinensis*), *Anopheles gambiae, Anopheles stephensi, Anopheles coluzzii, Anopheles albimanus, Anopheles sundaicus, Anopheles arabiensis, Anopheles funestus, Anopheles darlingi, Anopheles farauti, Anopheles minimus*, and the like;

from the family Simulidae, *Prosimulium yezoensis, Simulium ornatum*, and the like;

from the family Tabanidae, *Tabanus trigonus*, and the like;

from the family Muscidae, house fly (*Musca domestica*), false stable fly (*Muscina stabulans*), biting house fly (*Stomoxys calcitrans*), buffalo fly (*Haematobia irritans*), and the like;

from the family Calliphoridae;

from the family Sarcophagidae;

from the family Chironomidae, *Chironomus plumosus, Chironomus yoshimatsui, Glyptotendipes tokunagai*, and the like;

from the family Fannidae;

and the others.

Coleoptera:

from the family Chrysomelidae, western corn rootworm (*Diabrotica virgifera virgifera*), southern corn rootworm (*Diabrotica undecimpunctata howardi*), northern corn rootworm (*Diabrotica barberi*), Mexican corn rootworm (*Diabrotica virgifera zeae*), banded cucumber beetle (*Diabrotica balteata*), Cucurbit Beetle (*Diabrotica speciosa*), bean leaf beetle (*Cerotoma trifurcata*), barley leaf beetle (*Oulema melanopus*), cucurbit leaf beetle (*Aulacophora femoralis*), striped flea beetle (*Phyllotreta striolata*), Cabbage flea beetle (*Phyllotreta cruciferae*), Western black flea beetle (*Phyllotreta pusilla*), Cabbage stem flea beetle (*Psylliodes chrysocephala*), Colorado potato beetle (*Leptinotarsa decemlineata*), rice leaf beetle (*Oulema oryzae*), grape *colaspis* (*Colaspis brunnea*), corn flea beetle (*Chaetocnema pulicaria*), sweet-potato flea beetle (*Chaetocnema confinis*), potato flea beetle (*Epitrix cucumeris*), rice leaf beetle (*Dicladispa armigera*), southern corn leaf beetle (*Myochrous denticollis*), *Laccoptera quadrimaculata*, tobacco flea beetle (*Epitrix hirtipennis*), and the like;

from the family Carabidae, Seedcorn beetle (*Stenolophus lecontei*), Slender seedcorn beetle (*Clivina impressifrons*), and the like;

from the family Scarabaeidae, cupreus chafer (*Anomala cuprea*), soybean beetle (*Anomala rufocuprea*), *Anomala albopilosa*, Japanese beetle (*Popillia japonica*), yellowish elongate chafer (*Heptophylla picea*), European Chafer (*Rhizotrogus majalis*), *Tomarus gibbosus, Holotrichia* spp., *Rhyllophaga* spp. (such as June beetle (*Phyllophaga crinita*)), *Diloboderus* spp. (such as *Diloboderus abderus*), and the like;

from the family Curculionidae, coffee bean weevil (*Araecerus coffeae*), sweet-potato weevil (*Cylas formicarius*), West Indian sweet-potato weevil (*Euscepes postfasciatus*), alfalfa weevil (*Hypera postica*), maize weevil (*Sitophilus zeamais*), rice weevil (*Sitophilus oryzae*), grain weevil (*Sitophilus granarius*), rice plant weevil (*Echinocnemus squameus*), rice water weevil (*Lissorhoptrus oryzophilus*), *Rhabdoscelus lineatocollis*, boll weevil (*Anthonomus grandis*), nunting billbug (*Sphenophorus venatus*), Southern Corn Billbug (*Sphenophorus callosus*), Soybean stalk weevil (*Sternechus subsignatus*), Sugarcane weevil (*Sphenophorus levis*), rusty gourd-shaped weevil (*Scepticus griseus*), brown gourd-shaped weevil (*Scepticus uniformis*), Mexican bean weevil (*Zabrotes subfasciatus*), pine beetle (*Tomicus piniperda*), Coffee Berry Borer (*Hypothenemus hampei*), *Aracanthus* spp. (such as *Aracanthus mourei*), and cotton root borer (*Eutinobothrus brasiliensis*), and the like;

from the family Tenebrionidae, red meal beetle (*Tribolium castaneum*), mason beetle (*Tribolium confusum*), lesser mealworm (*Alphitobius diaperinus*), and the like;

from the family Coccinellidae, twenty-eight-spotted ladybird (*Epilachna vigintioctopunctata*), and the like;

from the family Bostrychidae, common powder-post beetle (*Lyctus brunneus*), lesser grain borer (*Rhyzopertha dominica*) and the like;

from the family Ptinidae;

from the family Cerambycidae, citrus long-horned beetle (*Anoplophora malasiaca*), *Migdolus fryanus*, and the like;

from the family Elateridae, *Melanotus okinawensis*, barley wireworm (*Agriotes fuscicollis*), *Melanotus legatus, Anchastus* spp., *Conoderus* spp., *Ctenicera* spp., *Limonius* spp., *Aeolus* spp., and the like;

from the family Staphylinidae, *Paederus fuscipes*, and the like;

from the family Dermestidae, varied carpet beetle (*Anthrenus verbasci*), hide beetle (*Dermestes maculates*), khapra beetle (*Trogoderma granarium*), and the like;

from the family Anobiidae, tobacco beetle (*Lasioderma serricorne*), biscuit beetle (*Stegobium paniceum*), and the like from the family Laemophloeidae, flat grain beetle (*Cryptolestes ferrugineus*), and the like;

from the family Silvanidae, saw-toothed grain beetle (*Oryzaephilus surinamensis*), and the like;

and the others.

Orthoptera:

from the family Acrididae, oriental migratory locust (*Locusta migratoria*), Moroccan locust (*Dociostaurus maroccanus*), Australian plague locust (*Chortoicetes terminifera*), red locust (*Nomadacris septemfasciata*), Brown Locust (*Locustana pardalina*), Tree Locust (*Anacridium melanorhodon*), Italian Locust (*Calliptamus italicus*), Differential grasshopper (*Melanoplus differentialis*), Two striped grasshopper (*Melanoplus bivittatus*), Migratory grasshopper (*Melanoplus sanguinipes*), Red-Legged grasshopper (*Melanoplus femurrubrum*), Clearwinged grasshopper (*Camnula pellucida*), desert locust (*Schistocerca gregaria*), Yellow-winged locust (*Gastrimargus musicus*), Spurthroated locust (*Austracris guttulosa*), Japanese grasshopper (*Oxya yezoensis*), rice grasshopper (*Oxya japonica*), Bombay locust (*Patanga succincta*), and the like;

from the family Gryllotalpidae, oriental mole cricket (*Gryllotalpa orientalis*), and the like;

from the family Gryllidae, house cricket (*Acheta domestica*), emma field cricket (*Teleogryllus emma*), and the like;

from the family Tettigoniidae, Mormon cricket (*Anabrus simplex*), and the like;

and the others.

Hymenoptera:

from the family Tenthredinidae, beet sawfly (*Athalia rosae*), nippon cabbage sawfly (*Athalia japonica*), and the like;

from the family Formicidae, *Solenopsis* spp. (such as red imported fire ant (*Solenopsis invicta*) and tropical fire ant (*Solenopsis geminata*)), *Atta* spp. (such as Brown leaf-cutting ant (*Atta capiguara*)), *Acromyrmex* spp., *Paraponera clavata*, black house ant (*Ochetellus glaber*), little red ant (*Monomorium pharaonis*), Argentine ant (*Linepithema humile*), *Formica fusca japonica, Pristomyrmex punctutus, Pheidole noda*, big-headed ant (*Pheidole megacephala*), *Camponotus* spp. (such as *Camponotus japonicus* and *Camponotus obscuripes*), *Pogonomyrmex* spp. (such as western harvester ant (*Pogonomyrmex occidentalis*)), *Wasmania* spp. (such as *Wasmania auropunctata*), long-legged ant (*Anoplolepis gracilipes*), and the like;

from the family Vespidae, Asian giant hornet (*Vespa mandarinia japonica*), *Vespa simillima, Vespa analis Fabriciusi*, Asian hornet (*Vespa velutina*), *Polistes jokahamae*, and the like;

from the family Siricidae, pine wood wasp (*Urocerus gigas*), and the like;

from the family Bethylidae;

and the others.

Blattodea:

from the family Blattellidae, German cockroach (*Blattella germanica*), and the like;

from the family Blattidae, smoky-brown cockroach (*Periplaneta fuliginosa*), American cockroach (*Periplaneta americana*), brown cockroach (*Periplaneta brunnea*), black cockroach (*Blatta orientalis*), and the like;

from the family Termitidae, Japanese termite (*Reticulitermes speratus*), Formosan termite (*Coptotermes formosanus*), western drywood termite (*Incisitermes minor*), *Cryptotermes domesticus*, *Odontotermes formosanus*, *Neotermes koshunensis*, *Glyptotermes satsumensis*, *Glyptotermes nakajimai*, *Glyptotermes fuscus*, *Hodotermopsis sjostedti*, *Coptotermes guangzhouensis*, *Reticulitermes amamianus*, *Reticulitermes miyatakei*, *Reticulitermes kanmonensis*, *Nasutitermes takasagoensis*, *Pericapritermes nitobei*, *Sinocapritermes mushae*, *Cornitermes cumulans*, and the like; and the others.

Siphonaptera:

*Pulex* spp. (such as human flea (*Pulex irritans*)), *Ctenocephalides* spp. (such as cat flea (*Ctenocephalides felis*) and dog flea (*Ctenocephalides canis*)), *Xenopsylla* spp. (such as oriental rat flea (*Xenopsylla cheopis*)), *Tunga* spp. (such as chigoe flea (*Tunga penetrans*)), *Echidnophaga* spp. (such as chicken flea (*Echidnophaga gallinacea*)), *Nosopsyllus* spp. (such as European rat flea (*Nosopsyllus fasciatus*)), and the like.

Psocodea:

*Pediculus* spp. (such as head louse (*Pediculus humanus capitis*)); *Pthirus* spp. (such as crab louse (*Pthirus pubis*)); *Haematopinus* spp. (such as short-nosed cattle louse (*Haematopinus eurysternus*) and pig louse (*Haematopinus suis*)); *Damalinia* spp. (such as *Dalmalinia ovis* and *Damalinia bovis*); *Linognathus* spp. (such as blue cattle louse (*Linognathus vituli*) and sheep face louse (*Linognathus ovillus*)); *Solenopotes* spp. (such as capillate louse (*Solenopotes capillatus*)); *Menopon* spp. (such as common chicken louse (*Menopon gallinae*)); *Trimenopon* spp.; *Trinoton* spp.; *Trichodectes* spp. (such as dog biting louse (*Trichodectes canis*)); *Felicola* spp. (such as cat louse (*Felicola subrostratus*)); *Bovicola* spp. (such as cattle biting louse (*Bovicola bovis*)); *Menacanthus* spp. (such as chicken body louse (*Menacanthus stramineus*)); *Werneckiella* spp.; *Lepikentron* spp.;

from the family Liposcelididae, book louse (*Liposcelis subfuscas*), *Liposcelis bostrychophilus*, *Liposcelis simulans*, *Liposcelis divinatorius*, *Liposcelis entomophila*, and the like;

and the others.

Thysanura:

from the family Lepismatidae, oriental silverfish (*Ctenolepisma villosa*), moth fish (*Lepisma saccharina*), and the like.

Acari:

from the family Tetranychidae, common red spider mite (*Tetranychus urticae*), kanzawa spider mite (*Tetranychus kanzawai*), red spider mite (*Tetranychus evansi*), citrus red mite (*Panonychus citri*), fruit-tree red spider mite (*Panonychus ulmi*), *Oligonychus* spp., and the like;

from the family Eriophyidae, Japanese citrus rust mite (*Aculops pelekassi*), *Phyllocoptruta citri*, tomato mite (*Aculops lycopersici*), purple mite (*Calacarus carinatus*), tea rust mite (*Acaphylla theavagrans*), *Eriophyes chibaensis*, apple bud mite (*Aculus schlechtendali*), *Aceria diospyri*, *Aceria tosichella*, *Shevtchenkella* sp., and the like;

from the family Tarsonemidae, broad mite (*Polyphagotarsonemus latus*), and the like;

from the family Tenuipalpidae, *Brevipalpus phoenicis*, and the like;

from the family Tuckerellidae;

from the family Ixodidae, *Haemaphysalis* spp. (such as *Haemaphysalis longicornis*, *Haemaphysalis flava*, and *Haemaphysalis campanulata*), *Dermacentor* spp. (such as American dog tick (*Dermacentor variabilis*), *Dermacentor taiwanicus*, and Rocky Mountain wood tick (*Dermacentor andersoni*)), *Ixodes* spp. (such as *Ixodes ovatus*, *Ixodes persulcatus*, black-legged tick (*Ixodes scapularis*), *Ixodes pacificus*, and *Ixodes holocyclus*), *Amblyomma* spp. (such as lone star tick (*Amblyomma americanum*) and gulf coast tick (*Amblyomma maculatum*)), *Boophilus* spp. (such as *Rhipicephalus* (*Boophilus*) *microplus* and *Boophilus annulatus*) and *Rhipicephalus* spp. (such as brown dog tick (*Rhipicephalus sanguineus*) and *Rhipicephalus appendiculatus*);

from the family Acaridae, cereal mite (*Tyrophagus putrescentiae*), grassland mite (*Tyrophagus similis*), and the like;

from the family Pyroglyphidae, American house dust mite (*Dermatophagoides farinae*), European house dust mite (*Dermatophagoides pteronyssinus*), and the like;

from the family Cheyletidae, *Cheyletus eruditus*, *Cheyletus malaccensis*, *Chelacaropsis moorei*, *Cheyletiella yasguri*, and the like;

*Argas* spp. (such as fowl tick (*Argas persicus*)), *Ornithodorus* spp. (such as *Ornithodorus hermsi* and *Ornithodorus turicata*), *Psoroptes* spp. (such as sheep scab mite (*Psoroptes ovis*) and horse psoroptic mange mite (*Psoroptes equi*)), *Knemidocoptes* spp. (such as *Knemidocoptes mutans*), *Notoedres* spp. (such as *Notoedres cati* and *Notoedres muris*), *Sarcoptes* spp. (such as itch mite (*Sarcoptes scabiei*)), *Otodectes* spp. (such as ear mange mite (*Otodectes* cynotis)), *Listrophorus* spp. (such as *Listrophorus gibbus*), *Chorioptes* spp., *Hypodectes* spp., *Pterolichus* spp., *Cytodites* spp., *Laminosioptes* spp., *Dermanyssus* spp. (such as bird mite (*Dermanyssus gallinae*)), *Ornithonyssus* spp. (such as feather mite (*Ornithonyssus sylviarum*) and tropical rat mite (*Ornithonyssus bacoti*)), *Varroa* spp. (such as *Varroa jacobsoni*), *Cheyletiella* spp. (such as *Cheyletiella yasguri* and *Cheyletiella blakei*), *Ornithocheyletia* spp., *Demodex* spp. (such as dog follicle mite (*Demodex canis*) and cat follicle mite (*Demodex cati*)), *Myobia* spp., *Psorergates* spp., and *Trombicula* spp. (such as *Trombicula akamushi*, *Trombicula pallida*, and *Trombicula scutellaris*);

and the others.

Araneae:

from the family Eutichuridae, *Cheiracanthium japonicum*, and the like;

from the family Theridiidae, red-back spider (*Latrodectus hasseltii*), and the like;

and the others.

Polydesmida:

from the family Paradoxosomatidae, flat-backed millipede (*Oxidus gracilis*), *Nedyopus tambanus*, and the like;

and the others.

Isopoda:

from the family Armadillidiidae, common pill bug (*Armadillidium vulgare*), and the like;

and the others.

Chilopoda:
  from the family Scutigeridae, *Thereuonema hilgendorfi*, and the like;
  from the family Scolopendridae, giant tropical centipede (*Scolopendra subspinipes*), and the like;
  from the family Ethopolyidae, *Bothropolys rugosus*, and the like;
and the others.
Gastropoda:
  from the family Limacidae, tree slug (*Limax marginatus*), garden tawny slug (*Limax flavus*), and the like;
  from the family Philomycidae, *Meghimatium bilineatum*, and the like;
  from the family Ampullariidae, golden apple snail (*Pomacea canaliculata*), and the like;
  from the family Lymnaeidae, *Austropeplea ollula*, and the like;
and the others.
Nematoda:
  from the family Aphelenchoididae, rice white-tip nematode (*Aphelenchoides besseyi*), and the like;
  from the family Pratylenchidae, root lesion nematode (*Pratylenchus coffeae*), *Pratylenchus brachyurus*, California meadow nematode (*Pratylenchus neglectus*), *Radopholus similis*, and the like;
  from the family Heteroderidae, javanese root-knot nematode (*Meloidogyne javanica*), southern root-knot nematode (*Meloidogyne incognita*), northern root-knot nematode (*Meloidogyne hapla*), soybean cyst nematode (*Heterodera glycines*), potato cyst nematode (*Globodera rostochiensis*), white potato cyst nematode (*Globodera pallida*), and the like; from the family Hoplolaimidae, *Rotylenchulus reniformis*, and the like;
  from the family Anguinidae, strawberry bud nematode (*Nothotylenchus acris*), stem nematode (*Ditylenchus dipsaci*), and the like;
  from the family Tylenchulidae, citrus nematode (*Tylenchulus semipenetrans*), and the like;
  from the family Longidoridae, dagger nematode (*Xiphinema index*), and the like;
  from the family Trichodoridae;
  from the family Parasitaphelenchidae, pine wilt disease (*Bursaphelenchus xylophilus*), and the like;
and the others.

The target harmful arthropods such as harmful insects and harmful mites, harmful mollusks, and harmful nematodes may have a reduced agent-sensitivity to or a developed agent-resistance to an insecticide, a miticide, a molluscicide, or a nematicide.

The method for controlling harmful arthropods of the present invention is carried out by applying an effective amount of the Present compound or the Composition A to harmful arthropods directly and/or habitats where harmful arthropods live (for example, plant bodies, soil, interiors of houses, and animal bodies). Examples of the method for controlling harmful arthropods of the present invention include foliage treatment, soil treatment, root treatment, shower treatment, smoking treatment, water surface treatment, and seed treatment.

The Present compound or the Composition A is usually mixed with inert carrier(s) such as solid carrier(s), liquid carrier(s), and gaseous carrier(s), and as needed, surfactant(s) and other auxiliary agent(s) for formulation is/are added thereto, to formulate into an emulsifiable concentrate, an oil solution, a dust formulation, a granule, a wettable powder, a granular wettable powder, a flowable, a dry flowable, a microcapsule, an aerosol, a poison bait, a resin formulation, a shampoo formulation, a paste-like formulation, a foam, a carbon dioxide formulation, a tablet, or the like to be used. Such formulation may be processed into and used as a mosquito repellent coil, an electric mosquito repellent mat, a liquid mosquito repellent formulation, a smoking agent, a fumigant, a sheet formulation, a spot-on formulation, or a formulation for oral treatment. These formulations usually comprise 0.0001 to 95% by weight of the Present compound or the Composition A.

Examples of the solid carrier(s) to be used in the formulation include fine powders and granules of clays (for example, kaolin clay, diatomaceous earth, bentonite, and acid white clay), dry silica, wet silica, talc, ceramic, other inorganic minerals (for example, sericite, quartz, sulfur, active carbon, and calcium carbonate), chemical fertilizers (for example, ammonium sulfate, ammonium phosphate, ammonium nitrate, urea, and ammonium chloride), and the others; as well as synthetic resins (for example, polyester resins such as polypropylene, polyacrylonitrile, polymethylmethacrylate, and polyethylene terephthalate; nylon resins such as nylon-6, nylon-11, and nylon-66; polyamide resins; polyvinyl chloride, polyvinylidene chloride, vinyl chloride-propylene copolymers, and the others).

Examples of the liquid carrier(s) include water; alcohols (for example, methanol, ethanol, isopropyl alcohol, butanol, hexanol, benzyl alcohol, ethylene glycol, propylene glycol, and phenoxy ethanol); ketones (for example, acetone, methyl ethyl ketone, and cyclohexanone); aromatic hydrocarbons (for example, toluene, xylene, ethyl benzene, dodecyl benzene, phenyl xylyl ethane, and methylnaphthalene); aliphatic hydrocarbons (for example, hexane, cyclohexane, kerosene, and light oil); esters (for example, ethyl acetate, butyl acetate, isopropyl myristate, ethyl oleate, diisopropyl adipate, diisobutyl adipate, and propylene glycol monomethyl ether acetate); nitriles (for example, acetonitrile and isobutyronitrile); ethers (for example, diisopropyl ether, 1,4-dioxane, 1,2-dimethoxyethane, diethylene glycol dimethyl ether, diethylene glycol monomethyl ether, propylene glycol monomethyl ether, dipropylene glycol monomethyl ether, and 3-methoxy-3-methyl-1-butanol); amides (for example, DMF and N,N-dimethylacetamide); sulfoxides (for example, DMSO); propylene carbonate; and vegetable oils (for example, soybean oil and cottonseed oil).

Examples of the gaseous carrier(s) include fluorocarbon, butane gas, LPG (liquefied petroleum gas), dimethyl ether, and carbon dioxide.

Examples of the surfactant(s) include nonionic surfactants such as polyoxyethylene alkyl ethers, polyoxyethylene alkyl aryl ethers, and polyethylene glycol fatty acid esters; and anionic surfactants such as alkyl sulfonates, alkylbenzene sulfonates, and alkyl sulfates.

Examples of the other auxiliary agent(s) for formulation include binders, dispersants, colorants, and stabilizers. Specific examples thereof include casein, gelatin, saccharides (for example, starch, gum arabic, cellulose derivatives, and alginic acid), lignin derivatives, bentonite, water-soluble synthetic polymers (for example, polyvinyl alcohol, polyvinyl pyrrolidone, and polyacrylic acids), acidic isopropyl phosphate, 2,6-di-tert-butyl-4-methylphenol, and BHA (a mixture of 2-tert-butyl-4-methoxyphenol and 3-tert-butyl-4-methoxyphenol).

Examples of the base material of the resin formulation include vinyl chloride polymers, polyurethane, and the others, and plasticizer(s) such as phthalic acid esters (for example, dimethyl phthalate and dioctyl phthalate), adipic acid esters, and stearic acid may also be added to these base materials, as needed. The resin formulation may be prepared by mixing a compound with the above-mentioned base material, kneading the mixture in a conventional kneading apparatus, followed by molding it by injection molding, extrusion molding, pressure molding, or the like. The resultant resin formulation may be subjected to further molding, cutting procedure, or the like, as needed, to be processed into a shape such as plate, film, tape, net, and string shapes. These resin formulations may be processed into an animal collar, an animal ear tag, a sheet formulation, a trap string, a gardening support, or other products.

Examples of the base material for the poison bait include grain powders, vegetable oils, saccharides, crystalline celluloses, and the others, and further, antioxidant(s) such as dibutylhydroxytoluene and nordihydroguaiaretic acid, preservative(s) such as dehydroacetic acid, accidental ingestion inhibitor(s) for children and pets such as chili powder, insect attraction fragrance(s) such as cheese flavor, onion flavor, and peanut oil, or the other ingredient(s) may be added thereto as needed.

In the present invention, examples of the plants include whole plants, foliages, flowers, ears, fruits, tree stems, branches, tree crowns, seeds, vegetative reproduction organs, and seedlings.

A vegetative reproduction organ means a part of plant such as root, stem, and leaf which has a growth capability even when said part is separated from the plant body and placed into soil. Examples of the vegetative reproduction organ include tuberous root, creeping root, bulb, corm or solid bulb, tuber, rhizome, stolon, rhizophore, cane cuttings, propagule, and vine cutting. Stolon is also referred to as "runner", and propagule is also referred to as "propagulum" and categorized into broad bud and bulbil. Vine cutting means a shoot (collective term of leaf and stem) of sweet potato, glutinous yam, or the like. Bulb, corm or solid bulb, tuber, rhizome, cane cuttings, rhizophore, and tuberous root are also collectively referred to as "bulb". For example, cultivation of potato starts with planting a tuber into soil, and the tuber to be used is generally referred to as "seed potato".

Examples of the method for controlling harmful arthropods by applying an effective amount of the Present compound or the Composition A to soil include a method for applying an effective amount of the Present compound or the Composition A to soil before or after planting plants, a method for applying an effective amount of the Present compound or the Composition A to rhizosphere of crops to be protected from harm such as eating by harmful arthropods, and, a method for controlling plant-eating harmful arthropods by impregnating an effective amount of the Present compound or the Composition A from roots or the like and migrating it to inside plant bodies. More specific examples thereof include planting hole treatments (for example, planting hole application and planting hole soil incorporation), plant foot treatments (for example, plant foot application, plant foot soil incorporation, plant foot irrigation, and plant foot treatment at latter half of raising of seedling period), planting trench treatments (for example, planting trench application and planting trench soil incorporation), row treatments (for example, row application, row soil incorporation, and row application at growing season), row treatments at seeding (for example, row application at seeding and row soil incorporation at seeding), overall treatments (for example, overall soil application and overall soil incorporation), side row treatments, water surface treatments (for example, water surface application and water surface application after flooding), other soil application treatments (for example, foliar application of granule at growing season, application under tree crown or around trunk, soil surface application, soil surface incorporation, seeding hole application, ridge area surface application, and intrarow spacing application), other irrigation treatments (for example, soil irrigation, irrigation at raising of seedling period, chemical injection treatment, ground area irrigation, chemical drip irrigation, and chemigation), raising seedling box treatments (for example, raising seedling box application, raising seedling box irrigation, raising seedling box chemical flooding), raising seedling tray treatments (for example, raising seedling tray application, raising seedling tray irrigation, and raising seedling tray chemical flooding), nursery treatments (for example, nursery application, nursery irrigation, flooded nursery application, and seedling soaking), bed soil incorporation treatments (for example, bed soil incorporation, bed soil incorporation before seeding, application at seeding before soil covering, application at seeding after soil covering, and soil covering incorporation), and other treatments (for example, culture soil incorporation, plowing, surface soil incorporation, rain dropping point soil incorporation, planting position treatment, flower cluster application of granule, and paste fertilizer incorporation).

Examples of the seed treatment include application of the Present compound or the Composition A to seeds or vegetative reproduction organs. Specific examples thereof include spray treatment wherein mist of a suspension of the Present compound or the Composition A is sprayed to seed surfaces or vegetative reproduction organ surfaces; smear treatment wherein the Present compound or the Composition A is smeared to seeds or vegetative reproduction organs; immersion treatment wherein seeds are immersed in a drug solution of the Present compound or the Composition A for a period of time; and methods for coating seeds or vegetative reproduction organs by a carrier comprising the Present compound or the Composition A (for example, film coat treatment and pellet coat treatment). Examples of the above vegetative reproduction organ include seed potato.

When the Composition A is applied to seeds or vegetative reproduction organs, a formulation of the Composition A may be applied to seeds or vegetative reproduction organs, or a plurality of different formulations of the Composition A may be applied separately in a plurality of times to seeds or vegetative reproduction organs. Examples of the method for applying a plurality of different formulations of the Composition A separately in a plurality of times include a method wherein a formulation comprising the Present compound only as an active ingredient is applied seeds or vegetative reproduction organs, said seeds or vegetative reproduction organs are air-dried, and a formulation comprising the Present ingredient(s) is applied thereto; and a method wherein a formulation comprising the Present compound and the Present ingredient(s) as active ingredients is applied to seeds or vegetative reproduction organs, said seeds or vegetative reproduction organs are air-dried, and then a formulation comprising the Present ingredient(s) other than the applied Present ingredient(s) is applied.

In the present invention, the seed or the vegetative reproduction organ holding the Present compound or the Composition A means a seed or a vegetative reproduction organ in which the Present compound or the Composition A is attached to the surface of the seed or the vegetative reproduction organ. A material other than the Present compound or the Composition A may be attached to the above seed or vegetative reproduction organ holding the Present compound or the Composition A before or after the Present compound or the Composition A is attached to the seed or the vegetative reproduction organ.

Also, when the Composition A is attached to surfaces of seeds or vegetative reproduction organs to form layer(s), said layer(s) consist(s) of a layer or a plurality of layers. When said layer(s) consist(s) of a plurality of layers, each layer consists of a layer comprising one or more active ingredient(s), or consists of a layer comprising one or more active ingredient(s) and a layer comprising no active ingredient.

The seeds or the vegetative reproduction organs holding the Present compound or the Composition A may be prepared by, for example, applying a formulation comprising the Present compound or the Composition A to seeds or vegetative reproduction organs by the above seed treatment method.

When the Present compound or the Composition A is used for controlling harmful arthropods in the agricultural field, the application dose as an amount of the Present compound is usually within the range from 1 to 10,000 g per 10,000 $m^2$. When the Present compound or the Composition A is applied to seeds or vegetative reproduction organs, the application dose as an amount of the Present compound is usually within the range from 0.001 to 100 g per 1 Kg of the seeds or vegetative reproduction organs. An emulsifiable concentrate, a wettable powder, a flowable, or the like of the Present compound or the Composition A is usually applied by diluting it with water in such a way that a concentration of the active ingredient is within the range from 0.01 to 10,000 ppm. A granule, a dust formulation, or the like is usually applied as itself without diluting it.

Also, a resin formulation of the Present compound or the Composition A processed into a sheet shape or a string shape may be wrapped around crops, stretched near crops, spread on plant foot soil, or the like.

When the Present compound or the Composition A is used to control harmful arthropods that live inside a house, the application dose as an amount of the Present compound is usually within the range from 0.01 to 1,000 mg per 1 $m^2$ of an area to be treated in the case of using it on a planar area. In the case of using it spatially, the application dose as an amount of the Present compound is usually within the range from 0.01 to 500 mg per 1 $m^3$ of the space to be treated. When the Present compound or the Composition A is formulated into an emulsifiable concentrate, a wettable powder, a flowable, or the like, such formulation is usually applied after diluting it with water in such a way that a concentration of the active ingredient is within the range from 0.1 to 10,000 ppm, and then sparging it. In the case of being formulated into an oil solution, an aerosol, a smoking agent, a poison bait, or the like, such formulation is used as itself without diluting it.

When the Present compound or the Composition A is used for controlling external parasites of livestock such as cows, horses, pigs, sheep, goats, and chickens, and small animals such as dogs, cats, rats, and mice, the Present compound or the Composition A may be applied to the animals by a known method in the veterinary field. Examples of the specific method for using the Present compound or the Composition A include administration by a tablet, a mixture with feed, a suppository, or an injection (for example, intramuscular, subcutaneous, intravenous, or intraperitoneal injection) when systemic control is intended, and include spraying of an oil solution or an aqueous liquid, pour-on treatment or spot-on treatment, washing of animals with a shampoo formulation, or application of a resin formulation in the form of a collar, an ear tag, or the like to animals when non-systemic control is intended. In case of administered to animals, the dose of the Present compound is usually within the range from 0.1 to 1,000 mg per 1 kg of animal body weight.

Also, the Present compound or the Composition A may be used as an agent for controlling harmful arthropods in croplands such as fields, paddy fields, grasses, and orchards. Examples of the plants include the followings.

corn, rice, wheat, barley, rye, oat, sorghum, cotton, soybean, peanut, buckwheat, beet, rapeseed, sunflower, sugar cane, tobacco, solanaceous vegetables (for example, eggplant, tomato, pimento, pepper, and potato), cucurbitaceous vegetables (for example, cucumber, pumpkin, zucchini, water melon, and melon), cruciferous vegetables (for example, Japanese radish, white turnip, horseradish, kohlrabi, Chinese cabbage, cabbage, leaf mustard, broccoli, and cauliflower), asteraceous vegetables (for example, burdock, crown daisy, artichoke, and lettuce), liliaceous vegetables (for example, welsh onion, onion, garlic, and asparagus), ammiaceous vegetables (for example, carrot, parsley, celery, and parsnip), chenopodiaceous vegetables (for example, spinach and Swiss chard), lamiaceous vegetables (for example, *perilla*, mint, and basil), strawberry, sweet potato, glutinous yam, eddoe, pomaceous fruits (for example, apple, pear, Japanese pear, Chinese quince, and quince), stone fleshy fruits (for example, peach, plum, nectarine, Japanese apricot (*Prunus mume*), cherry fruit, apricot, and prune), citrus fruits (for example, *Citrus unshiu*, orange, lemon, lime, and grapefruit), nuts (for example, chestnuts, walnuts, hazelnuts, almond, pistachio, cashew nuts, and macadamia nuts), berry fruits (for example, blueberry, cranberry, blackberry, and raspberry), grapes, Japanese persimmon, olive, Japanese plum, banana, coffee, date palm, coconuts, tea, mulberry, ornamental plants, forest plants, turfs, grasses, and the others.

The above plants also include plants which may be produced by natural breeding, plants which may be generated by mutation, F1 hybrid plants, and genetically modified crops. Examples of the genetically modified crops include plants which have resistance to HPPD (4-hydroxyphenylpyruvate dioxygenase enzyme) inhibitors such as isoxaflutole, ALS (acetolactate synthase) inhibitors such as imazethapyr and thifensulfuron-methyl, EPSP (5-enolpyruvylshikimate-3-phosphate synthase) inhibitors, glutamine synthetase inhibitors, PPO (protoporphyrinogen oxidase) inhibitors, or herbicide such as bromoxynil and dicamba; plants which can synthesize a selective toxin known in *Bacillus* such as *Bacillus thuringiensis* or the like; and plants which can synthesize a gene fragment or the like which is partially identical to an endogenous gene derived from a harmful insect, and induce a gene silencing (RNAi; RNA interference) in the target harmful insect to achieve a specific insecticidal activity.

The above plants are not specifically limited as long as they are generally cultivated cultivars.

EXAMPLES

Hereinafter, the present invention is illustrated more in detail by Preparation Examples, Formulation Examples, Test Examples, and the like, but the present invention is not limited to these Examples only.

In the present description, Me represents a methyl group, Et represents an ethyl group, Pr represents a propyl group, i-Pr represents an isopropyl group, c-Pr represents a cyclopropyl group, c-Bu represents a cyclobutyl group, c-Pen represents a cyclopentyl group, c-Hex represents a cyclohexyl group, Ph represents a phenyl group, Py2 represents a 2-pyridyl group, Py3 represents a 3-pyridyl group, Py4 represents a 4-pyridyl group, and Bn represents a benzyl group. When c-Pr, c-Bu, c-Pen, c-Hex, Ph, Py2, Py3, and Py4 have substituent(s), the substituent(s) is/are indicated before the symbols with the substitution position(s). For example, 1-CN-c-Pr represents a 1-cyanocyclopropyl group, 3,4-F2-Ph represents a 3,4-difluorophenyl group, 4-CF$_3$—Py2 represents a 4-(trifluoromethyl)-2-pyridyl group, and 5-OCH$_2$CF$_2$CF$_3$-Py2 represents a 5-(2,2,3,3,3-pentafluoropropoxy)-2-pyridyl group.

First, Preparation Examples of the Present compounds are shown below.

When a physical property of a compound is measured by liquid chromatography/mass spectrometry (hereinafter referred to as "LCMS"), the measured molecular ion value [M+H]$^+$ or [M−H]$^−$, and retention time (hereinafter referred to as "RT") are described. The conditions of liquid chromatography (hereinafter referred to as "LC") are as follows.

[Lc Conditions]
Column: L-column2 ODS, inner diameter: 4.6 mm, length: 30 mm, particle size: 3 μm (Chemicals Evaluation and Research Institute, Japan)
UV measurement wavelength: 254 nm
Mobile phase: Solution A: 0.1% formic acid in water, Solution B: 0.1% formic acid in acetonitrile
Flow rate: 2.0 mL/min
Pump: two LC-20AD (manufactured by Shimadzu Corporation) (high pressure gradient)
Gradient conditions: sending a solution with the concentration gradient described in Table LC1.

TABLE LC1

| Time (min) | Solution A (%) | Solution B (%) |
|---|---|---|
| 0.01 | 90 | 10 |
| 2.00 | 0 | 100 |
| 4.00 | 0 | 100 |
| 4.01 | 90 | 10 |

[Ms Conditions]
Detector: LCMS-2020 (manufactured by Shimadzu Corporation) Ionization method: DUIS Reference Preparation Example 1

To a mixture of chloroacetic acid (9.49 g) and water (15 mL) was added triethylamine (16.7 mL) at 0° C. over 30 minutes. To the resulting mixture was added 2-amino-5-(trifluoromethyl)pyridine (16.1 g), and the resulting mixture was stirred under reflux for 2 hours. The resulting mixture was filtered, and the filtered residue was washed with water. The resulting solids were dried to give a crude product of the Intermediate compound 1 represented by the following formula (11.0 g).

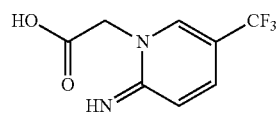

Intermediate compound 1: LCMS: 219 [M−H]$^−$, RT=0.42 min

Reference Preparation Example 2

A mixture of the crude product of the Intermediate compound 1 obtained in the Reference Preparation Example 1 (4.40 g), phosphorus oxybromide (22.37 g), and toluene (50 mL) was stirred under reflux for 5 hours. The resulting mixture was added dropwise to an aqueous solution of sodium hydroxide, and the resulting mixture was subjected to extraction with toluene. The resulting organic layer was dried over anhydrous sodium sulfate, and concentrated under reduced pressure to give the Intermediate compound 2 represented by the following formula (4.7 g).

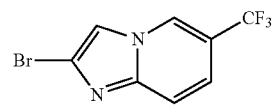

Intermediate compound 2: $^1$H-NMR (CDCl$_3$) δ: 8.45 (1H, d), 7.69 (1H, s), 7.67 (1H, dd), 7.36 (1H, d).

Reference Preparation Example 3

A mixture of the Intermediate compound 2 (2.39 g), 6-(trifluoromethyl)-1,2,4-triazolo[4,3-a]pyridin-3(2H)-one (1.83 g), pyridine-2-carboxylic acid (885 mg), copper(I) iodide (1.35 g), cesium carbonate (4.39 g), and NMP (30 mL) was stirred at 120° C. for 8 hours. To the resulting mixture was added water, and the resulting mixture was subjected to extraction with chloroform. The resulting organic layer was dried over anhydrous sodium sulfate, and concentrated under reduced pressure. The resulting residue was subjected to silica gel column chromatography to give a crude product of the Intermediate compound 3 represented by the following formula (comprising 85% of the Intermediate compound 2) (590 mg).

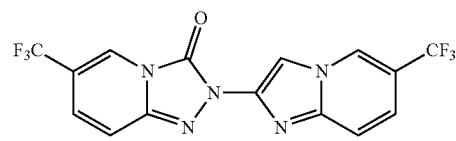 [SMILES: O=c1n(-c2cn3cc(C(F)(F)F)ccc3n2)nc2ccc(C(F)(F)F)cn12]

Intermediate compound 3: LCMS: 388 [M+H]$^+$, RT=1.84 min

Reference Preparation Example 4

To a mixture of the crude product of the Intermediate compound 3 prepared in the Reference Preparation Example 3 (comprising 85% of the Intermediate compound 2) (590 mg) and DMF (5 mL) was added N-iodosuccinimide (360 mg) under ice-cooling, and the resulting mixture was stirred at room temperature for 3 hours. To the resulting mixture was added an aqueous solution of sodium thiosulfate, and the resulting mixture was subjected to extraction with chloroform. The resulting organic layer was dried over anhydrous sodium sulfate, and concentrated under reduced pressure. The resulting residue was subjected to silica gel column chromatography to give the Intermediate compound 4 represented by the following formula (118 mg).

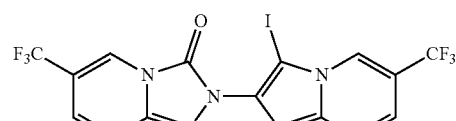

Intermediate compound 4: $^1$H-NMR (CDCl$_3$) δ: 8.59 (1H, s), 8.26 (1H, d), 7.78 (1H, d), 7.51 (1H, d), 7.30 (1H, s), 7.28 (1H, d).

Reference Preparation Example 5

The compounds prepared according to the Reference Preparation Example 1 and physical properties thereof are shown below.

A compound represented by formula (B-1):

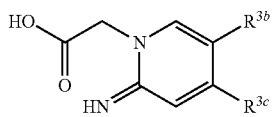

(B-1)

wherein the combination of R$^{3b}$ and R$^{3c}$ represents any one combination indicated in Table B-1.

TABLE B-1

| Intermediate compound | R$^{3b}$ | R$^{3c}$ |
|---|---|---|
| 5 | Br | H |
| 6 | Cl | H |
| 7 | H | CF$_3$ |
| 49 | H | Br |
| 50 | H | Cl |

Intermediate compound 5: LCMS: 229 [M−H]$^−$, RT=0.34 min

Intermediate compound 6: LCMS: 187 [M+H]$^+$, RT=0.34 min

Intermediate compound 7: LCMS: 219 [M−H]$^−$, RT=1.10 min

Intermediate compound 49: LCMS: 231 [M+H]$^+$, RT=0.40 min

Intermediate compound 50: LCMS: 187 [M+H]$^+$, RT=0.35 min

Reference Preparation Example 6

A mixture of the crude product of the Intermediate compound 1 prepared according to the Reference Preparation Example 1 (13.21 g), phosphorus oxychloride (18 mL), and toluene (150 mL) was stirred under reflux for 6 hours. The resulting mixture was added dropwise to an aqueous solution of sodium hydroxide, and the resulting mixture was subjected to extraction with toluene. The resulting organic layer was dried over anhydrous sodium sulfate, and concentrated under reduced pressure to give the Intermediate compound 8 represented by the following formula (13.2 g).

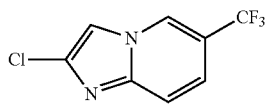

Intermediate compound 8: $^1$H-NMR (CDCl$_3$) δ: 8.44 (1H, s), 7.65 (1H, d), 7.62 (1H, s), 7.38 (1H, d).

Reference Preparation Example 7

The compounds prepared according to the Reference Preparation Example 6 and physical properties thereof are shown below.

A compound represented by formula (B-2):

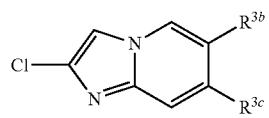

(B-2)

wherein the combination of R$^{3b}$ and R$^{3c}$ represents any one combination indicated in Table B-2.

TABLE B-2

| Intermediate compound | R$^{3b}$ | R$^{3c}$ |
|---|---|---|
| 9 | Br | H |
| 10 | Cl | H |
| 11 | H | CF$_3$ |
| 12 | H | Br |
| 13 | H | Cl |

Intermediate compound 9: $^1$H-NMR (CDCl$_3$) δ: 8.21 (1H, s), 7.48 (1H, s), 7.44 (1H, d), 7.28 (1H, d).

Intermediate compound 10: $^1$H-NMR (CDCl$_3$) δ: 8.11 (1H, s), 7.48-7.50 (2H, m), 7.19 (1H, d).

Intermediate compound 11: $^1$H-NMR (CDCl$_3$) δ: 8.17 (1H, d), 7.86 (1H, s), 7.64 (1H, s), 7.04 (1H, d).

Intermediate compound 12: $^1$H-NMR (CDCl$_3$) δ: 7.91 (1H, d), 7.72 (1H, s), 7.51 (1H, s), 6.96 (1H, d).

Intermediate compound 13: $^1$H-NMR (CDCl$_3$) δ: 7.97 (1H, d), 7.54 (1H, s), 7.49 (1H, s), 6.85 (1H, d).

Reference Preparation Example 8

To a mixture of the Intermediate compound 8 (15.44 g) prepared according to the Reference Preparation Example 6 and DMF (75 mL) was added N-iodosuccinimide (17.32 g) under ice-cooling, and the resulting mixture was stirred at 70° C. for 5 hours. To the resulting mixture was added an aqueous solution of sodium thiosulfate, and the precipitated solids were collected by filtration. The resulting solids were washed with water, and dried under reduced pressure to give the Intermediate compound 14 represented by the following formula (18.0 g).

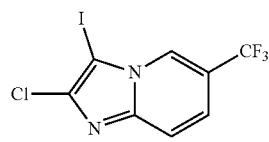 [SMILES: FC(F)(F)c1ccc2nc(Cl)c(I)n2c1]

Intermediate compound 14: $^1$H-NMR (CDCl$_3$) δ: 8.41 (1H, s), 7.65 (1H, d), 7.44 (1H, d).

Reference Preparation Example 9

The compounds prepared according to the Reference Preparation Example 8 and physical properties thereof are shown below.

A compound represented by formula (B-3):

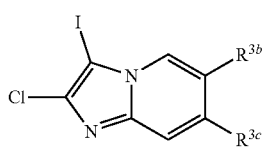

wherein the combination of $R^{3b}$ and $R^{3c}$ represents any one combination indicated in Table B-3.

TABLE B-3

| Intermediate compound | $R^{3b}$ | $R^{3c}$ |
|---|---|---|
| 15 | Br | H |
| 16 | Cl | H |
| 17 | H | CF$_3$ |
| 18 | H | Br |
| 19 | H | Cl |

Intermediate compound 15: $^1$H-NMR (CDCl$_3$) δ: 8.20 (1H, s), 7.43 (1H, d), 7.35 (1H, d).

Intermediate compound 16: $^1$H-NMR (CDCl$_3$) δ: 8.46 (1H, s), 7.64 (1H, d), 7.47 (1H, d).

Intermediate compound 17: $^1$H-NMR (CDCl$_3$) δ: 8.18 (1H, d), 7.84 (1H, s), 7.15 (1H, d).

Intermediate compound 18: $^1$H-NMR (CDCl$_3$) δ: 7.93 (1H, d), 7.72 (1H, s), 7.06 (1H, d).

Intermediate compound 19: $^1$H-NMR (CDCl$_3$) δ: 7.98 (1H, d), 7.55 (1H, s), 6.96 (1H, d).

Reference Preparation Example 10

A mixture of the Intermediate compound 14 (18.0 g), 1,4-dioxane (140 mL), tris(dibenzylideneacetone)dipalladium(0) (2.38 g), Xantphos (3.01 g), diisopropylethylamine (27.2 mL), and ethanethiol (3.75 mL) was stirred under reflux for 3 hours. The resulting mixture was cooled to room temperature, and concentrated under reduced pressure. The resulting residue was subjected to silica gel column chromatography to give the Intermediate compound 20 represented by the following formula (13.39 g).

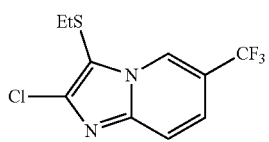

Intermediate compound 20: $^1$H-NMR (CDCl$_3$) δ: 8.74 (1H, s), 7.67 (1H, d), 7.48 (1H, d), 2.78 (2H, d), 1.24 (3H, t).

Reference Preparation Example 11

The compounds prepared according to the Reference Preparation Example 10 and physical properties thereof are shown below.

A compound represented by formula (B-4):

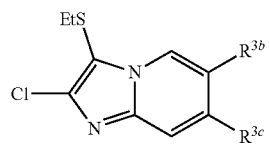

wherein the combination of $R^{3b}$ and $R^{3c}$ represents any one combination indicated in Table B-4.

TABLE B-4

| Intermediate compound | $R^{3b}$ | $R^{3c}$ |
|---|---|---|
| 21 | Br | H |
| 22 | Cl | H |
| 23 | H | CF$_3$ |
| 24 | H | Br |
| 25 | H | Cl |

Intermediate compound 21: $^1$H-NMR (CDCl$_3$) δ: 8.51 (1H, s), 7.46 (1H, d), 7.38 (1H, d), 2.73 (2H, d), 1.23 (3H, t).

Intermediate compound 22: $^1$H-NMR (CDCl$_3$) δ: 0.42 (1H, s), 7.51 (1H, d), 7.28 (1H, d), 2.75 (2H, d), 1.23 (3H, t).

Intermediate compound 23: LCMS: 281 [M+H]$^+$, RT=2.11 min

Intermediate compound 24: $^1$H-NMR (CDCl$_3$) δ: 8.25 (1H, d), 7.74 (1H, s), 7.07 (1H, d), 2.73 (2H, q), 1.21 (3H, t).

Intermediate compound 25: $^1$H-NMR (CDCl$_3$) δ: 8.31 (1H, d), 7.57 (1H, s), 6.96 (1H, d), 2.73 (2H, q), 1.21 (3H, t).

Reference Preparation Example 12

To a mixture of the Intermediate compound 21 (2.66 g) and chloroform (10 mL) was added mCPBA (purity: 70%, comprising 30% of water) (5.16 g) under ice-cooling, and the resulting mixture was stirred at room temperature for 2 hours. To the resulting mixture were sequentially added a saturated aqueous solution of sodium hydrogen carbonate and an aqueous solution of sodium thiosulfate, and the resulting mixture was subjected to extraction with chloroform. The resulting organic layer was dried over anhydrous sodium sulfate, and concentrated under reduced pressure. The resulting residue was subjected to silica gel column chromatography to give the Intermediate compound 26 represented by the following formula (1.79 g).

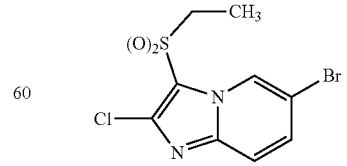

Intermediate compound 26: $^1$H-NMR (CDCl$_3$) δ: 9.15 (1H, s), 7.60 (1H, d), 7.57 (1H, d), 3.36 (2H, q), 1.36 (3H, t).

Reference Preparation Example 13

The compounds prepared according to the Reference Preparation Example 12 and physical properties thereof are shown below.

A compound represented by formula (B-5):

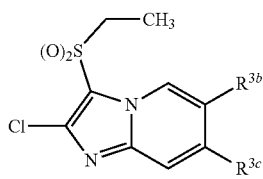

(B-5)

wherein the combination of $R^{3b}$ and $R^{3c}$ represents any one combination indicated in Table B-5.

TABLE B-5

| Intermediate compound | $R^{3b}$ | $R^{3c}$ |
|---|---|---|
| 27 | CF$_3$ | H |
| 28 | Cl | H |
| 29 | H | CF$_3$ |
| 30 | H | Br |
| 31 | H | Cl |

Intermediate compound 27: $^1$H-NMR (CDCl$_3$) δ: 9.39 (1H, s), 7.81 (1H, d), 7.67 (1H, d), 3.39 (2H, q), 1.37 (3H, t).

Intermediate compound 28: $^1$H-NMR (CDCl$_3$) δ: 9.07 (1H, s), 7.63 (1H, d), 7.49 (1H, d), 3.37 (2H, q), 1.36 (3H, t).

Intermediate compound 29: $^1$H-NMR (CDCl$_3$) δ: 9.16 (1H, d), 7.98 (1H, s), 7.27 (1H, d), 3.38 (2H, q), 1.35 (3H, t).

Intermediate compound 30: $^1$H-NMR (CDCl$_3$) δ: 8.87 (1H, d), 7.86 (1H, s), 7.20 (1H, d), 3.34 (2H, q), 1.33 (3H, t).

Intermediate compound 31: $^1$H-NMR (CDCl$_3$) δ: 8.93 (1H, d), 7.68 (1H, s), 7.08 (1H, d), 3.34 (2H, q), 1.33 (3H, t).

Reference Preparation Example 14

A mixture of the Intermediate compound 26 (324 mg), trans-N,N'-dimethylcyclohexane-1,2-diamine (0.32 mL), sodium iodide (225 mg), copper(I) iodide (190 mg), and toluene (4 mL) was stirred at 120° C. for 21 hours. The resulting mixture was cooled to room temperature, and then filtered. To the resulting filtrate was added water, and the resulting mixture was subjected to extraction with chloroform twice. The resulting organic layer was dried over anhydrous sodium sulfate, and concentrated under reduced pressure. The resulting residue was subjected to silica gel chromatography to give the Intermediate compound 32 represented by the following formula (70 mg).

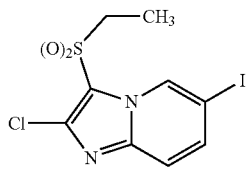

Intermediate compound 32: $^1$H-NMR (CDCl$_3$) δ: 9.23 (1H, s), 7.70 (1H, d), 7.46 (1H, d), 3.35 (2H, q), 1.35 (3H, t).

Reference Preparation Example 15

The Intermediate compound 27 (936 mg), cesium fluoride (4.56 g), and DMSO (10 mL) were stirred at 95° C. The resulting mixture was cooled to room temperature, then ethyl acetate and water were sequentially added thereto, and the resulting mixture was filtered. The resulting filtrate was separated, the resulting organic layer was dried over anhydrous sodium sulfate, and concentrated under reduced pressure. The resulting residue was subjected to silica gel column chromatography to give a crude product of the Intermediate compound 33 represented by the following formula (comprising 22% of the Intermediate compound 27) (330 mg).

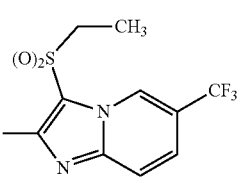

Intermediate compound 33: LCMS: 297 [M+H]$^+$, RT=1.76 min

Reference Preparation Example 16

The compounds prepared according to the Reference Preparation Example 15 and physical properties thereof are shown below.

A compound represented by formula (B-6):

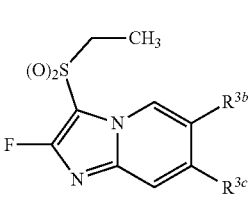

(B-6)

wherein the combination of $R^{3b}$ and $R^{3c}$ represents any one combination indicated in Table B-6.

TABLE B-6

| Intermediate compound | $R^{3b}$ | $R^{3c}$ |
|---|---|---|
| 34 | Br | H |
| 35 | Cl | H |
| 36 | H | CF$_3$ |
| 37 | H | Br |
| 38 | I | H |

Intermediate compound 34: LCMS: 307 [M+H]$^+$, RT=1.64 min

Intermediate compound 35: LCMS: 263 [M+H]$^+$, RT=1.61 min

Intermediate compound 36: LCMS: 297 [M+H]$^+$, RT=1.78 min

Intermediate compound 37: LCMS: 307 [M+H]+, RT=1.69 min

Intermediate compound 38: LCMS: 355 [M+H]+, RT=1.72 min

Reference Preparation Example 17

A mixture of the Intermediate compound 8 (60 g), sodium iodide (165 g), 57% hydroiodic acid (307 mL), and acetonitrile (600 mL) was stirred under reflux for 22 hours. Acetonitrile was distilled away under reduced pressure from the resulting mixture, and the precipitated solids were collected by filtration. The resulting solids were sequentially washed with water, a 10% aqueous solution of sodium hydroxide, and water. The resulting solids were dried to give the Intermediate compound 39 represented by the following formula (40 g).

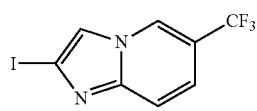 [SMILES: FC(F)(F)c1ccc2nc(I)cn2c1]

Intermediate compound 39: $^1$H-NMR (CDCl$_3$) δ: 8.46 (1H, s), 7.79 (1H, s), 7.68 (1H, d), 7.33 (1H, d).

Reference Preparation Example 18

The compound prepared according to the Reference Preparation Example 17 and a physical property thereof are shown below.

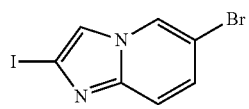

Intermediate compound 40: $^1$H-NMR (CDCl$_3$) δ: 8.23 (1H, dd), 7.64 (1H, s), 7.47 (1H, d), 7.24 (1H, dd).

Reference Preparation Example 19

To a mixture of 2-hydrazinyl-5-(trifluoromethyl)pyridine (3.1 g) and THF (20 mL) was added 1,1'-carbonyldiimidazole (4.2 g) at 0° C., and the resulting mixture was stirred at room temperature for 3 hours. To the resulting mixture was added water, and the resulting mixture was subjected to extraction with ethyl acetate. The resulting organic layer was dried over anhydrous sodium sulfate, and concentrated under reduced pressure. The resulting residue was subjected to silica gel chromatography to give the Intermediate compound 41 represented by the following formula (2.5 g).

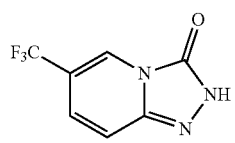

Intermediate compound 41: $^1$H-NMR (CDCl$_3$) δ: 10.55 (1H, s), 8.21 (1H, s), 7.27 (1H, d), 7.20 (1H, dd).

Reference Preparation Example 20

The compounds prepared according to the Reference Preparation Example 19 and physical properties thereof are shown below.

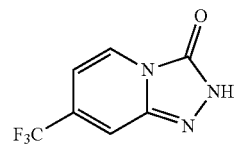

Intermediate compound 42: $^1$H-NMR (CDCl$_3$) δ: 9.83 (1H, s), 7.89 (1H, d), 7.48 (1H, d), 6.62 (1H, dd).

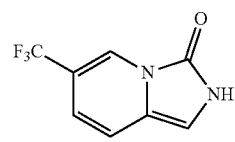

Intermediate compound 43: $^1$H-NMR (CDCl$_3$) δ: 11.12 (1H, s), 7.95 (1H, s), 6.96 (1H, d), 6.55 (1H, s), 6.47 (1H, dd).

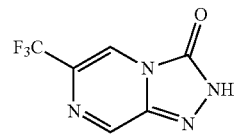

Intermediate compound 44: $^1$H-NMR (DMSO-d$_6$) δ: 8.99 (1H, s), 8.45 (1H, s).

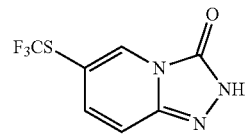

Intermediate compound 45: $^1$H-NMR (CDCl$_3$) δ: 9.27 (1H, s), 8.15 (1H, s), 7.21 (1H, d), 7.15 (1H, d).

Reference Preparation Example 21

To a mixture of methyl 2-chloro-5-(trifluoromethyl)pyridine-3-carboxylate (8.34 g) and ethanol (70 mL) was added dropwise methylhydrazine (5.5 mL) at 0° C., and the resulting mixture was stirred at room temperature for 30 minutes. The resulting mixture was concentrated under reduced pressure, then to the resulting residue was added 2N hydrochloric acid, and the resulting mixture was subjected to extraction with ethyl acetate. The resulting organic layer was dried over anhydrous sodium sulfate, and concentrated under reduced pressure. The resulting residue was subjected to silica gel chromatography to give the Intermediate compound 46 represented by the following formula (8.16 g).

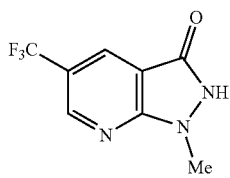 [SMILES: Cn1[nH]c(=O)c2cc(C(F)(F)F)cnc21]

Intermediate compound 46: ¹H-NMR (DMSO-d₆) δ: 8.75 (1H, s), 8.56 (1H, s), 3.85 (3H, s).

Reference Preparation Example 22

A mixture of the Intermediate compound 39 (2.18 g), the Intermediate compound 46 (1.52 g), pyridine-2-carboxylic acid (345 mg), copper(I) iodide (533 g), cesium carbonate (3.58 g), and NMP (20 mL) was stirred at 120° C. for 8 hours. To the resulting mixture was added water, and the resulting mixture was subjected to extraction with ethyl acetate. The resulting organic layer was dried over anhydrous sodium sulfate, and concentrated under reduced pressure. The resulting residue was subjected to silica gel column chromatography to give the Intermediate compound 47 represented by the following formula (70 mg).

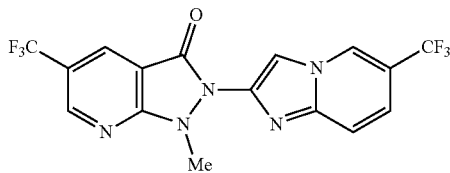

Intermediate compound 47: ¹H-NMR (CDCl₃) δ: 8.90 (1H, s), 8.57 (1H, s), 8.48 (1H, s), 8.35 (1H, s), 7.74 (1H, d), 7.43 (1H, d), 3.92 (3H, s).

Reference Preparation Example 23

The compound prepared according to the Reference Preparation Example 4 and a physical property thereof are shown below.

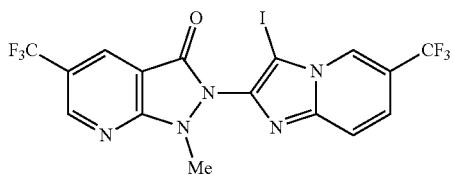 [SMILES: Cn1c2ncc(C(F)(F)F)cc2c(=O)n1-c1nc2ccc(C(F)(F)F)cn2c1I]

Intermediate compound 48: ¹H-NMR (CDCl₃) δ: 8.89 (1H, s), 8.59 (1H, s), 8.49 (1H, s), 7.75 (1H, d), 7.53 (1H, d), 3.55 (3H, s).

Preparation Example 1

A mixture of the Intermediate compound 4 (118 mg), 1,4-dioxane (1 mL), tris(dibenzylideneacetone)dipalladium (0) (21 mg), Xantphos (27 mg), diisopropylethylamine (0.060 mL), and ethanethiol (0.050 mL) was stirred under reflux for 3 hours. To the resulting mixture was added water, and the resulting mixture was subjected to extraction with chloroform. The resulting organic layer was dried over anhydrous sodium sulfate, and concentrated under reduced pressure. The resulting residue was subjected to silica gel column chromatography (chloroform:methanol=96:4) to give the Present compound 1 represented by the following formula (71 mg).

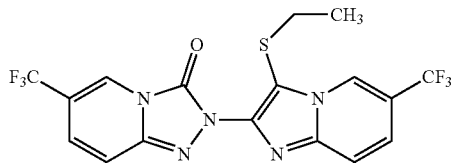 [SMILES: CCSc1c(-n2nc3ccc(C(F)(F)F)cn3c2=O)nc2ccc(C(F)(F)F)cn12]

Present compound 1: ¹H-NMR (DMSO-d₆) δ: 9.02 (1H, s), 8.49 (1H, d), 7.97 (1H, d), 7.81 (1H, d), 7.52 (2H, m), 2.88 (2H, q), 1.06 (3H, t).

Preparation Example 2

To a mixture of the Present compound 1 (71 mg) and chloroform (3 mL) was added mCPBA (purity: 70%, comprising 30% of water) (154 mg) under ice-cooling, and the resulting mixture was stirred at room temperature for 4 hours. To the resulting mixture were sequentially added a saturated aqueous solution of sodium hydrogen carbonate and an aqueous solution of sodium thiosulfate, and the resulting mixture was subjected to extraction with chloroform. The resulting organic layer was dried over anhydrous sodium sulfate, and concentrated under reduced pressure to give the Present compound 2 represented by the following formula (70 mg).

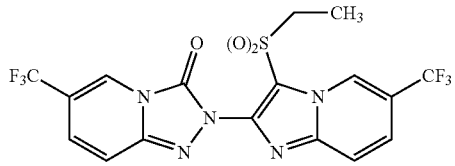

Present compound 2: ¹H-NMR (DMSO-d₆) δ: 9.18 (1H, s), 8.54 (1H, d), 8.15 (1H, d), 8.04 (1H, d), 7.55 (2H, m), 3.87 (2H, q), 1.32 (3H, t).

Preparation Example 3

The compound prepared according to the Preparation Example 1 and a physical property thereof are shown below.

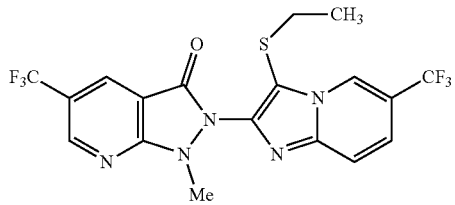 [SMILES: CCSc1c(-n2c(=O)c3cc(C(F)(F)F)cnc3n2C)nc2ccc(C(F)(F)F)cn12]

Present compound 3: ¹H-NMR (CDCl₃) δ: 8.89-8.88 (2H, m), 8.48 (1H, d), 7.78 (1H, d), 7.56 (1H, d), 3.54 (3H, s), 2.95 (2H, q), 1.26 (3H, t).

Preparation Example 4

The compound prepared according to the Preparation Example 2 and a physical property thereof are shown below.

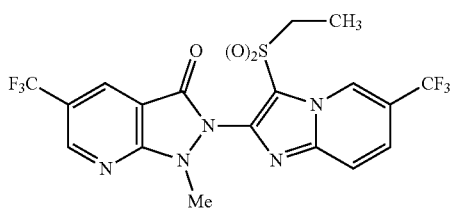

Present compound 4: ¹H-NMR (DMSO-d₆) δ: 9.39 (1H, s), 9.05 (1H, s), 8.58 (1H, s), 8.07 (1H, d), 7.97 (1H, d), 3.92 (2H, t), 3.59 (3H, s), 1.45 (3H, t).

Preparation Example 5

To a mixture of the Intermediate compound 41 (180 mg), the Intermediate compound 34 (comprising 30% of the Intermediate compound 26) (392 mg), and DMF (2 mL) was added sodium hydride (oil, 60%) (72 mg) at room temperature, and the resulting mixture was stirred at 70° C. for 2 hours. To the resulting mixture was added water, and the resulting mixture was subjected to extraction with ethyl acetate. The resulting organic layer was dried over anhydrous sodium sulfate, and concentrated under reduced pressure. The resulting residue was subjected to silica gel chromatography (ethyl acetate:hexane=40:60) to give the Present compound 5 represented by the following formula (147 mg).

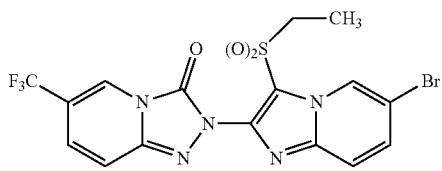

Present compound 5: ¹H-NMR (DMSO-d₆) δ: 8.98 (1H, s), 8.53 (1H, s), 7.94-7.92 (2H, m), 7.54-7.53 (2H, m), 3.79 (2H, q), 1.30 (3H, t).

Preparation Example 6

A mixture of the Intermediate compound 43 (69 mg), the Intermediate compound 34 (comprising 30% of the Intermediate compound 26) (150 mg), DMF (2 mL), and cesium carbonate (166 mg) was stirred at 70° C. for 2 hours. To the resulting mixture was added water, and the resulting mixture was subjected to extraction with ethyl acetate. The resulting organic layer was dried over anhydrous sodium sulfate, and concentrated under reduced pressure. The resulting residue was subjected to silica gel chromatography (ethyl acetate: hexane=40:60) to give the Present compound 6 represented by the following formula (49 mg).

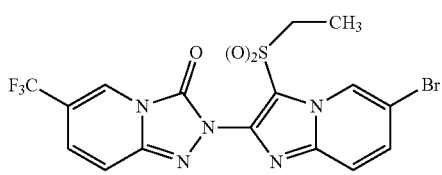

Present compound 6: ¹H-NMR (CDCl₃) δ: 9.03 (1H, s), 7.93 (1H, s), 7.63-7.62 (2H, m), 6.94 (1H, d), 6.86 (1H, s), 6.51 (1H, d), 3.85 (2H, q), 1.50 (3H, d).

Preparation Example 7

The compounds prepared according to the Preparation Example 6 and physical properties thereof are shown below.
A compound represented by formula (A-1):

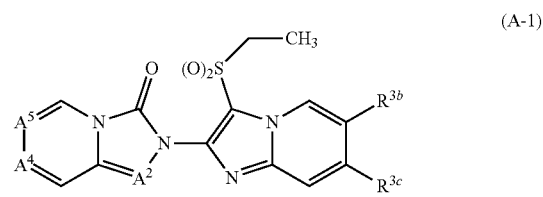

wherein the combination of $A^2$, A4, A5, $R^{3b}$, and $R^{3c}$ represents any one combination indicated in Table A-1.

TABLE A-1

| Present compound | $A^2$ | $A^4$ | $A^5$ | $R^{3b}$ | $R^{3c}$ |
|---|---|---|---|---|---|
| 7 | N | CCF₃ | CH | CF₃ | H |
| 8 | N | CH | CCF₃ | H | CF₃ |
| 9 | N | N | CCF₃ | Br | H |
| 10 | N | CH | CCF₃ | Cl | H |
| 11 | N | CH | CCF₃ | H | Br |
| 12 | N | CH | CSCF₃ | Cl | H |

Present compound 7: ¹H-NMR (CDCl₃) δ: 9.30 (1H, s), 7.94-7.89 (2H, m), 7.71 (1H, d), 7.49 (1H, s), 6.66 (1H, d), 3.83 (2H, q), 1.50 (3H, t).

Present compound 8: ¹H-NMR (DMSO-d₆) δ: 9.08 (1H, d), 8.54-8.51 (2H, m), 7.66 (1H, d), 7.55 (2H, m), 3.78 (2H, q), 1.31 (3H, t).

Present compound 9: ¹H-NMR (CDCl₃) δ: 9.05 (1H, s), 8.87 (1H, s), 8.14 (1H, s), 7.71 (1H, d), 7.68 (1H, d), 3.73 (2H, q), 1.51 (3H, t).

Present compound 10: ¹H-NMR (CDCl₃) δ: 8.97 (1H, s), 8.20 (1H, d), 7.76 (1H, d), 7.53 (1H, d), 7.27 (1H, s), 7.25 (1H, d), 3.78 (2H, q), 1.49 (3H, t).

Present compound 11: ¹H-NMR (DMSO-d₆) δ: 8.80 (1H, d), 8.52 (1H, s), 8.33 (1H, d), 7.57 (1H, d), 7.54-7.53 (2H, m), 3.73 (2H, q), 1.28 (3H, t).

Present compound 12: ¹H-NMR (DMSO-d₆) δ: 8.92 (1H, s), 8.54 (1H, s), 7.99 (1H, d), 7.86 (1H, d), 7.45-7.45 (2H, m), 3.77 (2H, q), 1.30 (3H, t).

Preparation Example 8

A mixture of the Present compound 5 (490 mg), bis (pinacolato)diboron (508 mg), potassium acetate (294 mg), 1,1'-bis(diphenylphosphino)ferrocene (37 mg), and toluene (10 mL) was stirred at 110° C. for 3 hours. To the resulting mixture was added water, and the resulting mixture was subjected to extraction with ethyl acetate. The resulting organic layer was dried over anhydrous sodium sulfate, and concentrated under reduced pressure. To the resulting mixture were added sodium acetate (615 mg), water (5 mL), and THF (5 mL). To the resulting mixture was added 30% hydrogen peroxide water (0.22 mL) at 0° C., and the resulting mixture was stirred at room temperature for 5 hours. To the resulting mixture was added an aqueous solution of sodium thiosulfate, and the resulting mixture was subjected to extraction with chloroform. The resulting organic layer was dried over anhydrous sodium sulfate, and concentrated under reduced pressure to give a crude product of the Present compound 13 represented by the following formula (500 mg).

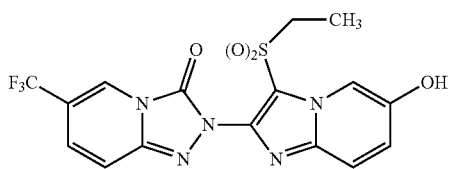

Present compound 13: LCMS: 426 [M−H]⁻, RT=1.54 min

Preparation Example 9

A mixture of the crude product of the Present compound 13 obtained in the Preparation Example 8 (500 mg), cesium carbonate (391 mg), DMF (4 mL), and iodoethane (0.100 mL) was stirred at room temperature for 6 hours. To the resulting mixture was added water, and the resulting mixture was subjected to extraction with chloroform. The resulting organic layer was dried over anhydrous sodium sulfate, and concentrated under reduced pressure. The resulting residue was subjected to silica gel chromatography (ethyl acetate: hexane=40:60) to give the Present compound 14 represented by the following formula (209 mg).

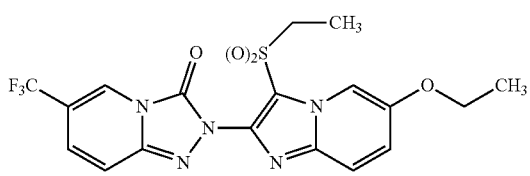

Present compound 14: $^1$H-NMR (DMSO-d$_6$) δ: 8.51 (1H, s), 8.33 (1H, d), 7.87 (1H, d), 7.58 (1H, d), 7.53-7.52 (2H, m), 4.15 (2H, q), 3.70 (2H, q), 1.41 (3H, t), 1.27 (3H, t).

Preparation Example 10

A mixture of the Present compound 5 (490 mg), 2-isopropenyl-4,4,5,5-tetramethyl-1,3,2-dioxaborolane (252 mg), tripotassium phosphate (637 mg), 1,1'-bis(diphenylphosphino)ferrocene (29 mg), 1,2-dimethoxyethane (8 mL), and water (0.8 mL) was stirred at 80° C. for 4 hours. To the resulting mixture was added water, and the resulting mixture was subjected to extraction with ethyl acetate. The resulting organic layer was dried over anhydrous sodium sulfate, and concentrated under reduced pressure. The resulting residue was subjected to silica gel chromatography (ethyl acetate hexane=63:37) to give the Present compound 15 represented by the following formula (150 mg).

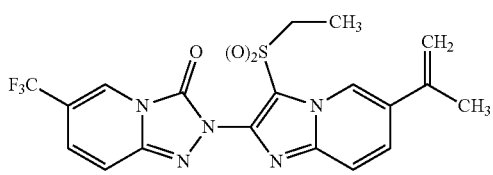

Present compound 15: $^1$H-NMR (CDCl$_3$) δ: 8.91 (1H, s), 8.20 (1H, d), 7.74-7.73 (2H, m), 7.27 (1H, s), 7.25 (1H, d), 5.52 (1H, s), 5.30 (1H, s), 3.77 (2H, q), 2.22 (3H, s), 1.49 (3H, t).

Preparation Example 11

The compounds prepared according to the Preparation Example 10 and physical properties thereof are shown below. A compound represented by formula (A-2):

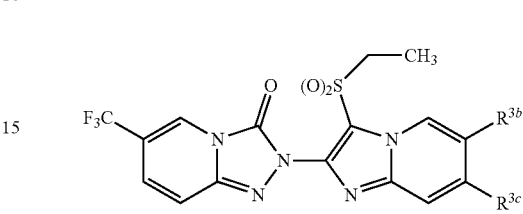

wherein the combination of R$^{3b}$ and R$^{3c}$ represents any one combination indicated in Table A-2.

TABLE A-2

| Present compound | R$^{3b}$ | R$^{3c}$ |
|---|---|---|
| 16 | c-Pr | H |
| 17 | 4-F—Ph | H |

Present compound 16: $^1$H-NMR (DMSO-d$_6$) δ: 8.67 (1H, s), 8.52 (1H, s), 7.83 (1H, d), 7.53-7.52 (2H, m), 7.43 (1H, d), 3.71 (2H, t), 2.21-2.17 (1H, m), 1.28 (3H, t), 1.06-1.04 (2H, m), 0.82-0.81 (2H, m).
Present compound 17: $^1$H-NMR (CDCl$_3$) δ: 9.03 (1H, s), 8.21 (1H, s), 7.86 (1H, d), 7.76 (1H, d), 7.58-7.55 (2H, m), 7.28 (1H, s), 7.25-7.20 (3H, m), 3.80 (2H, q), 1.51 (3H, t).

Preparation Example 12

A mixture of the Present compound 5 (490 mg), formic acid (0.057 mL), triethylamine (0.23 mL), tetrakis(triphenylphosphine)palladium(0) (116 mg), and N,N-dimethylacetamide (10 mL) was stirred at 100° C. for 3 hours. To the resulting mixture was added water, and the resulting mixture was subjected to extraction with ethyl acetate. The resulting organic layer was dried over anhydrous sodium sulfate, and concentrated under reduced pressure. The resulting residue was subjected to silica gel chromatography (ethyl acetate: hexane=71:29) to give the Present compound 18 represented by the following formula (390 mg).

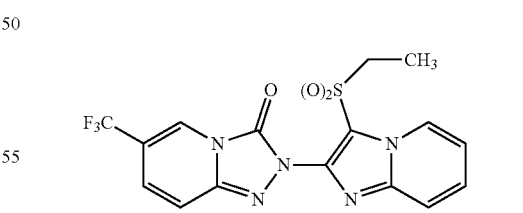

Present compound 18: $^1$H-NMR (CDCl$_3$) δ: 8.93 (1H, d), 8.20 (1H, s), 7.81 (1H, d), 7.58-7.56 (1H, m), 7.28-7.27 (1H, m), 7.25-7.23 (1H, m), 7.17-7.15 (1H, m), 3.77 (2H, q), 1.49 (3H, t).

Preparation Example 13

The Present compound 19 represented by the following formula was prepared according to the Reference Preparation Example 14 by using the Present compound 5 instead of the Intermediate compound 26.

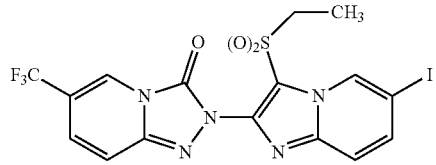

Present compound 19: $^1$H-NMR (CDCl$_3$) δ: 9.15 (1H, s), 8.19 (1H, s), 7.75 (1H, d), 7.58 (1H, d), 7.27 (1H, s), 7.25 (1H, s), 3.78 (2H, q), 1.50 (3H, t).

Next, examples of the Present compound prepared according to any one of the Preparation Examples described in the EXAMPLES and the Production methods described in the present description are shown below. Here, Q11 to Q30 represent the following groups.

Q11
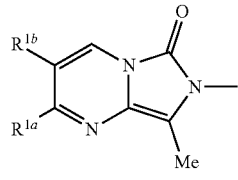

Q12
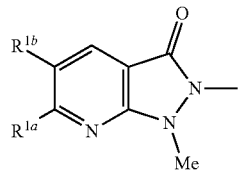

Q13
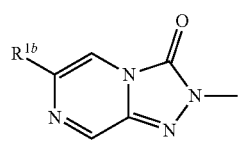

Q14
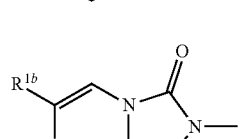

Q15
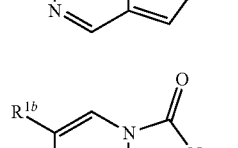

Q16
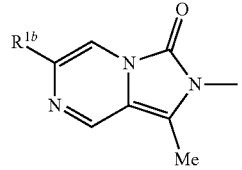

Q17

Q18

Q19

Q20
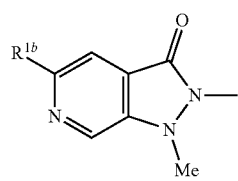

Q21
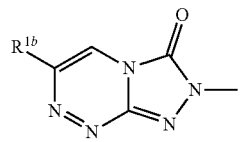

Q22
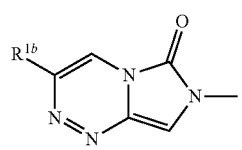

Q23

Q24

Q25
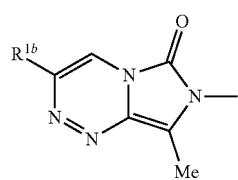

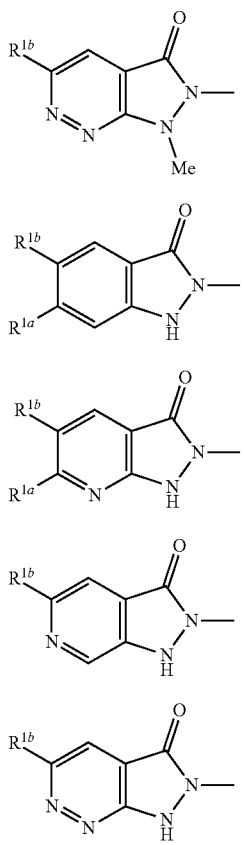

A compound represented by formula (L-1):

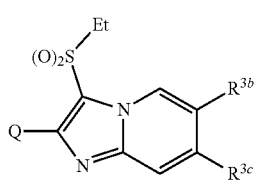

(hereinafter referred to as "Compound (L-1)"), wherein Q represents the group represented by Q11; $R^{1a}$ represents a hydrogen atom; $R^{1b}$ represents any one substituent described in Table 1A or Table 2A; $R^{3b}$ represents a hydrogen atom; and $R^{3c}$ represents a hydrogen atom (hereinafter referred to as "Compound group SX1").

TABLE 1A

| |
|---|
| $CF_3$ |
| $CHF_2$ |
| $CH_2CF_3$ |
| $CF_2CF_3$ |
| $CH_2CF_2CF_3$ |
| $CF_2CF_2CF_3$ |
| $CF_2CF_2CF_2CF_3$ |
| $CF_2CF_2CF_2CF_2CF_3$ |
| $C(CF_3)_3$ |
| $C(CH_3)_2CN$ |
| $OCF_3$ |
| $OCHF_2$ |
| $OCH_2CF_3$ |
| $OCH_2CHF_2$ |

TABLE 1A-continued

| |
|---|
| $OCF_2CF_3$ |
| $OCH(CH_3)CF_3$ |
| $OCH_2CF_2CHF_2$ |
| $OCH_2CF_2CF_3$ |
| $OCF_2CF_2CF_3$ |
| $OCH_2CF_2CHFCF_3$ |
| $OCH_2CF_2CF_2CF_3$ |
| $OCF_2CF_2CF_2CF_3$ |
| $OCH_2CF_2CF_2CF_2CF_3$ |
| $OS(O)_2CF_3$ |
| $OS(O)_2CF_2CF_3$ |
| $OS(O)_2CF_2CF_2CF_3$ |

TABLE 2A

| |
|---|
| $SCF_3$ |
| $SCH_2CF_3$ |
| $SCF_2CF_3$ |
| $SCH_2CF_2CF_3$ |
| $SCF_2CF_2CF_3$ |
| $SCH_2CF_2CF_2CF_3$ |
| $SCF_2CF_2CF_2CF_3$ |
| $S(O)CF_3$ |
| $S(O)CH_2CF_3$ |
| $S(O)CF_2CF_3$ |
| $S(O)CH_2CF_2CF_3$ |
| $S(O)CF_2CF_2CF_3$ |
| $S(O)CH_2CF_2CF_2CF_3$ |
| $S(O)CF_2CF_2CF_2CF_3$ |
| $S(O)_2CF_3$ |
| $S(O)_2CH_2CF_3$ |
| $S(O)_2CF_2CF_3$ |
| $S(O)_2CH_2CF_2CF_3$ |
| $S(O)_2CF_2CF_2CF_3$ |
| $S(O)_2CH_2CF_2CF_2CF_3$ |
| $S(O)_2CF_2CF_2CF_2CF_3$ |
| c-Pr |
| 1-CN—c-Pr |
| 2-CN—c-Pr |
| 1-CN—c-Bu |
| $CF(CF_3)_2$ |

The Compound (L-1), wherein Q represents the group represented by Q11; $R^{1a}$ represents any one substituent described in Table 1A or Table 2A; $R^{1b}$ represents a hydrogen atom; $R^{3b}$ represents a hydrogen atom; and $R^{3c}$ represents a hydrogen atom (hereinafter referred to as "Compound group SX2").

The Compound (L-1), wherein Q represents the group represented by Q12; $R^{1a}$ represents a hydrogen atom; $R^{1b}$ represents any one substituent described in Table 1A or Table 2A; $R^{3b}$ represents a hydrogen atom; and $R^{3c}$ represents a hydrogen atom (hereinafter referred to as "Compound group SX3").

The Compound (L-1), wherein Q represents the group represented by Q12; $R^{1a}$ represents any one substituent described in Table 1A or Table 2A; $R^{1b}$ represents a hydrogen atom; $R^{3b}$ represents a hydrogen atom; and $R^{3c}$ represents a hydrogen atom (hereinafter referred to as "Compound group SX4").

The Compound (L-1), wherein Q represents the group represented by Q13; $R^{1a}$ represents a hydrogen atom; $R^{1b}$ represents any one substituent described in Table 1A or Table 2A; $R^{3b}$ represents a hydrogen atom; and $R^{3c}$ represents a hydrogen atom (hereinafter referred to as "Compound group SX5").

The Compound (L-1), wherein Q represents the group represented by Q13; $R^{1a}$ represents any one substituent described in Table 1A or Table 2A; $R^{1b}$ represents a hydrogen atom; $R^{3b}$ represents a hydrogen atom; and $R^{3c}$ represents a hydrogen atom (hereinafter referred to as "Compound group SX6").

The Compound (L-1), wherein Q represents the group represented by Q14; $R^{1a}$ represents a hydrogen atom; $R^{1b}$ represents any one substituent described in Table 1A or Table 2A; $R^{3b}$ represents a hydrogen atom; and $R^{3c}$ represents a hydrogen atom (hereinafter referred to as "Compound group SX7").

The Compound (L-1), wherein Q represents the group represented by Q14; $R^{1a}$ represents any one substituent described in Table 1A or Table 2A; $R^{1b}$ represents a hydrogen atom; $R^{3b}$ represents a hydrogen atom; and $R^{3c}$ represents a hydrogen atom (hereinafter referred to as "Compound group SX8").

The Compound (L-1), wherein Q represents the group represented by Q15; $R^{1a}$ represents a hydrogen atom; $R^{1b}$ represents any one substituent described in Table 1A or Table 2A; $R^{3b}$ represents a hydrogen atom; and $R^{3c}$ represents a hydrogen atom (hereinafter referred to as "Compound group SX9").

The Compound (L-1), wherein Q represents the group represented by Q15; $R^{1a}$ represents any one substituent described in Table 1A or Table 2A; $R^{1b}$ represents a hydrogen atom; $R^{3b}$ represents a hydrogen atom; and $R^{3c}$ represents a hydrogen atom (hereinafter referred to as "Compound group SX10").

The Compound (L-1), wherein Q represents the group represented by Q16; $R^{1a}$ represents a hydrogen atom; $R^{1b}$ represents any one substituent described in Table 1A or Table 2A; $R^{3b}$ represents a hydrogen atom; and $R^{3c}$ represents a hydrogen atom (hereinafter referred to as "Compound group SX11").

The Compound (L-1), wherein Q represents the group represented by Q16; $R^{1a}$ represents any one substituent described in Table 1A or Table 2A; $R^{1b}$ represents a hydrogen atom; $R^{3b}$ represents a hydrogen atom; and $R^{3c}$ represents a hydrogen atom (hereinafter referred to as "Compound group SX12").

The Compound (L-1), wherein Q represents the group represented by Q17; $R^{1a}$ represents a hydrogen atom; $R^{1b}$ represents any one substituent described in Table 1A or Table 2A; $R^{3b}$ represents a hydrogen atom; and $R^{3c}$ represents a hydrogen atom (hereinafter referred to as "Compound group SX13").

The Compound (L-1), wherein Q represents the group represented by Q17; $R^{1a}$ represents any one substituent described in Table 1A or Table 2A; $R^{1b}$ represents a hydrogen atom; $R^{3b}$ represents a hydrogen atom; and $R^{3c}$ represents a hydrogen atom (hereinafter referred to as "Compound group SX14").

The Compound (L-1), wherein Q represents the group represented by Q18; $R^{1a}$ represents a hydrogen atom; $R^{1b}$ represents any one substituent described in Table 1A or Table 2A; $R^{3b}$ represents a hydrogen atom; and $R^{3c}$ represents a hydrogen atom (hereinafter referred to as "Compound group SX15").

The Compound (L-1), wherein Q represents the group represented by Q18; $R^{1a}$ represents any one substituent described in Table 1A or Table 2A; $R^{1b}$ represents a hydrogen atom; $R^{3b}$ represents a hydrogen atom; and $R^{3c}$ represents a hydrogen atom (hereinafter referred to as "Compound group SX16").

The Compound (L-1), wherein Q represents the group represented by Q19; $R^{1b}$ represents any one substituent described in Table 1A or Table 2A; $R^{3b}$ represents a hydrogen atom; and $R^{3c}$ represents a hydrogen atom (hereinafter referred to as "Compound group SX17").

The Compound (L-1), wherein Q represents the group represented by Q20; $R^{1b}$ represents any one substituent described in Table 1A or Table 2A; $R^{3b}$ represents a hydrogen atom; and $R^{3c}$ represents a hydrogen atom (hereinafter referred to as "Compound group SX18").

The Compound (L-1), wherein Q represents the group represented by Q21; $R^{1b}$ represents any one substituent described in Table 1A or Table 2A; $R^{3b}$ represents a hydrogen atom; and $R^{3c}$ represents a hydrogen atom (hereinafter referred to as "Compound group SX19").

The Compound (L-1), wherein Q represents the group represented by Q22; $R^{1b}$ represents any one substituent described in Table 1A or Table 2A; $R^{3b}$ represents a hydrogen atom; and $R^{3c}$ represents a hydrogen atom (hereinafter referred to as "Compound group SX20").

The Compound (L-1), wherein Q represents the group represented by Q23; $R^{1b}$ represents any one substituent described in Table 1A or Table 2A; $R^{3b}$ represents a hydrogen atom; and $R^{3c}$ represents a hydrogen atom (hereinafter referred to as "Compound group SX21").

The Compound (L-1), wherein Q represents the group represented by Q24; $R^{1b}$ represents any one substituent described in Table 1A or Table 2A; $R^{3b}$ represents a hydrogen atom; and $R^{3c}$ represents a hydrogen atom (hereinafter referred to as "Compound group SX22").

The Compound (L-1), wherein Q represents the group represented by Q25; $R^{1b}$ represents any one substituent described in Table 1A or Table 2A; $R^{3b}$ represents a hydrogen atom; and $R^{3c}$ represents a hydrogen atom (hereinafter referred to as "Compound group SX23").

The Compound (L-1), wherein Q represents the group represented by Q26; $R^{1b}$ represents any one substituent described in Table 1A or Table 2A; $R^{3b}$ represents a hydrogen atom; and $R^{3c}$ represents a hydrogen atom (hereinafter referred to as "Compound group SX24").

The Compound (L-1), wherein Q represents the group represented by Q27; $R^{1a}$ represents a hydrogen atom; $R^{1b}$ represents any one substituent described in Table 1A or Table 2A; $R^{3b}$ represents a hydrogen atom; and $R^{3c}$ represents a hydrogen atom (hereinafter referred to as "Compound group SX25").

The Compound (L-1), wherein Q represents the group represented by Q27; $R^{1a}$ represents any one substituent described in Table 1A or Table 2A; $R^{1b}$ represents a hydrogen atom; $R^{3b}$ represents a hydrogen atom; and $R^{3c}$ represents a hydrogen atom (hereinafter referred to as "Compound group SX26").

The Compound (L-1), wherein Q represents the group represented by Q28; $R^{1a}$ represents a hydrogen atom; $R^{1b}$ represents any one substituent described in Table 1A or Table 2A; $R^{3b}$ represents a hydrogen atom; and $R^{3c}$ represents a hydrogen atom (hereinafter referred to as "Compound group SX27").

The Compound (L-1), wherein Q represents the group represented by Q28; $R^{1a}$ represents any one substituent described in Table 1A or Table 2A; $R^{1b}$ represents a hydrogen atom; $R^{3b}$ represents a hydrogen atom; and $R^{3c}$ represents a hydrogen atom (hereinafter referred to as "Compound group SX28").

The Compound (L-1), wherein Q represents the group represented by Q29; $R^{1b}$ represents any one substituent described in Table 1A or Table 2A; $R^{3b}$ represents a hydrogen atom; and $R^{3c}$ represents a hydrogen atom (hereinafter referred to as "Compound group SX29").

The Compound (L-1), wherein Q represents the group represented by Q30; $R^{1b}$ represents any one substituent described in Table 1A or Table 2A; $R^{3b}$ represents a hydrogen atom; and $R^{3c}$ represents a hydrogen atom (hereinafter referred to as "Compound group SX30").

The Compound (L-1), wherein Q represents the group represented by Q11; $R^{1a}$ represents a hydrogen atom; $R^{1b}$ represents any one substituent described in Table 1A or Table 2A; $R^{3b}$ represents a trifluoromethyl group; and $R^{3c}$ represents a hydrogen atom (hereinafter referred to as "Compound group SX31").

The Compound (L-1), wherein Q represents the group represented by Q11; $R^{1a}$ represents any one substituent described in Table 1A or Table 2A; $R^{1b}$ represents a hydrogen atom; $R^{3b}$ represents a trifluoromethyl group; and $R^{3c}$ represents a hydrogen atom (hereinafter referred to as "Compound group SX32").

The Compound (L-1), wherein Q represents the group represented by Q12; $R^{1a}$ represents a hydrogen atom; $R^{1b}$ represents any one substituent described in Table 1A or Table 2A; $R^{3b}$ represents a trifluoromethyl group; and $R^{3c}$ represents a hydrogen atom (hereinafter referred to as "Compound group SX33").

The Compound (L-1), wherein Q represents the group represented by Q12; $R^{1a}$ represents any one substituent described in Table 1A or Table 2A; $R^{1b}$ represents a hydrogen atom; $R^{3b}$ represents a trifluoromethyl group; and $R^{3c}$ represents a hydrogen atom (hereinafter referred to as "Compound group SX34").

The Compound (L-1), wherein Q represents the group represented by Q13; $R^{1a}$ represents a hydrogen atom; $R^{1b}$ represents any one substituent described in Table 1A or Table 2A; $R^{3b}$ represents a trifluoromethyl group; and $R^{3c}$ represents a hydrogen atom (hereinafter referred to as "Compound group SX35").

The Compound (L-1), wherein Q represents the group represented by Q13; $R^{1a}$ represents any one substituent described in Table 1A or Table 2A; $R^{1b}$ represents a hydrogen atom; $R^{3b}$ represents a trifluoromethyl group; and $R^{3c}$ represents a hydrogen atom (hereinafter referred to as "Compound group SX36").

The Compound (L-1), wherein Q represents the group represented by Q14; $R^{1a}$ represents a hydrogen atom; $R^{1b}$ represents any one substituent described in Table 1A or Table 2A; $R^{3b}$ represents a trifluoromethyl group; and $R^{3c}$ represents a hydrogen atom (hereinafter referred to as "Compound group SX37").

The Compound (L-1), wherein Q represents the group represented by Q14; $R^{1a}$ represents any one substituent described in Table 1A or Table 2A; $R^{1b}$ represents a hydrogen atom; $R^{3b}$ represents a trifluoromethyl group; and $R^{3c}$ represents a hydrogen atom (hereinafter referred to as "Compound group SX38").

The Compound (L-1), wherein Q represents the group represented by Q15; $R^{1a}$ represents a hydrogen atom; $R^{1b}$ represents any one substituent described in Table 1A or Table 2A; $R^{3b}$ represents a trifluoromethyl group; and $R^{3G}$ represents a hydrogen atom (hereinafter referred to as "Compound group SX39").

The Compound (L-1), wherein Q represents the group represented by Q15; $R^{1a}$ represents any one substituent described in Table 1A or Table 2A; $R^{1b}$ represents a hydrogen atom; $R^{3b}$ represents a trifluoromethyl group; and $R^{3c}$ represents a hydrogen atom (hereinafter referred to as "Compound group SX40").

The Compound (L-1), wherein Q represents the group represented by Q16; $R^{1a}$ represents a hydrogen atom; $R^{1b}$ represents any one substituent described in Table 1A or Table 2A; $R^{3b}$ represents a trifluoromethyl group; and $R^{3c}$ represents a hydrogen atom (hereinafter referred to as "Compound group SX41").

The Compound (L-1), wherein Q represents the group represented by Q16; $R^{1a}$ represents any one substituent described in Table 1A or Table 2A; $R^{1b}$ represents a hydrogen atom; $R^{3b}$ represents a trifluoromethyl group; and $R^{3c}$ represents a hydrogen atom (hereinafter referred to as "Compound group SX42").

The Compound (L-1), wherein Q represents the group represented by Q17; $R^{1a}$ represents a hydrogen atom; $R^{1b}$ represents any one substituent described in Table 1A or Table 2A; $R^{3b}$ represents a trifluoromethyl group; and $R^{3c}$ represents a hydrogen atom (hereinafter referred to as "Compound group SX43").

The Compound (L-1), wherein Q represents the group represented by Q17; $R^{1a}$ represents any one substituent described in Table 1A or Table 2A; $R^{1b}$ represents a hydrogen atom; $R^{3b}$ represents a trifluoromethyl group; and $R^{3c}$ represents a hydrogen atom (hereinafter referred to as "Compound group SX44").

The Compound (L-1), wherein Q represents the group represented by Q18; $R^{1a}$ represents a hydrogen atom; $R^{1b}$ represents any one substituent described in Table 1A or Table 2A; $R^{3b}$ represents a trifluoromethyl group; and $R^{3c}$ represents a hydrogen atom (hereinafter referred to as "Compound group SX45").

The Compound (L-1), wherein Q represents the group represented by Q18; $R^{1a}$ represents any one substituent described in Table 1A or Table 2A; $R^{1b}$ represents a hydrogen atom; $R^{3b}$ represents a trifluoromethyl group; and $R^{3c}$ represents a hydrogen atom (hereinafter referred to as "Compound group SX46").

The Compound (L-1), wherein Q represents the group represented by Q19; $R^{1b}$ represents any one substituent described in Table 1A or Table 2A; $R^{3b}$ represents a trifluoromethyl group; and $R^{3c}$ represents a hydrogen atom (hereinafter referred to as "Compound group SX47").

The Compound (L-1), wherein Q represents the group represented by Q20; $R^{1b}$ represents any one substituent described in Table 1A or Table 2A; $R^{3b}$ represents a trifluoromethyl group; and $R^{3c}$ represents a hydrogen atom (hereinafter referred to as "Compound group SX48").

The Compound (L-1), wherein Q represents the group represented by Q21; $R^{1b}$ represents any one substituent described in Table 1A or Table 2A; $R^{3b}$ represents a trifluoromethyl group; and $R^{3c}$ represents a hydrogen atom (hereinafter referred to as "Compound group SX49").

The Compound (L-1), wherein Q represents the group represented by Q22; $R^{1b}$ represents any one substituent described in Table 1A or Table 2A; $R^{3b}$ represents a trifluoromethyl group; and $R^{3c}$ represents a hydrogen atom (hereinafter referred to as "Compound group SX50").

The Compound (L-1), wherein Q represents the group represented by Q23; $R^{1b}$ represents any one substituent described in Table 1A or Table 2A; $R^{3b}$ represents a trifluoromethyl group; and $R^{3c}$ represents a hydrogen atom (hereinafter referred to as "Compound group SX51").

The Compound (L-1), wherein Q represents the group represented by Q24; $R^{1b}$ represents any one substituent described in Table 1A or Table 2A; $R^{3b}$ represents a trifluoromethyl group; and $R^{3c}$ represents a hydrogen atom (hereinafter referred to as "Compound group SX52").

The Compound (L-1), wherein Q represents the group represented by Q25; $R^{1b}$ represents any one substituent described in Table 1A or Table 2A; $R^{3b}$ represents a trifluoromethyl group; and $R^{3c}$ represents a hydrogen atom (hereinafter referred to as "Compound group SX53").

The Compound (L-1), wherein Q represents the group represented by Q26; $R^{1b}$ represents any one substituent described in Table 1A or Table 2A; $R^{3b}$ represents a trifluoromethyl group; and $R^{3c}$ represents a hydrogen atom (hereinafter referred to as "Compound group SX54").

The Compound (L-1), wherein Q represents the group represented by Q27; $R^{1a}$ represents a hydrogen atom; $R^{1b}$ represents any one substituent described in Table 1A or Table 2A; $R^{3b}$ represents a trifluoromethyl group; and $R^{3c}$ represents a hydrogen atom (hereinafter referred to as "Compound group SX55").

The Compound (L-1), wherein Q represents the group represented by Q27; $R^{1a}$ represents any one substituent described in Table 1A or Table 2A; $R^{1b}$ represents a hydrogen atom; $R^{3b}$ represents a trifluoromethyl group; and $R^{3c}$ represents a hydrogen atom (hereinafter referred to as "Compound group SX56").

The Compound (L-1), wherein Q represents the group represented by Q28; $R^{1a}$ represents a hydrogen atom; $R^{1b}$ represents any one substituent described in Table 1A or Table 2A; $R^{3b}$ represents a trifluoromethyl group; and $R^{3G}$ represents a hydrogen atom (hereinafter referred to as "Compound group SX57").

The Compound (L-1), wherein Q represents the group represented by Q28; $R^{1a}$ represents any one substituent described in Table 1A or Table 2A; $R^{1b}$ represents a hydrogen atom; $R^{3b}$ represents a trifluoromethyl group; and $R^{3c}$ represents a hydrogen atom (hereinafter referred to as "Compound group SX58").

The Compound (L-1), wherein Q represents the group represented by Q29; $R^{1b}$ represents any one substituent described in Table 1A or Table 2A; $R^{3b}$ represents a trifluoromethyl group; and $R^{3c}$ represents a hydrogen atom (hereinafter referred to as "Compound group SX59").

The Compound (L-1), wherein Q represents the group represented by Q30; $R^{1b}$ represents any one substituent described in Table 1A or Table 2A; $R^{3b}$ represents a trifluoromethyl group; and $R^{3c}$ represents a hydrogen atom (hereinafter referred to as "Compound group SX60").

The Compound (L-1), wherein Q represents the group represented by Q11; $R^{1a}$ represents a hydrogen atom; $R^{1b}$ represents any one substituent described in Table 1A or Table 2A; $R^{3b}$ represents a chlorine atom; and $R^{3c}$ represents a hydrogen atom (hereinafter referred to as "Compound group SX61").

The Compound (L-1), wherein Q represents the group represented by Q11; $R^{1a}$ represents any one substituent described in Table 1A or Table 2A; $R^{1b}$ represents a hydrogen atom; $R^{3b}$ represents a chlorine atom; and $R^{3c}$ represents a hydrogen atom (hereinafter referred to as "Compound group SX62").

The Compound (L-1), wherein Q represents the group represented by Q12; $R^{1a}$ represents a hydrogen atom; $R^{1b}$ represents any one substituent described in Table 1A or Table 2A; $R^{3b}$ represents a chlorine atom; and $R^{3c}$ represents a hydrogen atom (hereinafter referred to as "Compound group SX63").

The Compound (L-1), wherein Q represents the group represented by Q12; $R^{1a}$ represents any one substituent described in Table 1A or Table 2A; $R^{1b}$ represents a hydrogen atom; $R^{3b}$ represents a chlorine atom; and $R^{3c}$ represents a hydrogen atom (hereinafter referred to as "Compound group SX64").

The Compound (L-1), wherein Q represents the group represented by Q13; $R^{1a}$ represents a hydrogen atom; $R^{1b}$ represents any one substituent described in Table 1A or Table 2A; $R^{3b}$ represents a chlorine atom; and $R^{3c}$ represents a hydrogen atom (hereinafter referred to as "Compound group SX65").

The Compound (L-1), wherein Q represents the group represented by Q13; $R^{1a}$ represents any one substituent described in Table 1A or Table 2A; $R^{1b}$ represents a hydrogen atom; $R^{3b}$ represents a chlorine atom; and $R^{3c}$ represents a hydrogen atom (hereinafter referred to as "Compound group SX66").

The Compound (L-1), wherein Q represents the group represented by Q14; $R^{1a}$ represents a hydrogen atom; $R^{1b}$ represents any one substituent described in Table 1A or Table 2A; $R^{3b}$ represents a chlorine atom; and $R^{3c}$ represents a hydrogen atom (hereinafter referred to as "Compound group SX67").

The Compound (L-1), wherein Q represents the group represented by Q14; $R^{1a}$ represents any one substituent described in Table 1A or Table 2A; $R^{1b}$ represents a hydrogen atom; $R^{3b}$ represents a chlorine atom; and $R^{3c}$ represents a hydrogen atom (hereinafter referred to as "Compound group SX68").

The Compound (L-1), wherein Q represents the group represented by Q15; $R^{1a}$ represents a hydrogen atom; $R^{1b}$ represents any one substituent described in Table 1A or Table 2A; $R^{3b}$ represents a chlorine atom; and $R^{3c}$ represents a hydrogen atom (hereinafter referred to as "Compound group SX69").

The Compound (L-1), wherein Q represents the group represented by Q15; $R^{1a}$ represents any one substituent described in Table 1A or Table 2A; $R^{1b}$ represents a hydrogen atom; $R^{3b}$ represents a chlorine atom; and $R^{3c}$ represents a hydrogen atom (hereinafter referred to as "Compound group SX70").

The Compound (L-1), wherein Q represents the group represented by Q16; $R^{1a}$ represents a hydrogen atom; $R^{1b}$ represents any one substituent described in Table 1A or Table 2A; $R^{3b}$ represents a chlorine atom; and $R^{3c}$ represents a hydrogen atom (hereinafter referred to as "Compound group SX71").

The Compound (L-1), wherein Q represents the group represented by Q16; $R^{1a}$ represents any one substituent described in Table 1A or Table 2A; $R^{1b}$ represents a hydrogen atom; $R^{3b}$ represents a chlorine atom; and $R^{3c}$ represents a hydrogen atom (hereinafter referred to as "Compound group SX72").

The Compound (L-1), wherein Q represents the group represented by Q17; $R^{1a}$ represents a hydrogen atom; $R^{1b}$ represents any one substituent described in Table 1A or Table 2A; $R^{3b}$ represents a chlorine atom; and $R^{3c}$ represents a hydrogen atom (hereinafter referred to as "Compound group SX73").

The Compound (L-1), wherein Q represents the group represented by Q17; $R^{1a}$ represents any one substituent described in Table 1A or Table 2A; $R^{1b}$ represents a hydrogen atom; $R^{3b}$ represents a chlorine atom; and $R^{3c}$ represents a hydrogen atom (hereinafter referred to as "Compound group SX74").

The Compound (L-1), wherein Q represents the group represented by Q18; $R^{1a}$ represents a hydrogen atom; $R^{1b}$ represents any one substituent described in Table 1A or Table 2A; $R^{3b}$ represents a chlorine atom; and $R^{3c}$ represents a hydrogen atom (hereinafter referred to as "Compound group SX75").

The Compound (L-1), wherein Q represents the group represented by Q18; $R^{1a}$ represents any one substituent described in Table 1A or Table 2A; $R^{1b}$ represents a hydrogen atom; $R^{3b}$ represents a chlorine atom; and $R^{3c}$ represents a hydrogen atom (hereinafter referred to as "Compound group SX76").

The Compound (L-1), wherein Q represents the group represented by Q19; $R^{1b}$ represents any one substituent described in Table 1A or Table 2A; $R^{3b}$ represents a chlorine atom; and $R^{3c}$ represents a hydrogen atom (hereinafter referred to as "Compound group SX77").

The Compound (L-1), wherein Q represents the group represented by Q20; $R^{1b}$ represents any one substituent described in Table 1A or Table 2A; $R^{3b}$ represents a chlorine atom; and $R^{3c}$ represents a hydrogen atom (hereinafter referred to as "Compound group SX78").

The Compound (L-1), wherein Q represents the group represented by Q21; $R^{1b}$ represents any one substituent described in Table 1A or Table 2A; $R^{3b}$ represents a chlorine atom; and $R^{3c}$ represents a hydrogen atom (hereinafter referred to as "Compound group SX79").

The Compound (L-1), wherein Q represents the group represented by Q22; $R^{1b}$ represents any one substituent described in Table 1A or Table 2A; $R^{3b}$ represents a chlorine atom; and $R^{3c}$ represents a hydrogen atom (hereinafter referred to as "Compound group SX80").

The Compound (L-1), wherein Q represents the group represented by Q23; $R^{1b}$ represents any one substituent described in Table 1A or Table 2A; $R^{3b}$ represents a chlorine atom; and $R^{3c}$ represents a hydrogen atom (hereinafter referred to as "Compound group SX81").

The Compound (L-1), wherein Q represents the group represented by Q24; $R^{1b}$ represents any one substituent described in Table 1A or Table 2A; $R^{3b}$ represents a chlorine atom; and $R^{3c}$ represents a hydrogen atom (hereinafter referred to as "Compound group SX82").

The Compound (L-1), wherein Q represents the group represented by Q25; $R^{1b}$ represents any one substituent described in Table 1A or Table 2A; $R^{3b}$ represents a chlorine atom; and $R^{3c}$ represents a hydrogen atom (hereinafter referred to as "Compound group SX83").

The Compound (L-1), wherein Q represents the group represented by Q26; $R^{1b}$ represents any one substituent described in Table 1A or Table 2A; $R^{3b}$ represents a chlorine atom; and $R^{3c}$ represents a hydrogen atom (hereinafter referred to as "Compound group SX84").

The Compound (L-1), wherein Q represents the group represented by Q27; $R^{1a}$ represents a hydrogen atom; $R^{1b}$ represents any one substituent described in Table 1A or Table 2A; $R^{3b}$ represents a chlorine atom; and $R^{3c}$ represents a hydrogen atom (hereinafter referred to as "Compound group SX85").

The Compound (L-1), wherein Q represents the group represented by Q27; $R^{1a}$ represents any one substituent described in Table 1A or Table 2A; $R^{1b}$ represents a hydrogen atom; $R^{3b}$ represents a chlorine atom; and $R^{3c}$ represents a hydrogen atom (hereinafter referred to as "Compound group SX86").

The Compound (L-1), wherein Q represents the group represented by Q28; $R^{1a}$ represents a hydrogen atom; $R^{1b}$ represents any one substituent described in Table 1A or Table 2A; $R^{3b}$ represents a chlorine atom; and $R^{3c}$ represents a hydrogen atom (hereinafter referred to as "Compound group SX87").

The Compound (L-1), wherein Q represents the group represented by Q28; $R^{1a}$ represents any one substituent described in Table 1A or Table 2A; $R^{1b}$ represents a hydrogen atom; $R^{3b}$ represents a chlorine atom; and $R^{3c}$ represents a hydrogen atom (hereinafter referred to as "Compound group SX88").

The Compound (L-1), wherein Q represents the group represented by Q29; $R^{1b}$ represents any one substituent described in Table 1A or Table 2A; $R^{3b}$ represents a chlorine atom; and $R^{3c}$ represents a hydrogen atom (hereinafter referred to as "Compound group SX89").

The Compound (L-1), wherein Q represents the group represented by Q30; $R^{1b}$ represents any one substituent described in Table 1A or Table 2A; $R^{3b}$ represents a chlorine atom; and $R^{3c}$ represents a hydrogen atom (hereinafter referred to as "Compound group SX90").

The Compound (L-1), wherein Q represents the group represented by Q11; $R^{1a}$ represents a hydrogen atom; $R^{1b}$ represents any one substituent described in Table 1A or Table 2A; $R^{3b}$ represents a bromine atom; and $R^{3c}$ represents a hydrogen atom (hereinafter referred to as "Compound group SX91").

The Compound (L-1), wherein Q represents the group represented by Q11; $R^{1a}$ represents any one substituent described in Table 1A or Table 2A; $R^{1b}$ represents a hydrogen atom; $R^{3b}$ represents a bromine atom; and $R^{3c}$ represents a hydrogen atom (hereinafter referred to as "Compound group SX92").

The Compound (L-1), wherein Q represents the group represented by Q12; $R^{1a}$ represents a hydrogen atom; $R^{1b}$ represents any one substituent described in Table 1A or Table 2A; $R^{3b}$ represents a bromine atom; and $R^{3c}$ represents a hydrogen atom (hereinafter referred to as "Compound group SX93").

The Compound (L-1), wherein Q represents the group represented by Q12; $R^{1a}$ represents any one substituent described in Table 1A or Table 2A; $R^{1b}$ represents a hydrogen atom; $R^{3b}$ represents a bromine atom; and $R^{3c}$ represents a hydrogen atom (hereinafter referred to as "Compound group SX94").

The Compound (L-1), wherein Q represents the group represented by Q13; $R^{1a}$ represents a hydrogen atom; $R^{1b}$ represents any one substituent described in Table 1A or Table 2A; $R^{3b}$ represents a bromine atom; and $R^{3c}$ represents a hydrogen atom (hereinafter referred to as "Compound group SX95").

The Compound (L-1), wherein Q represents the group represented by Q13; $R^{1a}$ represents any one substituent described in Table 1A or Table 2A; $R^{1b}$ represents a hydrogen atom; $R^{3b}$ represents a bromine atom; and $R^{3c}$ represents a hydrogen atom (hereinafter referred to as "Compound group SX96").

The Compound (L-1), wherein Q represents the group represented by Q14; $R^{1a}$ represents a hydrogen atom; $R^{1b}$ represents any one substituent described in Table 1A or Table 2A; $R^{3b}$ represents a bromine atom; and $R^{3c}$ represents a hydrogen atom (hereinafter referred to as "Compound group SX97").

The Compound (L-1), wherein Q represents the group represented by Q14; $R^{1a}$ represents any one substituent described in Table 1A or Table 2A; $R^{1b}$ represents a hydrogen atom; $R^{3b}$ represents a bromine atom; and $R^{3c}$ represents a hydrogen atom (hereinafter referred to as "Compound group SX98").

The Compound (L-1), wherein Q represents the group represented by Q15; $R^{1a}$ represents a hydrogen atom; $R^{1b}$ represents any one substituent described in Table 1A or Table 2A; $R^{3b}$ represents a bromine atom; and $R^{3c}$ represents a hydrogen atom (hereinafter referred to as "Compound group SX99").

The Compound (L-1), wherein Q represents the group represented by Q15; $R^{1a}$ represents any one substituent described in Table 1A or Table 2A; $R^{1b}$ represents a hydrogen atom; $R^{3b}$ represents a bromine atom; and $R^{3c}$ represents a hydrogen atom (hereinafter referred to as "Compound group SX100").

The Compound (L-1), wherein Q represents the group represented by Q16; $R^{1a}$ represents a hydrogen atom; $R^{1b}$ represents any one substituent described in Table 1A or Table 2A; $R^{3b}$ represents a bromine atom; and $R^{3c}$ represents a hydrogen atom (hereinafter referred to as "Compound group SX101").

The Compound (L-1), wherein Q represents the group represented by Q16; $R^{1a}$ represents any one substituent described in Table 1A or Table 2A; $R^{1b}$ represents a hydrogen atom; $R^{3b}$ represents a bromine atom; and $R^{3c}$ represents a hydrogen atom (hereinafter referred to as "Compound group SX102").

The Compound (L-1), wherein Q represents the group represented by Q17; $R^{1a}$ represents a hydrogen atom; $R^{1b}$ represents any one substituent described in Table 1A or Table 2A; $R^{3b}$ represents a bromine atom; and $R^{3c}$ represents a hydrogen atom (hereinafter referred to as "Compound group SX103").

The Compound (L-1), wherein Q represents the group represented by Q17; $R^{1a}$ represents any one substituent described in Table 1A or Table 2A; $R^{1b}$ represents a hydrogen atom; $R^{3b}$ represents a bromine atom; and $R^{3c}$ represents a hydrogen atom (hereinafter referred to as "Compound group SX104").

The Compound (L-1), wherein Q represents the group represented by Q18; $R^{1a}$ represents a hydrogen atom; $R^{1b}$ represents any one substituent described in Table 1A or Table 2A; $R^{3b}$ represents a bromine atom; and $R^{3c}$ represents a hydrogen atom (hereinafter referred to as "Compound group SX105").

The Compound (L-1), wherein Q represents the group represented by Q18; $R^{1a}$ represents any one substituent described in Table 1A or Table 2A; $R^{1b}$ represents a hydrogen atom; $R^{3b}$ represents a bromine atom; and $R^{3c}$ represents a hydrogen atom (hereinafter referred to as "Compound group SX106").

The Compound (L-1), wherein Q represents the group represented by Q19; $R^{1b}$ represents any one substituent described in Table 1A or Table 2A; $R^{3b}$ represents a bromine atom; and $R^{3c}$ represents a hydrogen atom (hereinafter referred to as "Compound group SX107").

The Compound (L-1), wherein Q represents the group represented by Q20; $R^{1b}$ represents any one substituent described in Table 1A or Table 2A; $R^{3b}$ represents a bromine atom; and $R^{3c}$ represents a hydrogen atom (hereinafter referred to as "Compound group SX108").

The Compound (L-1), wherein Q represents the group represented by Q21; $R^{1b}$ represents any one substituent described in Table 1A or Table 2A; $R^{3b}$ represents a bromine atom; and $R^{3c}$ represents a hydrogen atom (hereinafter referred to as "Compound group SX109").

The Compound (L-1), wherein Q represents the group represented by Q22; $R^{1b}$ represents any one substituent described in Table 1A or Table 2A; $R^{3b}$ represents a bromine atom; and $R^{3c}$ represents a hydrogen atom (hereinafter referred to as "Compound group SX110").

The Compound (L-1), wherein Q represents the group represented by Q23; $R^{1b}$ represents any one substituent described in Table 1A or Table 2A; $R^{3b}$ represents a bromine atom; and $R^{3c}$ represents a hydrogen atom (hereinafter referred to as "Compound group SX111").

The Compound (L-1), wherein Q represents the group represented by Q24; $R^{1b}$ represents any one substituent described in Table 1A or Table 2A; $R^{3b}$ represents a bromine atom; and $R^{3c}$ represents a hydrogen atom (hereinafter referred to as "Compound group SX112").

The Compound (L-1), wherein Q represents the group represented by Q25; $R^{1b}$ represents any one substituent described in Table 1A or Table 2A; $R^{3b}$ represents a bromine atom; and $R^{3c}$ represents a hydrogen atom (hereinafter referred to as "Compound group SX113").

The Compound (L-1), wherein Q represents the group represented by Q26; $R^{1b}$ represents any one substituent described in Table 1A or Table 2A; $R^{3b}$ represents a bromine atom; and $R^{3c}$ represents a hydrogen atom (hereinafter referred to as "Compound group SX114").

The Compound (L-1), wherein Q represents the group represented by Q27; $R^{1a}$ represents a hydrogen atom; $R^{1b}$ represents any one substituent described in Table 1A or Table 2A; $R^{3b}$ represents a bromine atom; and $R^{3c}$ represents a hydrogen atom (hereinafter referred to as "Compound group SX115").

The Compound (L-1), wherein Q represents the group represented by Q27; $R^{1a}$ represents any one substituent described in Table 1A or Table 2A; $R^{1b}$ represents a hydrogen atom; $R^{3b}$ represents a bromine atom; and $R^{3c}$ represents a hydrogen atom (hereinafter referred to as "Compound group SX116").

The Compound (L-1), wherein Q represents the group represented by Q28; $R^{1a}$ represents a hydrogen atom; $R^{1b}$ represents any one substituent described in Table 1A or Table 2A; $R^{3b}$ represents a bromine atom; and $R^{3c}$ represents a hydrogen atom (hereinafter referred to as "Compound group SX117").

The Compound (L-1), wherein Q represents the group represented by Q28; $R^{1a}$ represents any one substituent described in Table 1A or Table 2A; $R^{1b}$ represents a hydrogen atom; $R^{3b}$ represents a bromine atom; and $R^{3c}$ represents a hydrogen atom (hereinafter referred to as "Compound group SX118").

The Compound (L-1), wherein Q represents the group represented by Q29; $R^{1b}$ represents any one substituent described in Table 1A or Table 2A; $R^{3b}$ represents a bromine atom; and $R^{3c}$ represents a hydrogen atom (hereinafter referred to as "Compound group SX119").

The Compound (L-1), wherein Q represents the group represented by Q30; $R^{1b}$ represents any one substituent described in Table 1A or Table 2A; $R^{3b}$ represents a bromine atom; and $R^{3c}$ represents a hydrogen atom (hereinafter referred to as "Compound group SX120").

The Compound (L-1), wherein Q represents the group represented by Q11; $R^{1a}$ represents a hydrogen atom; $R^{1b}$ represents any one substituent described in Table 1A or Table 2A; $R^{3b}$ represents an iodine atom; and $R^{3c}$ represents a hydrogen atom (hereinafter referred to as "Compound group SX121").

The Compound (L-1), wherein Q represents the group represented by Q11; $R^{1a}$ represents any one substituent described in Table 1A or Table 2A; $R^{1b}$ represents a hydrogen atom; $R^{3b}$ represents an iodine atom; and $R^{3c}$ represents a hydrogen atom (hereinafter referred to as "Compound group SX122").

The Compound (L-1), wherein Q represents the group represented by Q12; $R^{1a}$ represents a hydrogen atom; $R^{1b}$ represents any one substituent described in Table 1A or Table 2A; $R^{3b}$ represents an iodine atom; and $R^{3c}$ represents a hydrogen atom (hereinafter referred to as "Compound group SX123").

The Compound (L-1), wherein Q represents the group represented by Q12; $R^{1a}$ represents any one substituent described in Table 1A or Table 2A; $R^{1b}$ represents a hydrogen atom; $R^{3b}$ represents an iodine atom; and $R^{3c}$ represents a hydrogen atom (hereinafter referred to as "Compound group SX124").

The Compound (L-1), wherein Q represents the group represented by Q13; $R^{1a}$ represents a hydrogen atom; $R^{1b}$ represents any one substituent described in Table 1A or Table 2A; $R^{3b}$ represents an iodine atom; and $R^{3c}$ represents a hydrogen atom (hereinafter referred to as "Compound group SX125").

The Compound (L-1), wherein Q represents the group represented by Q13; $R^{1a}$ represents any one substituent described in Table 1A or Table 2A; $R^{1b}$ represents a hydrogen atom; $R^{3b}$ represents an iodine atom; and $R^{3c}$ represents a hydrogen atom (hereinafter referred to as "Compound group SX126").

The Compound (L-1), wherein Q represents the group represented by Q14; $R^{1a}$ represents a hydrogen atom; $R^{1b}$ represents any one substituent described in Table 1A or Table 2A; $R^{3b}$ represents an iodine atom; and $R^{3c}$ represents a hydrogen atom (hereinafter referred to as "Compound group SX127").

The Compound (L-1), wherein Q represents the group represented by Q14; $R^{1a}$ represents any one substituent described in Table 1A or Table 2A; $R^{1b}$ represents a hydrogen atom; $R^{3b}$ represents an iodine atom; and $R^{3c}$ represents a hydrogen atom (hereinafter referred to as "Compound group SX128").

The Compound (L-1), wherein Q represents the group represented by Q15; $R^{1a}$ represents a hydrogen atom; $R^{1b}$ represents any one substituent described in Table 1A or Table 2A; $R^{3b}$ represents an iodine atom; and $R^{3c}$ represents a hydrogen atom (hereinafter referred to as "Compound group SX129").

The Compound (L-1), wherein Q represents the group represented by Q15; $R^{1a}$ represents any one substituent described in Table 1A or Table 2A; $R^{1b}$ represents a hydrogen atom; $R^{3b}$ represents an iodine atom; and $R^{3c}$ represents a hydrogen atom (hereinafter referred to as "Compound group SX130").

The Compound (L-1), wherein Q represents the group represented by Q16; $R^{1a}$ represents a hydrogen atom; $R^{1b}$ represents any one substituent described in Table 1A or Table 2A; $R^{3b}$ represents an iodine atom; and $R^{3c}$ represents a hydrogen atom (hereinafter referred to as "Compound group SX131").

The Compound (L-1), wherein Q represents the group represented by Q16; $R^{1a}$ represents any one substituent described in Table 1A or Table 2A; $R^{1b}$ represents a hydrogen atom; $R^{3b}$ represents an iodine atom; and $R^{3c}$ represents a hydrogen atom (hereinafter referred to as "Compound group SX132").

The Compound (L-1), wherein Q represents the group represented by Q17; $R^{1a}$ represents a hydrogen atom; $R^{1b}$ represents any one substituent described in Table 1A or Table 2A; $R^{3b}$ represents an iodine atom; and $R^{3c}$ represents a hydrogen atom (hereinafter referred to as "Compound group SX133").

The Compound (L-1), wherein Q represents the group represented by Q17; $R^{1a}$ represents any one substituent described in Table 1A or Table 2A; $R^{1b}$ represents a hydrogen atom; $R^{3b}$ represents an iodine atom; and $R^{3c}$ represents a hydrogen atom (hereinafter referred to as "Compound group SX134").

The Compound (L-1), wherein Q represents the group represented by Q18; $R^{1a}$ represents a hydrogen atom; $R^{1b}$ represents any one substituent described in Table 1A or Table 2A; $R^{3b}$ represents an iodine atom; and $R^{3c}$ represents a hydrogen atom (hereinafter referred to as "Compound group SX135").

The Compound (L-1), wherein Q represents the group represented by Q18; $R^{1a}$ represents any one substituent described in Table 1A or Table 2A; $R^{1b}$ represents a hydrogen atom; $R^{3b}$ represents an iodine atom; and $R^{3c}$ represents a hydrogen atom (hereinafter referred to as "Compound group SX136").

The Compound (L-1), wherein Q represents the group represented by Q19; $R^{1b}$ represents any one substituent described in Table 1A or Table 2A; $R^{3b}$ represents an iodine atom; and $R^{3c}$ represents a hydrogen atom (hereinafter referred to as "Compound group SX137").

The Compound (L-1), wherein Q represents the group represented by Q20; $R^{1b}$ represents any one substituent described in Table 1A or Table 2A; $R^{3b}$ represents an iodine atom; and $R^{3c}$ represents a hydrogen atom (hereinafter referred to as "Compound group SX138").

The Compound (L-1), wherein Q represents the group represented by Q21; $R^{1b}$ represents any one substituent described in Table 1A or Table 2A; $R^{3b}$ represents an iodine atom; and $R^{3c}$ represents a hydrogen atom (hereinafter referred to as "Compound group SX139").

The Compound (L-1), wherein Q represents the group represented by Q22; $R^{1b}$ represents any one substituent described in Table 1A or Table 2A; $R^{3b}$ represents an iodine atom; and $R^{3c}$ represents a hydrogen atom (hereinafter referred to as "Compound group SX140").

The Compound (L-1), wherein Q represents the group represented by Q23; $R^{1b}$ represents any one substituent described in Table 1A or Table 2A; $R^{3b}$ represents an iodine atom; and $R^{3c}$ represents a hydrogen atom (hereinafter referred to as "Compound group SX141").

The Compound (L-1), wherein Q represents the group represented by Q24; $R^{1b}$ represents any one substituent described in Table 1A or Table 2A; $R^{3b}$ represents an iodine atom; and $R^{3c}$ represents a hydrogen atom (hereinafter referred to as "Compound group SX142").

The Compound (L-1), wherein Q represents the group represented by Q25; $R^{1b}$ represents any one substituent described in Table 1A or Table 2A; $R^{3b}$ represents an iodine atom; and $R^{3c}$ represents a hydrogen atom (hereinafter referred to as "Compound group SX143").

The Compound (L-1), wherein Q represents the group represented by Q26; $R^{1b}$ represents any one substituent described in Table 1A or Table 2A; $R^{3b}$ represents an iodine atom; and $R^{3c}$ represents a hydrogen atom (hereinafter referred to as "Compound group SX144").

The Compound (L-1), wherein Q represents the group represented by Q27; $R^{1a}$ represents a hydrogen atom; $R^{1b}$ represents any one substituent described in Table 1A or Table 2A; $R^{3b}$ represents an iodine atom; and $R^{3c}$ represents a hydrogen atom (hereinafter referred to as "Compound group SX145").

The Compound (L-1), wherein Q represents the group represented by Q27; $R^{1a}$ represents any one substituent described in Table 1A or Table 2A; $R^{1b}$ represents a hydrogen atom; $R^{3b}$ represents an iodine atom; and $R^{3c}$ represents a hydrogen atom (hereinafter referred to as "Compound group SX146").

The Compound (L-1), wherein Q represents the group represented by Q28; $R^{1a}$ represents a hydrogen atom; $R^{1b}$ represents any one substituent described in Table 1A or Table 2A; $R^{3b}$ represents an iodine atom; and $R^{3c}$ represents a hydrogen atom (hereinafter referred to as "Compound group SX147").

The Compound (L-1), wherein Q represents the group represented by Q28; $R^{1a}$ represents any one substituent described in Table 1A or Table 2A; $R^{1b}$ represents a hydrogen atom; $R^{3b}$ represents an iodine atom; and $R^{3c}$ represents a hydrogen atom (hereinafter referred to as "Compound group SX148").

The Compound (L-1), wherein Q represents the group represented by Q29; $R^{1b}$ represents any one substituent described in Table 1A or Table 2A; $R^{3b}$ represents an iodine atom; and $R^{3c}$ represents a hydrogen atom (hereinafter referred to as "Compound group SX149").

The Compound (L-1), wherein Q represents the group represented by Q30; $R^{1b}$ represents any one substituent described in Table 1A or Table 2A; $R^{3b}$ represents an iodine atom; and $R^{3c}$ represents a hydrogen atom (hereinafter referred to as "Compound group SX150").

The Compound (L-1), wherein Q represents the group represented by Q11; $R^{1a}$ represents a hydrogen atom; $R^{1b}$ represents any one substituent described in Table 1A or Table 2A; $R^{3b}$ represents a hydrogen atom; and $R^{3c}$ represents a trifluoromethyl group (hereinafter referred to as "Compound group SX151").

The Compound (L-1), wherein Q represents the group represented by Q11; $R^{1a}$ represents any one substituent described in Table 1A or Table 2A; $R^{1b}$ represents a hydrogen atom; $R^{3b}$ represents a hydrogen atom; and $R^{3c}$ represents a trifluoromethyl group (hereinafter referred to as "Compound group SX152").

The Compound (L-1), wherein Q represents the group represented by Q12; $R^{1a}$ represents a hydrogen atom; $R^{1b}$ represents any one substituent described in Table 1A or Table 2A; $R^{3b}$ represents a hydrogen atom; and $R^{3c}$ represents a trifluoromethyl group (hereinafter referred to as "Compound group SX153").

The Compound (L-1), wherein Q represents the group represented by Q12; $R^{1a}$ represents any one substituent described in Table 1A or Table 2A; $R^{1b}$ represents a hydrogen atom; $R^{3b}$ represents a hydrogen atom; and $R^{3c}$ represents a trifluoromethyl group (hereinafter referred to as "Compound group SX154").

The Compound (L-1), wherein Q represents the group represented by Q13; $R^{1a}$ represents a hydrogen atom; $R^{1b}$ represents any one substituent described in Table 1A or Table 2A; $R^{3b}$ represents a hydrogen atom; and $R^{3c}$ represents a trifluoromethyl group (hereinafter referred to as "Compound group SX155").

The Compound (L-1), wherein Q represents the group represented by Q13; $R^{1a}$ represents any one substituent described in Table 1A or Table 2A; $R^{1b}$ represents a hydrogen atom; $R^{3b}$ represents a hydrogen atom; and $R^{3c}$ represents a trifluoromethyl group (hereinafter referred to as "Compound group SX156").

The Compound (L-1), wherein Q represents the group represented by Q14; $R^{1a}$ represents a hydrogen atom; $R^{1b}$ represents any one substituent described in Table 1A or Table 2A; $R^{3b}$ represents a hydrogen atom; and $R^{3c}$ represents a trifluoromethyl group (hereinafter referred to as "Compound group SX157").

The Compound (L-1), wherein Q represents the group represented by Q14; $R^{1a}$ represents any one substituent described in Table 1A or Table 2A; $R^{1b}$ represents a hydrogen atom; $R^{3b}$ represents a hydrogen atom; and $R^{3c}$ represents a trifluoromethyl group (hereinafter referred to as "Compound group SX158").

The Compound (L-1), wherein Q represents the group represented by Q15; $R^{1a}$ represents a hydrogen atom; $R^{1b}$ represents any one substituent described in Table 1A or Table 2A; $R^{3b}$ represents a hydrogen atom; and $R^{3c}$ represents a trifluoromethyl group (hereinafter referred to as "Compound group SX159").

The Compound (L-1), wherein Q represents the group represented by Q15; $R^{1a}$ represents any one substituent described in Table 1A or Table 2A; $R^{1b}$ represents a hydrogen atom; $R^{3b}$ represents a hydrogen atom; and $R^{3c}$ represents a trifluoromethyl group (hereinafter referred to as "Compound group SX160").

The Compound (L-1), wherein Q represents the group represented by Q16; $R^{1a}$ represents a hydrogen atom; $R^{1b}$ represents any one substituent described in Table 1A or Table 2A; $R^{3b}$ represents a hydrogen atom; and $R^{3c}$ represents a trifluoromethyl group (hereinafter referred to as "Compound group SX161").

The Compound (L-1), wherein Q represents the group represented by Q16; $R^{1a}$ represents any one substituent described in Table 1A or Table 2A; $R^{1b}$ represents a hydrogen atom; $R^{3b}$ represents a hydrogen atom; and $R^{3c}$ represents a trifluoromethyl group (hereinafter referred to as "Compound group SX162").

The Compound (L-1), wherein Q represents the group represented by Q17; $R^{1a}$ represents a hydrogen atom; $R^{1b}$ represents any one substituent described in Table 1A or Table 2A; $R^{3b}$ represents a hydrogen atom; and $R^{3c}$ represents a trifluoromethyl group (hereinafter referred to as "Compound group SX163").

The Compound (L-1), wherein Q represents the group represented by Q17; $R^{1a}$ represents any one substituent described in Table 1A or Table 2A; $R^{1b}$ represents a hydrogen atom; $R^{3b}$ represents a hydrogen atom; and $R^{3c}$ represents a trifluoromethyl group (hereinafter referred to as "Compound group SX164").

The Compound (L-1), wherein Q represents the group represented by Q18; $R^{1a}$ represents a hydrogen atom; $R^{1b}$ represents any one substituent described in Table 1A or Table 2A; $R^{3b}$ represents a hydrogen atom; and $R^{3c}$ represents a trifluoromethyl group (hereinafter referred to as "Compound group SX165").

The Compound (L-1), wherein Q represents the group represented by Q18; $R^{1a}$ represents any one substituent described in Table 1A or Table 2A; $R^{1b}$ represents a hydrogen atom; $R^{3b}$ represents a hydrogen atom; and $R^{3c}$ represents a trifluoromethyl group (hereinafter referred to as "Compound group SX166").

The Compound (L-1), wherein Q represents the group represented by Q19; $R^{1b}$ represents any one substituent described in Table 1A or Table 2A; $R^{3b}$ represents a hydrogen atom; and $R^{3c}$ represents a trifluoromethyl group (hereinafter referred to as "Compound group SX167").

The Compound (L-1), wherein Q represents the group represented by Q20; $R^{1b}$ represents any one substituent described in Table 1A or Table 2A; $R^{3b}$ represents a hydrogen atom; and $R^{3c}$ represents a trifluoromethyl group (hereinafter referred to as "Compound group SX168").

The Compound (L-1), wherein Q represents the group represented by Q21; $R^{1b}$ represents any one substituent described in Table 1A or Table 2A; $R^{3b}$ represents a hydrogen atom; and $R^{3c}$ represents a trifluoromethyl group (hereinafter referred to as "Compound group SX169").

The Compound (L-1), wherein Q represents the group represented by Q22; $R^{1b}$ represents any one substituent described in Table 1A or Table 2A; $R^{3b}$ represents a hydrogen atom; and $R^{3c}$ represents a trifluoromethyl group (hereinafter referred to as "Compound group SX170").

The Compound (L-1), wherein Q represents the group represented by Q23; $R^{1b}$ represents any one substituent described in Table 1A or Table 2A; $R^{3b}$ represents a hydrogen atom; and $R^{3c}$ represents a trifluoromethyl group (hereinafter referred to as "Compound group SX171").

The Compound (L-1), wherein Q represents the group represented by Q24; $R^{1b}$ represents any one substituent described in Table 1A or Table 2A; $R^{3b}$ represents a hydrogen atom; and $R^{3c}$ represents a trifluoromethyl group (hereinafter referred to as "Compound group SX172").

The Compound (L-1), wherein Q represents the group represented by Q25; $R^{1b}$ represents any one substituent described in Table 1A or Table 2A; $R^{3b}$ represents a hydrogen atom; and $R^{3c}$ represents a trifluoromethyl group (hereinafter referred to as "Compound group SX173").

The Compound (L-1), wherein Q represents the group represented by Q26; $R^{1b}$ represents any one substituent described in Table 1A or Table 2A; $R^{3b}$ represents a hydrogen atom; and $R^{3c}$ represents a trifluoromethyl group (hereinafter referred to as "Compound group SX174").

The Compound (L-1), wherein Q represents the group represented by Q27; $R^{1a}$ represents a hydrogen atom; $R^{1b}$ represents any one substituent described in Table 1A or Table 2A; $R^{3b}$ represents a hydrogen atom; and $R^{3c}$ represents a trifluoromethyl group (hereinafter referred to as "Compound group SX175").

The Compound (L-1), wherein Q represents the group represented by Q27; $R^{1a}$ represents any one substituent described in Table 1A or Table 2A; $R^{1b}$ represents a hydrogen atom; $R^{3b}$ represents a hydrogen atom; and $R^{3c}$ represents a trifluoromethyl group (hereinafter referred to as "Compound group SX176").

The Compound (L-1), wherein Q represents the group represented by Q28; $R^{1a}$ represents a hydrogen atom; $R^{1b}$ represents any one substituent described in Table 1A or Table 2A; $R^{3b}$ represents a hydrogen atom; and $R^{3c}$ represents a trifluoromethyl group (hereinafter referred to as "Compound group SX177").

The Compound (L-1), wherein Q represents the group represented by Q28; $R^{1a}$ represents any one substituent described in Table 1A or Table 2A; $R^{1b}$ represents a hydrogen atom; $R^{3b}$ represents a hydrogen atom; and $R^{3c}$ represents a trifluoromethyl group (hereinafter referred to as "Compound group SX178").

The Compound (L-1), wherein Q represents the group represented by Q29; $R^{1b}$ represents any one substituent described in Table 1A or Table 2A; $R^{3b}$ represents a hydrogen atom; and $R^{3c}$ represents a trifluoromethyl group (hereinafter referred to as "Compound group SX179").

The Compound (L-1), wherein Q represents the group represented by Q30; $R^{1b}$ represents any one substituent described in Table 1A or Table 2A; $R^{3b}$ represents a hydrogen atom; and $R^{3c}$ represents a trifluoromethyl group (hereinafter referred to as "Compound group SX180").

The Compound (L-1), wherein Q represents the group represented by Q11; $R^{1a}$ represents a hydrogen atom; $R^{1b}$ represents any one substituent described in Table 1A or Table 2A; $R^{3b}$ represents a hydrogen atom; and $R^{3c}$ represents a chlorine atom (hereinafter referred to as "Compound group SX181").

The Compound (L-1), wherein Q represents the group represented by Q11; $R^{1a}$ represents any one substituent described in Table 1A or Table 2A; $R^{1b}$ represents a hydrogen atom; $R^{3b}$ represents a hydrogen atom; and $R^{3c}$ represents a chlorine atom (hereinafter referred to as "Compound group SX182").

The Compound (L-1), wherein Q represents the group represented by Q12; $R^{1a}$ represents a hydrogen atom; $R^{1b}$ represents any one substituent described in Table 1A or Table 2A; $R^{3b}$ represents a hydrogen atom; and $R^{3c}$ represents a chlorine atom (hereinafter referred to as "Compound group SX183").

The Compound (L-1), wherein Q represents the group represented by Q12; $R^{1a}$ represents any one substituent described in Table 1A or Table 2A; $R^{1b}$ represents a hydrogen atom; $R^{3b}$ represents a hydrogen atom; and $R^{3c}$ represents a chlorine atom (hereinafter referred to as "Compound group SX184").

The Compound (L-1), wherein Q represents the group represented by Q13; $R^{1a}$ represents a hydrogen atom; $R^{1b}$ represents any one substituent described in Table 1A or Table 2A; $R^{3b}$ represents a hydrogen atom; and $R^{3c}$ represents a chlorine atom (hereinafter referred to as "Compound group SX185").

The Compound (L-1), wherein Q represents the group represented by Q13; $R^{1a}$ represents any one substituent described in Table 1A or Table 2A; $R^{1b}$ represents a hydrogen atom; $R^{3b}$ represents a hydrogen atom; and $R^{3c}$ represents a chlorine atom (hereinafter referred to as "Compound group SX186").

The Compound (L-1), wherein Q represents the group represented by Q14; $R^{1a}$ represents a hydrogen atom; $R^{1b}$ represents any one substituent described in Table 1A or Table 2A; $R^{3b}$ represents a hydrogen atom; and $R^{3c}$ represents a chlorine atom (hereinafter referred to as "Compound group SX187").

The Compound (L-1), wherein Q represents the group represented by Q14; $R^{1a}$ represents any one substituent described in Table 1A or Table 2A; $R^{1b}$ represents a hydrogen atom; $R^{3b}$ represents a hydrogen atom; and $R^{3c}$ represents a chlorine atom (hereinafter referred to as "Compound group SX188").

The Compound (L-1), wherein Q represents the group represented by Q15; $R^{1a}$ represents a hydrogen atom; $R^{1b}$ represents any one substituent described in Table 1A or Table 2A; $R^{3b}$ represents a hydrogen atom; and $R^{3c}$ represents a chlorine atom (hereinafter referred to as "Compound group SX189").

The Compound (L-1), wherein Q represents the group represented by Q15; $R^{1a}$ represents any one substituent described in Table 1A or Table 2A; $R^{1b}$ represents a hydrogen atom; $R^{3b}$ represents a hydrogen atom; and $R^{3c}$ represents a chlorine atom (hereinafter referred to as "Compound group SX190").

The Compound (L-1), wherein Q represents the group represented by Q16; $R^{1a}$ represents a hydrogen atom; $R^{1b}$ represents any one substituent described in Table 1A or Table 2A; $R^{3b}$ represents a hydrogen atom; and $R^{3c}$ represents a chlorine atom (hereinafter referred to as "Compound group SX191").

The Compound (L-1), wherein Q represents the group represented by Q16; $R^{1a}$ represents any one substituent described in Table 1A or Table 2A; $R^{1b}$ represents a hydrogen atom; $R^{3b}$ represents a hydrogen atom; and $R^{3c}$ represents a chlorine atom (hereinafter referred to as "Compound group SX192").

The Compound (L-1), wherein Q represents the group represented by Q17; $R^{1a}$ represents a hydrogen atom; $R^{1b}$ represents any one substituent described in Table 1A or Table 2A; $R^{3b}$ represents a hydrogen atom; and $R^{3c}$ represents a chlorine atom (hereinafter referred to as "Compound group SX193").

The Compound (L-1), wherein Q represents the group represented by Q17; $R^{1a}$ represents any one substituent described in Table 1A or Table 2A; $R^{1b}$ represents a hydrogen atom; $R^{3b}$ represents a hydrogen atom; and $R^{3c}$ represents a chlorine atom (hereinafter referred to as "Compound group SX194").

The Compound (L-1), wherein Q represents the group represented by Q18; $R^{1a}$ represents a hydrogen atom; $R^{1b}$ represents any one substituent described in Table 1A or Table 2A; $R^{3b}$ represents a hydrogen atom; and $R^{3c}$ represents a chlorine atom (hereinafter referred to as "Compound group SX195").

The Compound (L-1), wherein Q represents the group represented by Q18; $R^{1a}$ represents any one substituent described in Table 1A or Table 2A; $R^{1b}$ represents a hydrogen atom; $R^{3b}$ represents a hydrogen atom; and $R^{3c}$ represents a chlorine atom (hereinafter referred to as "Compound group SX196").

The Compound (L-1), wherein Q represents the group represented by Q19; $R^{1b}$ represents any one substituent described in Table 1A or Table 2A; $R^{3b}$ represents a hydrogen atom; and $R^{3c}$ represents a chlorine atom (hereinafter referred to as "Compound group SX197").

The Compound (L-1), wherein Q represents the group represented by Q20; $R^{1b}$ represents any one substituent described in Table 1A or Table 2A; $R^{3b}$ represents a hydrogen atom; and $R^{3c}$ represents a chlorine atom (hereinafter referred to as "Compound group SX198").

The Compound (L-1), wherein Q represents the group represented by Q21; $R^{1b}$ represents any one substituent described in Table 1A or Table 2A; $R^{3b}$ represents a hydrogen atom; and $R^{3c}$ represents a chlorine atom (hereinafter referred to as "Compound group SX199").

The Compound (L-1), wherein Q represents the group represented by Q22; $R^{1b}$ represents any one substituent described in Table 1A or Table 2A; $R^{3b}$ represents a hydrogen atom; and $R^{3c}$ represents a chlorine atom (hereinafter referred to as "Compound group SX200").

The Compound (L-1), wherein Q represents the group represented by Q23; $R^{1b}$ represents any one substituent described in Table 1A or Table 2A; $R^{3b}$ represents a hydrogen atom; and $R^{3c}$ represents a chlorine atom (hereinafter referred to as "Compound group SX201").

The Compound (L-1), wherein Q represents the group represented by Q24; $R^{1b}$ represents any one substituent described in Table 1A or Table 2A; $R^{3b}$ represents a hydrogen atom; and $R^{3c}$ represents a chlorine atom (hereinafter referred to as "Compound group SX202").

The Compound (L-1), wherein Q represents the group represented by Q25; $R^{1b}$ represents any one substituent described in Table 1A or Table 2A; $R^{3b}$ represents a hydrogen atom; and $R^{3c}$ represents a chlorine atom (hereinafter referred to as "Compound group SX203").

The Compound (L-1), wherein Q represents the group represented by Q26; $R^{1b}$ represents any one substituent described in Table 1A or Table 2A; $R^{3b}$ represents a hydrogen atom; and $R^{3c}$ represents a chlorine atom (hereinafter referred to as "Compound group SX204").

The Compound (L-1), wherein Q represents the group represented by Q27; $R^{1a}$ represents a hydrogen atom; $R^{1b}$ represents any one substituent described in Table 1A or Table 2A; $R^{3b}$ represents a hydrogen atom; and $R^{3c}$ represents a chlorine atom (hereinafter referred to as "Compound group SX205").

The Compound (L-1), wherein Q represents the group represented by Q27; $R^{1a}$ represents any one substituent described in Table 1A or Table 2A; $R^{1b}$ represents a hydrogen atom; $R^{3b}$ represents a hydrogen atom; and $R^{3c}$ represents a chlorine atom (hereinafter referred to as "Compound group SX206").

The Compound (L-1), wherein Q represents the group represented by Q28; $R^{1a}$ represents a hydrogen atom; $R^{1b}$ represents any one substituent described in Table 1A or Table 2A; $R^{3b}$ represents a hydrogen atom; and $R^{3c}$ represents a chlorine atom (hereinafter referred to as "Compound group SX207").

The Compound (L-1), wherein Q represents the group represented by Q28; $R^{1a}$ represents any one substituent described in Table 1A or Table 2A; $R^{1b}$ represents a hydrogen atom; $R^{3b}$ represents a hydrogen atom; and $R^{3c}$ represents a chlorine atom (hereinafter referred to as "Compound group SX208").

The Compound (L-1), wherein Q represents the group represented by Q29; $R^{1b}$ represents any one substituent described in Table 1A or Table 2A; $R^{3b}$ represents a hydrogen atom; and $R^{3c}$ represents a chlorine atom (hereinafter referred to as "Compound group SX209").

The Compound (L-1), wherein Q represents the group represented by Q30; $R^{1b}$ represents any one substituent described in Table 1A or Table 2A; $R^{3b}$ represents a hydrogen atom; and $R^{3c}$ represents a chlorine atom (hereinafter referred to as "Compound group SX210").

The Compound (L-1), wherein Q represents the group represented by Q11; $R^{1a}$ represents a hydrogen atom; $R^{1b}$ represents any one substituent described in Table 1A or Table 2A; $R^{3b}$ represents a hydrogen atom; and $R^{3c}$ represents a bromine atom (hereinafter referred to as "Compound group SX211").

The Compound (L-1), wherein Q represents the group represented by Q11; $R^{1a}$ represents any one substituent described in Table 1A or Table 2A; $R^{1b}$ represents a hydrogen atom; $R^{3b}$ represents a hydrogen atom; and $R^{3c}$ represents a bromine atom (hereinafter referred to as "Compound group SX212").

The Compound (L-1), wherein Q represents the group represented by Q12; $R^{1a}$ represents a hydrogen atom; $R^{1b}$ represents any one substituent described in Table 1A or Table 2A; $R^{3b}$ represents a hydrogen atom; and $R^{3c}$ represents a bromine atom (hereinafter referred to as "Compound group SX213").

The Compound (L-1), wherein Q represents the group represented by Q12; $R^{1a}$ represents any one substituent described in Table 1A or Table 2A; $R^{1b}$ represents a hydrogen atom; $R^{3b}$ represents a hydrogen atom; and $R^{3c}$ represents a bromine atom (hereinafter referred to as "Compound group SX214").

The Compound (L-1), wherein Q represents the group represented by Q13; $R^{1a}$ represents a hydrogen atom; $R^{1b}$ represents any one substituent described in Table 1A or Table 2A; $R^{3b}$ represents a hydrogen atom; and $R^{3c}$ represents a bromine atom (hereinafter referred to as "Compound group SX215").

The Compound (L-1), wherein Q represents the group represented by Q13; $R^{1a}$ represents any one substituent described in Table 1A or Table 2A; $R^{1b}$ represents a hydrogen atom; $R^{3b}$ represents a hydrogen atom; and $R^{3c}$ represents a bromine atom (hereinafter referred to as "Compound group SX216").

The Compound (L-1), wherein Q represents the group represented by Q14; $R^{1a}$ represents a hydrogen atom; $R^{1b}$ represents any one substituent described in Table 1A or Table 2A; $R^{3b}$ represents a hydrogen atom; and $R^{3c}$ represents a bromine atom (hereinafter referred to as "Compound group SX217").

The Compound (L-1), wherein Q represents the group represented by Q14; $R^{1a}$ represents any one substituent described in Table 1A or Table 2A; $R^{1b}$ represents a hydrogen atom; $R^{3b}$ represents a hydrogen atom; and $R^{3c}$ represents a bromine atom (hereinafter referred to as "Compound group SX218").

The Compound (L-1), wherein Q represents the group represented by Q15; $R^{1a}$ represents a hydrogen atom; $R^{1b}$ represents any one substituent described in Table 1A or Table 2A; $R^{3b}$ represents a hydrogen atom; and $R^{3c}$ represents a bromine atom (hereinafter referred to as "Compound group SX219").

The Compound (L-1), wherein Q represents the group represented by Q15; $R^{1a}$ represents any one substituent described in Table 1A or Table 2A; $R^{1b}$ represents a hydrogen atom; $R^{3b}$ represents a hydrogen atom; and $R^{3c}$ represents a bromine atom (hereinafter referred to as "Compound group SX220").

The Compound (L-1), wherein Q represents the group represented by Q16; $R^{1a}$ represents a hydrogen atom; $R^{1b}$ represents any one substituent described in Table 1A or Table 2A; $R^{3b}$ represents a hydrogen atom; and $R^{3c}$ represents a bromine atom (hereinafter referred to as "Compound group SX221").

The Compound (L-1), wherein Q represents the group represented by Q16; $R^{1a}$ represents any one substituent described in Table 1A or Table 2A; $R^{1b}$ represents a hydrogen atom; $R^{3b}$ represents a hydrogen atom; and $R^{3c}$ represents a bromine atom (hereinafter referred to as "Compound group SX222").

The Compound (L-1), wherein Q represents the group represented by Q17; $R^{1a}$ represents a hydrogen atom; $R^{1b}$ represents any one substituent described in Table 1A or Table 2A; $R^{3b}$ represents a hydrogen atom; and $R^{3c}$ represents a bromine atom (hereinafter referred to as "Compound group SX223").

The Compound (L-1), wherein Q represents the group represented by Q17; $R^{1a}$ represents any one substituent described in Table 1A or Table 2A; $R^{1b}$ represents a hydrogen atom; $R^{3b}$ represents a hydrogen atom; and $R^{3c}$ represents a bromine atom (hereinafter referred to as "Compound group SX224").

The Compound (L-1), wherein Q represents the group represented by Q18; $R^{1a}$ represents a hydrogen atom; $R^{1b}$ represents any one substituent described in Table 1A or Table 2A; $R^{3b}$ represents a hydrogen atom; and $R^{3c}$ represents a bromine atom (hereinafter referred to as "Compound group SX225").

The Compound (L-1), wherein Q represents the group represented by Q18; $R^{1a}$ represents any one substituent described in Table 1A or Table 2A; $R^{1b}$ represents a hydrogen atom; $R^{3b}$ represents a hydrogen atom; and $R^{3c}$ represents a bromine atom (hereinafter referred to as "Compound group SX226").

The Compound (L-1), wherein Q represents the group represented by Q19; $R^{1b}$ represents any one substituent described in Table 1A or Table 2A; $R^{3b}$ represents a hydrogen atom; and $R^{3c}$ represents a bromine atom (hereinafter referred to as "Compound group SX227").

The Compound (L-1), wherein Q represents the group represented by Q20; $R^{1b}$ represents any one substituent described in Table 1A or Table 2A; $R^{3b}$ represents a hydrogen atom; and $R^{3c}$ represents a bromine atom (hereinafter referred to as "Compound group SX228").

The Compound (L-1), wherein Q represents the group represented by Q21; $R^{1b}$ represents any one substituent described in Table 1A or Table 2A; $R^{3b}$ represents a hydrogen atom; and $R^{3c}$ represents a bromine atom (hereinafter referred to as "Compound group SX229").

The Compound (L-1), wherein Q represents the group represented by Q22; $R^{1b}$ represents any one substituent described in Table 1A or Table 2A; $R^{3b}$ represents a hydrogen atom; and $R^{3c}$ represents a bromine atom (hereinafter referred to as "Compound group SX230").

The Compound (L-1), wherein Q represents the group represented by Q23; $R^{1b}$ represents any one substituent described in Table 1A or Table 2A; $R^{3b}$ represents a hydrogen atom; and $R^{3c}$ represents a bromine atom (hereinafter referred to as "Compound group SX231").

The Compound (L-1), wherein Q represents the group represented by Q24; $R^{1b}$ represents any one substituent described in Table 1A or Table 2A; $R^{3b}$ represents a hydrogen atom; and $R^{3c}$ represents a bromine atom (hereinafter referred to as "Compound group SX232").

The Compound (L-1), wherein Q represents the group represented by Q25; $R^{1b}$ represents any one substituent described in Table 1A or Table 2A; $R^{3b}$ represents a hydrogen atom; and $R^{3c}$ represents a bromine atom (hereinafter referred to as "Compound group SX233").

The Compound (L-1), wherein Q represents the group represented by Q26; $R^{1b}$ represents any one substituent described in Table 1A or Table 2A; $R^{3b}$ represents a hydrogen atom; and $R^{3c}$ represents a bromine atom (hereinafter referred to as "Compound group SX234").

The Compound (L-1), wherein Q represents the group represented by Q27; $R^{1a}$ represents a hydrogen atom; $R^{1b}$ represents any one substituent described in Table 1A or Table 2A; $R^{3b}$ represents a hydrogen atom; and $R^{3c}$ represents a bromine atom (hereinafter referred to as "Compound group SX235").

The Compound (L-1), wherein Q represents the group represented by Q27; $R^{1a}$ represents any one substituent described in Table 1A or Table 2A; $R^{1b}$ represents a hydrogen atom; $R^{3b}$ represents a hydrogen atom; and $R^{3c}$ represents a bromine atom (hereinafter referred to as "Compound group SX236").

The Compound (L-1), wherein Q represents the group represented by Q28; $R^{1a}$ represents a hydrogen atom; $R^{1b}$ represents any one substituent described in Table 1A or Table 2A; $R^{3b}$ represents a hydrogen atom; and $R^{3c}$ represents a bromine atom (hereinafter referred to as "Compound group SX237").

The Compound (L-1), wherein Q represents the group represented by Q28; $R^{1a}$ represents any one substituent described in Table 1A or Table 2A; $R^{1b}$ represents a hydrogen atom; $R^{3b}$ represents a hydrogen atom; and $R^{3c}$ represents a bromine atom (hereinafter referred to as "Compound group SX238").

The Compound (L-1), wherein Q represents the group represented by Q29; $R^{1b}$ represents any one substituent described in Table 1A or Table 2A; $R^{3b}$ represents a hydrogen atom; and $R^{3c}$ represents a bromine atom (hereinafter referred to as "Compound group SX239").

The Compound (L-1), wherein Q represents the group represented by Q30; $R^{1b}$ represents any one substituent described in Table 1A or Table 2A; $R^{3b}$ represents a hydrogen atom; and $R^{3c}$ represents a bromine atom (hereinafter referred to as "Compound group SX240").

The Compound (L-1), wherein Q represents the group represented by Q11; $R^{1a}$ represents a hydrogen atom; $R^{1b}$ represents any one substituent described in Table 1A or Table 2A; $R^{3b}$ represents a hydrogen atom; and $R^{3c}$ represents an iodine atom (hereinafter referred to as "Compound group SX241").

The Compound (L-1), wherein Q represents the group represented by Q11; $R^{1a}$ represents any one substituent described in Table 1A or Table 2A; $R^{1b}$ represents a hydrogen atom; $R^{3b}$ represents a hydrogen atom; and $R^{3c}$ represents an iodine atom (hereinafter referred to as "Compound group SX242").

The Compound (L-1), wherein Q represents the group represented by Q12; $R^{1a}$ represents a hydrogen atom; $R^{1b}$ represents any one substituent described in Table 1A or Table 2A; $R^{3b}$ represents a hydrogen atom; and $R^{3c}$ represents an iodine atom (hereinafter referred to as "Compound group SX243").

The Compound (L-1), wherein Q represents the group represented by Q12; $R^{1a}$ represents any one substituent described in Table 1A or Table 2A; $R^{1b}$ represents a hydrogen atom; $R^{3b}$ represents a hydrogen atom; and $R^{3c}$ represents an iodine atom (hereinafter referred to as "Compound group SX244").

The Compound (L-1), wherein Q represents the group represented by Q13; $R^{1a}$ represents a hydrogen atom; $R^{1b}$ represents any one substituent described in Table 1A or Table 2A; $R^{3b}$ represents a hydrogen atom; and $R^{3c}$ represents an iodine atom (hereinafter referred to as "Compound group SX245").

The Compound (L-1), wherein Q represents the group represented by Q13; $R^{1a}$ represents any one substituent described in Table 1A or Table 2A; $R^{1b}$ represents a hydrogen atom; $R^{3b}$ represents a hydrogen atom; and $R^{3c}$ represents an iodine atom (hereinafter referred to as "Compound group SX246").

The Compound (L-1), wherein Q represents the group represented by Q14; $R^{1a}$ represents a hydrogen atom; $R^{1b}$ represents any one substituent described in Table 1A or Table 2A; $R^{3b}$ represents a hydrogen atom; and $R^{3c}$ represents an iodine atom (hereinafter referred to as "Compound group SX247").

The Compound (L-1), wherein Q represents the group represented by Q14; $R^{1a}$ represents any one substituent described in Table 1A or Table 2A; $R^{1b}$ represents a hydrogen atom; $R^{3b}$ represents a hydrogen atom; and $R^{3c}$ represents an iodine atom (hereinafter referred to as "Compound group SX248").

The Compound (L-1), wherein Q represents the group represented by Q15; $R^{1a}$ represents a hydrogen atom; $R^{1b}$ represents any one substituent described in Table 1A or Table 2A; $R^{3b}$ represents a hydrogen atom; and $R^{3c}$ represents an iodine atom (hereinafter referred to as "Compound group SX249").

The Compound (L-1), wherein Q represents the group represented by Q15; $R^{1a}$ represents any one substituent described in Table 1A or Table 2A; $R^{1b}$ represents a hydrogen atom; $R^{3b}$ represents a hydrogen atom; and $R^{3c}$ represents an iodine atom (hereinafter referred to as "Compound group SX250").

The Compound (L-1), wherein Q represents the group represented by Q16; $R^{1a}$ represents a hydrogen atom; $R^{1b}$ represents any one substituent described in Table 1A or Table 2A; $R^{3b}$ represents a hydrogen atom; and $R^{3c}$ represents an iodine atom (hereinafter referred to as "Compound group SX251").

The Compound (L-1), wherein Q represents the group represented by Q16; $R^{1a}$ represents any one substituent described in Table 1A or Table 2A; $R^{1b}$ represents a hydrogen atom; $R^{3b}$ represents a hydrogen atom; and $R^{3c}$ represents an iodine atom (hereinafter referred to as "Compound group SX252").

The Compound (L-1), wherein Q represents the group represented by Q17; $R^{1a}$ represents a hydrogen atom; $R^{1b}$ represents any one substituent described in Table 1A or Table 2A; $R^{3b}$ represents a hydrogen atom; and $R^{3c}$ represents an iodine atom (hereinafter referred to as "Compound group SX253").

The Compound (L-1), wherein Q represents the group represented by Q17; $R^{1a}$ represents any one substituent described in Table 1A or Table 2A; $R^{1b}$ represents a hydrogen atom; $R^{3b}$ represents a hydrogen atom; and $R^{3c}$ represents an iodine atom (hereinafter referred to as "Compound group SX254").

The Compound (L-1), wherein Q represents the group represented by Q18; $R^{1a}$ represents a hydrogen atom; $R^{1b}$ represents any one substituent described in Table 1A or Table 2A; $R^{3b}$ represents a hydrogen atom; and $R^{3c}$ represents an iodine atom (hereinafter referred to as "Compound group SX255").

The Compound (L-1), wherein Q represents the group represented by Q18; $R^{1a}$ represents any one substituent described in Table 1A or Table 2A; $R^{1b}$ represents a hydrogen atom; $R^{3b}$ represents a hydrogen atom; and $R^{3c}$ represents an iodine atom (hereinafter referred to as "Compound group SX256").

The Compound (L-1), wherein Q represents the group represented by Q19; $R^{1b}$ represents any one substituent described in Table 1A or Table 2A; $R^{3b}$ represents a hydrogen atom; and $R^{3c}$ represents an iodine atom (hereinafter referred to as "Compound group SX257").

The Compound (L-1), wherein Q represents the group represented by Q20; $R^{1b}$ represents any one substituent described in Table 1A or Table 2A; $R^{3b}$ represents a hydrogen atom; and $R^{3c}$ represents an iodine atom (hereinafter referred to as "Compound group SX258").

The Compound (L-1), wherein Q represents the group represented by Q21; $R^{1b}$ represents any one substituent described in Table 1A or Table 2A; $R^{3b}$ represents a hydrogen atom; and $R^{3c}$ represents an iodine atom (hereinafter referred to as "Compound group SX259").

The Compound (L-1), wherein Q represents the group represented by Q22; $R^{1b}$ represents any one substituent described in Table 1A or Table 2A; $R^{3b}$ represents a hydrogen atom; and $R^{3c}$ represents an iodine atom (hereinafter referred to as "Compound group SX260").

The Compound (L-1), wherein Q represents the group represented by Q23; $R^{1b}$ represents any one substituent described in Table 1A or Table 2A; $R^{3b}$ represents a hydrogen atom; and $R^{3c}$ represents an iodine atom (hereinafter referred to as "Compound group SX261").

The Compound (L-1), wherein Q represents the group represented by Q24; $R^{1b}$ represents any one substituent described in Table 1A or Table 2A; $R^{3b}$ represents a hydrogen atom; and $R^{3c}$ represents an iodine atom (hereinafter referred to as "Compound group SX262").

The Compound (L-1), wherein Q represents the group represented by Q25; $R^{1b}$ represents any one substituent described in Table 1A or Table 2A; $R^{3b}$ represents a hydrogen atom; and $R^{3c}$ represents an iodine atom (hereinafter referred to as "Compound group SX263").

The Compound (L-1), wherein Q represents the group represented by Q26; $R^{1b}$ represents any one substituent described in Table 1A or Table 2A; $R^{3b}$ represents a hydrogen atom; and $R^{3c}$ represents an iodine atom (hereinafter referred to as "Compound group SX264").

The Compound (L-1), wherein Q represents the group represented by Q27; $R^{1a}$ represents a hydrogen atom; $R^{1b}$ represents any one substituent described in Table 1A or Table 2A; $R^{3b}$ represents a hydrogen atom; and $R^{3c}$ represents an iodine atom (hereinafter referred to as "Compound group SX265").

The Compound (L-1), wherein Q represents the group represented by Q27; $R^{1a}$ represents any one substituent described in Table 1A or Table 2A; $R^{1b}$ represents a hydrogen atom; $R^{3b}$ represents a hydrogen atom; and $R^{3c}$ represents an iodine atom (hereinafter referred to as "Compound group SX266").

The Compound (L-1), wherein Q represents the group represented by Q28; $R^{1a}$ represents a hydrogen atom; $R^{1b}$ represents any one substituent described in Table 1A or Table 2A; $R^{3b}$ represents a hydrogen atom; and $R^{3c}$ represents an iodine atom (hereinafter referred to as "Compound group SX267").

The Compound (L-1), wherein Q represents the group represented by Q28; $R^{1a}$ represents any one substituent described in Table 1A or Table 2A; $R^{1b}$ represents a hydrogen atom; $R^{3b}$ represents a hydrogen atom; and $R^{3c}$ represents an iodine atom (hereinafter referred to as "Compound group SX268").

The Compound (L-1), wherein Q represents the group represented by Q29; $R^{1b}$ represents any one substituent described in Table 1A or Table 2A; $R^{3b}$ represents a hydrogen atom; and $R^{3c}$ represents an iodine atom (hereinafter referred to as "Compound group SX269").

The Compound (L-1), wherein Q represents the group represented by Q30; $R^{1b}$ represents any one substituent described in Table 1A or Table 2A; $R^{3b}$ represents a hydrogen atom; and $R^{3c}$ represents an iodine atom (hereinafter referred to as "Compound group SX270").

A compound represented by formula (L-2):

(L2)

(hereinafter referred to as "Compound (L-2)"), wherein Q represents the group represented by Q11; $R^{1a}$ represents a hydrogen atom; $R^{1b}$ represents any one substituent described in Table 1A or Table 2A; $R^{3b}$ represents a hydrogen atom; and $R^{3c}$ represents a hydrogen atom (hereinafter referred to as "Compound group SX271").

The Compound (L-2), wherein Q represents the group represented by Q11; $R^{1a}$ represents any one substituent described in Table 1A or Table 2A; $R^{1b}$ represents a hydrogen atom; $R^{3b}$ represents a hydrogen atom; and $R^{3c}$ represents a hydrogen atom (hereinafter referred to as "Compound group SX272").

The Compound (L-2), wherein Q represents the group represented by Q12; $R^{1a}$ represents a hydrogen atom; $R^{1b}$ represents any one substituent described in Table 1A or Table 2A; $R^{3b}$ represents a hydrogen atom; and $R^{3c}$ represents a hydrogen atom (hereinafter referred to as "Compound group SX273").

The Compound (L-2), wherein Q represents the group represented by Q12; $R^{1a}$ represents any one substituent described in Table 1A or Table 2A; $R^{1b}$ represents a hydrogen atom; $R^{3b}$ represents a hydrogen atom; and $R^{3c}$ represents a hydrogen atom (hereinafter referred to as "Compound group SX274").

The Compound (L-2), wherein Q represents the group represented by Q13; $R^{1a}$ represents a hydrogen atom; $R^{1b}$ represents any one substituent described in Table 1A or Table 2A; $R^{3b}$ represents a hydrogen atom; and $R^{3c}$ represents a hydrogen atom (hereinafter referred to as "Compound group SX275").

The Compound (L-2), wherein Q represents the group represented by Q13; $R^{1a}$ represents any one substituent described in Table 1A or Table 2A; $R^{1b}$ represents a hydrogen atom; $R^{3b}$ represents a hydrogen atom; and $R^{3c}$ represents a hydrogen atom (hereinafter referred to as "Compound group SX276").

The Compound (L-2), wherein Q represents the group represented by Q14; $R^{1a}$ represents a hydrogen atom; $R^{1b}$ represents any one substituent described in Table 1A or Table 2A; $R^{3b}$ represents a hydrogen atom; and $R^{3c}$ represents a hydrogen atom (hereinafter referred to as "Compound group SX277").

The Compound (L-2), wherein Q represents the group represented by Q14; $R^{1a}$ represents any one substituent described in Table 1A or Table 2A; $R^{1b}$ represents a hydrogen atom; $R^{3b}$ represents a hydrogen atom; and $R^{3c}$ represents a hydrogen atom (hereinafter referred to as "Compound group SX278").

The Compound (L-2), wherein Q represents the group represented by Q15; $R^{1a}$ represents a hydrogen atom; $R^{1b}$ represents any one substituent described in Table 1A or Table 2A; $R^{3b}$ represents a hydrogen atom; and $R^{3c}$ represents a hydrogen atom (hereinafter referred to as "Compound group SX279").

The Compound (L-2), wherein Q represents the group represented by Q15; $R^{1a}$ represents any one substituent described in Table 1A or Table 2A; $R^{1b}$ represents a hydrogen atom; $R^{3b}$ represents a hydrogen atom; and $R^{3c}$ represents a hydrogen atom (hereinafter referred to as "Compound group SX280").

The Compound (L-2), wherein Q represents the group represented by Q16; $R^{1a}$ represents a hydrogen atom; $R^{1b}$ represents any one substituent described in Table 1A or Table 2A; $R^{3b}$ represents a hydrogen atom; and $R^{3c}$ represents a hydrogen atom (hereinafter referred to as "Compound group SX281").

The Compound (L-2), wherein Q represents the group represented by Q16; $R^{1a}$ represents any one substituent described in Table 1A or Table 2A; $R^{1b}$ represents a hydrogen atom; $R^{3b}$ represents a hydrogen atom; and $R^{3c}$ represents a hydrogen atom (hereinafter referred to as "Compound group SX282").

The Compound (L-2), wherein Q represents the group represented by Q17; $R^{1a}$ represents a hydrogen atom; $R^{1b}$ represents any one substituent described in Table 1A or Table 2A; $R^{3b}$ represents a hydrogen atom; and $R^{3c}$ represents a hydrogen atom (hereinafter referred to as "Compound group SX283").

The Compound (L-2), wherein Q represents the group represented by Q17; $R^{1a}$ represents any one substituent described in Table 1A or Table 2A; $R^{1b}$ represents a hydrogen atom; $R^{3b}$ represents a hydrogen atom; and $R^{3c}$ represents a hydrogen atom (hereinafter referred to as "Compound group SX284").

The Compound (L-2), wherein Q represents the group represented by Q18; $R^{1a}$ represents a hydrogen atom; $R^{1b}$ represents any one substituent described in Table 1A or Table 2A; $R^{3b}$ represents a hydrogen atom; and $R^{3c}$ represents a hydrogen atom (hereinafter referred to as "Compound group SX285").

The Compound (L-2), wherein Q represents the group represented by Q18; $R^{1a}$ represents any one substituent described in Table 1A or Table 2A; $R^{1b}$ represents a hydrogen atom; $R^{3b}$ represents a hydrogen atom; and $R^{3c}$ represents a hydrogen atom (hereinafter referred to as "Compound group SX286").

The Compound (L-2), wherein Q represents the group represented by Q19; $R^{1b}$ represents any one substituent described in Table 1A or Table 2A; $R^{3b}$ represents a hydrogen atom; and $R^{3c}$ represents a hydrogen atom (hereinafter referred to as "Compound group SX287").

The Compound (L-2), wherein Q represents the group represented by Q20; $R^{1b}$ represents any one substituent described in Table 1A or Table 2A; $R^{3b}$ represents a hydrogen atom; and $R^{3c}$ represents a hydrogen atom (hereinafter referred to as "Compound group SX288").

The Compound (L-2), wherein Q represents the group represented by Q21; $R^{1b}$ represents any one substituent described in Table 1A or Table 2A; $R^{3b}$ represents a hydrogen atom; and $R^{3c}$ represents a hydrogen atom (hereinafter referred to as "Compound group SX289").

The Compound (L-2), wherein Q represents the group represented by Q22; $R^{1b}$ represents any one substituent described in Table 1A or Table 2A; $R^{3b}$ represents a hydrogen atom; and $R^{3c}$ represents a hydrogen atom (hereinafter referred to as "Compound group SX290").

The Compound (L-2), wherein Q represents the group represented by Q23; $R^{1b}$ represents any one substituent described in Table 1A or Table 2A; $R^{3b}$ represents a hydrogen atom; and $R^{3c}$ represents a hydrogen atom (hereinafter referred to as "Compound group SX291").

The Compound (L-2), wherein Q represents the group represented by Q24; $R^{1b}$ represents any one substituent described in Table 1A or Table 2A; $R^{3b}$ represents a hydrogen atom; and $R^{3c}$ represents a hydrogen atom (hereinafter referred to as "Compound group SX292").

The Compound (L-2), wherein Q represents the group represented by Q25; $R^{1b}$ represents any one substituent described in Table 1A or Table 2A; $R^{3b}$ represents a hydrogen atom; and $R^{3c}$ represents a hydrogen atom (hereinafter referred to as "Compound group SX293").

The Compound (L-2), wherein Q represents the group represented by Q26; $R^{1b}$ represents any one substituent described in Table 1A or Table 2A; $R^{3b}$ represents a hydrogen atom; and $R^{3c}$ represents a hydrogen atom (hereinafter referred to as "Compound group SX294").

The Compound (L-2), wherein Q represents the group represented by Q27; $R^{1a}$ represents a hydrogen atom; $R^{1b}$ represents any one substituent described in Table 1A or Table 2A; $R^{3b}$ represents a hydrogen atom; and $R^{3c}$ represents a hydrogen atom (hereinafter referred to as "Compound group SX295").

The Compound (L-2), wherein Q represents the group represented by Q27; $R^{1a}$ represents any one substituent described in Table 1A or Table 2A; $R^{1b}$ represents a hydrogen atom; $R^{3b}$ represents a hydrogen atom; and $R^{3c}$ represents a hydrogen atom (hereinafter referred to as "Compound group SX296").

The Compound (L-2), wherein Q represents the group represented by Q28; $R^{1a}$ represents a hydrogen atom; $R^{1b}$ represents any one substituent described in Table 1A or Table 2A; $R^{3b}$ represents a hydrogen atom; and $R^{3c}$ represents a hydrogen atom (hereinafter referred to as "Compound group SX297").

The Compound (L-2), wherein Q represents the group represented by Q28; $R^{1a}$ represents any one substituent described in Table 1A or Table 2A; $R^{1b}$ represents a hydrogen atom; $R^{3b}$ represents a hydrogen atom; and $R^{3c}$ represents a hydrogen atom (hereinafter referred to as "Compound group SX298").

The Compound (L-2), wherein Q represents the group represented by Q29; $R^{1b}$ represents any one substituent described in Table 1A or Table 2A; $R^{3b}$ represents a hydrogen atom; and $R^{3c}$ represents a hydrogen atom (hereinafter referred to as "Compound group SX299").

The Compound (L-2), wherein Q represents the group represented by Q30; $R^{1b}$ represents any one substituent described in Table 1A or Table 2A; $R^{3b}$ represents a hydrogen atom; and $R^{3c}$ represents a hydrogen atom (hereinafter referred to as "Compound group SX300").

The Compound (L-2), wherein Q represents the group represented by Q11; $R^{1a}$ represents a hydrogen atom; $R^{1b}$ represents any one substituent described in Table 1A or Table 2A; $R^{3b}$ represents a trifluoromethyl group; and $R^{3c}$ represents a hydrogen atom (hereinafter referred to as "Compound group SX301").

The Compound (L-2), wherein Q represents the group represented by Q11; $R^{1a}$ represents any one substituent described in Table 1A or Table 2A; $R^{1b}$ represents a hydrogen atom; $R^{3b}$ represents a trifluoromethyl group; and $R^{3c}$ represents a hydrogen atom (hereinafter referred to as "Compound group SX302").

The Compound (L-2), wherein Q represents the group represented by Q12; $R^{1a}$ represents a hydrogen atom; $R^{1b}$ represents any one substituent described in Table 1A or Table 2A; $R^{3b}$ represents a trifluoromethyl group; and $R^{3c}$ represents a hydrogen atom (hereinafter referred to as "Compound group SX303").

The Compound (L-2), wherein Q represents the group represented by Q12; $R^{1a}$ represents any one substituent described in Table 1A or Table 2A; $R^{1b}$ represents a hydrogen atom; $R^{3b}$ represents a trifluoromethyl group; and $R^{3c}$ represents a hydrogen atom (hereinafter referred to as "Compound group SX304").

The Compound (L-2), wherein Q represents the group represented by Q13; $R^{1a}$ represents a hydrogen atom; $R^{1b}$ represents any one substituent described in Table 1A of Table 2A; $R^{3b}$ represents a trifluoromethyl group; and $R^{3c}$ represents a hydrogen atom (hereinafter referred to as "Compound group SX305").

The Compound (L-2), wherein Q represents the group represented by Q13; $R^{1a}$ represents any one substituent described in Table 1A or Table 2A; $R^{1b}$ represents a hydrogen atom; $R^{3b}$ represents a trifluoromethyl group; and $R^{3c}$ represents a hydrogen atom (hereinafter referred to as "Compound group SX306").

The Compound (L-2), wherein Q represents the group represented by Q14; $R^{1a}$ represents a hydrogen atom; $R^{1b}$ represents any one substituent described in Table 1A or Table 2A; $R^{3b}$ represents a trifluoromethyl group; and $R^{3c}$ represents a hydrogen atom (hereinafter referred to as "Compound group SX307").

The Compound (L-2), wherein Q represents the group represented by Q14; $R^{1a}$ represents any one substituent described in Table 1A or Table 2A; $R^{1b}$ represents a hydrogen atom; $R^{3b}$ represents a trifluoromethyl group; and $R^{3c}$ represents a hydrogen atom (hereinafter referred to as "Compound group SX308").

The Compound (L-2), wherein Q represents the group represented by Q15; $R^{1a}$ represents a hydrogen atom; $R^{1b}$ represents any one substituent described in Table 1A or Table 2A; $R^{3b}$ represents a trifluoromethyl group; and $R^{3c}$ represents a hydrogen atom (hereinafter referred to as "Compound group SX309").

The Compound (L-2), wherein Q represents the group represented by Q15; $R^{1a}$ represents any one substituent described in Table 1A or Table 2A; $R^{1b}$ represents a hydrogen atom; $R^{3b}$ represents a trifluoromethyl group; and $R^{3c}$ represents a hydrogen atom (hereinafter referred to as "Compound group SX310").

The Compound (L-2), wherein Q represents the group represented by Q16; $R^{1a}$ represents a hydrogen atom; $R^{1b}$ represents any one substituent described in Table 1A or Table 2A; $R^{3b}$ represents a trifluoromethyl group; and $R^{3c}$ represents a hydrogen atom (hereinafter referred to as "Compound group SX311").

The Compound (L-2), wherein Q represents the group represented by Q16; $R^{1a}$ represents any one substituent described in Table 1A or Table 2A; $R^{1b}$ represents a hydrogen atom; $R^{3b}$ represents a trifluoromethyl group; and $R^{3c}$ represents a hydrogen atom (hereinafter referred to as "Compound group SX312").

The Compound (L-2), wherein Q represents the group represented by Q17; $R^{1a}$ represents a hydrogen atom; $R^{1b}$ represents any one substituent described in Table 1A or Table 2A; $R^{3b}$ represents a trifluoromethyl group; and $R^{3c}$ represents a hydrogen atom (hereinafter referred to as "Compound group SX313").

The Compound (L-2), wherein Q represents the group represented by Q17; $R^{1a}$ represents any one substituent described in Table 1A or Table 2A; $R^{1b}$ represents a hydrogen atom; $R^{3b}$ represents a trifluoromethyl group; and $R^{3c}$ represents a hydrogen atom (hereinafter referred to as "Compound group SX314").

The Compound (L-2), wherein Q represents the group represented by Q18; $R^{1a}$ represents a hydrogen atom; $R^{1b}$ represents any one substituent described in Table 1A or Table 2A; $R^{3b}$ represents a trifluoromethyl group; and $R^{3c}$ represents a hydrogen atom (hereinafter referred to as "Compound group SX315").

The Compound (L-2), wherein Q represents the group represented by Q18; $R^{1a}$ represents any one substituent described in Table 1A or Table 2A; $R^{1b}$ represents a hydrogen atom; $R^{3b}$ represents a trifluoromethyl group; and $R^{3c}$ represents a hydrogen atom (hereinafter referred to as "Compound group SX316").

The Compound (L-2), wherein Q represents the group represented by Q19; $R^{1b}$ represents any one substituent described in Table 1A or Table 2A; $R^{3b}$ represents a trifluoromethyl group; and $R^{3c}$ represents a hydrogen atom (hereinafter referred to as "Compound group SX317").

The Compound (L-2), wherein Q represents the group represented by Q20; $R^{1b}$ represents any one substituent described in Table 1A or Table 2A; $R^{3b}$ represents a trifluoromethyl group; and $R^{3c}$ represents a hydrogen atom (hereinafter referred to as "Compound group SX318").

The Compound (L-2), wherein Q represents the group represented by Q21; $R^{1b}$ represents any one substituent described in Table 1A or Table 2A; $R^{3b}$ represents a trifluoromethyl group; and $R^{3c}$ represents a hydrogen atom (hereinafter referred to as "Compound group SX319").

The Compound (L-2), wherein Q represents the group represented by Q22; $R^{1b}$ represents any one substituent described in Table 1A or Table 2A; $R^{3b}$ represents a trifluoromethyl group; and $R^{3c}$ represents a hydrogen atom (hereinafter referred to as "Compound group SX320").

The Compound (L-2), wherein Q represents the group represented by Q23; $R^{1b}$ represents any one substituent described in Table 1A or Table 2A; $R^{3b}$ represents a trifluoromethyl group; and $R^{3c}$ represents a hydrogen atom (hereinafter referred to as "Compound group SX321").

The Compound (L-2), wherein Q represents the group represented by Q24; $R^{1b}$ represents any one substituent described in Table 1A or Table 2A; $R^{3b}$ represents a trifluoromethyl group; and $R^{3c}$ represents a hydrogen atom (hereinafter referred to as "Compound group SX322").

The Compound (L-2), wherein Q represents the group represented by Q25; $R^{1b}$ represents any one substituent described in Table 1A or Table 2A; $R^{3b}$ represents a trifluoromethyl group; and $R^{3c}$ represents a hydrogen atom (hereinafter referred to as "Compound group SX323").

The Compound (L-2), wherein Q represents the group represented by Q26; $R^{1b}$ represents any one substituent described in Table 1A or Table 2A; $R^{3b}$ represents a trifluoromethyl group; and $R^{3c}$ represents a hydrogen atom (hereinafter referred to as "Compound group SX324").

The Compound (L-2), wherein Q represents the group represented by Q27; $R^{1a}$ represents a hydrogen atom; $R^{1b}$ represents any one substituent described in Table 1A or Table 2A; $R^{3b}$ represents a trifluoromethyl group; and $R^{3c}$ represents a hydrogen atom (hereinafter referred to as "Compound group SX325").

The Compound (L-2), wherein Q represents the group represented by Q27; $R^{1a}$ represents any one substituent described in Table 1A or Table 2A; $R^{1b}$ represents a hydrogen atom; $R^{3b}$ represents a trifluoromethyl group; and $R^{3c}$ represents a hydrogen atom (hereinafter referred to as "Compound group SX326").

The Compound (L-2), wherein Q represents the group represented by Q28; $R^{1a}$ represents a hydrogen atom; $R^{1b}$ represents any one substituent described in Table 1A or Table 2A; $R^{3b}$ represents a trifluoromethyl group; and $R^{3c}$ represents a hydrogen atom (hereinafter referred to as "Compound group SX327").

The Compound (L-2), wherein Q represents the group represented by Q28; $R^{1a}$ represents any one substituent described in Table 1A or Table 2A; $R^{1b}$ represents a hydrogen atom; $R^{3b}$ represents a trifluoromethyl group; and $R^{3c}$ represents a hydrogen atom (hereinafter referred to as "Compound group SX328").

The Compound (L-2), wherein Q represents the group represented by Q29; $R^{1b}$ represents any one substituent described in Table 1A or Table 2A; $R^{3b}$ represents a trifluoromethyl group; and $R^{3c}$ represents a hydrogen atom (hereinafter referred to as "Compound group SX329").

The Compound (L-2), wherein Q represents the group represented by Q30; $R^{1b}$ represents any one substituent described in Table 1A or Table 2A; $R^{3b}$ represents a trifluoromethyl group; and $R^{3c}$ represents a hydrogen atom (hereinafter referred to as "Compound group SX330").

The Compound (L-2), wherein Q represents the group represented by Q11; $R^{1a}$ represents a hydrogen atom; $R^{1b}$ represents any one substituent described in Table 1A or Table 2A; $R^{3b}$ represents a chlorine atom; and $R^{3c}$ represents a hydrogen atom (hereinafter referred to as "Compound group SX331").

The Compound (L-2), wherein Q represents the group represented by Q11; $R^{1a}$ represents any one substituent described in Table 1A or Table 2A; $R^{1b}$ represents a hydrogen atom; $R^{3b}$ represents a chlorine atom; and $R^{3c}$ represents a hydrogen atom (hereinafter referred to as "Compound group SX332").

The Compound (L-2), wherein Q represents the group represented by Q12; $R^{1a}$ represents a hydrogen atom; $R^{1b}$ represents any one substituent described in Table 1A or Table 2A; $R^{3b}$ represents a chlorine atom; and $R^{3c}$ represents a hydrogen atom (hereinafter referred to as "Compound group SX333").

The Compound (L-2), wherein Q represents the group represented by Q12; $R^{1a}$ represents any one substituent described in Table 1A or Table 2A; $R^{1b}$ represents a hydrogen atom; $R^{3b}$ represents a chlorine atom; and $R^{3c}$ represents a hydrogen atom (hereinafter referred to as "Compound group SX334").

The Compound (L-2), wherein Q represents the group represented by Q13; $R^{1a}$ represents a hydrogen atom; $R^{1b}$ represents any one substituent described in Table 1A or Table 2A; $R^{3b}$ represents a chlorine atom; and $R^{3c}$ represents a hydrogen atom (hereinafter referred to as "Compound group SX335").

The Compound (L-2), wherein Q represents the group represented by Q13; $R^{1a}$ represents any one substituent described in Table 1A or Table 2A; $R^{1b}$ represents a hydrogen atom; $R^{3b}$ represents a chlorine atom; and $R^{3c}$ represents a hydrogen atom (hereinafter referred to as "Compound group SX336").

The Compound (L-2), wherein Q represents the group represented by Q14; $R^{1a}$ represents a hydrogen atom; $R^{1b}$ represents any one substituent described in Table 1A or Table 2A; $R^{3b}$ represents a chlorine atom; and $R^{3c}$ represents a hydrogen atom (hereinafter referred to as "Compound group SX337").

The Compound (L-2), wherein Q represents the group represented by Q14; $R^{1a}$ represents any one substituent described in Table 1A or Table 2A; $R^{1b}$ represents a hydrogen atom; $R^{3b}$ represents a chlorine atom; and $R^{3c}$ represents a hydrogen atom (hereinafter referred to as "Compound group SX338").

The Compound (L-2), wherein Q represents the group represented by Q15; $R^{1a}$ represents a hydrogen atom; $R^{1b}$ represents any one substituent described in Table 1A or Table 2A; $R^{3b}$ represents a chlorine atom; and $R^{3c}$ represents a hydrogen atom (hereinafter referred to as "Compound group SX339").

The Compound (L-2), wherein Q represents the group represented by Q15; $R^{1a}$ represents any one substituent described in Table 1A or Table 2A; $R^{1b}$ represents a hydrogen atom; $R^{3b}$ represents a chlorine atom; and $R^{3c}$ represents a hydrogen atom (hereinafter referred to as "Compound group SX340").

The Compound (L-2), wherein Q represents the group represented by Q16; $R^{1a}$ represents a hydrogen atom; $R^{1b}$ represents any one substituent described in Table 1A or Table 2A; $R^{3b}$ represents a chlorine atom; and $R^{3c}$ represents a hydrogen atom (hereinafter referred to as "Compound group SX341").

The Compound (L-2), wherein Q represents the group represented by Q16; $R^{1a}$ represents any one substituent described in Table 1A or Table 2A; $R^{1b}$ represents a hydrogen atom; $R^{3b}$ represents a chlorine atom; and $R^{3c}$ represents a hydrogen atom (hereinafter referred to as "Compound group SX342").

The Compound (L-2), wherein Q represents the group represented by Q17; $R^{1a}$ represents a hydrogen atom; $R^{1b}$ represents any one substituent described in Table 1A or Table 2A; $R^{3b}$ represents a chlorine atom; and $R^{3c}$ represents a hydrogen atom (hereinafter referred to as "Compound group SX343").

The Compound (L-2), wherein Q represents the group represented by Q17; $R^{1a}$ represents any one substituent described in Table 1A or Table 2A; $R^{1b}$ represents a hydrogen atom; $R^{3b}$ represents a chlorine atom; and $R^{3c}$ represents a hydrogen atom (hereinafter referred to as "Compound group SX344").

The Compound (L-2), wherein Q represents the group represented by Q18; $R^{1a}$ represents a hydrogen atom; $R^{1b}$ represents any one substituent described in Table 1A or Table 2A; $R^{3b}$ represents a chlorine atom; and $R^{3c}$ represents a hydrogen atom (hereinafter referred to as "Compound group SX345").

The Compound (L-2), wherein Q represents the group represented by Q18; $R^{1a}$ represents any one substituent described in Table 1A or Table 2A; $R^{1b}$ represents a hydrogen atom; $R^{3b}$ represents a chlorine atom; and $R^{3c}$ represents a hydrogen atom (hereinafter referred to as "Compound group SX346").

The Compound (L-2), wherein Q represents the group represented by Q19; $R^{1b}$ represents any one substituent described in Table 1A or Table 2A; $R^{3b}$ represents a chlorine atom; and $R^{3c}$ represents a hydrogen atom (hereinafter referred to as "Compound group SX347").

The Compound (L-2), wherein Q represents the group represented by Q20; $R^{1b}$ represents any one substituent described in Table 1A or Table 2A; $R^{3b}$ represents a chlorine atom; and $R^{3c}$ represents a hydrogen atom (hereinafter referred to as "Compound group SX348").

The Compound (L-2), wherein Q represents the group represented by Q21; $R^{1b}$ represents any one substituent described in Table 1A or Table 2A; $R^{3b}$ represents a chlorine atom; and $R^{3c}$ represents a hydrogen atom (hereinafter referred to as "Compound group SX349").

The Compound (L-2), wherein Q represents the group represented by Q22; $R^{1b}$ represents any one substituent described in Table 1A or Table 2A; $R^{3b}$ represents a chlorine atom; and $R^{3c}$ represents a hydrogen atom (hereinafter referred to as "Compound group SX350").

The Compound (L-2), wherein Q represents the group represented by Q23; $R^{1b}$ represents any one substituent described in Table 1A or Table 2A; $R^{3b}$ represents a chlorine atom; and $R^{3c}$ represents a hydrogen atom (hereinafter referred to as "Compound group SX351").

The Compound (L-2), wherein Q represents the group represented by Q24; $R^{1b}$ represents any one substituent described in Table 1A or Table 2A; $R^{3b}$ represents a chlorine atom; and $R^{3c}$ represents a hydrogen atom (hereinafter referred to as "Compound group SX352").

The Compound (L-2), wherein Q represents the group represented by Q25; $R^{1b}$ represents any one substituent described in Table 1A or Table 2A; $R^{3b}$ represents a chlorine atom; and $R^{3c}$ represents a hydrogen atom (hereinafter referred to as "Compound group SX353").

The Compound (L-2), wherein Q represents the group represented by Q26; $R^{1b}$ represents any one substituent described in Table 1A or Table 2A; $R^{3b}$ represents a chlorine atom; and $R^{3c}$ represents a hydrogen atom (hereinafter referred to as "Compound group SX354").

The Compound (L-2), wherein Q represents the group represented by Q27; $R^{1a}$ represents a hydrogen atom; $R^{1b}$ represents any one substituent described in Table 1A or Table 2A; $R^{3b}$ represents a chlorine atom; and $R^{3c}$ represents a hydrogen atom (hereinafter referred to as "Compound group SX355").

The Compound (L-2), wherein Q represents the group represented by Q27; $R^{1a}$ represents any one substituent described in Table 1A or Table 2A; $R^{1b}$ represents a hydrogen atom; $R^{3b}$ represents a chlorine atom; and $R^{3c}$ represents a hydrogen atom (hereinafter referred to as "Compound group SX356").

The Compound (L-2), wherein Q represents the group represented by Q28; $R^{1a}$ represents a hydrogen atom; $R^{1b}$ represents any one substituent described in Table 1A or Table 2A; $R^{3b}$ represents a chlorine atom; and $R^{3c}$ represents a hydrogen atom (hereinafter referred to as "Compound group SX357").

The Compound (L-2), wherein Q represents the group represented by Q28; $R^{1a}$ represents any one substituent described in Table 1A or Table 2A; $R^{1b}$ represents a hydrogen atom; $R^{3b}$ represents a chlorine atom; and $R^{3c}$ represents a hydrogen atom (hereinafter referred to as "Compound group SX358").

The Compound (L-2), wherein Q represents the group represented by Q29; $R^{1b}$ represents any one substituent described in Table 1A or Table 2A; $R^{3b}$ represents a chlorine atom; and $R^{3c}$ represents a hydrogen atom (hereinafter referred to as "Compound group SX359").

The Compound (L-2), wherein Q represents the group represented by Q30; $R^{1b}$ represents any one substituent described in Table 1A or Table 2A; $R^{3b}$ represents a chlorine atom; and $R^{3c}$ represents a hydrogen atom (hereinafter referred to as "Compound group SX360").

The Compound (L-2), wherein Q represents the group represented by Q11; $R^{1a}$ represents a hydrogen atom; $R^{1b}$ represents any one substituent described in Table 1A or Table 2A; $R^{3b}$ represents a bromine atom; and $R^{3c}$ represents a hydrogen atom (hereinafter referred to as "Compound group SX361").

The Compound (L-2), wherein Q represents the group represented by Q11; $R^{1a}$ represents any one substituent described in Table 1A or Table 2A; $R^{1b}$ represents a hydrogen atom; $R^{3b}$ represents a bromine atom; and $R^{3c}$ represents a hydrogen atom (hereinafter referred to as "Compound group SX362").

The Compound (L-2), wherein Q represents the group represented by Q12; $R^{1a}$ represents a hydrogen atom; $R^{1b}$ represents any one substituent described in Table 1A or Table 2A; $R^{3b}$ represents a bromine atom; and $R^{3c}$ represents a hydrogen atom (hereinafter referred to as "Compound group SX363").

The Compound (L-2), wherein Q represents the group represented by Q12; $R^{1a}$ represents any one substituent described in Table 1A or Table 2A; $R^{1b}$ represents a hydrogen atom; $R^{3b}$ represents a bromine atom; and $R^{3c}$ represents a hydrogen atom (hereinafter referred to as "Compound group SX364").

The Compound (L-2), wherein Q represents the group represented by Q13; $R^{1a}$ represents a hydrogen atom; $R^{1b}$ represents any one substituent described in Table 1A or Table 2A; $R^{3b}$ represents a bromine atom; and $R^{3c}$ represents a hydrogen atom (hereinafter referred to as "Compound group SX365").

The Compound (L-2), wherein Q represents the group represented by Q13; $R^{1a}$ represents any one substituent described in Table 1A or Table 2A; $R^{1b}$ represents a hydrogen atom; $R^{3b}$ represents a bromine atom; and $R^{3c}$ represents a hydrogen atom (hereinafter referred to as "Compound group SX366").

The Compound (L-2), wherein Q represents the group represented by Q14; $R^{1a}$ represents a hydrogen atom; $R^{1b}$ represents any one substituent described in Table 1A or Table 2A; $R^{3b}$ represents a bromine atom; and $R^{3c}$ represents a hydrogen atom (hereinafter referred to as "Compound group SX367").

The Compound (L-2), wherein Q represents the group represented by Q14; $R^{1a}$ represents any one substituent described in Table 1A or Table 2A; $R^{1b}$ represents a hydrogen atom; $R^{3b}$ represents a bromine atom; and $R^{3c}$ represents a hydrogen atom (hereinafter referred to as "Compound group SX368").

The Compound (L-2), wherein Q represents the group represented by Q15; $R^{1a}$ represents a hydrogen atom; $R^{1b}$ represents any one substituent described in Table 1A or Table 2A; $R^{3b}$ represents a bromine atom; and $R^{3c}$ represents a hydrogen atom (hereinafter referred to as "Compound group SX369").

The Compound (L-2), wherein Q represents the group represented by Q15; $R^{1a}$ represents any one substituent described in Table 1A or Table 2A; $R^{1b}$ represents a hydrogen atom; $R^{3b}$ represents a bromine atom; and $R^{3c}$ represents a hydrogen atom (hereinafter referred to as "Compound group SX370").

The Compound (L-2), wherein Q represents the group represented by Q16; $R^{1a}$ represents a hydrogen atom; $R^{1b}$ represents any one substituent described in Table 1A or Table 2A; $R^{3b}$ represents a bromine atom; and $R^{3c}$ represents a hydrogen atom (hereinafter referred to as "Compound group SX371").

The Compound (L-2), wherein Q represents the group represented by Q16; $R^{1a}$ represents any one substituent described in Table 1A or Table 2A; $R^{1b}$ represents a hydrogen atom; $R^{3b}$ represents a bromine atom; and $R^{3c}$ represents a hydrogen atom (hereinafter referred to as "Compound group SX372").

The Compound (L-2), wherein Q represents the group represented by Q17; $R^{1a}$ represents a hydrogen atom; $R^{1b}$ represents any one substituent described in Table 1A or Table 2A; $R^{3b}$ represents a bromine atom; and $R^{3c}$ represents a hydrogen atom (hereinafter referred to as "Compound group SX373").

The Compound (L-2), wherein Q represents the group represented by Q17; $R^{1a}$ represents any one substituent described in Table 1A or Table 2A; $R^{1b}$ represents a hydrogen atom; $R^{3b}$ represents a bromine atom; and $R^{3c}$ represents a hydrogen atom (hereinafter referred to as "Compound group SX374").

The Compound (L-2), wherein Q represents the group represented by Q18; $R^{1a}$ represents a hydrogen atom; $R^{1b}$ represents any one substituent described in Table 1A or Table 2A; $R^{3b}$ represents a bromine atom; and $R^{3c}$ represents a hydrogen atom (hereinafter referred to as "Compound group SX375").

The Compound (L-2), wherein Q represents the group represented by Q18; $R^{1a}$ represents any one substituent described in Table 1A or Table 2A; $R^{1b}$ represents a hydrogen atom; $R^{3b}$ represents a bromine atom; and $R^{3c}$ represents a hydrogen atom (hereinafter referred to as "Compound group SX376").

The Compound (L-2), wherein Q represents the group represented by Q19; $R^{1b}$ represents any one substituent described in Table 1A or Table 2A; $R^{3b}$ represents a bromine atom; and $R^{3c}$ represents a hydrogen atom (hereinafter referred to as "Compound group SX377").

The Compound (L-2), wherein Q represents the group represented by Q20; $R^{1b}$ represents any one substituent described in Table 1A or Table 2A; $R^{3b}$ represents a bromine atom; and $R^{3c}$ represents a hydrogen atom (hereinafter referred to as "Compound group SX378").

The Compound (L-2), wherein Q represents the group represented by Q21; $R^{1b}$ represents any one substituent described in Table 1A or Table 2A; $R^{3b}$ represents a bromine atom; and $R^{3c}$ represents a hydrogen atom (hereinafter referred to as "Compound group SX379").

The Compound (L-2), wherein Q represents the group represented by Q22; $R^{1b}$ represents any one substituent described in Table 1A or Table 2A; $R^{3b}$ represents a bromine atom; and $R^{3c}$ represents a hydrogen atom (hereinafter referred to as "Compound group SX380").

The Compound (L-2), wherein Q represents the group represented by Q23; $R^{1b}$ represents any one substituent described in Table 1A or Table 2A; $R^{3b}$ represents a bromine atom; and $R^{3c}$ represents a hydrogen atom (hereinafter referred to as "Compound group SX381").

The Compound (L-2), wherein Q represents the group represented by Q24; $R^{1b}$ represents any one substituent described in Table 1A or Table 2A; $R^{3b}$ represents a bromine atom; and $R^{3c}$ represents a hydrogen atom (hereinafter referred to as "Compound group SX382").

The Compound (L-2), wherein Q represents the group represented by Q25; $R^{1b}$ represents any one substituent described in Table 1A or Table 2A; $R^{3b}$ represents a bromine atom; and $R^{3c}$ represents a hydrogen atom (hereinafter referred to as "Compound group SX383").

The Compound (L-2), wherein Q represents the group represented by Q26; $R^{1b}$ represents any one substituent described in Table 1A or Table 2A; $R^{3b}$ represents a bromine atom; and $R^{3c}$ represents a hydrogen atom (hereinafter referred to as "Compound group SX384").

The Compound (L-2), wherein Q represents the group represented by Q27; $R^{1a}$ represents a hydrogen atom; $R^{1b}$ represents any one substituent described in Table 1A or Table 2A; $R^{3b}$ represents a bromine atom; and $R^{3c}$ represents a hydrogen atom (hereinafter referred to as "Compound group SX385").

The Compound (L-2), wherein Q represents the group represented by Q27; $R^{1a}$ represents any one substituent described in Table 1A or Table 2A; $R^{1b}$ represents a hydrogen atom; $R^{3b}$ represents a bromine atom; and $R^{3c}$ represents a hydrogen atom (hereinafter referred to as "Compound group SX386").

The Compound (L-2), wherein Q represents the group represented by Q28; $R^{1a}$ represents a hydrogen atom; $R^{1b}$ represents any one substituent described in Table 1A or Table 2A; $R^{3b}$ represents a bromine atom; and $R^{3c}$ represents a hydrogen atom (hereinafter referred to as "Compound group SX387").

The Compound (L-2), wherein Q represents the group represented by Q28; $R^{1a}$ represents any one substituent described in Table 1A or Table 2A; $R^{1b}$ represents a hydrogen atom; $R^{3b}$ represents a bromine atom; and $R^{3c}$ represents a hydrogen atom (hereinafter referred to as "Compound group SX388").

The Compound (L-2), wherein Q represents the group represented by Q29; $R^{1b}$ represents any one substituent described in Table 1A or Table 2A; $R^{3b}$ represents a bromine atom; and $R^{3c}$ represents a hydrogen atom (hereinafter referred to as "Compound group SX389").

The Compound (L-2), wherein Q represents the group represented by Q30; $R^{1b}$ represents any one substituent described in Table 1A or Table 2A; $R^{3b}$ represents a bromine atom; and $R^{3c}$ represents a hydrogen atom (hereinafter referred to as "Compound group SX390").

The Compound (L-2), wherein Q represents the group represented by Q11; $R^{1a}$ represents a hydrogen atom; $R^{1b}$ represents any one substituent described in Table 1A or Table 2A; $R^{3b}$ represents an iodine atom; and $R^{3c}$ represents a hydrogen atom (hereinafter referred to as "Compound group SX391").

The Compound (L-2), wherein Q represents the group represented by Q11; $R^{1a}$ represents any one substituent described in Table 1A or Table 2A; $R^{1b}$ represents a hydrogen atom; $R^{3b}$ represents an iodine atom; and $R^{3c}$ represents a hydrogen atom (hereinafter referred to as "Compound group SX392").

The Compound (L-2), wherein Q represents the group represented by Q12; $R^{1a}$ represents a hydrogen atom; $R^{1b}$ represents any one substituent described in Table 1A or Table 2A; $R^{3b}$ represents an iodine atom; and $R^{3c}$ represents a hydrogen atom (hereinafter referred to as "Compound group SX393").

The Compound (L-2), wherein Q represents the group represented by Q12; $R^{1a}$ represents any one substituent described in Table 1A or Table 2A; $R^{1b}$ represents a hydrogen atom; $R^{3b}$ represents an iodine atom; and $R^{3c}$ represents a hydrogen atom (hereinafter referred to as "Compound group SX394").

The Compound (L-2), wherein Q represents the group represented by Q13; $R^{1a}$ represents a hydrogen atom; $R^{1b}$ represents any one substituent described in Table 1A or Table 2A; $R^{3b}$ represents an iodine atom; and $R^{3c}$ represents a hydrogen atom (hereinafter referred to as "Compound group SX395").

The Compound (L-2), wherein Q represents the group represented by Q13; $R^{1a}$ represents any one substituent described in Table 1A or Table 2A; $R^{1b}$ represents a hydrogen atom; $R^{3b}$ represents an iodine atom; and $R^{3c}$ represents a hydrogen atom (hereinafter referred to as "Compound group SX396").

The Compound (L-2), wherein Q represents the group represented by Q14; $R^{1a}$ represents a hydrogen atom; $R^{1b}$ represents any one substituent described in Table 1A or Table 2A; $R^{3b}$ represents an iodine atom; and $R^{3c}$ represents a hydrogen atom (hereinafter referred to as "Compound group SX397").

The Compound (L-2), wherein Q represents the group represented by Q14; $R^{1a}$ represents any one substituent described in Table 1A or Table 2A; $R^{1b}$ represents a hydrogen atom; $R^{3b}$ represents an iodine atom; and $R^{3c}$ represents a hydrogen atom (hereinafter referred to as "Compound group SX398").

The Compound (L-2), wherein Q represents the group represented by Q15; $R^{1a}$ represents a hydrogen atom; $R^{1b}$ represents any one substituent described in Table 1A or Table 2A; $R^{3b}$ represents an iodine atom; and $R^{3c}$ represents a hydrogen atom (hereinafter referred to as "Compound group SX399").

The Compound (L-2), wherein Q represents the group represented by Q15; $R^{1a}$ represents any one substituent described in Table 1A or Table 2A; $R^{1b}$ represents a hydrogen atom; $R^{3b}$ represents an iodine atom; and $R^{3c}$ represents a hydrogen atom (hereinafter referred to as "Compound group SX400").

The Compound (L-2), wherein Q represents the group represented by Q16; $R^{1a}$ represents a hydrogen atom; $R^{1b}$ represents any one substituent described in Table 1A or Table 2A; $R^{3b}$ represents an iodine atom; and $R^{3c}$ represents a hydrogen atom (hereinafter referred to as "Compound group SX401").

The Compound (L-2), wherein Q represents the group represented by Q16; $R^{1a}$ represents any one substituent described in Table 1A or Table 2A; $R^{1b}$ represents a hydrogen atom; $R^{3b}$ represents an iodine atom; and $R^{3c}$ represents a hydrogen atom (hereinafter referred to as "Compound group SX402").

The Compound (L-2), wherein Q represents the group represented by Q17; $R^{1a}$ represents a hydrogen atom; $R^{1b}$ represents any one substituent described in Table 1A or Table 2A; $R^{3b}$ represents an iodine atom; and $R^{3c}$ represents a hydrogen atom (hereinafter referred to as "Compound group SX403").

The Compound (L-2), wherein Q represents the group represented by Q17; $R^{1a}$ represents any one substituent described in Table 1A or Table 2A; $R^{1b}$ represents a hydrogen atom; $R^{3b}$ represents an iodine atom; and $R^{3c}$ represents a hydrogen atom (hereinafter referred to as "Compound group SX404").

The Compound (L-2), wherein Q represents the group represented by Q18; $R^{1a}$ represents a hydrogen atom; $R^{1b}$ represents any one substituent described in Table 1A or Table 2A; $R^{3b}$ represents an iodine atom; and $R^{3c}$ represents a hydrogen atom (hereinafter referred to as "Compound group SX405").

The Compound (L-2), wherein Q represents the group represented by Q18; $R^{1a}$ represents any one substituent described in Table 1A or Table 2A; $R^{1b}$ represents a hydrogen atom; $R^{3b}$ represents an iodine atom; and $R^{3c}$ represents a hydrogen atom (hereinafter referred to as "Compound group SX406").

The Compound (L-2), wherein Q represents the group represented by Q19; $R^{1b}$ represents any one substituent described in Table 1A or Table 2A; $R^{3b}$ represents an iodine atom; and $R^{3c}$ represents a hydrogen atom (hereinafter referred to as "Compound group SX407").

The Compound (L-2), wherein Q represents the group represented by Q20; $R^{1b}$ represents any one substituent described in Table 1A or Table 2A; $R^{3b}$ represents an iodine atom; and $R^{3c}$ represents a hydrogen atom (hereinafter referred to as "Compound group SX408").

The Compound (L-2), wherein Q represents the group represented by Q21; $R^{1b}$ represents any one substituent described in Table 1A or Table 2A; $R^{3b}$ represents an iodine atom; and $R^{3c}$ represents a hydrogen atom (hereinafter referred to as "Compound group SX409").

The Compound (L-2), wherein Q represents the group represented by Q22; $R^{1b}$ represents any one substituent described in Table 1A or Table 2A; $R^{3b}$ represents an iodine atom; and $R^{3c}$ represents a hydrogen atom (hereinafter referred to as "Compound group SX410").

The Compound (L-2), wherein Q represents the group represented by Q23; $R^{1b}$ represents any one substituent described in Table 1A or Table 2A; $R^{3b}$ represents an iodine atom; and $R^{3c}$ represents a hydrogen atom (hereinafter referred to as "Compound group SX411").

The Compound (L-2), wherein Q represents the group represented by Q24; $R^{1b}$ represents any one substituent described in Table 1A or Table 2A; $R^{3b}$ represents an iodine atom; and $R^{3c}$ represents a hydrogen atom (hereinafter referred to as "Compound group SX412").

The Compound (L-2), wherein Q represents the group represented by Q25; $R^{1b}$ represents any one substituent described in Table 1A or Table 2A; $R^{3b}$ represents an iodine atom; and $R^{3c}$ represents a hydrogen atom (hereinafter referred to as "Compound group SX413").

The Compound (L-2), wherein Q represents the group represented by Q26; $R^{1b}$ represents any one substituent described in Table 1A or Table 2A; $R^{3b}$ represents an iodine atom; and $R^{3c}$ represents a hydrogen atom (hereinafter referred to as "Compound group SX414").

The Compound (L-2), wherein Q represents the group represented by Q27; $R^{1a}$ represents a hydrogen atom; $R^{1b}$ represents any one substituent described in Table 1A or Table 2A; $R^{3b}$ represents an iodine atom; and $R^{3c}$ represents a hydrogen atom (hereinafter referred to as "Compound group SX415").

The Compound (L-2), wherein Q represents the group represented by Q27; $R^{1a}$ represents any one substituent described in Table 1A or Table 2A; $R^{1b}$ represents a hydrogen atom; $R^{3b}$ represents an iodine atom; and $R^{3c}$ represents a hydrogen atom (hereinafter referred to as "Compound group SX416").

The Compound (L-2), wherein Q represents the group represented by Q28; $R^{1a}$ represents a hydrogen atom; $R^{1b}$ represents any one substituent described in Table 1A or Table 2A; $R^{3b}$ represents an iodine atom; and $R^{3c}$ represents a hydrogen atom (hereinafter referred to as "Compound group SX417").

The Compound (L-2), wherein Q represents the group represented by Q28; $R^{1a}$ represents any one substituent described in Table 1A or Table 2A; $R^{1b}$ represents a hydrogen atom; $R^{3b}$ represents an iodine atom; and $R^{3c}$ represents a hydrogen atom (hereinafter referred to as "Compound group SX418").

The Compound (L-2), wherein Q represents the group represented by Q29; $R^{1b}$ represents any one substituent described in Table 1A or Table 2A; $R^{3b}$ represents an iodine atom; and $R^{3c}$ represents a hydrogen atom (hereinafter referred to as "Compound group SX419").

The Compound (L-2), wherein Q represents the group represented by Q30; $R^{1b}$ represents any one substituent described in Table 1A or Table 2A; $R^{3b}$ represents an iodine atom; and $R^{3c}$ represents a hydrogen atom (hereinafter referred to as "Compound group SX420").

The Compound (L-2), wherein Q represents the group represented by Q11; $R^{1a}$ represents a hydrogen atom; $R^{1b}$ represents any one substituent described in Table 1A or Table 2A; $R^{3b}$ represents a hydrogen atom; and $R^{3c}$ represents a trifluoromethyl group (hereinafter referred to as "Compound group SX421").

The Compound (L-2), wherein Q represents the group represented by Q11; $R^{1a}$ represents any one substituent described in Table 1A or Table 2A; $R^{1b}$ represents a hydrogen atom; $R^{3b}$ represents a hydrogen atom; and $R^{3c}$ represents a trifluoromethyl group (hereinafter referred to as "Compound group SX422").

The Compound (L-2), wherein Q represents the group represented by Q12; $R^{1a}$ represents a hydrogen atom; $R^{1b}$ represents any one substituent described in Table 1A or Table 2A; $R^{3b}$ represents a hydrogen atom; and $R^{3c}$ represents a trifluoromethyl group (hereinafter referred to as "Compound group SX423").

The Compound (L-2), wherein Q represents the group represented by Q12; $R^{1a}$ represents any one substituent described in Table 1A or Table 2A; $R^{1b}$ represents a hydrogen atom; $R^{3b}$ represents a hydrogen atom; and $R^{3c}$ represents a trifluoromethyl group (hereinafter referred to as "Compound group SX424").

The Compound (L-2), wherein Q represents the group represented by Q13; $R^{1a}$ represents a hydrogen atom; $R^{1b}$ represents any one substituent described in Table 1A or Table 2A; $R^{3b}$ represents a hydrogen atom; and $R^{3c}$ represents a trifluoromethyl group (hereinafter referred to as "Compound group SX425").

The Compound (L-2), wherein Q represents the group represented by Q13; $R^{1a}$ represents any one substituent described in Table 1A or Table 2A; $R^{1b}$ represents a hydrogen atom; $R^{3b}$ represents a hydrogen atom; and $R^{3c}$ represents a trifluoromethyl group (hereinafter referred to as "Compound group SX426").

The Compound (L-2), wherein Q represents the group represented by Q14; $R^{1a}$ represents a hydrogen atom; $R^{1b}$ represents any one substituent described in Table 1A or Table 2A; $R^{3b}$ represents a hydrogen atom; and $R^{3c}$ represents a trifluoromethyl group (hereinafter referred to as "Compound group SX427").

The Compound (L-2), wherein Q represents the group represented by Q14; $R^{1a}$ represents any one substituent described in Table 1A or Table 2A; $R^{1b}$ represents a hydrogen atom; $R^{3b}$ represents a hydrogen atom; and $R^{3c}$ represents a trifluoromethyl group (hereinafter referred to as "Compound group SX428").

The Compound (L-2), wherein Q represents the group represented by Q15; $R^{1a}$ represents a hydrogen atom; $R^{1b}$ represents any one substituent described in Table 1A or Table 2A; $R^{3b}$ represents a hydrogen atom; and $R^{3c}$ represents a trifluoromethyl group (hereinafter referred to as "Compound group SX429").

The Compound (L-2), wherein Q represents the group represented by Q15; $R^{1a}$ represents any one substituent described in Table 1A or Table 2A; $R^{1b}$ represents a hydrogen atom; $R^{3b}$ represents a hydrogen atom; and $R^{3c}$ represents a trifluoromethyl group (hereinafter referred to as "Compound group SX430").

The Compound (L-2), wherein Q represents the group represented by Q16; $R^{1a}$ represents a hydrogen atom; $R^{1b}$ represents any one substituent described in Table 1A or Table 2A; $R^{3b}$ represents a hydrogen atom; and $R^{3c}$ represents a trifluoromethyl group (hereinafter referred to as "Compound group SX431").

The Compound (L-2), wherein Q represents the group represented by Q16; $R^{1a}$ represents any one substituent described in Table 1A or Table 2A; $R^{1b}$ represents a hydrogen atom; $R^{3b}$ represents a hydrogen atom; and $R^{3c}$ represents a trifluoromethyl group (hereinafter referred to as "Compound group SX432").

The Compound (L-2), wherein Q represents the group represented by Q17; $R^{1a}$ represents a hydrogen atom; $R^{1b}$ represents any one substituent described in Table 1A or Table 2A; $R^{3b}$ represents a hydrogen atom; and $R^{3c}$ represents a trifluoromethyl group (hereinafter referred to as "Compound group SX433").

The Compound (L-2), wherein Q represents the group represented by Q17; $R^{1a}$ represents any one substituent described in Table 1A or Table 2A; $R^{1b}$ represents a hydrogen atom; $R^{3b}$ represents a hydrogen atom; and $R^{3c}$ represents a trifluoromethyl group (hereinafter referred to as "Compound group SX434").

The Compound (L-2), wherein Q represents the group represented by Q18; $R^{1a}$ represents a hydrogen atom; $R^{1b}$ represents any one substituent described in Table 1A or Table 2A; $R^{3b}$ represents a hydrogen atom; and $R^{3c}$ represents a trifluoromethyl group (hereinafter referred to as "Compound group SX435").

The Compound (L-2), wherein Q represents the group represented by Q18; $R^{1a}$ represents any one substituent described in Table 1A or Table 2A; $R^{1b}$ represents a hydrogen atom; $R^{3b}$ represents a hydrogen atom; and $R^{3c}$ represents a trifluoromethyl group (hereinafter referred to as "Compound group SX436").

The Compound (L-2), wherein Q represents the group represented by Q19; $R^{1b}$ represents any one substituent described in Table 1A or Table 2A; $R^{3b}$ represents a hydrogen atom; and $R^{3c}$ represents a trifluoromethyl group (hereinafter referred to as "Compound group SX437").

The Compound (L-2), wherein Q represents the group represented by Q20; $R^{1b}$ represents any one substituent described in Table 1A or Table 2A; $R^{3b}$ represents a hydrogen atom; and $R^{3c}$ represents a trifluoromethyl group (hereinafter referred to as "Compound group SX438").

The Compound (L-2), wherein Q represents the group represented by Q21; $R^{1b}$ represents any one substituent described in Table 1A or Table 2A; $R^{3b}$ represents a hydrogen atom; and $R^{3c}$ represents a trifluoromethyl group (hereinafter referred to as "Compound group SX439").

The Compound (L-2), wherein Q represents the group represented by Q22; $R^{1b}$ represents any one substituent described in Table 1A or Table 2A; $R^{3b}$ represents a hydrogen atom; and $R^{3c}$ represents a trifluoromethyl group (hereinafter referred to as "Compound group SX440").

The Compound (L-2), wherein Q represents the group represented by Q23; $R^{1b}$ represents any one substituent described in Table 1A or Table 2A; $R^{3b}$ represents a hydrogen atom; and $R^{3c}$ represents a trifluoromethyl group (hereinafter referred to as "Compound group SX441").

The Compound (L-2), wherein Q represents the group represented by Q24; $R^{1b}$ represents any one substituent described in Table 1A or Table 2A; $R^{3b}$ represents a hydrogen atom; and $R^{3c}$ represents a trifluoromethyl group (hereinafter referred to as "Compound group SX442").

The Compound (L-2), wherein Q represents the group represented by Q25; $R^{1b}$ represents any one substituent described in Table 1A or Table 2A; $R^{3b}$ represents a hydrogen atom; and $R^{3c}$ represents a trifluoromethyl group (hereinafter referred to as "Compound group SX443").

The Compound (L-2), wherein Q represents the group represented by Q26; $R^{1b}$ represents any one substituent described in Table 1A or Table 2A; $R^{3b}$ represents a hydrogen atom; and $R^{3c}$ represents a trifluoromethyl group (hereinafter referred to as "Compound group SX444").

The Compound (L-2), wherein Q represents the group represented by Q27; $R^{1a}$ represents a hydrogen atom; $R^{1b}$ represents any one substituent described in Table 1A or Table 2A; $R^{3b}$ represents a hydrogen atom; and $R^{3c}$ represents a trifluoromethyl group (hereinafter referred to as "Compound group SX445").

The Compound (L-2), wherein Q represents the group represented by Q27; $R^{1a}$ represents any one substituent described in Table 1A or Table 2A; $R^{1b}$ represents a hydrogen atom; $R^{3b}$ represents a hydrogen atom; and $R^{3c}$ represents a trifluoromethyl group (hereinafter referred to as "Compound group SX446").

The Compound (L-2), wherein Q represents the group represented by Q28; $R^{1a}$ represents a hydrogen atom; $R^{1b}$ represents any one substituent described in Table 1A or Table 2A; $R^{3b}$ represents a hydrogen atom; and $R^{3c}$ represents a trifluoromethyl group (hereinafter referred to as "Compound group SX447").

The Compound (L-2), wherein Q represents the group represented by Q28; $R^{1a}$ represents any one substituent described in Table 1A or Table 2A; $R^{1b}$ represents a hydrogen atom; $R^{3b}$ represents a hydrogen atom; and $R^{3c}$ represents a trifluoromethyl group (hereinafter referred to as "Compound group SX448").

The Compound (L-2), wherein Q represents the group represented by Q29; $R^{1b}$ represents any one substituent described in Table 1A or Table 2A; $R^{3b}$ represents a hydrogen atom; and $R^{3c}$ represents a trifluoromethyl group (hereinafter referred to as "Compound group SX449").

The Compound (L-2), wherein Q represents the group represented by Q30; $R^{1b}$ represents any one substituent described in Table 1A or Table 2A; $R^{3b}$ represents a hydrogen atom; and $R^{3c}$ represents a trifluoromethyl group (hereinafter referred to as "Compound group SX450").

The Compound (L-2), wherein Q represents the group represented by Q11; $R^{1a}$ represents a hydrogen atom; $R^{1b}$ represents any one substituent described in Table 1A or Table 2A; $R^{3b}$ represents a hydrogen atom; and $R^{3c}$ represents a chlorine atom (hereinafter referred to as "Compound group SX451").

The Compound (L-2), wherein Q represents the group represented by Q11; $R^{1a}$ represents any one substituent described in Table 1A or Table 2A; $R^{1b}$ represents a hydrogen atom; $R^{3b}$ represents a hydrogen atom; and $R^{3c}$ represents a chlorine atom (hereinafter referred to as "Compound group SX452").

The Compound (L-2), wherein Q represents the group represented by Q12; $R^{1a}$ represents a hydrogen atom; $R^{1b}$ represents any one substituent described in Table 1A or Table 2A; $R^{3b}$ represents a hydrogen atom; and $R^{3c}$ represents a chlorine atom (hereinafter referred to as "Compound group SX453").

The Compound (L-2), wherein Q represents the group represented by Q12; $R^{1a}$ represents any one substituent described in Table 1A or Table 2A; $R^{1b}$ represents a hydrogen atom; $R^{3b}$ represents a hydrogen atom; and $R^{3c}$ represents a chlorine atom (hereinafter referred to as "Compound group SX454").

The Compound (L-2), wherein Q represents the group represented by Q13; $R^{1a}$ represents a hydrogen atom; $R^{1b}$ represents any one substituent described in Table 1A or Table 2A; $R^{3b}$ represents a hydrogen atom; and $R^{3c}$ represents a chlorine atom (hereinafter referred to as "Compound group SX455").

The Compound (L-2), wherein Q represents the group represented by Q13; $R^{1a}$ represents any one substituent described in Table 1A or Table 2A; $R^{1b}$ represents a hydrogen atom; $R^{3b}$ represents a hydrogen atom; and $R^{3c}$ represents a chlorine atom (hereinafter referred to as "Compound group SX456").

The Compound (L-2), wherein Q represents the group represented by Q14; $R^{1a}$ represents a hydrogen atom; $R^{1b}$ represents any one substituent described in Table 1A or Table 2A; $R^{3b}$ represents a hydrogen atom; and $R^{3c}$ represents a chlorine atom (hereinafter referred to as "Compound group SX457").

The Compound (L-2), wherein Q represents the group represented by Q14; $R^{1a}$ represents any one substituent described in Table 1A or Table 2A; $R^{1b}$ represents a hydrogen atom; $R^{3b}$ represents a hydrogen atom; and $R^{3c}$ represents a chlorine atom (hereinafter referred to as "Compound group SX458").

The Compound (L-2), wherein Q represents the group represented by Q15; $R^{1a}$ represents a hydrogen atom; $R^{1b}$ represents any one substituent described in Table 1A or Table 2A; $R^{3b}$ represents a hydrogen atom; and $R^{3c}$ represents a chlorine atom (hereinafter referred to as "Compound group SX459").

The Compound (L-2), wherein Q represents the group represented by Q15; $R^{1a}$ represents any one substituent described in Table 1A or Table 2A; $R^{1b}$ represents a hydrogen atom; $R^{3b}$ represents a hydrogen atom; and $R^{3c}$ represents a chlorine atom (hereinafter referred to as "Compound group SX460").

The Compound (L-2), wherein Q represents the group represented by Q16; $R^{1a}$ represents a hydrogen atom; $R^{1b}$ represents any one substituent described in Table 1A or Table 2A; $R^{3b}$ represents a hydrogen atom; and $R^{3c}$ represents a chlorine atom (hereinafter referred to as "Compound group SX461").

The Compound (L-2), wherein Q represents the group represented by Q16; $R^{1a}$ represents any one substituent described in Table 1A or Table 2A; $R^{1b}$ represents a hydrogen atom; $R^{3b}$ represents a hydrogen atom; and $R^{3c}$ represents a chlorine atom (hereinafter referred to as "Compound group SX462").

The Compound (L-2), wherein Q represents the group represented by Q17; $R^{1a}$ represents a hydrogen atom; $R^{1b}$ represents any one substituent described in Table 1A or Table 2A; $R^{3b}$ represents a hydrogen atom; and $R^{3c}$ represents a chlorine atom (hereinafter referred to as "Compound group SX463").

The Compound (L-2), wherein Q represents the group represented by Q17; $R^{1a}$ represents any one substituent described in Table 1A or Table 2A; $R^{1b}$ represents a hydrogen atom; $R^{3b}$ represents a hydrogen atom; and $R^{3c}$ represents a chlorine atom (hereinafter referred to as "Compound group SX464").

The Compound (L-2), wherein Q represents the group represented by Q18; $R^{1a}$ represents a hydrogen atom; $R^{1b}$ represents any one substituent described in Table 1A or Table 2A; $R^{3b}$ represents a hydrogen atom; and $R^{3c}$ represents a chlorine atom (hereinafter referred to as "Compound group SX465").

The Compound (L-2), wherein Q represents the group represented by Q18; $R^{1a}$ represents any one substituent described in Table 1A or Table 2A; $R^{1b}$ represents a hydrogen atom; $R^{3b}$ represents a hydrogen atom; and $R^{3c}$ represents a chlorine atom (hereinafter referred to as "Compound group SX466").

The Compound (L-2), wherein Q represents the group represented by Q19; $R^{1b}$ represents any one substituent described in Table 1A or Table 2A; $R^{3b}$ represents a hydrogen atom; and $R^{3c}$ represents a chlorine atom (hereinafter referred to as "Compound group SX467").

The Compound (L-2), wherein Q represents the group represented by Q20; $R^{1b}$ represents any one substituent described in Table 1A or Table 2A; $R^{3b}$ represents a hydrogen atom; and $R^{3c}$ represents a chlorine atom (hereinafter referred to as "Compound group SX468").

The Compound (L-2), wherein Q represents the group represented by Q21; $R^{1b}$ represents any one substituent described in Table 1A or Table 2A; $R^{3b}$ represents a hydrogen atom; and $R^{3c}$ represents a chlorine atom (hereinafter referred to as "Compound group SX469").

The Compound (L-2), wherein Q represents the group represented by Q22; $R^{1b}$ represents any one substituent described in Table 1A or Table 2A; $R^{3b}$ represents a hydrogen atom; and $R^{3c}$ represents a chlorine atom (hereinafter referred to as "Compound group SX470").

The Compound (L-2), wherein Q represents the group represented by Q23; $R^{1b}$ represents any one substituent described in Table 1A or Table 2A; $R^{3b}$ represents a hydrogen atom; and $R^{3c}$ represents a chlorine atom (hereinafter referred to as "Compound group SX471").

The Compound (L-2), wherein Q represents the group represented by Q24; $R^{1b}$ represents any one substituent described in Table 1A or Table 2A; $R^{3b}$ represents a hydrogen atom; and $R^{3c}$ represents a chlorine atom (hereinafter referred to as "Compound group SX472").

The Compound (L-2), wherein Q represents the group represented by Q25; $R^{1b}$ represents any one substituent described in Table 1A or Table 2A; $R^{3b}$ represents a hydrogen atom; and $R^{3c}$ represents a chlorine atom (hereinafter referred to as "Compound group SX473").

The Compound (L-2), wherein Q represents the group represented by Q26; $R^{1b}$ represents any one substituent described in Table 1A or Table 2A; $R^{3b}$ represents a hydrogen atom; and $R^{3c}$ represents a chlorine atom (hereinafter referred to as "Compound group SX474").

The Compound (L-2), wherein Q represents the group represented by Q27; $R^{1a}$ represents a hydrogen atom; $R^{1b}$ represents any one substituent described in Table 1A or Table 2A; $R^{3b}$ represents a hydrogen atom; and $R^{3c}$ represents a chlorine atom (hereinafter referred to as "Compound group SX475").

The Compound (L-2), wherein Q represents the group represented by Q27; $R^{1a}$ represents any one substituent described in Table 1A or Table 2A; $R^{1b}$ represents a hydrogen atom; $R^{3b}$ represents a hydrogen atom; and $R^{3c}$ represents a chlorine atom (hereinafter referred to as "Compound group SX476").

The Compound (L-2), wherein Q represents the group represented by Q28; $R^{1a}$ represents a hydrogen atom; $R^{1b}$ represents any one substituent described in Table 1A or Table 2A; $R^{3b}$ represents a hydrogen atom; and $R^{3c}$ represents a chlorine atom (hereinafter referred to as "Compound group SX477").

The Compound (L-2), wherein Q represents the group represented by Q28; $R^{1a}$ represents any one substituent described in Table 1A or Table 2A; $R^{1b}$ represents a hydrogen atom; $R^{3b}$ represents a hydrogen atom; and $R^{3c}$ represents a chlorine atom (hereinafter referred to as "Compound group SX478").

The Compound (L-2), wherein Q represents the group represented by Q29; $R^{1b}$ represents any one substituent described in Table 1A or Table 2A; $R^{3b}$ represents a hydrogen atom; and $R^{3c}$ represents a chlorine atom (hereinafter referred to as "Compound group SX479").

The Compound (L-2), wherein Q represents the group represented by Q30; $R^{1b}$ represents any one substituent described in Table 1A or Table 2A; $R^{3b}$ represents a hydrogen atom; and $R^{3c}$ represents a chlorine atom (hereinafter referred to as "Compound group SX480").

The Compound (L-2), wherein Q represents the group represented by Q11; $R^{1a}$ represents a hydrogen atom; $R^{1b}$ represents any one substituent described in Table 1A or Table 2A; $R^{3b}$ represents a hydrogen atom; and $R^{3c}$ represents a bromine atom (hereinafter referred to as "Compound group SX481").

The Compound (L-2), wherein Q represents the group represented by Q11; $R^{1a}$ represents any one substituent described in Table 1A or Table 2A; $R^{1b}$ represents a hydrogen atom; $R^{3b}$ represents a hydrogen atom; and $R^{3c}$ represents a bromine atom (hereinafter referred to as "Compound group SX482").

The Compound (L-2), wherein Q represents the group represented by Q12; $R^{1a}$ represents a hydrogen atom; $R^{1b}$ represents any one substituent described in Table 1A or Table 2A; $R^{3b}$ represents a hydrogen atom; and $R^{3c}$ represents a bromine atom (hereinafter referred to as "Compound group SX483").

The Compound (L-2), wherein Q represents the group represented by Q12; $R^{1a}$ represents any one substituent described in Table 1A or Table 2A; $R^{1b}$ represents a hydrogen atom; $R^{3b}$ represents a hydrogen atom; and $R^{3c}$ represents a bromine atom (hereinafter referred to as "Compound group SX484").

The Compound (L-2), wherein Q represents the group represented by Q13; $R^{1a}$ represents a hydrogen atom; $R^{1b}$ represents any one substituent described in Table 1A or Table 2A; $R^{3b}$ represents a hydrogen atom; and $R^{3c}$ represents a bromine atom (hereinafter referred to as "Compound group SX485").

The Compound (L-2), wherein Q represents the group represented by Q13; $R^{1a}$ represents any one substituent described in Table 1A or Table 2A; $R^{1b}$ represents a hydrogen atom; $R^{3b}$ represents a hydrogen atom; and $R^{3c}$ represents a bromine atom (hereinafter referred to as "Compound group SX486").

The Compound (L-2), wherein Q represents the group represented by Q14; $R^{1a}$ represents a hydrogen atom; $R^{1b}$ represents any one substituent described in Table 1A or Table 2A; $R^{3b}$ represents a hydrogen atom; and $R^{3c}$ represents a bromine atom (hereinafter referred to as "Compound group SX487").

The Compound (L-2), wherein Q represents the group represented by Q14; $R^{1a}$ represents any one substituent described in Table 1A or Table 2A; $R^{1b}$ represents a hydrogen atom; $R^{3b}$ represents a hydrogen atom; and $R^{3c}$ represents a bromine atom (hereinafter referred to as "Compound group SX488").

The Compound (L-2), wherein Q represents the group represented by Q15; $R^{1a}$ represents a hydrogen atom; $R^{1b}$ represents any one substituent described in Table 1A or Table 2A; $R^{3b}$ represents a hydrogen atom; and $R^{3c}$ represents a bromine atom (hereinafter referred to as "Compound group SX489").

The Compound (L-2), wherein Q represents the group represented by Q15; $R^{1a}$ represents any one substituent described in Table 1A or Table 2A; $R^{1b}$ represents a hydrogen atom; $R^{3b}$ represents a hydrogen atom; and $R^{3c}$ represents a bromine atom (hereinafter referred to as "Compound group SX490").

The Compound (L-2), wherein Q represents the group represented by Q16; $R^{1a}$ represents a hydrogen atom; $R^{1b}$ represents any one substituent described in Table 1A or Table 2A; $R^{3b}$ represents a hydrogen atom; and $R^{3c}$ represents a bromine atom (hereinafter referred to as "Compound group SX491").

The Compound (L-2), wherein Q represents the group represented by Q16; $R^{1a}$ represents any one substituent described in Table 1A or Table 2A; $R^{1b}$ represents a hydrogen atom; $R^{3b}$ represents a hydrogen atom; and $R^{3c}$ represents a bromine atom (hereinafter referred to as "Compound group SX492").

The Compound (L-2), wherein Q represents the group represented by Q17; $R^{1a}$ represents a hydrogen atom; $R^{1b}$ represents any one substituent described in Table 1A or Table 2A; $R^{3b}$ represents a hydrogen atom; and $R^{3c}$ represents a bromine atom (hereinafter referred to as "Compound group SX493").

The Compound (L-2), wherein Q represents the group represented by Q17; $R^{1a}$ represents any one substituent described in Table 1A or Table 2A; $R^{1b}$ represents a hydrogen atom; $R^{3b}$ represents a hydrogen atom; and $R^{3c}$ represents a bromine atom (hereinafter referred to as "Compound group SX494").

The Compound (L-2), wherein Q represents the group represented by Q18; $R^{1a}$ represents a hydrogen atom; $R^{1b}$ represents any one substituent described in Table 1A or Table 2A; $R^{3b}$ represents a hydrogen atom; and $R^{3c}$ represents a bromine atom (hereinafter referred to as "Compound group SX495").

The Compound (L-2), wherein Q represents the group represented by Q18; $R^{1a}$ represents any one substituent described in Table 1A or Table 2A; $R^{1b}$ represents a hydrogen atom; $R^{3b}$ represents a hydrogen atom; and $R^{3c}$ represents a bromine atom (hereinafter referred to as "Compound group SX496").

The Compound (L-2), wherein Q represents the group represented by Q19; $R^{1b}$ represents any one substituent described in Table 1A or Table 2A; $R^{3b}$ represents a hydrogen atom; and $R^{3c}$ represents a bromine atom (hereinafter referred to as "Compound group SX497").

The Compound (L-2), wherein Q represents the group represented by Q20; $R^{1b}$ represents any one substituent described in Table 1A or Table 2A; $R^{3b}$ represents a hydrogen atom; and $R^{3c}$ represents a bromine atom (hereinafter referred to as "Compound group SX498").

The Compound (L-2), wherein Q represents the group represented by Q21; $R^{1b}$ represents any one substituent described in Table 1A or Table 2A; $R^{3b}$ represents a hydrogen atom; and $R^{3c}$ represents a bromine atom (hereinafter referred to as "Compound group SX499").

The Compound (L-2), wherein Q represents the group represented by Q22; $R^{1b}$ represents any one substituent described in Table 1A or Table 2A; $R^{3b}$ represents a hydrogen atom; and $R^{3c}$ represents a bromine atom (hereinafter referred to as "Compound group SX500").

The Compound (L-2), wherein Q represents the group represented by Q23; $R^{1b}$ represents any one substituent described in Table 1A or Table 2A; $R^{3b}$ represents a hydrogen atom; and $R^{3c}$ represents a bromine atom (hereinafter referred to as "Compound group SX501").

The Compound (L-2), wherein Q represents the group represented by Q24; $R^{1b}$ represents any one substituent described in Table 1A or Table 2A; $R^{3b}$ represents a hydrogen atom; and $R^{3c}$ represents a bromine atom (hereinafter referred to as "Compound group SX502").

The Compound (L-2), wherein Q represents the group represented by Q25; $R^{1b}$ represents any one substituent described in Table 1A or Table 2A; $R^{3b}$ represents a hydrogen atom; and $R^{3c}$ represents a bromine atom (hereinafter referred to as "Compound group SX503").

The Compound (L-2), wherein Q represents the group represented by Q26; $R^{1b}$ represents any one substituent described in Table 1A or Table 2A; $R^{3b}$ represents a hydrogen atom; and $R^{3c}$ represents a bromine atom (hereinafter referred to as "Compound group SX504").

The Compound (L-2), wherein Q represents the group represented by Q27; $R^{1a}$ represents a hydrogen atom; $R^{1b}$ represents any one substituent described in Table 1A or Table 2A; $R^{3b}$ represents a hydrogen atom; and $R^{3c}$ represents a bromine atom (hereinafter referred to as "Compound group SX505").

The Compound (L-2), wherein Q represents the group represented by Q27; $R^{1a}$ represents any one substituent described in Table 1A or Table 2A; $R^{1b}$ represents a hydrogen atom; $R^{3b}$ represents a hydrogen atom; and $R^{3c}$ represents a bromine atom (hereinafter referred to as "Compound group SX506").

The Compound (L-2), wherein Q represents the group represented by Q28; $R^{1a}$ represents a hydrogen atom; $R^{1b}$ represents any one substituent described in Table 1A or Table 2A; $R^{3b}$ represents a hydrogen atom; and $R^{3c}$ represents a bromine atom (hereinafter referred to as "Compound group SX507").

The Compound (L-2), wherein Q represents the group represented by Q28; $R^{1a}$ represents any one substituent described in Table 1A or Table 2A; $R^{1b}$ represents a hydrogen atom; $R^{3b}$ represents a hydrogen atom; and $R^{3c}$ represents a bromine atom (hereinafter referred to as "Compound group SX508").

The Compound (L-2), wherein Q represents the group represented by Q29; $R^{1b}$ represents any one substituent described in Table 1A or Table 2A; $R^{3b}$ represents a hydrogen atom; and $R^{3c}$ represents a bromine atom (hereinafter referred to as "Compound group SX509").

The Compound (L-2), wherein Q represents the group represented by Q30; $R^{1b}$ represents any one substituent described in Table 1A or Table 2A; $R^{3b}$ represents a hydrogen atom; and $R^{3c}$ represents a bromine atom (hereinafter referred to as "Compound group SX510").

The Compound (L-2), wherein Q represents the group represented by Q11; $R^{1a}$ represents a hydrogen atom; $R^{1b}$ represents any one substituent described in Table 1A or Table 2A; $R^{3b}$ represents a hydrogen atom; and $R^{3c}$ represents an iodine atom (hereinafter referred to as "Compound group SX511").

The Compound (L-2), wherein Q represents the group represented by Q11; $R^{1a}$ represents any one substituent described in Table 1A or Table 2A; $R^{1b}$ represents a hydrogen atom; $R^{3b}$ represents a hydrogen atom; and $R^{3c}$ represents an iodine atom (hereinafter referred to as "Compound group SX512").

The Compound (L-2), wherein Q represents the group represented by Q12; $R^{1a}$ represents a hydrogen atom; $R^{1b}$ represents any one substituent described in Table 1A or Table 2A; $R^{3b}$ represents a hydrogen atom; and $R^{3c}$ represents an iodine atom (hereinafter referred to as "Compound group SX513").

The Compound (L-2), wherein Q represents the group represented by Q12; $R^{1a}$ represents any one substituent described in Table 1A or Table 2A; $R^{1b}$ represents a hydrogen atom; $R^{3b}$ represents a hydrogen atom; and $R^{3c}$ represents an iodine atom (hereinafter referred to as "Compound group SX514").

The Compound (L-2), wherein Q represents the group represented by Q13; $R^{1a}$ represents a hydrogen atom; $R^{1b}$ represents any one substituent described in Table 1A or Table 2A; $R^{3b}$ represents a hydrogen atom; and $R^{3c}$ represents an iodine atom (hereinafter referred to as "Compound group SX515").

The Compound (L-2), wherein Q represents the group represented by Q13; $R^{1a}$ represents any one substituent described in Table 1A or Table 2A; $R^{1b}$ represents a hydrogen atom; $R^{3b}$ represents a hydrogen atom; and $R^{3c}$ represents an iodine atom (hereinafter referred to as "Compound group SX516").

The Compound (L-2), wherein Q represents the group represented by Q14; $R^{1a}$ represents a hydrogen atom; $R^{1b}$ represents any one substituent described in Table 1A or Table 2A; $R^{3b}$ represents a hydrogen atom; and $R^{3c}$ represents an iodine atom (hereinafter referred to as "Compound group SX517").

The Compound (L-2), wherein Q represents the group represented by Q14; $R^{1a}$ represents any one substituent described in Table 1A or Table 2A; $R^{1b}$ represents a hydrogen atom; $R^{3b}$ represents a hydrogen atom; and $R^{3c}$ represents an iodine atom (hereinafter referred to as "Compound group SX518").

The Compound (L-2), wherein Q represents the group represented by Q15; $R^{1a}$ represents a hydrogen atom; $R^{1b}$ represents any one substituent described in Table 1A or Table 2A; $R^{3b}$ represents a hydrogen atom; and $R^{3c}$ represents an iodine atom (hereinafter referred to as "Compound group SX519").

The Compound (L-2), wherein Q represents the group represented by Q15; $R^{1a}$ represents any one substituent described in Table 1A or Table 2A; $R^{1b}$ represents a hydrogen atom; $R^{3b}$ represents a hydrogen atom; and $R^{3c}$ represents an iodine atom (hereinafter referred to as "Compound group SX520").

The Compound (L-2), wherein Q represents the group represented by Q16; $R^{1a}$ represents a hydrogen atom; $R^{1b}$ represents any one substituent described in Table 1A or Table 2A; $R^{3b}$ represents a hydrogen atom; and $R^{3c}$ represents an iodine atom (hereinafter referred to as "Compound group SX521").

The Compound (L-2), wherein Q represents the group represented by Q16; $R^{1a}$ represents any one substituent described in Table 1A or Table 2A; $R^{1b}$ represents a hydrogen atom; $R^{3b}$ represents a hydrogen atom; and $R^{3c}$ represents an iodine atom (hereinafter referred to as "Compound group SX522").

The Compound (L-2), wherein Q represents the group represented by Q17; $R^{1a}$ represents a hydrogen atom; $R^{1b}$ represents any one substituent described in Table 1A or Table 2A; $R^{3b}$ represents a hydrogen atom; and $R^{3c}$ represents an iodine atom (hereinafter referred to as "Compound group SX523").

The Compound (L-2), wherein Q represents the group represented by Q17; $R^{1a}$ represents any one substituent described in Table 1A or Table 2A; $R^{1b}$ represents a hydrogen atom; $R^{3b}$ represents a hydrogen atom; and $R^{3c}$ represents an iodine atom (hereinafter referred to as "Compound group SX524").

The Compound (L-2), wherein Q represents the group represented by Q18; $R^{1a}$ represents a hydrogen atom; $R^{1b}$ represents any one substituent described in Table 1A or Table 2A; $R^{3b}$ represents a hydrogen atom; and $R^{3c}$ represents an iodine atom (hereinafter referred to as "Compound group SX525").

The Compound (L-2), wherein Q represents the group represented by Q18; $R^{1a}$ represents any one substituent described in Table 1A or Table 2A; $R^{1b}$ represents a hydrogen atom; $R^{3b}$ represents a hydrogen atom; and $R^{3c}$ represents an iodine atom (hereinafter referred to as "Compound group SX526").

The Compound (L-2), wherein Q represents the group represented by Q19; $R^{1b}$ represents any one substituent described in Table 1A or Table 2A; $R^{3b}$ represents a hydrogen atom; and $R^{3c}$ represents an iodine atom (hereinafter referred to as "Compound group SX527").

The Compound (L-2), wherein Q represents the group represented by Q20; $R^{1b}$ represents any one substituent described in Table 1A or Table 2A; $R^{3b}$ represents a hydrogen atom; and $R^{3c}$ represents an iodine atom (hereinafter referred to as "Compound group SX528").

The Compound (L-2), wherein Q represents the group represented by Q21; $R^{1b}$ represents any one substituent described in Table 1A or Table 2A; $R^{3b}$ represents a hydrogen atom; and $R^{3c}$ represents an iodine atom (hereinafter referred to as "Compound group SX529").

The Compound (L-2), wherein Q represents the group represented by Q22; $R^{1b}$ represents any one substituent described in Table 1A or Table 2A; $R^{3b}$ represents a hydrogen atom; and $R^{3c}$ represents an iodine atom (hereinafter referred to as "Compound group SX530").

The Compound (L-2), wherein Q represents the group represented by Q23; $R^{1b}$ represents any one substituent described in Table 1A or Table 2A; $R^{3b}$ represents a hydrogen atom; and $R^{3c}$ represents an iodine atom (hereinafter referred to as "Compound group SX531").

The Compound (L-2), wherein Q represents the group represented by Q24; $R^{1b}$ represents any one substituent described in Table 1A or Table 2A; $R^{3b}$ represents a hydrogen atom; and $R^{3c}$ represents an iodine atom (hereinafter referred to as "Compound group SX532").

The Compound (L-2), wherein Q represents the group represented by Q25; $R^{1b}$ represents any one substituent described in Table 1A or Table 2A; $R^{3b}$ represents a hydrogen atom; and $R^{3c}$ represents an iodine atom (hereinafter referred to as "Compound group SX533").

The Compound (L-2), wherein Q represents the group represented by Q26; $R^{1b}$ represents any one substituent described in Table 1A or Table 2A; $R^{3b}$ represents a hydrogen atom; and $R^{3c}$ represents an iodine atom (hereinafter referred to as "Compound group SX534").

The Compound (L-2), wherein Q represents the group represented by Q27; $R^{1a}$ represents a hydrogen atom; $R^{1b}$ represents any one substituent described in Table 1A or Table 2A; $R^{3b}$ represents a hydrogen atom; and $R^{3c}$ represents an iodine atom (hereinafter referred to as "Compound group SX535").

The Compound (L-2), wherein Q represents the group represented by Q27; $R^{1a}$ represents any one substituent described in Table 1A or Table 2A; $R^{1b}$ represents a hydrogen atom; $R^{3b}$ represents a hydrogen atom; and $R^{3c}$ represents an iodine atom (hereinafter referred to as "Compound group SX536").

The Compound (L-2), wherein Q represents the group represented by Q28; $R^{1a}$ represents a hydrogen atom; $R^{1b}$ represents any one substituent described in Table 1A or Table 2A; $R^{3b}$ represents a hydrogen atom; and $R^{3c}$ represents an iodine atom (hereinafter referred to as "Compound group SX537").

The Compound (L-2), wherein Q represents the group represented by Q28; $R^{1a}$ represents any one substituent described in Table 1A or Table 2A; $R^{1b}$ represents a hydrogen atom; $R^{3b}$ represents a hydrogen atom; and $R^{3c}$ represents an iodine atom (hereinafter referred to as "Compound group SX538").

The Compound (L-2), wherein Q represents the group represented by Q29; $R^{1b}$ represents any one substituent described in Table 1A or Table 2A; $R^{3b}$ represents a hydrogen atom; and $R^{3c}$ represents an iodine atom (hereinafter referred to as "Compound group SX539").

The Compound (L-2), wherein Q represents the group represented by Q30; $R^{1b}$ represents any one substituent described in Table 1A or Table 2A; $R^{3b}$ represents a hydrogen atom; and $R^{3c}$ represents an iodine atom (hereinafter referred to as "Compound group SX540").

A compound represented by formula (L-3):

(L-3)

(hereinafter referred to as "Compound (L-3)"), wherein Q represents the group represented by Q11; $R^{1a}$ represents a hydrogen atom; $R^{1b}$ represents any one substituent described in Table 1A or Table 2A; $R^{3b}$ represents a hydrogen atom; and $R^{3c}$ represents a hydrogen atom (hereinafter referred to as "Compound group SX541").

The Compound (L-3), wherein Q represents the group represented by Q11; $R^{1a}$ represents any one substituent described in Table 1A or Table 2A; $R^{1b}$ represents a hydrogen atom; $R^{3b}$ represents a hydrogen atom; and $R^{3c}$ represents a hydrogen atom (hereinafter referred to as "Compound group SX542").

The Compound (L-3), wherein Q represents the group represented by Q12; $R^{1a}$ represents a hydrogen atom; $R^{1b}$ represents any one substituent described in Table 1A or Table 2A; $R^{3b}$ represents a hydrogen atom; and $R^{3c}$ represents a hydrogen atom (hereinafter referred to as "Compound group SX543").

The Compound (L-3), wherein Q represents the group represented by Q12; $R^{1a}$ represents any one substituent described in Table 1A or Table 2A; $R^{1b}$ represents a hydrogen atom; $R^{3b}$ represents a hydrogen atom; and $R^{3c}$ represents a hydrogen atom (hereinafter referred to as "Compound group SX544").

The Compound (L-3), wherein Q represents the group represented by Q13; $R^{1a}$ represents a hydrogen atom; $R^{1b}$ represents any one substituent described in Table 1A or Table 2A; $R^{3b}$ represents a hydrogen atom; and $R^{3c}$ represents a hydrogen atom (hereinafter referred to as "Compound group SX545").

The Compound (L-3), wherein Q represents the group represented by Q13; $R^{1a}$ represents any one substituent described in Table 1A or Table 2A; $R^{1b}$ represents a hydrogen atom; $R^{3b}$ represents a hydrogen atom; and $R^{3c}$ represents a hydrogen atom (hereinafter referred to as "Compound group SX546").

The Compound (L-3), wherein Q represents the group represented by Q14; $R^{1a}$ represents a hydrogen atom; $R^{1b}$ represents any one substituent described in Table 1A or Table 2A; $R^{3b}$ represents a hydrogen atom; and $R^{3c}$ represents a hydrogen atom (hereinafter referred to as "Compound group SX547").

The Compound (L-3), wherein Q represents the group represented by Q14; $R^{1a}$ represents any one substituent described in Table 1A or Table 2A; $R^{1b}$ represents a hydrogen atom; $R^{3b}$ represents a hydrogen atom; and $R^{3c}$ represents a hydrogen atom (hereinafter referred to as "Compound group SX548").

The Compound (L-3), wherein Q represents the group represented by Q15; $R^{1a}$ represents a hydrogen atom; $R^{1b}$ represents any one substituent described in Table 1A or Table 2A; $R^{3b}$ represents a hydrogen atom; and $R^{3c}$ represents a hydrogen atom (hereinafter referred to as "Compound group SX549").

The Compound (L-3), wherein Q represents the group represented by Q15; $R^{1a}$ represents any one substituent described in Table 1A or Table 2A; $R^{1b}$ represents a hydrogen atom; $R^{3b}$ represents a hydrogen atom; and $R^{3c}$ represents a hydrogen atom (hereinafter referred to as "Compound group SX550").

The Compound (L-3), wherein Q represents the group represented by Q16; $R^{1a}$ represents a hydrogen atom; $R^{1b}$ represents any one substituent described in Table 1A or Table 2A; $R^{3b}$ represents a hydrogen atom; and $R^{3c}$ represents a hydrogen atom (hereinafter referred to as "Compound group SX551").

The Compound (L-3), wherein Q represents the group represented by Q16; $R^{1a}$ represents any one substituent described in Table 1A or Table 2A; $R^{1b}$ represents a hydrogen atom; $R^{3b}$ represents a hydrogen atom; and $R^{3c}$ represents a hydrogen atom (hereinafter referred to as "Compound group SX552").

The Compound (L-3), wherein Q represents the group represented by Q17; $R^{1a}$ represents a hydrogen atom; $R^{1b}$ represents any one substituent described in Table 1A or Table 2A; $R^{3b}$ represents a hydrogen atom; and $R^{3c}$ represents a hydrogen atom (hereinafter referred to as "Compound group SX553").

The Compound (L-3), wherein Q represents the group represented by Q17; $R^{1a}$ represents any one substituent described in Table 1A or Table 2A; $R^{1b}$ represents a hydrogen atom; $R^{3b}$ represents a hydrogen atom; and $R^{3c}$ represents a hydrogen atom (hereinafter referred to as "Compound group SX554").

The Compound (L-3), wherein Q represents the group represented by Q18; $R^{1a}$ represents a hydrogen atom; $R^{1b}$ represents any one substituent described in Table 1A or Table 2A; $R^{3b}$ represents a hydrogen atom; and $R^{3c}$ represents a hydrogen atom (hereinafter referred to as "Compound group SX555").

The Compound (L-3), wherein Q represents the group represented by Q18; $R^{1a}$ represents any one substituent described in Table 1A or Table 2A; $R^{1b}$ represents a hydrogen atom; $R^{3b}$ represents a hydrogen atom; and $R^{3c}$ represents a hydrogen atom (hereinafter referred to as "Compound group SX556").

The Compound (L-3), wherein Q represents the group represented by Q19; $R^{1b}$ represents any one substituent described in Table 1A or Table 2A; $R^{3b}$ represents a hydrogen atom; and $R^{3c}$ represents a hydrogen atom (hereinafter referred to as "Compound group SX557").

The Compound (L-3), wherein Q represents the group represented by Q20; $R^{1b}$ represents any one substituent described in Table 1A or Table 2A; $R^{3b}$ represents a hydrogen atom; and $R^{3c}$ represents a hydrogen atom (hereinafter referred to as "Compound group SX558").

The Compound (L-3), wherein Q represents the group represented by Q21; $R^{1b}$ represents any one substituent described in Table 1A or Table 2A; $R^{3b}$ represents a hydrogen atom; and $R^{3c}$ represents a hydrogen atom (hereinafter referred to as "Compound group SX559").

The Compound (L-3), wherein Q represents the group represented by Q22; $R^{1b}$ represents any one substituent described in Table 1A or Table 2A; $R^{3b}$ represents a hydrogen atom; and $R^{3c}$ represents a hydrogen atom (hereinafter referred to as "Compound group SX560").

The Compound (L-3), wherein Q represents the group represented by Q23; $R^{1b}$ represents any one substituent described in Table 1A or Table 2A; $R^{3b}$ represents a hydrogen atom; and $R^{3c}$ represents a hydrogen atom (hereinafter referred to as "Compound group SX561").

The Compound (L-3), wherein Q represents the group represented by Q24; $R^{1b}$ represents any one substituent described in Table 1A or Table 2A; $R^{3b}$ represents a hydrogen atom; and $R^{3c}$ represents a hydrogen atom (hereinafter referred to as "Compound group SX562").

The Compound (L-3), wherein Q represents the group represented by Q25; $R^{1b}$ represents any one substituent described in Table 1A or Table 2A; $R^{3b}$ represents a hydrogen atom; and $R^{3c}$ represents a hydrogen atom (hereinafter referred to as "Compound group SX563").

The Compound (L-3), wherein Q represents the group represented by Q26; $R^{1b}$ represents any one substituent described in Table 1A or Table 2A; $R^{3b}$ represents a hydrogen atom; and $R^{3c}$ represents a hydrogen atom (hereinafter referred to as "Compound group SX564").

The Compound (L-3), wherein Q represents the group represented by Q27; $R^{1a}$ represents a hydrogen atom; $R^{1b}$ represents any one substituent described in Table 1A or Table 2A; $R^{3b}$ represents a hydrogen atom; and $R^{3c}$ represents a hydrogen atom (hereinafter referred to as "Compound group SX565").

The Compound (L-3), wherein Q represents the group represented by Q27; $R^{1a}$ represents any one substituent described in Table 1A or Table 2A; $R^{1b}$ represents a hydrogen atom; $R^{3b}$ represents a hydrogen atom; and $R^{3c}$ represents a hydrogen atom (hereinafter referred to as "Compound group SX566").

The Compound (L-3), wherein Q represents the group represented by Q28; $R^{1a}$ represents a hydrogen atom; $R^{1b}$ represents any one substituent described in Table 1A or Table 2A; $R^{3b}$ represents a hydrogen atom; and $R^{3c}$ represents a hydrogen atom (hereinafter referred to as "Compound group SX567").

The Compound (L-3), wherein Q represents the group represented by Q28; $R^{1a}$ represents any one substituent described in Table 1A or Table 2A; $R^{1b}$ represents a hydrogen atom; $R^{3b}$ represents a hydrogen atom; and $R^{3c}$ represents a hydrogen atom (hereinafter referred to as "Compound group SX568").

The Compound (L-3), wherein Q represents the group represented by Q29; $R^{1b}$ represents any one substituent described in Table 1A or Table 2A; $R^{3b}$ represents a hydrogen atom; and $R^{3c}$ represents a hydrogen atom (hereinafter referred to as "Compound group SX569").

The Compound (L-3), wherein Q represents the group represented by Q30; $R^{1b}$ represents any one substituent described in Table 1A or Table 2A; $R^{3b}$ represents a hydrogen atom; and $R^{3c}$ represents a hydrogen atom (hereinafter referred to as "Compound group SX570").

The Compound (L-3), wherein Q represents the group represented by Q11; $R^{1a}$ represents a hydrogen atom; $R^{1b}$ represents any one substituent described in Table 1A or Table 2A; $R^{3b}$ represents a trifluoromethyl group; and $R^{3c}$ represents a hydrogen atom (hereinafter referred to as "Compound group SX571").

The Compound (L-3), wherein Q represents the group represented by Q11; $R^{1a}$ represents any one substituent described in Table 1A or Table 2A; $R^{1b}$ represents a hydrogen atom; $R^{3b}$ represents a trifluoromethyl group; and $R^{3c}$ represents a hydrogen atom (hereinafter referred to as "Compound group SX572").

The Compound (L-3), wherein Q represents the group represented by Q12; $R^{1a}$ represents a hydrogen atom; $R^{1b}$ represents any one substituent described in Table 1A or Table 2A; $R^{3b}$ represents a trifluoromethyl group; and $R^{3G}$ represents a hydrogen atom (hereinafter referred to as "Compound group SX573").

The Compound (L-3), wherein Q represents the group represented by Q12; $R^{1a}$ represents any one substituent described in Table 1A or Table 2A; $R^{1b}$ represents a hydrogen atom; $R^{3b}$ represents a trifluoromethyl group; and $R^{3c}$ represents a hydrogen atom (hereinafter referred to as "Compound group SX574").

The Compound (L-3), wherein Q represents the group represented by Q13; $R^{1a}$ represents a hydrogen atom; $R^{1b}$ represents any one substituent described in Table 1A or Table 2A; $R^{3b}$ represents a trifluoromethyl group; and $R^{3c}$ represents a hydrogen atom (hereinafter referred to as "Compound group SX575").

The Compound (L-3), wherein Q represents the group represented by Q13; $R^{1a}$ represents any one substituent described in Table 1A or Table 2A; $R^{1b}$ represents a hydrogen atom; $R^{3b}$ represents a trifluoromethyl group; and $R^{3c}$ represents a hydrogen atom (hereinafter referred to as "Compound group SX576").

The Compound (L-3), wherein Q represents the group represented by Q14; $R^{1a}$ represents a hydrogen atom; $R^{1b}$ represents any one substituent described in Table 1A or Table 2A; $R^{3b}$ represents a trifluoromethyl group; and $R^{3c}$ represents a hydrogen atom (hereinafter referred to as "Compound group SX577").

The Compound (L-3), wherein Q represents the group represented by Q14; $R^{1a}$ represents any one substituent described in Table 1A or Table 2A; $R^{1b}$ represents a hydrogen atom; $R^{3b}$ represents a trifluoromethyl group; and $R^{3c}$ represents a hydrogen atom (hereinafter referred to as "Compound group SX578").

The Compound (L-3), wherein Q represents the group represented by Q15; $R^{1a}$ represents a hydrogen atom; $R^{1b}$ represents any one substituent described in Table 1A or Table 2A; $R^{3b}$ represents a trifluoromethyl group; and $R^{3c}$ represents a hydrogen atom (hereinafter referred to as "Compound group SX579").

The Compound (L-3), wherein Q represents the group represented by Q15; $R^{1a}$ represents any one substituent described in Table 1A or Table 2A; $R^{1b}$ represents a hydrogen atom; $R^{3b}$ represents a trifluoromethyl group; and $R^{3c}$ represents a hydrogen atom (hereinafter referred to as "Compound group SX580").

The Compound (L-3), wherein Q represents the group represented by Q16; $R^{1a}$ represents a hydrogen atom; $R^{1b}$ represents any one substituent described in Table 1A or Table 2A; $R^{3b}$ represents a trifluoromethyl group; and $R^{3c}$ represents a hydrogen atom (hereinafter referred to as "Compound group SX581").

The Compound (L-3), wherein Q represents the group represented by Q16; $R^{1a}$ represents any one substituent described in Table 1A or Table 2A; $R^{1b}$ represents a hydrogen atom; $R^{3b}$ represents a trifluoromethyl group; and $R^{3c}$ represents a hydrogen atom (hereinafter referred to as "Compound group SX582").

The Compound (L-3), wherein Q represents the group represented by Q17; $R^{1a}$ represents a hydrogen atom; $R^{1b}$ represents any one substituent described in Table 1A or Table 2A; $R^{3b}$ represents a trifluoromethyl group; and $R^{3c}$ represents a hydrogen atom (hereinafter referred to as "Compound group SX583").

The Compound (L-3), wherein Q represents the group represented by Q17; $R^{1a}$ represents any one substituent described in Table 1A or Table 2A; $R^{1b}$ represents a hydrogen atom; $R^{3b}$ represents a trifluoromethyl group; and $R^{3c}$ represents a hydrogen atom (hereinafter referred to as "Compound group SX584").

The Compound (L-3), wherein Q represents the group represented by Q18; $R^{1a}$ represents a hydrogen atom; $R^{1b}$ represents any one substituent described in Table 1A or Table 2A; $R^{3b}$ represents a trifluoromethyl group; and $R^{3G}$ represents a hydrogen atom (hereinafter referred to as "Compound group SX585").

The Compound (L-3), wherein Q represents the group represented by Q18; $R^{1a}$ represents any one substituent described in Table 1A or Table 2A; $R^{1b}$ represents a hydrogen atom; $R^{3b}$ represents a trifluoromethyl group; and $R^{3c}$ represents a hydrogen atom (hereinafter referred to as "Compound group SX586").

The Compound (L-3), wherein Q represents the group represented by Q19; $R^{1b}$ represents any one substituent described in Table 1A or Table 2A; $R^{3b}$ represents a trifluoromethyl group; and $R^{3c}$ represents a hydrogen atom (hereinafter referred to as "Compound group SX587").

The Compound (L-3), wherein Q represents the group represented by Q20; $R^{1b}$ represents any one substituent described in Table 1A or Table 2A; $R^{3b}$ represents a trifluoromethyl group; and $R^{3c}$ represents a hydrogen atom (hereinafter referred to as "Compound group SX588").

The Compound (L-3), wherein Q represents the group represented by Q21; $R^{1b}$ represents any one substituent described in Table 1A or Table 2A; $R^{3b}$ represents a trifluoromethyl group; and $R^{3c}$ represents a hydrogen atom (hereinafter referred to as "Compound group SX589").

The Compound (L-3), wherein Q represents the group represented by Q22; $R^{1b}$ represents any one substituent described in Table 1A or Table 2A; $R^{3b}$ represents a trifluoromethyl group; and $R^{3c}$ represents a hydrogen atom (hereinafter referred to as "Compound group SX590").

The Compound (L-3), wherein Q represents the group represented by Q23; $R^{1b}$ represents any one substituent described in Table 1A or Table 2A; $R^{3b}$ represents a trifluoromethyl group; and $R^{3c}$ represents a hydrogen atom (hereinafter referred to as "Compound group SX591").

The Compound (L-3), wherein Q represents the group represented by Q24; $R^{1b}$ represents any one substituent described in Table 1A or Table 2A; $R^{3b}$ represents a trifluoromethyl group; and $R^{3c}$ represents a hydrogen atom (hereinafter referred to as "Compound group SX592").

The Compound (L-3), wherein Q represents the group represented by Q25; $R^{1b}$ represents any one substituent described in Table 1A or Table 2A; $R^{3b}$ represents a trifluoromethyl group; and $R^{3c}$ represents a hydrogen atom (hereinafter referred to as "Compound group SX593").

The Compound (L-3), wherein Q represents the group represented by Q26; $R^{1b}$ represents any one substituent described in Table 1A or Table 2A; $R^{3b}$ represents a trifluoromethyl group; and $R^{3c}$ represents a hydrogen atom (hereinafter referred to as "Compound group SX594").

The Compound (L-3), wherein Q represents the group represented by Q27; $R^{1a}$ represents a hydrogen atom; $R^{1b}$ represents any one substituent described in Table 1A or Table 2A; $R^{3b}$ represents a trifluoromethyl group; and $R^{3c}$ represents a hydrogen atom (hereinafter referred to as "Compound group SX595").

The Compound (L-3), wherein Q represents the group represented by Q27; $R^{1a}$ represents any one substituent described in Table 1A or Table 2A; $R^{1b}$ represents a hydrogen atom; $R^{3b}$ represents a trifluoromethyl group; and $R^{3c}$ represents a hydrogen atom (hereinafter referred to as "Compound group SX596").

The Compound (L-3), wherein Q represents the group represented by Q28; $R^{1a}$ represents a hydrogen atom; $R^{1b}$ represents any one substituent described in Table 1A or Table 2A; $R^{3b}$ represents a trifluoromethyl group; and $R^{3c}$ represents a hydrogen atom (hereinafter referred to as "Compound group SX597").

The Compound (L-3), wherein Q represents the group represented by Q28; $R^{1a}$ represents any one substituent described in Table 1A or Table 2A; $R^{1b}$ represents a hydrogen atom; $R^{3b}$ represents a trifluoromethyl group; and $R^{3c}$ represents a hydrogen atom (hereinafter referred to as "Compound group SX598").

The Compound (L-3), wherein Q represents the group represented by Q29; $R^{1b}$ represents any one substituent described in Table 1A or Table 2A; $R^{3b}$ represents a trifluoromethyl group; and $R^{3c}$ represents a hydrogen atom (hereinafter referred to as "Compound group SX599").

The Compound (L-3), wherein Q represents the group represented by Q30; $R^{1b}$ represents any one substituent described in Table 1A or Table 2A; $R^{3b}$ represents a trifluoromethyl group; and $R^{3c}$ represents a hydrogen atom (hereinafter referred to as "Compound group SX600").

The Compound (L-3), wherein Q represents the group represented by Q11; $R^{1a}$ represents a hydrogen atom; $R^{1b}$ represents any one substituent described in Table 1A or Table 2A; $R^{3b}$ represents a chlorine atom; and $R^{3c}$ represents a hydrogen atom (hereinafter referred to as "Compound group SX601").

The Compound (L-3), wherein Q represents the group represented by Q11; $R^{1a}$ represents any one substituent described in Table 1A or Table 2A; $R^{1b}$ represents a hydrogen atom; $R^{3b}$ represents a chlorine atom; and $R^{3c}$ represents a hydrogen atom (hereinafter referred to as "Compound group SX602").

The Compound (L-3), wherein Q represents the group represented by Q12; $R^{1a}$ represents a hydrogen atom; $R^{1b}$ represents any one substituent described in Table 1A or Table 2A; $R^{3b}$ represents a chlorine atom; and $R^{3c}$ represents a hydrogen atom (hereinafter referred to as "Compound group SX603").

The Compound (L-3), wherein Q represents the group represented by Q12; $R^{1a}$ represents any one substituent described in Table 1A or Table 2A; $R^{1b}$ represents a hydrogen atom; $R^{3b}$ represents a chlorine atom; and $R^{3c}$ represents a hydrogen atom (hereinafter referred to as "Compound group SX604").

The Compound (L-3), wherein Q represents the group represented by Q13; $R^{1a}$ represents a hydrogen atom; $R^{1b}$ represents any one substituent described in Table 1A or Table 2A; $R^{3b}$ represents a chlorine atom; and $R^{3c}$ represents a hydrogen atom (hereinafter referred to as "Compound group SX605").

The Compound (L-3), wherein Q represents the group represented by Q13; $R^{1a}$ represents any one substituent described in Table 1A or Table 2A; $R^{1b}$ represents a hydrogen atom; $R^{3b}$ represents a chlorine atom; and $R^{3c}$ represents a hydrogen atom (hereinafter referred to as "Compound group SX606").

The Compound (L-3), wherein Q represents the group represented by Q14; $R^{1a}$ represents a hydrogen atom; $R^{1b}$ represents any one substituent described in Table 1A or Table 2A; $R^{3b}$ represents a chlorine atom; and $R^{3c}$ represents a hydrogen atom (hereinafter referred to as "Compound group SX607").

The Compound (L-3), wherein Q represents the group represented by Q14; $R^{1a}$ represents any one substituent described in Table 1A or Table 2A; $R^{1b}$ represents a hydrogen atom; $R^{3b}$ represents a chlorine atom; and $R^{3c}$ represents a hydrogen atom (hereinafter referred to as "Compound group SX608").

The Compound (L-3), wherein Q represents the group represented by Q15; $R^{1a}$ represents a hydrogen atom; $R^{1b}$ represents any one substituent described in Table 1A or Table 2A; $R^{3b}$ represents a chlorine atom; and $R^{3c}$ represents a hydrogen atom (hereinafter referred to as "Compound group SX609").

The Compound (L-3), wherein Q represents the group represented by Q15; $R^{1a}$ represents any one substituent described in Table 1A or Table 2A; $R^{1b}$ represents a hydrogen atom; $R^{3b}$ represents a chlorine atom; and $R^{3c}$ represents a hydrogen atom (hereinafter referred to as "Compound group SX610").

The Compound (L-3), wherein Q represents the group represented by Q16; $R^{1a}$ represents a hydrogen atom; $R^{1b}$ represents any one substituent described in Table 1A or Table 2A; $R^{3b}$ represents a chlorine atom; and $R^{3c}$ represents a hydrogen atom (hereinafter referred to as "Compound group SX611").

The Compound (L-3), wherein Q represents the group represented by Q16; $R^{1a}$ represents any one substituent described in Table 1A or Table 2A; $R^{1b}$ represents a hydrogen atom; $R^{3b}$ represents a chlorine atom; and $R^{3c}$ represents a hydrogen atom (hereinafter referred to as "Compound group SX612").

The Compound (L-3), wherein Q represents the group represented by Q17; $R^{1a}$ represents a hydrogen atom; $R^{1b}$ represents any one substituent described in Table 1A or Table 2A; $R^{3b}$ represents a chlorine atom; and $R^{3c}$ represents a hydrogen atom (hereinafter referred to as "Compound group SX613").

The Compound (L-3), wherein Q represents the group represented by Q17; $R^{1a}$ represents any one substituent described in Table 1A or Table 2A; $R^{1b}$ represents a hydrogen atom; $R^{3b}$ represents a chlorine atom; and $R^{3c}$ represents a hydrogen atom (hereinafter referred to as "Compound group SX614").

The Compound (L-3), wherein Q represents the group represented by Q18; $R^{1a}$ represents a hydrogen atom; $R^{1b}$ represents any one substituent described in Table 1A or Table 2A; $R^{3b}$ represents a chlorine atom; and $R^{3c}$ represents a hydrogen atom (hereinafter referred to as "Compound group SX615").

The Compound (L-3), wherein Q represents the group represented by Q18; $R^{1a}$ represents any one substituent described in Table 1A or Table 2A; $R^{1b}$ represents a hydrogen atom; $R^{3b}$ represents a chlorine atom; and $R^{3c}$ represents a hydrogen atom (hereinafter referred to as "Compound group SX616").

The Compound (L-3), wherein Q represents the group represented by Q19; $R^{1b}$ represents any one substituent described in Table 1A or Table 2A; $R^{3b}$ represents a chlorine atom; and $R^{3c}$ represents a hydrogen atom (hereinafter referred to as "Compound group SX617").

The Compound (L-3), wherein Q represents the group represented by Q20; $R^{1b}$ represents any one substituent described in Table 1A or Table 2A; $R^{3b}$ represents a chlorine atom; and $R^{3c}$ represents a hydrogen atom (hereinafter referred to as "Compound group SX618").

The Compound (L-3), wherein Q represents the group represented by Q21; $R^{1b}$ represents any one substituent described in Table 1A or Table 2A; $R^{3b}$ represents a chlorine atom; and $R^{3c}$ represents a hydrogen atom (hereinafter referred to as "Compound group SX619").

The Compound (L-3), wherein Q represents the group represented by Q22; $R^{1b}$ represents any one substituent described in Table 1A or Table 2A; $R^{3b}$ represents a chlorine atom; and $R^{3c}$ represents a hydrogen atom (hereinafter referred to as "Compound group SX620").

The Compound (L-3), wherein Q represents the group represented by Q23; $R^{1b}$ represents any one substituent described in Table 1A or Table 2A; $R^{3b}$ represents a chlorine atom; and $R^{3c}$ represents a hydrogen atom (hereinafter referred to as "Compound group SX621").

The Compound (L-3), wherein Q represents the group represented by Q24; $R^{1b}$ represents any one substituent described in Table 1A or Table 2A; $R^{3b}$ represents a chlorine atom; and $R^{3c}$ represents a hydrogen atom (hereinafter referred to as "Compound group SX622").

The Compound (L-3), wherein Q represents the group represented by Q25; $R^{1b}$ represents any one substituent described in Table 1A or Table 2A; $R^{3b}$ represents a chlorine atom; and $R^{3c}$ represents a hydrogen atom (hereinafter referred to as "Compound group SX623").

The Compound (L-3), wherein Q represents the group represented by Q26; $R^{1b}$ represents any one substituent described in Table 1A or Table 2A; $R^{3b}$ represents a chlorine atom; and $R^{3c}$ represents a hydrogen atom (hereinafter referred to as "Compound group SX624").

The Compound (L-3), wherein Q represents the group represented by Q27; $R^{1a}$ represents a hydrogen atom; $R^{1b}$ represents any one substituent described in Table 1A or Table 2A; $R^{3b}$ represents a chlorine atom; and $R^{3c}$ represents a hydrogen atom (hereinafter referred to as "Compound group SX625").

The Compound (L-3), wherein Q represents the group represented by Q27; $R^{1a}$ represents any one substituent described in Table 1A or Table 2A; $R^{1b}$ represents a hydrogen atom; $R^{3b}$ represents a chlorine atom; and $R^{3c}$ represents a hydrogen atom (hereinafter referred to as "Compound group SX626").

The Compound (L-3), wherein Q represents the group represented by Q28; $R^{1a}$ represents a hydrogen atom; $R^{1b}$ represents any one substituent described in Table 1A or Table 2A; $R^{3b}$ represents a chlorine atom; and $R^{3c}$ represents a hydrogen atom (hereinafter referred to as "Compound group SX627").

The Compound (L-3), wherein Q represents the group represented by Q28; $R^{1a}$ represents any one substituent described in Table 1A or Table 2A; $R^{1b}$ represents a hydrogen atom; $R^{3b}$ represents a chlorine atom; and $R^{3c}$ represents a hydrogen atom (hereinafter referred to as "Compound group SX628").

The Compound (L-3), wherein Q represents the group represented by Q29; $R^{1b}$ represents any one substituent described in Table 1A or Table 2A; $R^{3b}$ represents a chlorine atom; and $R^{3c}$ represents a hydrogen atom (hereinafter referred to as "Compound group SX629").

The Compound (L-3), wherein Q represents the group represented by Q30; $R^{1b}$ represents any one substituent described in Table 1A or Table 2A; $R^{3b}$ represents a chlorine atom; and $R^{3c}$ represents a hydrogen atom (hereinafter referred to as "Compound group SX630").

The Compound (L-3), wherein Q represents the group represented by Q11; $R^{1a}$ represents a hydrogen atom; $R^{1b}$ represents any one substituent described in Table 1A or Table 2A; $R^{3b}$ represents a bromine atom; and $R^{3c}$ represents a hydrogen atom (hereinafter referred to as "Compound group SX631").

The Compound (L-3), wherein Q represents the group represented by Q11; $R^{1a}$ represents any one substituent described in Table 1A or Table 2A; $R^{1b}$ represents a hydrogen atom; $R^{3b}$ represents a bromine atom; and $R^{3c}$ represents a hydrogen atom (hereinafter referred to as "Compound group SX632").

The Compound (L-3), wherein Q represents the group represented by Q12; $R^{1a}$ represents a hydrogen atom; $R^{1b}$ represents any one substituent described in Table 1A or Table 2A; $R^{3b}$ represents a bromine atom; and $R^{3c}$ represents a hydrogen atom (hereinafter referred to as "Compound group SX633").

The Compound (L-3), wherein Q represents the group represented by Q12; $R^{1a}$ represents any one substituent described in Table 1A or Table 2A; $R^{1b}$ represents a hydrogen atom; $R^{3b}$ represents a bromine atom; and $R^{3c}$ represents a hydrogen atom (hereinafter referred to as "Compound group SX634").

The Compound (L-3), wherein Q represents the group represented by Q13; $R^{1a}$ represents a hydrogen atom; $R^{1b}$ represents any one substituent described in Table 1A or Table 2A; $R^{3b}$ represents a bromine atom; and $R^{3c}$ represents a hydrogen atom (hereinafter referred to as "Compound group SX635").

The Compound (L-3), wherein Q represents the group represented by Q13; $R^{1a}$ represents any one substituent described in Table 1A or Table 2A; $R^{1b}$ represents a hydrogen atom; $R^{3b}$ represents a bromine atom; and $R^{3c}$ represents a hydrogen atom (hereinafter referred to as "Compound group SX636").

The Compound (L-3), wherein Q represents the group represented by Q14; $R^{1a}$ represents a hydrogen atom; $R^{1b}$ represents any one substituent described in Table 1A or Table 2A; $R^{3b}$ represents a bromine atom; and $R^{3c}$ represents a hydrogen atom (hereinafter referred to as "Compound group SX637").

The Compound (L-3), wherein Q represents the group represented by Q14; $R^{1a}$ represents any one substituent described in Table 1A or Table 2A; $R^{1b}$ represents a hydrogen atom; $R^{3b}$ represents a bromine atom; and $R^{3c}$ represents a hydrogen atom (hereinafter referred to as "Compound group SX638").

The Compound (L-3), wherein Q represents the group represented by Q15; $R^{1a}$ represents a hydrogen atom; $R^{1b}$ represents any one substituent described in Table 1A or Table 2A; $R^{3b}$ represents a bromine atom; and $R^{3c}$ represents a hydrogen atom (hereinafter referred to as "Compound group SX639").

The Compound (L-3), wherein Q represents the group represented by Q15; $R^{1a}$ represents any one substituent described in Table 1A or Table 2A; $R^{1b}$ represents a hydrogen atom; $R^{3b}$ represents a bromine atom; and $R^{3c}$ represents a hydrogen atom (hereinafter referred to as "Compound group SX640").

The Compound (L-3), wherein Q represents the group represented by Q16; $R^{1a}$ represents a hydrogen atom; $R^{1b}$ represents any one substituent described in Table 1A or Table 2A; $R^{3b}$ represents a bromine atom; and $R^{3c}$ represents a hydrogen atom (hereinafter referred to as "Compound group SX641").

The Compound (L-3), wherein Q represents the group represented by Q16; $R^{1a}$ represents any one substituent described in Table 1A or Table 2A; $R^{1b}$ represents a hydrogen atom; $R^{3b}$ represents a bromine atom; and $R^{3c}$ represents a hydrogen atom (hereinafter referred to as "Compound group SX642").

The Compound (L-3), wherein Q represents the group represented by Q17; $R^{1a}$ represents a hydrogen atom; $R^{1b}$ represents any one substituent described in Table 1A or Table 2A; $R^{3b}$ represents a bromine atom; and $R^{3c}$ represents a hydrogen atom (hereinafter referred to as "Compound group SX643").

The Compound (L-3), wherein Q represents the group represented by Q17; $R^{1a}$ represents any one substituent described in Table 1A or Table 2A; $R^{1b}$ represents a hydrogen atom; $R^{3b}$ represents a bromine atom; and $R^{3c}$ represents a hydrogen atom (hereinafter referred to as "Compound group SX644").

The Compound (L-3), wherein Q represents the group represented by Q18; $R^{1a}$ represents a hydrogen atom; $R^{1b}$ represents any one substituent described in Table 1A or Table 2A; $R^{3b}$ represents a bromine atom; and $R^{3c}$ represents a hydrogen atom (hereinafter referred to as "Compound group SX645").

The Compound (L-3), wherein Q represents the group represented by Q18; $R^{1a}$ represents any one substituent described in Table 1A or Table 2A; $R^{1b}$ represents a hydrogen atom; $R^{3b}$ represents a bromine atom; and $R^{3c}$ represents a hydrogen atom (hereinafter referred to as "Compound group SX646").

The Compound (L-3), wherein Q represents the group represented by Q19; $R^{1b}$ represents any one substituent described in Table 1A or Table 2A; $R^{3b}$ represents a bromine atom; and $R^{3c}$ represents a hydrogen atom (hereinafter referred to as "Compound group SX647").

The Compound (L-3), wherein Q represents the group represented by Q20; $R^{1b}$ represents any one substituent described in Table 1A or Table 2A; $R^{3b}$ represents a bromine atom; and $R^{3c}$ represents a hydrogen atom (hereinafter referred to as "Compound group SX648").

The Compound (L-3), wherein Q represents the group represented by Q21; $R^{1b}$ represents any one substituent described in Table 1A or Table 2A; $R^{3b}$ represents a bromine atom; and $R^{3c}$ represents a hydrogen atom (hereinafter referred to as "Compound group SX649").

The Compound (L-3), wherein Q represents the group represented by Q22; $R^{1b}$ represents any one substituent described in Table 1A or Table 2A; $R^{3b}$ represents a bromine atom; and $R^{3c}$ represents a hydrogen atom (hereinafter referred to as "Compound group SX650").

The Compound (L-3), wherein Q represents the group represented by Q23; $R^{1b}$ represents any one substituent described in Table 1A or Table 2A; $R^{3b}$ represents a bromine atom; and $R^{3c}$ represents a hydrogen atom (hereinafter referred to as "Compound group SX651").

The Compound (L-3), wherein Q represents the group represented by Q24; $R^{1b}$ represents any one substituent described in Table 1A or Table 2A; $R^{3b}$ represents a bromine atom; and $R^{3c}$ represents a hydrogen atom (hereinafter referred to as "Compound group SX652").

The Compound (L-3), wherein Q represents the group represented by Q25; $R^{1b}$ represents any one substituent described in Table 1A or Table 2A; $R^{3b}$ represents a bromine atom; and $R^{3c}$ represents a hydrogen atom (hereinafter referred to as "Compound group SX653").

The Compound (L-3), wherein Q represents the group represented by Q26; $R^{1b}$ represents any one substituent described in Table 1A or Table 2A; $R^{3b}$ represents a bromine atom; and $R^{3c}$ represents a hydrogen atom (hereinafter referred to as "Compound group SX654").

The Compound (L-3), wherein Q represents the group represented by Q27; $R^{1a}$ represents a hydrogen atom; $R^{1b}$ represents any one substituent described in Table 1A or Table 2A; $R^{3b}$ represents a bromine atom; and $R^{3c}$ represents a hydrogen atom (hereinafter referred to as "Compound group SX655").

The Compound (L-3), wherein Q represents the group represented by Q27; $R^{1a}$ represents any one substituent described in Table 1A or Table 2A; $R^{1b}$ represents a hydrogen atom; $R^{3b}$ represents a bromine atom; and $R^{3c}$ represents a hydrogen atom (hereinafter referred to as "Compound group SX656").

The Compound (L-3), wherein Q represents the group represented by Q28; $R^{1a}$ represents a hydrogen atom; $R^{1b}$ represents any one substituent described in Table 1A or Table 2A; $R^{3b}$ represents a bromine atom; and $R^{3c}$ represents a hydrogen atom (hereinafter referred to as "Compound group SX657").

The Compound (L-3), wherein Q represents the group represented by Q28; $R^{1a}$ represents any one substituent described in Table 1A or Table 2A; $R^{1b}$ represents a hydrogen atom; $R^{3b}$ represents a bromine atom; and $R^{3c}$ represents a hydrogen atom (hereinafter referred to as "Compound group SX658").

The Compound (L-3), wherein Q represents the group represented by Q29; $R^{1b}$ represents any one substituent described in Table 1A or Table 2A; $R^{3b}$ represents a bromine atom; and $R^{3c}$ represents a hydrogen atom (hereinafter referred to as "Compound group SX659").

The Compound (L-3), wherein Q represents the group represented by Q30; $R^{1b}$ represents any one substituent described in Table 1A or Table 2A; $R^{3b}$ represents a bromine atom; and $R^{3c}$ represents a hydrogen atom (hereinafter referred to as "Compound group SX660").

The Compound (L-3), wherein Q represents the group represented by Q11; $R^{1a}$ represents a hydrogen atom; $R^{1b}$ represents any one substituent described in Table 1A or Table 2A; $R^{3b}$ represents an iodine atom; and $R^{3c}$ represents a hydrogen atom (hereinafter referred to as "Compound group SX661").

The Compound (L-3), wherein Q represents the group represented by Q11; $R^{1a}$ represents any one substituent described in Table 1A or Table 2A; $R^{1b}$ represents a hydrogen atom; $R^{3b}$ represents an iodine atom; and $R^{3c}$ represents a hydrogen atom (hereinafter referred to as "Compound group SX662").

The Compound (L-3), wherein Q represents the group represented by Q12; $R^{1a}$ represents a hydrogen atom; $R^{1b}$ represents any one substituent described in Table 1A or Table 2A; $R^{3b}$ represents an iodine atom; and $R^{3c}$ represents a hydrogen atom (hereinafter referred to as "Compound group SX663").

The Compound (L-3), wherein Q represents the group represented by Q12; $R^{1a}$ represents any one substituent described in Table 1A or Table 2A; $R^{1b}$ represents a hydrogen atom; $R^{3b}$ represents an iodine atom; and $R^{3c}$ represents a hydrogen atom (hereinafter referred to as "Compound group SX664").

The Compound (L-3), wherein Q represents the group represented by Q13; $R^{1a}$ represents a hydrogen atom; $R^{1b}$ represents any one substituent described in Table 1A or Table 2A; $R^{3b}$ represents an iodine atom; and $R^{3c}$ represents a hydrogen atom (hereinafter referred to as "Compound group SX665").

The Compound (L-3), wherein Q represents the group represented by Q13; $R^{1a}$ represents any one substituent described in Table 1A or Table 2A; $R^{1b}$ represents a hydrogen atom; $R^{3b}$ represents an iodine atom; and $R^{3c}$ represents a hydrogen atom (hereinafter referred to as "Compound group SX666").

The Compound (L-3), wherein Q represents the group represented by Q14; $R^{1a}$ represents a hydrogen atom; $R^{1b}$ represents any one substituent described in Table 1A or Table 2A; $R^{3b}$ represents an iodine atom; and $R^{3c}$ represents a hydrogen atom (hereinafter referred to as "Compound group SX667").

The Compound (L-3), wherein Q represents the group represented by Q14; $R^{1a}$ represents any one substituent described in Table 1A or Table 2A; $R^{1b}$ represents a hydrogen atom; $R^{3b}$ represents an iodine atom; and $R^{3c}$ represents a hydrogen atom (hereinafter referred to as "Compound group SX668").

The Compound (L-3), wherein Q represents the group represented by Q15; $R^{1a}$ represents a hydrogen atom; $R^{1b}$ represents any one substituent described in Table 1A or Table 2A; $R^{3b}$ represents an iodine atom; and $R^{3c}$ represents a hydrogen atom (hereinafter referred to as "Compound group SX669").

The Compound (L-3), wherein Q represents the group represented by Q15; $R^{1a}$ represents any one substituent described in Table 1A or Table 2A; $R^{1b}$ represents a hydrogen atom; $R^{3b}$ represents an iodine atom; and $R^{3c}$ represents a hydrogen atom (hereinafter referred to as "Compound group SX670").

The Compound (L-3), wherein Q represents the group represented by Q16; $R^{1a}$ represents a hydrogen atom; $R^{1b}$ represents any one substituent described in Table 1A or Table 2A; $R^{3b}$ represents an iodine atom; and $R^{3c}$ represents a hydrogen atom (hereinafter referred to as "Compound group SX671").

The Compound (L-3), wherein Q represents the group represented by Q16; $R^{1a}$ represents any one substituent described in Table 1A or Table 2A; $R^{1b}$ represents a hydrogen atom; $R^{3b}$ represents an iodine atom; and $R^{3c}$ represents a hydrogen atom (hereinafter referred to as "Compound group SX672").

The Compound (L-3), wherein Q represents the group represented by Q17; $R^{1a}$ represents a hydrogen atom; $R^{1b}$ represents any one substituent described in Table 1A or Table 2A; $R^{3b}$ represents an iodine atom; and $R^{3c}$ represents a hydrogen atom (hereinafter referred to as "Compound group SX673").

The Compound (L-3), wherein Q represents the group represented by Q17; $R^{1a}$ represents any one substituent described in Table 1A or Table 2A; $R^{1b}$ represents a hydrogen atom; $R^{3b}$ represents an iodine atom; and $R^{3c}$ represents a hydrogen atom (hereinafter referred to as "Compound group SX674").

The Compound (L-3), wherein Q represents the group represented by Q18; $R^{1a}$ represents a hydrogen atom; $R^{1b}$ represents any one substituent described in Table 1A or Table 2A; $R^{3b}$ represents an iodine atom; and $R^{3c}$ represents a hydrogen atom (hereinafter referred to as "Compound group SX675").

The Compound (L-3), wherein Q represents the group represented by Q18; $R^{1a}$ represents any one substituent described in Table 1A or Table 2A; $R^{1b}$ represents a hydrogen atom; $R^{3b}$ represents an iodine atom; and $R^{3c}$ represents a hydrogen atom (hereinafter referred to as "Compound group SX676").

The Compound (L-3), wherein Q represents the group represented by Q19; $R^{1b}$ represents any one substituent described in Table 1A or Table 2A; $R^{3b}$ represents an iodine atom; and $R^{3c}$ represents a hydrogen atom (hereinafter referred to as "Compound group SX677").

The Compound (L-3), wherein Q represents the group represented by Q20; $R^{1b}$ represents any one substituent described in Table 1A or Table 2A; $R^{3b}$ represents an iodine atom; and $R^{3c}$ represents a hydrogen atom (hereinafter referred to as "Compound group SX678").

The Compound (L-3), wherein Q represents the group represented by Q21; $R^{1b}$ represents any one substituent described in Table 1A or Table 2A; $R^{3b}$ represents an iodine atom; and $R^{3c}$ represents a hydrogen atom (hereinafter referred to as "Compound group SX679").

The Compound (L-3), wherein Q represents the group represented by Q22; $R^{1b}$ represents any one substituent described in Table 1A or Table 2A; $R^{3b}$ represents an iodine atom; and $R^{3c}$ represents a hydrogen atom (hereinafter referred to as "Compound group SX680").

The Compound (L-3), wherein Q represents the group represented by Q23; $R^{1b}$ represents any one substituent described in Table 1A or Table 2A; $R^{3b}$ represents an iodine atom; and $R^{3c}$ represents a hydrogen atom (hereinafter referred to as "Compound group SX681").

The Compound (L-3), wherein Q represents the group represented by Q24; $R^{1b}$ represents any one substituent described in Table 1A or Table 2A; $R^{3b}$ represents an iodine atom; and $R^{3c}$ represents a hydrogen atom (hereinafter referred to as "Compound group SX682").

The Compound (L-3), wherein Q represents the group represented by Q25; $R^{1b}$ represents any one substituent described in Table 1A or Table 2A; $R^{3b}$ represents an iodine atom; and $R^{3c}$ represents a hydrogen atom (hereinafter referred to as "Compound group SX683").

The Compound (L-3), wherein Q represents the group represented by Q26; $R^{1b}$ represents any one substituent described in Table 1A or Table 2A; $R^{3b}$ represents an iodine atom; and $R^{3c}$ represents a hydrogen atom (hereinafter referred to as "Compound group SX684").

The Compound (L-3), wherein Q represents the group represented by Q27; $R^{1a}$ represents a hydrogen atom; $R^{1b}$ represents any one substituent described in Table 1A or Table 2A; $R^{3b}$ represents an iodine atom; and $R^{3c}$ represents a hydrogen atom (hereinafter referred to as "Compound group SX685").

The Compound (L-3), wherein Q represents the group represented by Q27; $R^{1a}$ represents any one substituent described in Table 1A or Table 2A; $R^{1b}$ represents a hydrogen atom; $R^{3b}$ represents an iodine atom; and $R^{3c}$ represents a hydrogen atom (hereinafter referred to as "Compound group SX686").

The Compound (L-3), wherein Q represents the group represented by Q28; $R^{1a}$ represents a hydrogen atom; $R^{1b}$ represents any one substituent described in Table 1A or Table 2A; $R^{3b}$ represents an iodine atom; and $R^{3c}$ represents a hydrogen atom (hereinafter referred to as "Compound group SX687").

The Compound (L-3), wherein Q represents the group represented by Q28; $R^{1a}$ represents any one substituent described in Table 1A or Table 2A; $R^{1b}$ represents a hydrogen atom; $R^{3b}$ represents an iodine atom; and $R^{3c}$ represents a hydrogen atom (hereinafter referred to as "Compound group SX688").

The Compound (L-3), wherein Q represents the group represented by Q29; $R^{1b}$ represents any one substituent described in Table 1A or Table 2A; $R^{3b}$ represents an iodine atom; and $R^{3c}$ represents a hydrogen atom (hereinafter referred to as "Compound group SX689").

The Compound (L-3), wherein Q represents the group represented by Q30; $R^{1b}$ represents any one substituent described in Table 1A or Table 2A; $R^{3b}$ represents an iodine atom; and $R^{3c}$ represents a hydrogen atom (hereinafter referred to as "Compound group SX690").

The Compound (L-3), wherein Q represents the group represented by Q11; $R^{1a}$ represents a hydrogen atom; $R^{1b}$ represents any one substituent described in Table 1A or Table 2A; $R^{3b}$ represents a hydrogen atom; and $R^{3c}$ represents a trifluoromethyl group (hereinafter referred to as "Compound group SX691").

The Compound (L-3), wherein Q represents the group represented by Q11; $R^{1a}$ represents any one substituent described in Table 1A or Table 2A; $R^{1b}$ represents a hydrogen atom; $R^{3b}$ represents a hydrogen atom; and $R^{3c}$ represents a trifluoromethyl group (hereinafter referred to as "Compound group SX692").

The Compound (L-3), wherein Q represents the group represented by Q12; $R^{1a}$ represents a hydrogen atom; $R^{1b}$ represents any one substituent described in Table 1A or Table 2A; $R^{3b}$ represents a hydrogen atom; and $R^{3c}$ represents a trifluoromethyl group (hereinafter referred to as "Compound group SX693").

The Compound (L-3), wherein Q represents the group represented by Q12; $R^{1a}$ represents any one substituent described in Table 1A or Table 2A; $R^{1b}$ represents a hydrogen atom; $R^{3b}$ represents a hydrogen atom; and $R^{3c}$ represents a trifluoromethyl group (hereinafter referred to as "Compound group SX694").

The Compound (L-3), wherein Q represents the group represented by Q13; $R^{1a}$ represents a hydrogen atom; $R^{1b}$ represents any one substituent described in Table 1A or Table 2A; $R^{3b}$ represents a hydrogen atom; and $R^{3c}$ represents a trifluoromethyl group (hereinafter referred to as "Compound group SX695").

The Compound (L-3), wherein Q represents the group represented by Q13; $R^{1a}$ represents any one substituent described in Table 1A or Table 2A; $R^{1b}$ represents a hydrogen atom; $R^{3b}$ represents a hydrogen atom; and $R^{3c}$ represents a trifluoromethyl group (hereinafter referred to as "Compound group SX696").

The Compound (L-3), wherein Q represents the group represented by Q14; $R^{1a}$ represents a hydrogen atom; $R^{1b}$ represents any one substituent described in Table 1A or Table 2A; $R^{3b}$ represents a hydrogen atom; and $R^{3c}$ represents a trifluoromethyl group (hereinafter referred to as "Compound group SX697").

The Compound (L-3), wherein Q represents the group represented by Q14; $R^{1a}$ represents any one substituent described in Table 1A or Table 2A; $R^{1b}$ represents a hydrogen atom; $R^{3b}$ represents a hydrogen atom; and $R^{3c}$ represents a trifluoromethyl group (hereinafter referred to as "Compound group SX698").

The Compound (L-3), wherein Q represents the group represented by Q15; $R^{1a}$ represents a hydrogen atom; $R^{1b}$ represents any one substituent described in Table 1A or Table 2A; $R^{3b}$ represents a hydrogen atom; and $R^{3c}$ represents a trifluoromethyl group (hereinafter referred to as "Compound group SX699").

The Compound (L-3), wherein Q represents the group represented by Q15; $R^{1a}$ represents any one substituent described in Table 1A or Table 2A; $R^{1b}$ represents a hydrogen atom; $R^{3b}$ represents a hydrogen atom; and $R^{3c}$ represents a trifluoromethyl group (hereinafter referred to as "Compound group SX700").

The Compound (L-3), wherein Q represents the group represented by Q16; $R^{1a}$ represents a hydrogen atom; $R^{1b}$ represents any one substituent described in Table 1A or Table 2A; $R^{3b}$ represents a hydrogen atom; and $R^{3c}$ represents a trifluoromethyl group (hereinafter referred to as "Compound group SX701").

The Compound (L-3), wherein Q represents the group represented by Q16; $R^{1a}$ represents any one substituent described in Table 1A or Table 2A; $R^{1b}$ represents a hydrogen atom; $R^{3b}$ represents a hydrogen atom; and $R^{3c}$ represents a trifluoromethyl group (hereinafter referred to as "Compound group SX702").

The Compound (L-3), wherein Q represents the group represented by Q17; $R^{1a}$ represents a hydrogen atom; $R^{1b}$ represents any one substituent described in Table 1A or Table 2A; $R^{3b}$ represents a hydrogen atom; and $R^{3c}$ represents a trifluoromethyl group (hereinafter referred to as "Compound group SX703").

The Compound (L-3), wherein Q represents the group represented by Q17; $R^{1a}$ represents any one substituent described in Table 1A or Table 2A; $R^{1b}$ represents a hydrogen atom; $R^{3b}$ represents a hydrogen atom; and $R^{3c}$ represents a trifluoromethyl group (hereinafter referred to as "Compound group SX704").

The Compound (L-3), wherein Q represents the group represented by Q18; $R^{1a}$ represents a hydrogen atom; $R^{1b}$ represents any one substituent described in Table 1A or Table 2A; $R^{3b}$ represents a hydrogen atom; and $R^{3c}$ represents a trifluoromethyl group (hereinafter referred to as "Compound group SX705").

The Compound (L-3), wherein Q represents the group represented by Q18; $R^{1a}$ represents any one substituent described in Table 1A or Table 2A; $R^{1b}$ represents a hydrogen atom; $R^{3b}$ represents a hydrogen atom; and $R^{3c}$ represents a trifluoromethyl group (hereinafter referred to as "Compound group SX706").

The Compound (L-3), wherein Q represents the group represented by Q19; $R^{1b}$ represents any one substituent described in Table 1A or Table 2A; $R^{3b}$ represents a hydrogen atom; and $R^{3c}$ represents a trifluoromethyl group (hereinafter referred to as "Compound group SX707").

The Compound (L-3), wherein Q represents the group represented by Q20; $R^{1b}$ represents any one substituent described in Table 1A or Table 2A; $R^{3b}$ represents a hydrogen atom; and $R^{3c}$ represents a trifluoromethyl group (hereinafter referred to as "Compound group SX708").

The Compound (L-3), wherein Q represents the group represented by Q21; $R^{1b}$ represents any one substituent described in Table 1A or Table 2A; $R^{3b}$ represents a hydrogen atom; and $R^{3c}$ represents a trifluoromethyl group (hereinafter referred to as "Compound group SX709").

The Compound (L-3), wherein Q represents the group represented by Q22; $R^{1b}$ represents any one substituent described in Table 1A or Table 2A; $R^{3b}$ represents a hydrogen atom; and $R^{3c}$ represents a trifluoromethyl group (hereinafter referred to as "Compound group SX710").

The Compound (L-3), wherein Q represents the group represented by Q23; $R^{1b}$ represents any one substituent described in Table 1A or Table 2A; $R^{3b}$ represents a hydrogen atom; and $R^{3c}$ represents a trifluoromethyl group (hereinafter referred to as "Compound group SX711").

The Compound (L-3), wherein Q represents the group represented by Q24; $R^{1b}$ represents any one substituent described in Table 1A or Table 2A; $R^{3b}$ represents a hydrogen atom; and $R^{3c}$ represents a trifluoromethyl group (hereinafter referred to as "Compound group SX712").

The Compound (L-3), wherein Q represents the group represented by Q25; $R^{1b}$ represents any one substituent described in Table 1A or Table 2A; $R^{3b}$ represents a hydrogen atom; and $R^{3c}$ represents a trifluoromethyl group (hereinafter referred to as "Compound group SX713").

The Compound (L-3), wherein Q represents the group represented by Q26; $R^{1b}$ represents any one substituent described in Table 1A or Table 2A; $R^{3b}$ represents a hydrogen atom; and $R^{3c}$ represents a trifluoromethyl group (hereinafter referred to as "Compound group SX714").

The Compound (L-3), wherein Q represents the group represented by Q27; $R^{1a}$ represents a hydrogen atom; $R^{1b}$ represents any one substituent described in Table 1A or Table 2A; $R^{3b}$ represents a hydrogen atom; and $R^{3c}$ represents a trifluoromethyl group (hereinafter referred to as "Compound group SX715").

The Compound (L-3), wherein Q represents the group represented by Q27; $R^{1a}$ represents any one substituent described in Table 1A or Table 2A; $R^{1b}$ represents a hydrogen atom; $R^{3b}$ represents a hydrogen atom; and $R^{3c}$ represents a trifluoromethyl group (hereinafter referred to as "Compound group SX716").

The Compound (L-3), wherein Q represents the group represented by Q28; $R^{1a}$ represents a hydrogen atom; $R^{1b}$ represents any one substituent described in Table 1A or Table 2A; $R^{3b}$ represents a hydrogen atom; and $R^{3c}$ represents a trifluoromethyl group (hereinafter referred to as "Compound group SX717").

The Compound (L-3), wherein Q represents the group represented by Q28; $R^{1a}$ represents any one substituent described in Table 1A or Table 2A; $R^{1b}$ represents a hydrogen atom; $R^{3b}$ represents a hydrogen atom; and $R^{3c}$ represents a trifluoromethyl group (hereinafter referred to as "Compound group SX718").

The Compound (L-3), wherein Q represents the group represented by Q29; $R^{1b}$ represents any one substituent described in Table 1A or Table 2A; $R^{3b}$ represents a hydrogen atom; and $R^{3c}$ represents a trifluoromethyl group (hereinafter referred to as "Compound group SX719").

The Compound (L-3), wherein Q represents the group represented by Q30; $R^{1b}$ represents any one substituent described in Table 1A or Table 2A; $R^{3b}$ represents a hydrogen atom; and $R^{3c}$ represents a trifluoromethyl group (hereinafter referred to as "Compound group SX720").

The Compound (L-3), wherein Q represents the group represented by Q11; $R^{1a}$ represents a hydrogen atom; $R^{1b}$ represents any one substituent described in Table 1A or Table 2A; $R^{3b}$ represents a hydrogen atom; and $R^{3c}$ represents a chlorine atom (hereinafter referred to as "Compound group SX721").

The Compound (L-3), wherein Q represents the group represented by Q11; $R^{1a}$ represents any one substituent described in Table 1A or Table 2A; $R^{1b}$ represents a hydrogen atom; $R^{3b}$ represents a hydrogen atom; and $R^{3c}$ represents a chlorine atom (hereinafter referred to as "Compound group SX722").

The Compound (L-3), wherein Q represents the group represented by Q12; $R^{1a}$ represents a hydrogen atom; $R^{1b}$ represents any one substituent described in Table 1A or Table 2A; $R^{3b}$ represents a hydrogen atom; and $R^{3c}$ represents a chlorine atom (hereinafter referred to as "Compound group SX723").

The Compound (L-3), wherein Q represents the group represented by Q12; $R^{1a}$ represents any one substituent described in Table 1A or Table 2A; $R^{1b}$ represents a hydrogen atom; $R^{3b}$ represents a hydrogen atom; and $R^{3c}$ represents a chlorine atom (hereinafter referred to as "Compound group SX724").

The Compound (L-3), wherein Q represents the group represented by Q13; $R^{1a}$ represents a hydrogen atom; $R^{1b}$ represents any one substituent described in Table 1A or Table 2A; $R^{3b}$ represents a hydrogen atom; and $R^{3c}$ represents a chlorine atom (hereinafter referred to as "Compound group SX725").

The Compound (L-3), wherein Q represents the group represented by Q13; $R^{1a}$ represents any one substituent described in Table 1A or Table 2A; $R^{1b}$ represents a hydrogen atom; $R^{3b}$ represents a hydrogen atom; and $R^{3c}$ represents a chlorine atom (hereinafter referred to as "Compound group SX726").

The Compound (L-3), wherein Q represents the group represented by Q14; $R^{1a}$ represents a hydrogen atom; $R^{1b}$ represents any one substituent described in Table 1A or Table 2A; $R^{3b}$ represents a hydrogen atom; and $R^{3c}$ represents a chlorine atom (hereinafter referred to as "Compound group SX727").

The Compound (L-3), wherein Q represents the group represented by Q14; $R^{1a}$ represents any one substituent described in Table 1A or Table 2A; $R^{1b}$ represents a hydrogen atom; $R^{3b}$ represents a hydrogen atom; and $R^{3c}$ represents a chlorine atom (hereinafter referred to as "Compound group SX728").

The Compound (L-3), wherein Q represents the group represented by Q15; $R^{1a}$ represents a hydrogen atom; $R^{1b}$ represents any one substituent described in Table 1A or Table 2A; $R^{3b}$ represents a hydrogen atom; and $R^{3c}$ represents a chlorine atom (hereinafter referred to as "Compound group SX729").

The Compound (L-3), wherein Q represents the group represented by Q15; $R^{1a}$ represents any one substituent described in Table 1A or Table 2A; $R^{1b}$ represents a hydrogen atom; $R^{3b}$ represents a hydrogen atom; and $R^{3c}$ represents a chlorine atom (hereinafter referred to as "Compound group SX730").

The Compound (L-3), wherein Q represents the group represented by Q16; $R^{1a}$ represents a hydrogen atom; $R^{1b}$ represents any one substituent described in Table 1A or Table 2A; $R^{3b}$ represents a hydrogen atom; and $R^{3c}$ represents a chlorine atom (hereinafter referred to as "Compound group SX731").

The Compound (L-3), wherein Q represents the group represented by Q16; $R^{1a}$ represents any one substituent described in Table 1A or Table 2A; $R^{1b}$ represents a hydrogen atom; $R^{3b}$ represents a hydrogen atom; and $R^{3c}$ represents a chlorine atom (hereinafter referred to as "Compound group SX732").

The Compound (L-3), wherein Q represents the group represented by Q17; $R^{1a}$ represents a hydrogen atom; $R^{1b}$ represents any one substituent described in Table 1A or Table 2A; $R^{3b}$ represents a hydrogen atom; and $R^{3c}$ represents a chlorine atom (hereinafter referred to as "Compound group SX733").

The Compound (L-3), wherein Q represents the group represented by Q17; $R^{1a}$ represents any one substituent described in Table 1A or Table 2A; $R^{1b}$ represents a hydrogen atom; $R^{3b}$ represents a hydrogen atom; and $R^{3c}$ represents a chlorine atom (hereinafter referred to as "Compound group SX734").

The Compound (L-3), wherein Q represents the group represented by Q18; $R^{1a}$ represents a hydrogen atom; $R^{1b}$ represents any one substituent described in Table 1A or Table 2A; $R^{3b}$ represents a hydrogen atom; and $R^{3c}$ represents a chlorine atom (hereinafter referred to as "Compound group SX735").

The Compound (L-3), wherein Q represents the group represented by Q18; $R^{1a}$ represents any one substituent described in Table 1A or Table 2A; $R^{1b}$ represents a hydrogen atom; $R^{3b}$ represents a hydrogen atom; and $R^{3c}$ represents a chlorine atom (hereinafter referred to as "Compound group SX736").

The Compound (L-3), wherein Q represents the group represented by Q19; $R^{1b}$ represents any one substituent described in Table 1A or Table 2A; $R^{3b}$ represents a hydrogen atom; and $R^{3c}$ represents a chlorine atom (hereinafter referred to as "Compound group SX737").

The Compound (L-3), wherein Q represents the group represented by Q20; $R^{1b}$ represents any one substituent described in Table 1A or Table 2A; $R^{3b}$ represents a hydrogen atom; and $R^{3c}$ represents a chlorine atom (hereinafter referred to as "Compound group SX738").

The Compound (L-3), wherein Q represents the group represented by Q21; $R^{1b}$ represents any one substituent described in Table 1A or Table 2A; $R^{3b}$ represents a hydrogen atom; and $R^{3c}$ represents a chlorine atom (hereinafter referred to as "Compound group SX739").

The Compound (L-3), wherein Q represents the group represented by Q22; $R^{1b}$ represents any one substituent described in Table 1A or Table 2A; $R^{3b}$ represents a hydrogen atom; and $R^{3c}$ represents a chlorine atom (hereinafter referred to as "Compound group SX740").

The Compound (L-3), wherein Q represents the group represented by Q23; $R^{1b}$ represents any one substituent described in Table 1A or Table 2A; $R^{3b}$ represents a hydrogen atom; and $R^{3c}$ represents a chlorine atom (hereinafter referred to as "Compound group SX741").

The Compound (L-3), wherein Q represents the group represented by Q24; $R^{1b}$ represents any one substituent described in Table 1A or Table 2A; $R^{3b}$ represents a hydrogen atom; and $R^{3c}$ represents a chlorine atom (hereinafter referred to as "Compound group SX742").

The Compound (L-3), wherein Q represents the group represented by Q25; $R^{1b}$ represents any one substituent described in Table 1A or Table 2A; $R^{3b}$ represents a hydrogen atom; and $R^{3c}$ represents a chlorine atom (hereinafter referred to as "Compound group SX743").

The Compound (L-3), wherein Q represents the group represented by Q26; $R^{1b}$ represents any one substituent described in Table 1A or Table 2A; $R^{3b}$ represents a hydrogen atom; and $R^{3c}$ represents a chlorine atom (hereinafter referred to as "Compound group SX744").

The Compound (L-3), wherein Q represents the group represented by Q27; $R^{1a}$ represents a hydrogen atom; $R^{1b}$ represents any one substituent described in Table 1A or Table 2A; $R^{3b}$ represents a hydrogen atom; and $R^{3c}$ represents a chlorine atom (hereinafter referred to as "Compound group SX745").

The Compound (L-3), wherein Q represents the group represented by Q27; $R^{1a}$ represents any one substituent described in Table 1A or Table 2A; $R^{1b}$ represents a hydrogen atom; $R^{3b}$ represents a hydrogen atom; and $R^{3c}$ represents a chlorine atom (hereinafter referred to as "Compound group SX746").

The Compound (L-3), wherein Q represents the group represented by Q28; $R^{1a}$ represents a hydrogen atom; $R^{1b}$ represents any one substituent described in Table 1A or Table 2A; $R^{3b}$ represents a hydrogen atom; and $R^{3c}$ represents a chlorine atom (hereinafter referred to as "Compound group SX747").

The Compound (L-3), wherein Q represents the group represented by Q28; $R^{1a}$ represents any one substituent described in Table 1A or Table 2A; $R^{1b}$ represents a hydrogen atom; $R^{3b}$ represents a hydrogen atom; and $R^{3c}$ represents a chlorine atom (hereinafter referred to as "Compound group SX748").

The Compound (L-3), wherein Q represents the group represented by Q29; $R^{1b}$ represents any one substituent described in Table 1A or Table 2A; $R^{3b}$ represents a hydrogen atom; and $R^{3c}$ represents a chlorine atom (hereinafter referred to as "Compound group SX749").

The Compound (L-3), wherein Q represents the group represented by Q30; $R^{1b}$ represents any one substituent described in Table 1A or Table 2A; $R^{3b}$ represents a hydrogen atom; and $R^{3c}$ represents a chlorine atom (hereinafter referred to as "Compound group SX750").

The Compound (L-3), wherein Q represents the group represented by Q11; $R^{1a}$ represents a hydrogen atom; $R^{1b}$ represents any one substituent described in Table 1A or Table 2A; $R^{3b}$ represents a hydrogen atom; and $R^{3c}$ represents a bromine atom (hereinafter referred to as "Compound group SX751").

The Compound (L-3), wherein Q represents the group represented by Q11; $R^{1a}$ represents any one substituent described in Table 1A or Table 2A; $R^{1b}$ represents a hydrogen atom; $R^{3b}$ represents a hydrogen atom; and $R^{3c}$ represents a bromine atom (hereinafter referred to as "Compound group SX752").

The Compound (L-3), wherein Q represents the group represented by Q12; $R^{1a}$ represents a hydrogen atom; $R^{1b}$ represents any one substituent described in Table 1A or Table 2A; $R^{3b}$ represents a hydrogen atom; and $R^{3c}$ represents a bromine atom (hereinafter referred to as "Compound group SX753").

The Compound (L-3), wherein Q represents the group represented by Q12; $R^{1a}$ represents any one substituent described in Table 1A or Table 2A; $R^{1b}$ represents a hydrogen atom; $R^{3b}$ represents a hydrogen atom; and $R^{3c}$ represents a bromine atom (hereinafter referred to as "Compound group SX754").

The Compound (L-3), wherein Q represents the group represented by Q13; $R^{1a}$ represents a hydrogen atom; $R^{1b}$ represents any one substituent described in Table 1A or Table 2A; $R^{3b}$ represents a hydrogen atom; and $R^{3c}$ represents a bromine atom (hereinafter referred to as "Compound group SX755").

The Compound (L-3), wherein Q represents the group represented by Q13; $R^{1a}$ represents any one substituent described in Table 1A or Table 2A; $R^{1b}$ represents a hydrogen atom; $R^{3b}$ represents a hydrogen atom; and $R^{3c}$ represents a bromine atom (hereinafter referred to as "Compound group SX756").

The Compound (L-3), wherein Q represents the group represented by Q14; $R^{1a}$ represents a hydrogen atom; $R^{1b}$ represents any one substituent described in Table 1A or Table 2A; $R^{3b}$ represents a hydrogen atom; and $R^{3c}$ represents a bromine atom (hereinafter referred to as "Compound group SX757").

The Compound (L-3), wherein Q represents the group represented by Q14; $R^{1a}$ represents any one substituent described in Table 1A or Table 2A; $R^{1b}$ represents a hydrogen atom; $R^{3b}$ represents a hydrogen atom; and $R^{3c}$ represents a bromine atom (hereinafter referred to as "Compound group SX758").

The Compound (L-3), wherein Q represents the group represented by Q15; $R^{1a}$ represents a hydrogen atom; $R^{1b}$ represents any one substituent described in Table 1A or Table 2A; $R^{3b}$ represents a hydrogen atom; and $R^{3c}$ represents a bromine atom (hereinafter referred to as "Compound group SX759").

The Compound (L-3), wherein Q represents the group represented by Q15; $R^{1a}$ represents any one substituent described in Table 1A or Table 2A; $R^{1b}$ represents a hydrogen atom; $R^{3b}$ represents a hydrogen atom; and $R^{3c}$ represents a bromine atom (hereinafter referred to as "Compound group SX760").

The Compound (L-3), wherein Q represents the group represented by Q16; $R^{1a}$ represents a hydrogen atom; $R^{1b}$ represents any one substituent described in Table 1A or Table 2A; $R^{3b}$ represents a hydrogen atom; and $R^{3c}$ represents a bromine atom (hereinafter referred to as "Compound group SX761").

The Compound (L-3), wherein Q represents the group represented by Q16; $R^{1a}$ represents any one substituent described in Table 1A or Table 2A; $R^{1b}$ represents a hydrogen atom; $R^{3b}$ represents a hydrogen atom; and $R^{3c}$ represents a bromine atom (hereinafter referred to as "Compound group SX762").

The Compound (L-3), wherein Q represents the group represented by Q17; $R^{1a}$ represents a hydrogen atom; $R^{1b}$ represents any one substituent described in Table 1A or Table 2A; $R^{3b}$ represents a hydrogen atom; and $R^{3c}$ represents a bromine atom (hereinafter referred to as "Compound group SX763").

The Compound (L-3), wherein Q represents the group represented by Q17; $R^{1a}$ represents any one substituent described in Table 1A or Table 2A; $R^{1b}$ represents a hydrogen atom; $R^{3b}$ represents a hydrogen atom; and $R^{3c}$ represents a bromine atom (hereinafter referred to as "Compound group SX764").

The Compound (L-3), wherein Q represents the group represented by Q18; $R^{1a}$ represents a hydrogen atom; $R^{1b}$ represents any one substituent described in Table 1A or Table 2A; $R^{3b}$ represents a hydrogen atom; and $R^{3c}$ represents a bromine atom (hereinafter referred to as "Compound group SX765").

The Compound (L-3), wherein Q represents the group represented by Q18; $R^{1a}$ represents any one substituent described in Table 1A or Table 2A; $R^{1b}$ represents a hydrogen atom; $R^{3b}$ represents a hydrogen atom; and $R^{3c}$ represents a bromine atom (hereinafter referred to as "Compound group SX766").

The Compound (L-3), wherein Q represents the group represented by Q19; $R^{1b}$ represents any one substituent described in Table 1A or Table 2A; $R^{3b}$ represents a hydrogen atom; and $R^{3c}$ represents a bromine atom (hereinafter referred to as "Compound group SX767").

The Compound (L-3), wherein Q represents the group represented by Q20; $R^{1b}$ represents any one substituent described in Table 1A or Table 2A; $R^{3b}$ represents a hydrogen atom; and $R^{3c}$ represents a bromine atom (hereinafter referred to as "Compound group SX768").

The Compound (L-3), wherein Q represents the group represented by Q21; $R^{1b}$ represents any one substituent described in Table 1A or Table 2A; $R^{3b}$ represents a hydrogen atom; and $R^{3c}$ represents a bromine atom (hereinafter referred to as "Compound group SX769").

The Compound (L-3), wherein Q represents the group represented by Q22; $R^{1b}$ represents any one substituent described in Table 1A or Table 2A; $R^{3b}$ represents a hydrogen atom; and $R^{3c}$ represents a bromine atom (hereinafter referred to as "Compound group SX770").

The Compound (L-3), wherein Q represents the group represented by Q23; $R^{1b}$ represents any one substituent described in Table 1A or Table 2A; $R^{3b}$ represents a hydrogen atom; and $R^{3c}$ represents a bromine atom (hereinafter referred to as "Compound group SX771").

The Compound (L-3), wherein Q represents the group represented by Q24; $R^{1b}$ represents any one substituent described in Table 1A or Table 2A; $R^{3b}$ represents a hydrogen atom; and $R^{3c}$ represents a bromine atom (hereinafter referred to as "Compound group SX772").

The Compound (L-3), wherein Q represents the group represented by Q25; $R^{1b}$ represents any one substituent described in Table 1A or Table 2A; $R^{3b}$ represents a hydrogen atom; and $R^{3c}$ represents a bromine atom (hereinafter referred to as "Compound group SX773").

The Compound (L-3), wherein Q represents the group represented by Q26; $R^{1b}$ represents any one substituent described in Table 1A or Table 2A; $R^{3b}$ represents a hydrogen atom; and $R^{3c}$ represents a bromine atom (hereinafter referred to as "Compound group SX774").

The Compound (L-3), wherein Q represents the group represented by Q27; $R^{1a}$ represents a hydrogen atom; $R^{1b}$ represents any one substituent described in Table 1A or Table 2A; $R^{3b}$ represents a hydrogen atom; and $R^{3c}$ represents a bromine atom (hereinafter referred to as "Compound group SX775").

The Compound (L-3), wherein Q represents the group represented by Q27; $R^{1a}$ represents any one substituent described in Table 1A or Table 2A; $R^{1b}$ represents a hydrogen atom; $R^{3b}$ represents a hydrogen atom; and $R^{3c}$ represents a bromine atom (hereinafter referred to as "Compound group SX776").

The Compound (L-3), wherein Q represents the group represented by Q28; $R^{1a}$ represents a hydrogen atom; $R^{1b}$ represents any one substituent described in Table 1A or Table 2A; $R^{3b}$ represents a hydrogen atom; and $R^{3c}$ represents a bromine atom (hereinafter referred to as "Compound group SX777").

The Compound (L-3), wherein Q represents the group represented by Q28; $R^{1a}$ represents any one substituent described in Table 1A or Table 2A; $R^{1b}$ represents a hydrogen atom; $R^{3b}$ represents a hydrogen atom; and $R^{3c}$ represents a bromine atom (hereinafter referred to as "Compound group SX778").

The Compound (L-3), wherein Q represents the group represented by Q29; $R^{1b}$ represents any one substituent described in Table 1A or Table 2A; $R^{3b}$ represents a hydrogen atom; and $R^{3c}$ represents a bromine atom (hereinafter referred to as "Compound group SX779").

The Compound (L-3), wherein Q represents the group represented by Q30; $R^{1b}$ represents any one substituent described in Table 1A or Table 2A; $R^{3b}$ represents a hydrogen atom; and $R^{3c}$ represents a bromine atom (hereinafter referred to as "Compound group SX780").

The Compound (L-3), wherein Q represents the group represented by Q11; $R^{1a}$ represents a hydrogen atom; $R^{1b}$ represents any one substituent described in Table 1A or Table 2A; $R^{3b}$ represents a hydrogen atom; and $R^{3c}$ represents an iodine atom (hereinafter referred to as "Compound group SX781").

The Compound (L-3), wherein Q represents the group represented by Q11; $R^{1a}$ represents any one substituent described in Table 1A or Table 2A; $R^{1b}$ represents a hydrogen atom; $R^{3b}$ represents a hydrogen atom; and $R^{3c}$ represents an iodine atom (hereinafter referred to as "Compound group SX782").

The Compound (L-3), wherein Q represents the group represented by Q12; $R^{1a}$ represents a hydrogen atom; $R^{1b}$ represents any one substituent described in Table 1A or Table 2A; $R^{3b}$ represents a hydrogen atom; and $R^{3c}$ represents an iodine atom (hereinafter referred to as "Compound group SX783").

The Compound (L-3), wherein Q represents the group represented by Q12; $R^{1a}$ represents any one substituent described in Table 1A or Table 2A; $R^{1b}$ represents a hydrogen atom; $R^{3b}$ represents a hydrogen atom; and $R^{3c}$ represents an iodine atom (hereinafter referred to as "Compound group SX784").

The Compound (L-3), wherein Q represents the group represented by Q13; $R^{1a}$ represents a hydrogen atom; $R^{1b}$ represents any one substituent described in Table 1A or Table 2A; $R^{3b}$ represents a hydrogen atom; and $R^{3c}$ represents an iodine atom (hereinafter referred to as "Compound group SX785").

The Compound (L-3), wherein Q represents the group represented by Q13; $R^{1a}$ represents any one substituent described in Table 1A or Table 2A; $R^{1b}$ represents a hydrogen atom; $R^{3b}$ represents a hydrogen atom; and $R^{3c}$ represents an iodine atom (hereinafter referred to as "Compound group SX786").

The Compound (L-3), wherein Q represents the group represented by Q14; $R^{1a}$ represents a hydrogen atom; $R^{1b}$ represents any one substituent described in Table 1A or Table 2A; $R^{3b}$ represents a hydrogen atom; and $R^{3c}$ represents an iodine atom (hereinafter referred to as "Compound group SX787").

The Compound (L-3), wherein Q represents the group represented by Q14; $R^{1a}$ represents any one substituent described in Table 1A or Table 2A; $R^{1b}$ represents a hydrogen atom; $R^{3b}$ represents a hydrogen atom; and $R^{3c}$ represents an iodine atom (hereinafter referred to as "Compound group SX788").

The Compound (L-3), wherein Q represents the group represented by Q15; $R^{1a}$ represents a hydrogen atom; $R^{1b}$ represents any one substituent described in Table 1A or Table 2A; $R^{3b}$ represents a hydrogen atom; and $R^{3c}$ represents an iodine atom (hereinafter referred to as "Compound group SX789").

The Compound (L-3), wherein Q represents the group represented by Q15; $R^{1a}$ represents any one substituent described in Table 1A or Table 2A; $R^{1b}$ represents a hydrogen atom; $R^{3b}$ represents a hydrogen atom; and $R^{3c}$ represents an iodine atom (hereinafter referred to as "Compound group SX790").

The Compound (L-3), wherein Q represents the group represented by Q16; $R^{1a}$ represents a hydrogen atom; $R^{1b}$ represents any one substituent described in Table 1A or Table 2A; $R^{3b}$ represents a hydrogen atom; and $R^{3c}$ represents an iodine atom (hereinafter referred to as "Compound group SX791").

The Compound (L-3), wherein Q represents the group represented by Q16; $R^{1a}$ represents any one substituent described in Table 1A or Table 2A; $R^{1b}$ represents a hydrogen atom; $R^{3b}$ represents a hydrogen atom; and $R^{3c}$ represents an iodine atom (hereinafter referred to as "Compound group SX792").

The Compound (L-3), wherein Q represents the group represented by Q17; $R^{1a}$ represents a hydrogen atom; $R^{1b}$ represents any one substituent described in Table 1A or Table 2A; $R^{3b}$ represents a hydrogen atom; and $R^{3c}$ represents an iodine atom (hereinafter referred to as "Compound group SX793").

The Compound (L-3), wherein Q represents the group represented by Q17; $R^{1a}$ represents any one substituent described in Table 1A or Table 2A; $R^{1b}$ represents a hydrogen atom; $R^{3b}$ represents a hydrogen atom; and $R^{3c}$ represents an iodine atom (hereinafter referred to as "Compound group SX794").

The Compound (L-3), wherein Q represents the group represented by Q18; $R^{1a}$ represents a hydrogen atom; $R^{1b}$ represents any one substituent described in Table 1A or Table 2A; $R^{3b}$ represents a hydrogen atom; and $R^{3c}$ represents an iodine atom (hereinafter referred to as "Compound group SX795").

The Compound (L-3), wherein Q represents the group represented by Q18; $R^{1a}$ represents any one substituent described in Table 1A or Table 2A; $R^{1b}$ represents a hydrogen atom; $R^{3b}$ represents a hydrogen atom; and $R^{3c}$ represents an iodine atom (hereinafter referred to as "Compound group SX796").

The Compound (L-3), wherein Q represents the group represented by Q19; $R^{1b}$ represents any one substituent described in Table 1A or Table 2A; $R^{3b}$ represents a hydrogen atom; and $R^{3c}$ represents an iodine atom (hereinafter referred to as "Compound group SX797").

The Compound (L-3), wherein Q represents the group represented by Q20; $R^{1b}$ represents any one substituent described in Table 1A or Table 2A; $R^{3b}$ represents a hydrogen atom; and $R^{3c}$ represents an iodine atom (hereinafter referred to as "Compound group SX798").

The Compound (L-3), wherein Q represents the group represented by Q21; $R^{1b}$ represents any one substituent described in Table 1A or Table 2A; $R^{3b}$ represents a hydrogen atom; and $R^{3c}$ represents an iodine atom (hereinafter referred to as "Compound group SX799").

The Compound (L-3), wherein Q represents the group represented by Q22; $R^{1b}$ represents any one substituent described in Table 1A or Table 2A; $R^{3b}$ represents a hydrogen atom; and $R^{3c}$ represents an iodine atom (hereinafter referred to as "Compound group SX800").

The Compound (L-3), wherein Q represents the group represented by Q23; $R^{1b}$ represents any one substituent described in Table 1A or Table 2A; $R^{3b}$ represents a hydrogen atom; and $R^{3c}$ represents an iodine atom (hereinafter referred to as "Compound group SX801").

The Compound (L-3), wherein Q represents the group represented by Q24; $R^{1b}$ represents any one substituent described in Table 1A or Table 2A; $R^{3b}$ represents a hydrogen atom; and $R^{3c}$ represents an iodine atom (hereinafter referred to as "Compound group SX802").

The Compound (L-3), wherein Q represents the group represented by Q25; $R^{1b}$ represents any one substituent described in Table 1A or Table 2A; $R^{3b}$ represents a hydrogen atom; and $R^{3c}$ represents an iodine atom (hereinafter referred to as "Compound group SX803").

The Compound (L-3), wherein Q represents the group represented by Q26; $R^{1b}$ represents any one substituent described in Table 1A or Table 2A; $R^{3b}$ represents a hydrogen atom; and $R^{3c}$ represents an iodine atom (hereinafter referred to as "Compound group SX804").

The Compound (L-3), wherein Q represents the group represented by Q27; $R^{1a}$ represents a hydrogen atom; $R^{1b}$ represents any one substituent described in Table 1A or Table 2A; $R^{3b}$ represents a hydrogen atom; and $R^{3c}$ represents an iodine atom (hereinafter referred to as "Compound group SX805").

The Compound (L-3), wherein Q represents the group represented by Q27; $R^{1a}$ represents any one substituent described in Table 1A or Table 2A; $R^{1b}$ represents a hydrogen atom; $R^{3b}$ represents a hydrogen atom; and $R^{3c}$ represents an iodine atom (hereinafter referred to as "Compound group SX806").

The Compound (L-3), wherein Q represents the group represented by Q28; $R^{1a}$ represents a hydrogen atom; $R^{1b}$ represents any one substituent described in Table 1A or Table 2A; $R^{3b}$ represents a hydrogen atom; and $R^{3c}$ represents an iodine atom (hereinafter referred to as "Compound group SX807").

The Compound (L-3), wherein Q represents the group represented by Q28; $R^{1a}$ represents any one substituent described in Table 1A or Table 2A; $R^{1b}$ represents a hydrogen atom; $R^{3b}$ represents a hydrogen atom; and $R^{3c}$ represents an iodine atom (hereinafter referred to as "Compound group SX808").

The Compound (L-3), wherein Q represents the group represented by Q29; $R^{1b}$ represents any one substituent described in Table 1A or Table 2A; $R^{3b}$ represents a hydrogen atom; and $R^{3c}$ represents an iodine atom (hereinafter referred to as "Compound group SX809").

The Compound (L-3), wherein Q represents the group represented by Q30; $R^{1b}$ represents any one substituent described in Table 1A or Table 2A; $R^{3b}$ represents a hydrogen atom; and $R^{3c}$ represents an iodine atom (hereinafter referred to as "Compound group SX810").

A compound represented by formula (L-4):

$$(L-4)$$

(hereinafter referred to as "Compound (L-4)"), wherein Q represents the group represented by Q11; $R^{1a}$ represents a hydrogen atom; $R^{1b}$ represents any one substituent described in Table 1A or Table 2A; and $R^{3c}$ represents a hydrogen atom (hereinafter referred to as "Compound group SX811").

The Compound (L-4), wherein Q represents the group represented by Q11; $R^{1a}$ represents any one substituent described in Table 1A or Table 2A; $R^{1b}$ represents a hydrogen atom; $R^{3b}$ represents a hydrogen atom; and $R^{3c}$ represents a hydrogen atom (hereinafter referred to as "Compound group SX812").

The Compound (L-4), wherein Q represents the group represented by Q12; $R^{1a}$ represents a hydrogen atom; $R^{1b}$ represents any one substituent described in Table 1A or Table 2A; and $R^{3c}$ represents a hydrogen atom (hereinafter referred to as "Compound group SX813").

The Compound (L-4), wherein Q represents the group represented by Q12; $R^{1a}$ represents any one substituent described in Table 1A or Table 2A; $R^{1b}$ represents a hydrogen atom; and $R^{3c}$ represents a hydrogen atom (hereinafter referred to as "Compound group SX814").

The Compound (L-4), wherein Q represents the group represented by Q13; $R^{1a}$ represents a hydrogen atom; $R^{1b}$ represents any one substituent described in Table 1A or Table 2A; and $R^{3c}$ represents a hydrogen atom (hereinafter referred to as "Compound group SX815").

The Compound (L-4), wherein Q represents the group represented by Q13; $R^{1a}$ represents any one substituent described in Table 1A or Table 2A; $R^{1b}$ represents a hydrogen atom; and $R^{3c}$ represents a hydrogen atom (hereinafter referred to as "Compound group SX816").

The Compound (L-4), wherein Q represents the group represented by Q14; $R^{1a}$ represents a hydrogen atom; $R^{1b}$ represents any one substituent described in Table 1A or Table 2A; and $R^{3c}$ represents a hydrogen atom (hereinafter referred to as "Compound group SX817").

The Compound (L-4), wherein Q represents the group represented by Q14; $R^{1a}$ represents any one substituent described in Table 1A or Table 2A; $R^{1b}$ represents a hydrogen atom; and $R^{3c}$ represents a hydrogen atom (hereinafter referred to as "Compound group SX818").

The Compound (L-4), wherein Q represents the group represented by Q15; $R^{1a}$ represents a hydrogen atom; $R^{1b}$ represents any one substituent described in Table 1A or Table 2A; and $R^{3c}$ represents a hydrogen atom (hereinafter referred to as "Compound group SX819").

The Compound (L-4), wherein Q represents the group represented by Q15; $R^{1a}$ represents any one substituent described in Table 1A or Table 2A; $R^{1b}$ represents a hydrogen atom; and $R^{3c}$ represents a hydrogen atom (hereinafter referred to as "Compound group SX820").

The Compound (L-4), wherein Q represents the group represented by Q16; $R^{1a}$ represents a hydrogen atom; $R^{1b}$ represents any one substituent described in Table 1A or Table 2A; and $R^{3c}$ represents a hydrogen atom (hereinafter referred to as "Compound group SX821").

The Compound (L-4), wherein Q represents the group represented by Q16; $R^{1a}$ represents any one substituent described in Table 1A or Table 2A; $R^{1b}$ represents a hydrogen atom; and $R^{3c}$ represents a hydrogen atom (hereinafter referred to as "Compound group SX822").

The Compound (L-4), wherein Q represents the group represented by Q17; $R^{1a}$ represents a hydrogen atom; $R^{1b}$ represents any one substituent described in Table 1A or Table 2A; and $R^{3c}$ represents a hydrogen atom (hereinafter referred to as "Compound group SX823").

The Compound (L-4), wherein Q represents the group represented by Q17; $R^{1a}$ represents any one substituent described in Table 1A or Table 2A; $R^{1b}$ represents a hydrogen atom; and $R^{3c}$ represents a hydrogen atom (hereinafter referred to as "Compound group SX824").

The Compound (L-4), wherein Q represents the group represented by Q18; $R^{1a}$ represents a hydrogen atom; $R^{1b}$ represents any one substituent described in Table 1A or Table 2A; and $R^{3c}$ represents a hydrogen atom (hereinafter referred to as "Compound group SX825").

The Compound (L-4), wherein Q represents the group represented by Q18; $R^{1a}$ represents any one substituent described in Table 1A or Table 2A; $R^{1b}$ represents a hydrogen atom; and $R^{3c}$ represents a hydrogen atom (hereinafter referred to as "Compound group SX826").

The Compound (L-4), wherein Q represents the group represented by Q19; $R^{1b}$ represents any one substituent described in Table 1A or Table 2A; and $R^{3c}$ represents a hydrogen atom (hereinafter referred to as "Compound group SX827").

The Compound (L-4), wherein Q represents the group represented by Q20; $R^{1b}$ represents any one substituent described in Table 1A or Table 2A; and $R^{3c}$ represents a hydrogen atom (hereinafter referred to as "Compound group SX828").

The Compound (L-4), wherein Q represents the group represented by Q21; $R^{1b}$ represents any one substituent described in Table 1A or Table 2A; and $R^{3c}$ represents a hydrogen atom (hereinafter referred to as "Compound group SX829").

The Compound (L-4), wherein Q represents the group represented by Q22; $R^{1b}$ represents any one substituent described in Table 1A or Table 2A; and $R^{3c}$ represents a hydrogen atom (hereinafter referred to as "Compound group SX830").

The Compound (L-4), wherein Q represents the group represented by Q23; $R^{1b}$ represents any one substituent described in Table 1A or Table 2A; and $R^{3c}$ represents a hydrogen atom (hereinafter referred to as "Compound group SX831").

The Compound (L-4), wherein Q represents the group represented by Q24; $R^{1b}$ represents any one substituent described in Table 1A or Table 2A; and $R^{3c}$ represents a hydrogen atom (hereinafter referred to as "Compound group SX832").

The Compound (L-4), wherein Q represents the group represented by Q25; $R^{1b}$ represents any one substituent described in Table 1A or Table 2A; and $R^{3c}$ represents a hydrogen atom (hereinafter referred to as "Compound group SX833").

The Compound (L-4), wherein Q represents the group represented by Q26; $R^{1b}$ represents any one substituent described in Table 1A or Table 2A; and $R^{3c}$ represents a hydrogen atom (hereinafter referred to as "Compound group SX834").

The Compound (L-4), wherein Q represents the group represented by Q27; $R^{1a}$ represents a hydrogen atom; $R^{1b}$ represents any one substituent described in Table 1A or Table 2A; and $R^{3c}$ represents a hydrogen atom (hereinafter referred to as "Compound group SX835").

The Compound (L-4), wherein Q represents the group represented by Q27; $R^{1a}$ represents any one substituent described in Table 1A or Table 2A; $R^{1b}$ represents a hydrogen atom; and $R^{3c}$ represents a hydrogen atom (hereinafter referred to as "Compound group SX836").

The Compound (L-4), wherein Q represents the group represented by Q28; $R^{1a}$ represents a hydrogen atom; $R^{1b}$ represents any one substituent described in Table 1A or Table 2A; and $R^{3c}$ represents a hydrogen atom (hereinafter referred to as "Compound group SX837").

The Compound (L-4), wherein Q represents the group represented by Q28; $R^{1a}$ represents any one substituent described in Table 1A or Table 2A; $R^{1b}$ represents a hydrogen atom; and $R^{3c}$ represents a hydrogen atom (hereinafter referred to as "Compound group SX838").

The Compound (L-4), wherein Q represents the group represented by Q29; $R^{1b}$ represents any one substituent described in Table 1A or Table 2A; and $R^{3c}$ represents a hydrogen atom (hereinafter referred to as "Compound group SX839").

The Compound (L-4), wherein Q represents the group represented by Q30; $R^{1b}$ represents any one substituent described in Table 1A or Table 2A; and $R^{3c}$ represents a hydrogen atom (hereinafter referred to as "Compound group SX840").

The Compound (L-4), wherein Q represents the group represented by Q11; $R^{1a}$ represents a hydrogen atom; $R^{1b}$ represents any one substituent described in Table 1A or Table 2A; and $R^{3c}$ represents a trifluoromethyl group (hereinafter referred to as "Compound group SX841").

The Compound (L-4), wherein Q represents the group represented by Q11; $R^{1a}$ represents any one substituent described in Table 1A or Table 2A; $R^{1b}$ represents a hydrogen atom; and $R^{3c}$ represents a trifluoromethyl group (hereinafter referred to as "Compound group SX842").

The Compound (L-4), wherein Q represents the group represented by Q12; $R^{1a}$ represents a hydrogen atom; $R^{1b}$ represents any one substituent described in Table 1A or Table 2A; and $R^{3c}$ represents a trifluoromethyl group (hereinafter referred to as "Compound group SX843").

The Compound (L-4), wherein Q represents the group represented by Q12; $R^{1a}$ represents any one substituent described in Table 1A or Table 2A; $R^{1b}$ represents a hydrogen atom; and $R^{3c}$ represents a trifluoromethyl group (hereinafter referred to as "Compound group SX844").

The Compound (L-4), wherein Q represents the group represented by Q13; $R^{1a}$ represents a hydrogen atom; $R^{1b}$ represents any one substituent described in Table 1A or Table 2A; and $R^{3c}$ represents a trifluoromethyl group (hereinafter referred to as "Compound group SX845").

The Compound (L-4), wherein Q represents the group represented by Q13; $R^{1a}$ represents any one substituent described in Table 1A or Table 2A; $R^{1b}$ represents a hydrogen atom; and $R^{3c}$ represents a trifluoromethyl group (hereinafter referred to as "Compound group SX846").

The Compound (L-4), wherein Q represents the group represented by Q14; $R^{1a}$ represents a hydrogen atom; $R^{1b}$ represents any one substituent described in Table 1A or Table 2A; and $R^{3c}$ represents a trifluoromethyl group (hereinafter referred to as "Compound group SX847").

The Compound (L-4), wherein Q represents the group represented by Q14; $R^{1a}$ represents any one substituent described in Table 1A or Table 2A; $R^{1b}$ represents a hydrogen atom; and $R^{3c}$ represents a trifluoromethyl group (hereinafter referred to as "Compound group SX848").

The Compound (L-4), wherein Q represents the group represented by Q15; $R^{1a}$ represents a hydrogen atom; $R^{1b}$ represents any one substituent described in Table 1A or Table 2A; and $R^{3c}$ represents a trifluoromethyl group (hereinafter referred to as "Compound group SX849").

The Compound (L-4), wherein Q represents the group represented by Q15; $R^{1a}$ represents any one substituent described in Table 1A or Table 2A; $R^{1b}$ represents a hydrogen atom; and $R^{3c}$ represents a trifluoromethyl group (hereinafter referred to as "Compound group SX850").

The Compound (L-4), wherein Q represents the group represented by Q16; $R^{1a}$ represents a hydrogen atom; $R^{1b}$ represents any one substituent described in Table 1A or Table 2A; and $R^{3c}$ represents a trifluoromethyl group (hereinafter referred to as "Compound group SX851").

The Compound (L-4), wherein Q represents the group represented by Q16; $R^{1a}$ represents any one substituent described in Table 1A or Table 2A; $R^{1b}$ represents a hydrogen atom; and $R^{3c}$ represents a trifluoromethyl group (hereinafter referred to as "Compound group SX852").

The Compound (L-4), wherein Q represents the group represented by Q17; $R^{1a}$ represents a hydrogen atom; $R^{1b}$ represents any one substituent described in Table 1A or Table 2A; and $R^{3c}$ represents a trifluoromethyl group (hereinafter referred to as "Compound group SX853").

The Compound (L-4), wherein Q represents the group represented by Q17; $R^{1a}$ represents any one substituent described in Table 1A or Table 2A; $R^{1b}$ represents a hydrogen atom; and $R^{3c}$ represents a trifluoromethyl group (hereinafter referred to as "Compound group SX854").

The Compound (L-4), wherein Q represents the group represented by Q18; $R^{1a}$ represents a hydrogen atom; $R^{1b}$ represents any one substituent described in Table 1A or Table 2A; and $R^{3c}$ represents a trifluoromethyl group (hereinafter referred to as "Compound group SX855").

The Compound (L-4), wherein Q represents the group represented by Q18; $R^{1a}$ represents any one substituent described in Table 1A or Table 2A; $R^{1b}$ represents a hydrogen atom; and $R^{3c}$ represents a trifluoromethyl group (hereinafter referred to as "Compound group SX856").

The Compound (L-4), wherein Q represents the group represented by Q19; $R^{1b}$ represents any one substituent described in Table 1A or Table 2A; and $R^{3c}$ represents a trifluoromethyl group (hereinafter referred to as "Compound group SX857").

The Compound (L-4), wherein Q represents the group represented by Q20; $R^{1b}$ represents any one substituent described in Table 1A or Table 2A; and $R^{3c}$ represents a trifluoromethyl group (hereinafter referred to as "Compound group SX858").

The Compound (L-4), wherein Q represents the group represented by Q21; $R^{1b}$ represents any one substituent described in Table 1A or Table 2A; and $R^{3c}$ represents a trifluoromethyl group (hereinafter referred to as "Compound group SX859").

The Compound (L-4), wherein Q represents the group represented by Q22; $R^{1b}$ represents any one substituent described in Table 1A or Table 2A; and $R^{3c}$ represents a trifluoromethyl group (hereinafter referred to as "Compound group SX860").

The Compound (L-4), wherein Q represents the group represented by Q23; $R^{1b}$ represents any one substituent described in Table 1A or Table 2A; and $R^{3c}$ represents a trifluoromethyl group (hereinafter referred to as "Compound group SX861").

The Compound (L-4), wherein Q represents the group represented by Q24; $R^{1b}$ represents any one substituent described in Table 1A or Table 2A; and $R^{3c}$ represents a trifluoromethyl group (hereinafter referred to as "Compound group SX862").

The Compound (L-4), wherein Q represents the group represented by Q25; $R^{1b}$ represents any one substituent described in Table 1A or Table 2A; and $R^{3c}$ represents a trifluoromethyl group (hereinafter referred to as "Compound group SX863").

The Compound (L-4), wherein Q represents the group represented by Q26; $R^{1b}$ represents any one substituent described in Table 1A or Table 2A; and $R^{3c}$ represents a trifluoromethyl group (hereinafter referred to as "Compound group SX864").

The Compound (L-4), wherein Q represents the group represented by Q27; $R^{1a}$ represents a hydrogen atom; $R^{1b}$ represents any one substituent described in Table 1A or Table 2A; and $R^{3c}$ represents a trifluoromethyl group (hereinafter referred to as "Compound group SX865").

The Compound (L-4), wherein Q represents the group represented by Q27; $R^{1a}$ represents any one substituent described in Table 1A or Table 2A; $R^{1b}$ represents a hydrogen atom; and $R^{3c}$ represents a trifluoromethyl group (hereinafter referred to as "Compound group SX866").

The Compound (L-4), wherein Q represents the group represented by Q28; $R^{1a}$ represents a hydrogen atom; $R^{1b}$ represents any one substituent described in Table 1A or Table 2A; and $R^{3c}$ represents a trifluoromethyl group (hereinafter referred to as "Compound group SX867").

The Compound (L-4), wherein Q represents the group represented by Q28; $R^{1a}$ represents any one substituent described in Table 1A or Table 2A; $R^{1b}$ represents a hydrogen atom; and $R^{3c}$ represents a trifluoromethyl group (hereinafter referred to as "Compound group SX868").

The Compound (L-4), wherein Q represents the group represented by Q29; $R^{1b}$ represents any one substituent described in Table 1A or Table 2A; and $R^{3c}$ represents a trifluoromethyl group (hereinafter referred to as "Compound group SX869").

The Compound (L-4), wherein Q represents the group represented by Q30; $R^{1b}$ represents any one substituent described in Table 1A or Table 2A; and $R^{3c}$ represents a trifluoromethyl group (hereinafter referred to as "Compound group SX870").

The Compound (L-4), wherein Q represents the group represented by Q11; $R^{1a}$ represents a hydrogen atom; $R^{1b}$ represents any one substituent described in Table 1A or Table 2A; and $R^{3c}$ represents a chlorine atom (hereinafter referred to as "Compound group SX871").

The Compound (L-4), wherein Q represents the group represented by Q11; $R^{1a}$ represents any one substituent described in Table 1A or Table 2A; $R^{1b}$ represents a hydrogen atom; and $R^{3c}$ represents a chlorine atom (hereinafter referred to as "Compound group SX872").

The Compound (L-4), wherein Q represents the group represented by Q12; $R^{1a}$ represents a hydrogen atom; $R^{1b}$ represents any one substituent described in Table 1A or Table 2A; and $R^{3c}$ represents a chlorine atom (hereinafter referred to as "Compound group SX873").

The Compound (L-4), wherein Q represents the group represented by Q12; $R^{1a}$ represents any one substituent described in Table 1A or Table 2A; $R^{1b}$ represents a hydrogen atom; and $R^{3c}$ represents a chlorine atom (hereinafter referred to as "Compound group SX874").

The Compound (L-4), wherein Q represents the group represented by Q13; $R^{1a}$ represents a hydrogen atom; $R^{1b}$ represents any one substituent described in Table 1A or Table 2A; and $R^{3c}$ represents a chlorine atom (hereinafter referred to as "Compound group SX875").

The Compound (L-4), wherein Q represents the group represented by Q13; $R^{1a}$ represents any one substituent described in Table 1A or Table 2A; $R^{1b}$ represents a hydrogen atom; and $R^{3c}$ represents a chlorine atom (hereinafter referred to as "Compound group SX876").

The Compound (L-4), wherein Q represents the group represented by Q14; $R^{1a}$ represents a hydrogen atom; $R^{1b}$ represents any one substituent described in Table 1A or Table 2A; and $R^{3c}$ represents a chlorine atom (hereinafter referred to as "Compound group SX877").

The Compound (L-4), wherein Q represents the group represented by Q14; $R^{1a}$ represents any one substituent described in Table 1A or Table 2A; $R^{1b}$ represents a hydrogen atom; and $R^{3c}$ represents a chlorine atom (hereinafter referred to as "Compound group SX878").

The Compound (L-4), wherein Q represents the group represented by Q15; $R^{1a}$ represents a hydrogen atom; $R^{1b}$ represents any one substituent described in Table 1A or Table 2A; and $R^{3c}$ represents a chlorine atom (hereinafter referred to as "Compound group SX879").

The Compound (L-4), wherein Q represents the group represented by Q15; $R^{1a}$ represents any one substituent described in Table 1A or Table 2A; $R^{1b}$ represents a hydrogen atom; and $R^{3c}$ represents a chlorine atom (hereinafter referred to as "Compound group SX880").

The Compound (L-4), wherein Q represents the group represented by Q16; $R^{1a}$ represents a hydrogen atom; $R^{1b}$ represents any one substituent described in Table 1A or Table 2A; and $R^{3c}$ represents a chlorine atom (hereinafter referred to as "Compound group SX881").

The Compound (L-4), wherein Q represents the group represented by Q16; $R^{1a}$ represents any one substituent described in Table 1A or Table 2A; $R^{1b}$ represents a hydrogen atom; and $R^{3c}$ represents a chlorine atom (hereinafter referred to as "Compound group SX882").

The Compound (L-4), wherein Q represents the group represented by Q17; $R^{1a}$ represents a hydrogen atom; $R^{1b}$ represents any one substituent described in Table 1A or Table 2A; and $R^{3c}$ represents a chlorine atom (hereinafter referred to as "Compound group SX883").

The Compound (L-4), wherein Q represents the group represented by Q17; $R^{1a}$ represents any one substituent described in Table 1A or Table 2A; $R^{1b}$ represents a hydrogen atom; and $R^{3c}$ represents a chlorine atom (hereinafter referred to as "Compound group SX884").

The Compound (L-4), wherein Q represents the group represented by Q18; $R^{1a}$ represents a hydrogen atom; $R^{1b}$ represents any one substituent described in Table 1A or Table 2A; and $R^{3c}$ represents a chlorine atom (hereinafter referred to as "Compound group SX885").

The Compound (L-4), wherein Q represents the group represented by Q18; $R^{1a}$ represents any one substituent described in Table 1A or Table 2A; $R^{1b}$ represents a hydrogen atom; and $R^{3c}$ represents a chlorine atom (hereinafter referred to as "Compound group SX886").

The Compound (L-4), wherein Q represents the group represented by Q19; $R^{1b}$ represents any one substituent described in Table 1A or Table 2A; and $R^{3c}$ represents a chlorine atom (hereinafter referred to as "Compound group SX887").

The Compound (L-4), wherein Q represents the group represented by Q20; $R^{1b}$ represents any one substituent described in Table 1A or Table 2A; and $R^{3c}$ represents a chlorine atom (hereinafter referred to as "Compound group SX888").

The Compound (L-4), wherein Q represents the group represented by Q21; $R^{1b}$ represents any one substituent described in Table 1A or Table 2A; and $R^{3c}$ represents a chlorine atom (hereinafter referred to as "Compound group SX889").

The Compound (L-4), wherein Q represents the group represented by Q22; $R^{1b}$ represents any one substituent described in Table 1A or Table 2A; and $R^{3c}$ represents a chlorine atom (hereinafter referred to as "Compound group SX890").

The Compound (L-4), wherein Q represents the group represented by Q23; $R^{1b}$ represents any one substituent described in Table 1A or Table 2A; and $R^{3c}$ represents a chlorine atom (hereinafter referred to as "Compound group SX891").

The Compound (L-4), wherein Q represents the group represented by Q24; $R^{1b}$ represents any one substituent described in Table 1A or Table 2A; and $R^{3c}$ represents a chlorine atom (hereinafter referred to as "Compound group SX892").

The Compound (L-4), wherein Q represents the group represented by Q25; $R^{1b}$ represents any one substituent described in Table 1A or Table 2A; and $R^{3c}$ represents a chlorine atom (hereinafter referred to as "Compound group SX893").

The Compound (L-4), wherein Q represents the group represented by Q26; $R^{1b}$ represents any one substituent described in Table 1A or Table 2A; and $R^{3c}$ represents a chlorine atom (hereinafter referred to as "Compound group SX894").

The Compound (L-4), wherein Q represents the group represented by Q27; $R^{1a}$ represents a hydrogen atom; $R^{1b}$ represents any one substituent described in Table 1A or Table 2A; and $R^{3c}$ represents a chlorine atom (hereinafter referred to as "Compound group SX895").

The Compound (L-4), wherein Q represents the group represented by Q27; $R^{1a}$ represents any one substituent described in Table 1A or Table 2A; $R^{1b}$ represents a hydrogen atom; and $R^{3c}$ represents a chlorine atom (hereinafter referred to as "Compound group SX896").

The Compound (L-4), wherein Q represents the group represented by Q28; $R^{1a}$ represents a hydrogen atom; $R^{1b}$ represents any one substituent described in Table 1A or Table 2A; and $R^{3c}$ represents a chlorine atom (hereinafter referred to as "Compound group SX897").

The Compound (L-4), wherein Q represents the group represented by Q28; $R^{1a}$ represents any one substituent described in Table 1A or Table 2A; $R^{1b}$ represents a hydrogen atom; and $R^{3c}$ represents a chlorine atom (hereinafter referred to as "Compound group SX898").

The Compound (L-4), wherein Q represents the group represented by Q29; $R^{1b}$ represents any one substituent described in Table 1A or Table 2A; and $R^{3c}$ represents a chlorine atom (hereinafter referred to as "Compound group SX899").

The Compound (L-4), wherein Q represents the group represented by Q30; $R^{1b}$ represents any one substituent described in Table 1A or Table 2A; and $R^{3c}$ represents a chlorine atom (hereinafter referred to as "Compound group SX900").

The Compound (L-4), wherein Q represents the group represented by Q11; $R^{1a}$ represents a hydrogen atom; $R^{1b}$ represents any one substituent described in Table 1A or Table 2A; and $R^{3c}$ represents a bromine atom (hereinafter referred to as "Compound group SX901").

The Compound (L-4), wherein Q represents the group represented by Q11; $R^{1a}$ represents any one substituent described in Table 1A or Table 2A; $R^{1b}$ represents a hydrogen atom; and $R^{3c}$ represents a bromine atom (hereinafter referred to as "Compound group SX902").

The Compound (L-4), wherein Q represents the group represented by Q12; $R^{1a}$ represents a hydrogen atom; $R^{1b}$ represents any one substituent described in Table 1A or Table 2A; and $R^{3c}$ represents a bromine atom (hereinafter referred to as "Compound group SX903").

The Compound (L-4), wherein Q represents the group represented by Q12; $R^{1a}$ represents any one substituent described in Table 1A or Table 2A; $R^{1b}$ represents a hydrogen atom; and $R^{3c}$ represents a bromine atom (hereinafter referred to as "Compound group SX904").

The Compound (L-4), wherein Q represents the group represented by Q13; $R^{1a}$ represents a hydrogen atom; $R^{1b}$ represents any one substituent described in Table 1A or Table 2A; and $R^{3c}$ represents a bromine atom (hereinafter referred to as "Compound group SX905").

The Compound (L-4), wherein Q represents the group represented by Q13; $R^{1a}$ represents any one substituent described in Table 1A or Table 2A; $R^{1b}$ represents a hydrogen atom; and $R^{3c}$ represents a bromine atom (hereinafter referred to as "Compound group SX906").

The Compound (L-4), wherein Q represents the group represented by Q14; $R^{1a}$ represents a hydrogen atom; $R^{1b}$ represents any one substituent described in Table 1A or Table 2A; and $R^{3c}$ represents a bromine atom (hereinafter referred to as "Compound group SX907").

The Compound (L-4), wherein Q represents the group represented by Q14; $R^{1a}$ represents any one substituent described in Table 1A or Table 2A; $R^{1b}$ represents a hydrogen atom; and $R^{3c}$ represents a bromine atom (hereinafter referred to as "Compound group SX908").

The Compound (L-4), wherein Q represents the group represented by Q15; $R^{1a}$ represents a hydrogen atom; $R^{1b}$ represents any one substituent described in Table 1A or Table 2A; and $R^{3c}$ represents a bromine atom (hereinafter referred to as "Compound group SX909").

The Compound (L-4), wherein Q represents the group represented by Q15; $R^{1a}$ represents any one substituent described in Table 1A or Table 2A; $R^{1b}$ represents a hydrogen atom; and $R^{3c}$ represents a bromine atom (hereinafter referred to as "Compound group SX910").

The Compound (L-4), wherein Q represents the group represented by Q16; $R^{1a}$ represents a hydrogen atom; $R^{1b}$ represents any one substituent described in Table 1A or Table 2A; and $R^{3c}$ represents a bromine atom (hereinafter referred to as "Compound group SX911").

The Compound (L-4), wherein Q represents the group represented by Q16; $R^{1a}$ represents any one substituent described in Table 1A or Table 2A; $R^{1b}$ represents a hydrogen atom; and $R^{3c}$ represents a bromine atom (hereinafter referred to as "Compound group SX912").

The Compound (L-4), wherein Q represents the group represented by Q17; $R^{1a}$ represents a hydrogen atom; $R^{1b}$ represents any one substituent described in Table 1A or Table 2A; and $R^{3c}$ represents a bromine atom (hereinafter referred to as "Compound group SX913").

The Compound (L-4), wherein Q represents the group represented by Q17; $R^{1a}$ represents any one substituent described in Table 1A or Table 2A; $R^{1b}$ represents a hydrogen atom; and $R^{3c}$ represents a bromine atom (hereinafter referred to as "Compound group SX914").

The Compound (L-4), wherein Q represents the group represented by Q18; $R^{1a}$ represents a hydrogen atom; $R^{1b}$ represents any one substituent described in Table 1A or Table 2A; and $R^{3c}$ represents a bromine atom (hereinafter referred to as "Compound group SX915").

The Compound (L-4), wherein Q represents the group represented by Q18; $R^{1a}$ represents any one substituent described in Table 1A or Table 2A; $R^{1b}$ represents a hydrogen atom; and $R^{3c}$ represents a bromine atom (hereinafter referred to as "Compound group SX916").

The Compound (L-4), wherein Q represents the group represented by Q19; $R^{1b}$ represents any one substituent described in Table 1A or Table 2A; and $R^{3c}$ represents a bromine atom (hereinafter referred to as "Compound group SX917").

The Compound (L-4), wherein Q represents the group represented by Q20; $R^{1b}$ represents any one substituent described in Table 1A or Table 2A; and $R^{3c}$ represents a bromine atom (hereinafter referred to as "Compound group SX918").

The Compound (L-4), wherein Q represents the group represented by Q21; $R^{1b}$ represents any one substituent described in Table 1A or Table 2A; and $R^{3c}$ represents a bromine atom (hereinafter referred to as "Compound group SX919").

The Compound (L-4), wherein Q represents the group represented by Q22; $R^{1b}$ represents any one substituent described in Table 1A or Table 2A; and $R^{3c}$ represents a bromine atom (hereinafter referred to as "Compound group SX920").

The Compound (L-4), wherein Q represents the group represented by Q23; $R^{1b}$ represents any one substituent described in Table 1A or Table 2A; and $R^{3c}$ represents a bromine atom (hereinafter referred to as "Compound group SX921").

The Compound (L-4), wherein Q represents the group represented by Q24; $R^{1b}$ represents any one substituent described in Table 1A or Table 2A; and $R^{3c}$ represents a bromine atom (hereinafter referred to as "Compound group SX922").

The Compound (L-4), wherein Q represents the group represented by Q25; $R^{1b}$ represents any one substituent described in Table 1A or Table 2A; and $R^{3c}$ represents a bromine atom (hereinafter referred to as "Compound group SX923").

The Compound (L-4), wherein Q represents the group represented by Q26; $R^{1b}$ represents any one substituent described in Table 1A or Table 2A; and $R^{3c}$ represents a bromine atom (hereinafter referred to as "Compound group SX924").

The Compound (L-4), wherein Q represents the group represented by Q27; $R^{1a}$ represents a hydrogen atom; $R^{1b}$ represents any one substituent described in Table 1A or Table 2A; and $R^{3c}$ represents a bromine atom (hereinafter referred to as "Compound group SX925").

The Compound (L-4), wherein Q represents the group represented by Q27; $R^{1a}$ represents any one substituent described in Table 1A or Table 2A; $R^{1b}$ represents a hydrogen atom; and $R^{3c}$ represents a bromine atom (hereinafter referred to as "Compound group SX926").

The Compound (L-4), wherein Q represents the group represented by Q28; $R^{1a}$ represents a hydrogen atom; $R^{1b}$ represents any one substituent described in Table 1A or Table 2A; and $R^{3c}$ represents a bromine atom (hereinafter referred to as "Compound group SX927").

The Compound (L-4), wherein Q represents the group represented by Q28; $R^{1a}$ represents any one substituent described in Table 1A or Table 2A; $R^{1b}$ represents a hydrogen atom; and $R^{3c}$ represents a bromine atom (hereinafter referred to as "Compound group SX928").

The Compound (L-4), wherein Q represents the group represented by Q29; $R^{1b}$ represents any one substituent described in Table 1A or Table 2A; and $R^{3c}$ represents a bromine atom (hereinafter referred to as "Compound group SX929").

The Compound (L-4), wherein Q represents the group represented by Q30; $R^{1b}$ represents any one substituent described in Table 1A or Table 2A; and $R^{3c}$ represents a bromine atom (hereinafter referred to as "Compound group SX930").

The Compound (L-4), wherein Q represents the group represented by Q11; $R^{1a}$ represents a hydrogen atom; $R^{1b}$ represents any one substituent described in Table 1A or Table 2A; and $R^{3c}$ represents an iodine atom (hereinafter referred to as "Compound group SX931").

The Compound (L-4), wherein Q represents the group represented by Q11; $R^{1a}$ represents any one substituent described in Table 1A or Table 2A; $R^{1b}$ represents a hydrogen atom; and $R^{3c}$ represents an iodine atom (hereinafter referred to as "Compound group SX932").

The Compound (L-4), wherein Q represents the group represented by Q12; $R^{1a}$ represents a hydrogen atom; $R^{1b}$ represents any one substituent described in Table 1A or Table 2A; and $R^{3c}$ represents an iodine atom (hereinafter referred to as "Compound group SX933").

The Compound (L-4), wherein Q represents the group represented by Q12; $R^{1a}$ represents any one substituent described in Table 1A or Table 2A; $R^{1b}$ represents a hydrogen atom; and $R^{3c}$ represents an iodine atom (hereinafter referred to as "Compound group SX934").

The Compound (L-4), wherein Q represents the group represented by Q13; $R^{1a}$ represents a hydrogen atom; $R^{1b}$ represents any one substituent described in Table 1A or Table 2A; and $R^{3c}$ represents an iodine atom (hereinafter referred to as "Compound group SX935").

The Compound (L-4), wherein Q represents the group represented by Q13; $R^{1a}$ represents any one substituent described in Table 1A or Table 2A; $R^{1b}$ represents a hydrogen atom; and $R^{3c}$ represents an iodine atom (hereinafter referred to as "Compound group SX936").

The Compound (L-4), wherein Q represents the group represented by Q14; $R^{1a}$ represents a hydrogen atom; $R^{1b}$ represents any one substituent described in Table 1A or Table 2A; and $R^{3c}$ represents an iodine atom (hereinafter referred to as "Compound group SX937").

The Compound (L-4), wherein Q represents the group represented by Q14; $R^{1a}$ represents any one substituent described in Table 1A or Table 2A; $R^{1b}$ represents a hydrogen atom; and $R^{3c}$ represents an iodine atom (hereinafter referred to as "Compound group SX938").

The Compound (L-4), wherein Q represents the group represented by Q15; $R^{1a}$ represents a hydrogen atom; $R^{1b}$ represents any one substituent described in Table 1A or Table 2A; and $R^{3c}$ represents an iodine atom (hereinafter referred to as "Compound group SX939").

The Compound (L-4), wherein Q represents the group represented by Q15; $R^{1a}$ represents any one substituent described in Table 1A or Table 2A; $R^{1b}$ represents a hydrogen atom; and $R^{3c}$ represents an iodine atom (hereinafter referred to as "Compound group SX940").

The Compound (L-4), wherein Q represents the group represented by Q16; $R^{1a}$ represents a hydrogen atom; $R^{1b}$ represents any one substituent described in Table 1A or Table 2A; and $R^{3c}$ represents an iodine atom (hereinafter referred to as "Compound group SX941").

The Compound (L-4), wherein Q represents the group represented by Q16; $R^{1a}$ represents any one substituent described in Table 1A or Table 2A; $R^{1b}$ represents a hydrogen atom; and $R^{3c}$ represents an iodine atom (hereinafter referred to as "Compound group SX942").

The Compound (L-4), wherein Q represents the group represented by Q17; $R^{1a}$ represents a hydrogen atom; $R^{1b}$ represents any one substituent described in Table 1A or Table 2A; and $R^{3c}$ represents an iodine atom (hereinafter referred to as "Compound group SX943").

The Compound (L-4), wherein Q represents the group represented by Q17; $R^{1a}$ represents any one substituent described in Table 1A or Table 2A; $R^{1b}$ represents a hydrogen atom; and $R^{3c}$ represents an iodine atom (hereinafter referred to as "Compound group SX944").

The Compound (L-4), wherein Q represents the group represented by Q18; $R^{1a}$ represents a hydrogen atom; $R^{1b}$ represents any one substituent described in Table 1A or Table 2A; and $R^{3c}$ represents an iodine atom (hereinafter referred to as "Compound group SX945").

The Compound (L-4), wherein Q represents the group represented by Q18; $R^{1a}$ represents any one substituent described in Table 1A or Table 2A; $R^{1b}$ represents a hydrogen atom; and $R^{3c}$ represents an iodine atom (hereinafter referred to as "Compound group SX946").

The Compound (L-4), wherein Q represents the group represented by Q19; $R^{1b}$ represents any one substituent described in Table 1A or Table 2A; and $R^{3c}$ represents an iodine atom (hereinafter referred to as "Compound group SX947").

The Compound (L-4), wherein Q represents the group represented by Q20; $R^{1b}$ represents any one substituent described in Table 1A or Table 2A; and $R^{3c}$ represents an iodine atom (hereinafter referred to as "Compound group SX948").

The Compound (L-4), wherein Q represents the group represented by Q21; $R^{1b}$ represents any one substituent described in Table 1A or Table 2A; and $R^{3c}$ represents an iodine atom (hereinafter referred to as "Compound group SX949").

The Compound (L-4), wherein Q represents the group represented by Q22; $R^{1b}$ represents any one substituent described in Table 1A or Table 2A; and $R^{3c}$ represents an iodine atom (hereinafter referred to as "Compound group SX950").

The Compound (L-4), wherein Q represents the group represented by Q23; $R^{1b}$ represents any one substituent described in Table 1A or Table 2A; and $R^{3c}$ represents an iodine atom (hereinafter referred to as "Compound group SX951").

The Compound (L-4), wherein Q represents the group represented by Q24; $R^{1b}$ represents any one substituent described in Table 1A or Table 2A; and $R^{3c}$ represents an iodine atom (hereinafter referred to as "Compound group SX952").

The Compound (L-4), wherein Q represents the group represented by Q25; $R^{1b}$ represents any one substituent described in Table 1A or Table 2A; and $R^{3c}$ represents an iodine atom (hereinafter referred to as "Compound group SX953").

The Compound (L-4), wherein Q represents the group represented by Q26; $R^{1b}$ represents any one substituent described in Table 1A or Table 2A; and $R^{3c}$ represents an iodine atom (hereinafter referred to as "Compound group SX954").

The Compound (L-4), wherein Q represents the group represented by Q27; $R^{1a}$ represents a hydrogen atom; $R^{1b}$ represents any one substituent described in Table 1A or Table 2A; and $R^{3c}$ represents an iodine atom (hereinafter referred to as "Compound group SX955").

The Compound (L-4), wherein Q represents the group represented by Q27; $R^{1a}$ represents any one substituent described in Table 1A or Table 2A; $R^{1b}$ represents a hydrogen atom; and $R^{3c}$ represents an iodine atom (hereinafter referred to as "Compound group SX956").

The Compound (L-4), wherein Q represents the group represented by Q28; $R^{1a}$ represents a hydrogen atom; $R^{1b}$ represents any one substituent described in Table 1A or Table 2A; and $R^{3c}$ represents an iodine atom (hereinafter referred to as "Compound group SX957").

The Compound (L-4), wherein Q represents the group represented by Q28; $R^{1a}$ represents any one substituent described in Table 1A or Table 2A; $R^{1b}$ represents a hydrogen atom; and $R^{3c}$ represents an iodine atom (hereinafter referred to as "Compound group SX958").

The Compound (L-4), wherein Q represents the group represented by Q29; $R^{1b}$ represents any one substituent described in Table 1A or Table 2A; and $R^{3c}$ represents an iodine atom (hereinafter referred to as "Compound group SX959").

The Compound (L-4), wherein Q represents the group represented by Q30; $R^{1b}$ represents any one substituent described in Table 1A or Table 2A; and $R^{3c}$ represents an iodine atom (hereinafter referred to as "Compound group SX960").

A compound represented by formula (L-5):

$$\text{(L-5)}$$

(hereinafter referred to as "Compound (L-5)"), wherein Q represents the group represented by Q11; $R^{1a}$ represents a hydrogen atom; $R^{1b}$ represents any one substituent described in Table 1A or Table 2A; and $R^{3b}$ represents a hydrogen atom (hereinafter referred to as "Compound group SX961").

The Compound (L-5), wherein Q represents the group represented by Q11; $R^{1a}$ represents any one substituent described in Table 1A or Table 2A; $R^{1b}$ represents a hydrogen atom; and $R^{3b}$ represents a hydrogen atom (hereinafter referred to as "Compound group SX962").

The Compound (L-5), wherein Q represents the group represented by Q12; $R^{1a}$ represents a hydrogen atom; $R^{1b}$ represents any one substituent described in Table 1A or Table 2A; and $R^{3b}$ represents a hydrogen atom (hereinafter referred to as "Compound group SX963").

The Compound (L-5), wherein Q represents the group represented by Q12; $R^{1a}$ represents any one substituent described in Table 1A or Table 2A; $R^{1b}$ represents a hydrogen atom; and $R^{3b}$ represents a hydrogen atom (hereinafter referred to as "Compound group SX964").

The Compound (L-5), wherein Q represents the group represented by Q13; $R^{1a}$ represents a hydrogen atom; $R^{1b}$ represents any one substituent described in Table 1A or Table 2A; and $R^{3b}$ represents a hydrogen atom (hereinafter referred to as "Compound group SX965").

The Compound (L-5), wherein Q represents the group represented by Q13; $R^{1a}$ represents any one substituent described in Table 1A or Table 2A; $R^{1b}$ represents a hydrogen atom; and $R^{3b}$ represents a hydrogen atom (hereinafter referred to as "Compound group SX966").

The Compound (L-5), wherein Q represents the group represented by Q14; $R^{1a}$ represents a hydrogen atom; $R^{1b}$ represents any one substituent described in Table 1A or Table 2A; and $R^{3b}$ represents a hydrogen atom (hereinafter referred to as "Compound group SX967").

The Compound (L-5), wherein Q represents the group represented by Q14; $R^{1a}$ represents any one substituent described in Table 1A or Table 2A; $R^{1b}$ represents a hydrogen atom; and $R^{3b}$ represents a hydrogen atom (hereinafter referred to as "Compound group SX968").

The Compound (L-5), wherein Q represents the group represented by Q15; $R^{1a}$ represents a hydrogen atom; $R^{1b}$ represents any one substituent described in Table 1A or Table 2A; and $R^{3b}$ represents a hydrogen atom (hereinafter referred to as "Compound group SX969").

The Compound (L-5), wherein Q represents the group represented by Q15; $R^{1a}$ represents any one substituent described in Table 1A or Table 2A; $R^{1b}$ represents a hydrogen atom; and $R^{3b}$ represents a hydrogen atom (hereinafter referred to as "Compound group SX970").

The Compound (L-5), wherein Q represents the group represented by Q16; $R^{1a}$ represents a hydrogen atom; $R^{1b}$ represents any one substituent described in Table 1A or Table 2A; and $R^{3b}$ represents a hydrogen atom (hereinafter referred to as "Compound group SX971").

The Compound (L-5), wherein Q represents the group represented by Q16; $R^{1a}$ represents any one substituent described in Table 1A or Table 2A; $R^{1b}$ represents a hydrogen atom; and $R^{3b}$ represents a hydrogen atom (hereinafter referred to as "Compound group SX972").

The Compound (L-5), wherein Q represents the group represented by Q17; $R^{1a}$ represents a hydrogen atom; $R^{1b}$ represents any one substituent described in Table 1A or Table 2A; and $R^{3b}$ represents a hydrogen atom (hereinafter referred to as "Compound group SX973").

The Compound (L-5), wherein Q represents the group represented by Q17; $R^{1a}$ represents any one substituent described in Table 1A or Table 2A; $R^{1b}$ represents a hydrogen atom; and $R^{3b}$ represents a hydrogen atom (hereinafter referred to as "Compound group SX974").

The Compound (L-5), wherein Q represents the group represented by Q18; $R^{1a}$ represents a hydrogen atom; $R^{1b}$ represents any one substituent described in Table 1A or Table 2A; and $R^{3b}$ represents a hydrogen atom (hereinafter referred to as "Compound group SX975").

The Compound (L-5), wherein Q represents the group represented by Q18; $R^{1a}$ represents any one substituent described in Table 1A or Table 2A; $R^{1b}$ represents a hydrogen atom; and $R^{3b}$ represents a hydrogen atom (hereinafter referred to as "Compound group SX976").

The Compound (L-5), wherein Q represents the group represented by Q19; $R^{1b}$ represents any one substituent described in Table 1A or Table 2A; and $R^{3b}$ represents a hydrogen atom (hereinafter referred to as "Compound group SX977").

The Compound (L-5), wherein Q represents the group represented by Q20; $R^{1b}$ represents any one substituent described in Table 1A or Table 2A; and $R^{3b}$ represents a hydrogen atom (hereinafter referred to as "Compound group SX978").

The Compound (L-5), wherein Q represents the group represented by Q21; $R^{1b}$ represents any one substituent described in Table 1A or Table 2A; and $R^{3b}$ represents a hydrogen atom (hereinafter referred to as "Compound group SX979").

The Compound (L-5), wherein Q represents the group represented by Q22; $R^{1b}$ represents any one substituent described in Table 1A or Table 2A; and $R^{3b}$ represents a hydrogen atom (hereinafter referred to as "Compound group SX980").

The Compound (L-5), wherein Q represents the group represented by Q23; $R^{1b}$ represents any one substituent described in Table 1A or Table 2A; and $R^{3b}$ represents a hydrogen atom (hereinafter referred to as "Compound group SX981").

The Compound (L-5), wherein Q represents the group represented by Q24; $R^{1b}$ represents any one substituent described in Table 1A or Table 2A; and $R^{3b}$ represents a hydrogen atom (hereinafter referred to as "Compound group SX982").

The Compound (L-5), wherein Q represents the group represented by Q25; $R^{1b}$ represents any one substituent described in Table 1A or Table 2A; and $R^{3b}$ represents a hydrogen atom (hereinafter referred to as "Compound group SX983").

The Compound (L-5), wherein Q represents the group represented by Q26; $R^{1b}$ represents any one substituent described in Table 1A or Table 2A; and $R^{3b}$ represents a hydrogen atom (hereinafter referred to as "Compound group SX984").

The Compound (L-5), wherein Q represents the group represented by Q27; $R^{1a}$ represents a hydrogen atom; $R^{1b}$ represents any one substituent described in Table 1A or Table 2A; and $R^{3b}$ represents a hydrogen atom (hereinafter referred to as "Compound group SX985").

The Compound (L-5), wherein Q represents the group represented by Q27; $R^{1a}$ represents any one substituent described in Table 1A or Table 2A; $R^{1b}$ represents a hydrogen atom; and $R^{3b}$ represents a hydrogen atom (hereinafter referred to as "Compound group SX986").

The Compound (L-5), wherein Q represents the group represented by Q28; $R^{1a}$ represents a hydrogen atom; $R^{1b}$ represents any one substituent described in Table 1A or Table 2A; and $R^{3b}$ represents a hydrogen atom (hereinafter referred to as "Compound group SX987").

The Compound (L-5), wherein Q represents the group represented by Q28; $R^{1a}$ represents any one substituent described in Table 1A or Table 2A; $R^{1b}$ represents a hydrogen atom; and $R^{3b}$ represents a hydrogen atom (hereinafter referred to as "Compound group SX988").

The Compound (L-5), wherein Q represents the group represented by Q29; $R^{1b}$ represents any one substituent described in Table 1A or Table 2A; and $R^{3b}$ represents a hydrogen atom (hereinafter referred to as "Compound group SX989").

The Compound (L-5), wherein Q represents the group represented by Q30; $R^{1b}$ represents any one substituent described in Table 1A or Table 2A; and $R^{3b}$ represents a hydrogen atom (hereinafter referred to as "Compound group SX990").

The Compound (L-5), wherein Q represents the group represented by Q11; $R^{1a}$ represents a hydrogen atom; $R^{1b}$ represents any one substituent described in Table 1A or Table 2A; and $R^{3b}$ represents a trifluoromethyl group (hereinafter referred to as "Compound group SX991").

The Compound (L-5), wherein Q represents the group represented by Q11; $R^{1a}$ represents any one substituent described in Table 1A or Table 2A; $R^{1b}$ represents a hydrogen atom; and $R^{3b}$ represents a trifluoromethyl group (hereinafter referred to as "Compound group SX992").

The Compound (L-5), wherein Q represents the group represented by Q12; $R^{1a}$ represents a hydrogen atom; $R^{1b}$ represents any one substituent described in Table 1A or Table 2A; and $R^{3b}$ represents a trifluoromethyl group (hereinafter referred to as "Compound group SX993").

The Compound (L-5), wherein Q represents the group represented by Q12; $R^{1a}$ represents any one substituent described in Table 1A or Table 2A; $R^{1b}$ represents a hydrogen atom; and $R^{3b}$ represents a trifluoromethyl group (hereinafter referred to as "Compound group SX994").

The Compound (L-5), wherein Q represents the group represented by Q13; $R^{1a}$ represents a hydrogen atom; $R^{1b}$ represents any one substituent described in Table 1A or Table 2A; and $R^{3b}$ represents a trifluoromethyl group (hereinafter referred to as "Compound group SX995").

The Compound (L-5), wherein Q represents the group represented by Q13; $R^{1a}$ represents any one substituent described in Table 1A or Table 2A; $R^{1b}$ represents a hydrogen atom; and $R^{3b}$ represents a trifluoromethyl group (hereinafter referred to as "Compound group SX996").

The Compound (L-5), wherein Q represents the group represented by Q14; $R^{1a}$ represents a hydrogen atom; $R^{1b}$ represents any one substituent described in Table 1A or Table 2A; and $R^{3b}$ represents a trifluoromethyl group (hereinafter referred to as "Compound group SX997").

The Compound (L-5), wherein Q represents the group represented by Q14; $R^{1a}$ represents any one substituent described in Table 1A or Table 2A; $R^{1b}$ represents a hydrogen atom; and $R^{3b}$ represents a trifluoromethyl group (hereinafter referred to as "Compound group SX998").

The Compound (L-5), wherein Q represents the group represented by Q15; $R^{1a}$ represents a hydrogen atom; $R^{1b}$ represents any one substituent described in Table 1A or Table 2A; and $R^{3b}$ represents a trifluoromethyl group (hereinafter referred to as "Compound group SX999").

The Compound (L-5), wherein Q represents the group represented by Q15; $R^{1a}$ represents any one substituent described in Table 1A or Table 2A; $R^{1b}$ represents a hydrogen atom; and $R^{3b}$ represents a trifluoromethyl group (hereinafter referred to as "Compound group SX1000").

The Compound (L-5), wherein Q represents the group represented by Q16; $R^{1a}$ represents a hydrogen atom; $R^{1b}$ represents any one substituent described in Table 1A or Table 2A; and $R^{3b}$ represents a trifluoromethyl group (hereinafter referred to as "Compound group SX1001").

The Compound (L-5), wherein Q represents the group represented by Q16; $R^{1a}$ represents any one substituent described in Table 1A or Table 2A; $R^{1b}$ represents a hydrogen atom; and $R^{3b}$ represents a trifluoromethyl group (hereinafter referred to as "Compound group SX1002").

The Compound (L-5), wherein Q represents the group represented by Q17; $R^{1a}$ represents a hydrogen atom; $R^{1b}$ represents any one substituent described in Table 1A or Table 2A; and $R^{3b}$ represents a trifluoromethyl group (hereinafter referred to as "Compound group SX1003").

The Compound (L-5), wherein Q represents the group represented by Q17; $R^{1a}$ represents any one substituent described in Table 1A or Table 2A; $R^{1b}$ represents a hydrogen atom; and $R^{3b}$ represents a trifluoromethyl group (hereinafter referred to as "Compound group SX1004").

The Compound (L-5), wherein Q represents the group represented by Q18; $R^{1a}$ represents a hydrogen atom; $R^{1b}$ represents any one substituent described in Table 1A or Table 2A; and $R^{3b}$ represents a trifluoromethyl group (hereinafter referred to as "Compound group SX1005").

The Compound (L-5), wherein Q represents the group represented by Q18; $R^{1a}$ represents any one substituent described in Table 1A or Table 2A; $R^{1b}$ represents a hydrogen atom; and $R^{3b}$ represents a trifluoromethyl group (hereinafter referred to as "Compound group SX1006").

The Compound (L-5), wherein Q represents the group represented by Q19; $R^{1b}$ represents any one substituent described in Table 1A or Table 2A; and $R^{3b}$ represents a trifluoromethyl group (hereinafter referred to as "Compound group SX1007").

The Compound (L-5), wherein Q represents the group represented by Q20; $R^{1b}$ represents any one substituent described in Table 1A or Table 2A; and $R^{3b}$ represents a trifluoromethyl group (hereinafter referred to as "Compound group SX1008").

The Compound (L-5), wherein Q represents the group represented by Q21; $R^{1b}$ represents any one substituent described in Table 1A or Table 2A; and $R^{3b}$ represents a trifluoromethyl group (hereinafter referred to as "Compound group SX1009").

The Compound (L-5), wherein Q represents the group represented by Q22; $R^{1b}$ represents any one substituent described in Table 1A or Table 2A; and $R^{3b}$ represents a trifluoromethyl group (hereinafter referred to as "Compound group SX1010").

The Compound (L-5), wherein Q represents the group represented by Q23; $R^{1b}$ represents any one substituent described in Table 1A or Table 2A; and $R^{3b}$ represents a trifluoromethyl group (hereinafter referred to as "Compound group SX1011").

The Compound (L-5), wherein Q represents the group represented by Q24; $R^{1b}$ represents any one substituent described in Table 1A or Table 2A; and $R^{3b}$ represents a trifluoromethyl group (hereinafter referred to as "Compound group SX1012").

The Compound (L-5), wherein Q represents the group represented by Q25; $R^{1b}$ represents any one substituent described in Table 1A or Table 2A; and $R^{3b}$ represents a trifluoromethyl group (hereinafter referred to as "Compound group SX1013").

The Compound (L-5), wherein Q represents the group represented by Q26; $R^{1b}$ represents any one substituent described in Table 1A or Table 2A; and $R^{3b}$ represents a trifluoromethyl group (hereinafter referred to as "Compound group SX1014").

The Compound (L-5), wherein Q represents the group represented by Q27; $R^{1a}$ represents a hydrogen atom; $R^{1b}$ represents any one substituent described in Table 1A or Table 2A; and $R^{3b}$ represents a trifluoromethyl group (hereinafter referred to as "Compound group SX1015").

The Compound (L-5), wherein Q represents the group represented by Q27; $R^{1a}$ represents any one substituent described in Table 1A or Table 2A; $R^{1b}$ represents a hydrogen atom; and $R^{3b}$ represents a trifluoromethyl group (hereinafter referred to as "Compound group SX1016").

The Compound (L-5), wherein Q represents the group represented by Q28; $R^{1a}$ represents a hydrogen atom; $R^{1b}$ represents any one substituent described in Table 1A or Table 2A; and $R^{3b}$ represents a trifluoromethyl group (hereinafter referred to as "Compound group SX1017").

The Compound (L-5), wherein Q represents the group represented by Q28; $R^{1a}$ represents any one substituent described in Table 1A or Table 2A; $R^{1b}$ represents a hydrogen atom; and $R^{3b}$ represents a trifluoromethyl group (hereinafter referred to as "Compound group SX1018").

The Compound (L-5), wherein Q represents the group represented by Q29; $R^{1b}$ represents any one substituent described in Table 1A or Table 2A; and $R^{3b}$ represents a trifluoromethyl group (hereinafter referred to as "Compound group SX1019").

The Compound (L-5), wherein Q represents the group represented by Q30; $R^{1b}$ represents any one substituent described in Table 1A or Table 2A; and $R^{3b}$ represents a trifluoromethyl group (hereinafter referred to as "Compound group SX1020").

The Compound (L-5), wherein Q represents the group represented by Q11; $R^{1a}$ represents a hydrogen atom; $R^{1b}$ represents any one substituent described in Table 1A or Table 2A; and $R^{3b}$ represents a chlorine atom (hereinafter referred to as "Compound group SX1021").

The Compound (L-5), wherein Q represents the group represented by Q11; $R^{1a}$ represents any one substituent described in Table 1A or Table 2A; $R^{1b}$ represents a hydrogen atom; and $R^{3b}$ represents a chlorine atom (hereinafter referred to as "Compound group SX1022").

The Compound (L-5), wherein Q represents the group represented by Q12; $R^{1a}$ represents a hydrogen atom; $R^{1b}$ represents any one substituent described in Table 1A or Table 2A; and $R^{3b}$ represents a chlorine atom (hereinafter referred to as "Compound group SX1023").

The Compound (L-5), wherein Q represents the group represented by Q12; $R^{1a}$ represents any one substituent described in Table 1A or Table 2A; $R^{1b}$ represents a hydrogen atom; and $R^{3b}$ represents a chlorine atom (hereinafter referred to as "Compound group SX1024").

The Compound (L-5), wherein Q represents the group represented by Q13; $R^{1a}$ represents a hydrogen atom; $R^{1b}$ represents any one substituent described in Table 1A or Table 2A; and $R^{3b}$ represents a chlorine atom (hereinafter referred to as "Compound group SX1025").

The Compound (L-5), wherein Q represents the group represented by Q13; $R^{1a}$ represents any one substituent described in Table 1A or Table 2A; $R^{1b}$ represents a hydrogen atom; and $R^{3b}$ represents a chlorine atom (hereinafter referred to as "Compound group SX1026").

The Compound (L-5), wherein Q represents the group represented by Q14; $R^{1a}$ represents a hydrogen atom; $R^{1b}$ represents any one substituent described in Table 1A or Table 2A; and $R^{3b}$ represents a chlorine atom (hereinafter referred to as "Compound group SX1027").

The Compound (L-5), wherein Q represents the group represented by Q14; $R^{1a}$ represents any one substituent described in Table 1A or Table 2A; $R^{1b}$ represents a hydrogen atom; and $R^{3b}$ represents a chlorine atom (hereinafter referred to as "Compound group SX1028").

The Compound (L-5), wherein Q represents the group represented by Q15; $R^{1a}$ represents a hydrogen atom; $R^{1b}$ represents any one substituent described in Table 1A or Table 2A; and $R^{3b}$ represents a chlorine atom (hereinafter referred to as "Compound group SX1029").

The Compound (L-5), wherein Q represents the group represented by Q15; $R^{1a}$ represents any one substituent described in Table 1A or Table 2A; $R^{1b}$ represents a hydrogen atom; and $R^{3b}$ represents a chlorine atom (hereinafter referred to as "Compound group SX1030").

The Compound (L-5), wherein Q represents the group represented by Q16; $R^{1a}$ represents a hydrogen atom; $R^{1b}$ represents any one substituent described in Table 1A or Table 2A; and $R^{3b}$ represents a chlorine atom (hereinafter referred to as "Compound group SX1031").

The Compound (L-5), wherein Q represents the group represented by Q16; $R^{1a}$ represents any one substituent described in Table 1A or Table 2A; $R^{1b}$ represents a hydrogen atom; and $R^{3b}$ represents a chlorine atom (hereinafter referred to as "Compound group SX1032").

The Compound (L-5), wherein Q represents the group represented by Q17; $R^{1a}$ represents a hydrogen atom; $R^{1b}$ represents any one substituent described in Table 1A or Table 2A; and $R^{3b}$ represents a chlorine atom (hereinafter referred to as "Compound group SX1033").

The Compound (L-5), wherein Q represents the group represented by Q17; $R^{1a}$ represents any one substituent described in Table 1A or Table 2A; $R^{1b}$ represents a hydrogen atom; and $R^{3b}$ represents a chlorine atom (hereinafter referred to as "Compound group SX1034").

The Compound (L-5), wherein Q represents the group represented by Q18; $R^{1a}$ represents a hydrogen atom; $R^{1b}$ represents any one substituent described in Table 1A or Table 2A; and $R^{3b}$ represents a chlorine atom (hereinafter referred to as "Compound group SX1035").

The Compound (L-5), wherein Q represents the group represented by Q18; $R^{1a}$ represents any one substituent described in Table 1A or Table 2A; $R^{1b}$ represents a hydrogen atom; and $R^{3b}$ represents a chlorine atom (hereinafter referred to as "Compound group SX1036").

The Compound (L-5), wherein Q represents the group represented by Q19; $R^{1b}$ represents any one substituent described in Table 1A or Table 2A; and $R^{3b}$ represents a chlorine atom (hereinafter referred to as "Compound group SX1037").

The Compound (L-5), wherein Q represents the group represented by Q20; $R^{1b}$ represents any one substituent described in Table 1A or Table 2A; and $R^{3b}$ represents a chlorine atom (hereinafter referred to as "Compound group SX1038").

The Compound (L-5), wherein Q represents the group represented by Q21; $R^{1b}$ represents any one substituent described in Table 1A or Table 2A; and $R^{3b}$ represents a chlorine atom (hereinafter referred to as "Compound group SX1039").

The Compound (L-5), wherein Q represents the group represented by Q22; $R^{1b}$ represents any one substituent described in Table 1A or Table 2A; and $R^{3b}$ represents a chlorine atom (hereinafter referred to as "Compound group SX1040").

The Compound (L-5), wherein Q represents the group represented by Q23; $R^{1b}$ represents any one substituent described in Table 1A or Table 2A; and $R^{3b}$ represents a chlorine atom (hereinafter referred to as "Compound group SX1041").

The Compound (L-5), wherein Q represents the group represented by Q24; $R^{1b}$ represents any one substituent described in Table 1A or Table 2A; and $R^{3b}$ represents a chlorine atom (hereinafter referred to as "Compound group SX1042").

The Compound (L-5), wherein Q represents the group represented by Q25; $R^{1b}$ represents any one substituent described in Table 1A or Table 2A; and $R^{3b}$ represents a chlorine atom (hereinafter referred to as "Compound group SX1043").

The Compound (L-5), wherein Q represents the group represented by Q26; $R^{1b}$ represents any one substituent described in Table 1A or Table 2A; and $R^{3b}$ represents a chlorine atom (hereinafter referred to as "Compound group SX1044").

The Compound (L-5), wherein Q represents the group represented by Q27; $R^{1a}$ represents a hydrogen atom; $R^{1b}$ represents any one substituent described in Table 1A or Table 2A; and $R^{3b}$ represents a chlorine atom (hereinafter referred to as "Compound group SX1045").

The Compound (L-5), wherein Q represents the group represented by Q27; $R^{1a}$ represents any one substituent described in Table 1A or Table 2A; $R^{1b}$ represents a hydrogen atom; and $R^{3b}$ represents a chlorine atom (hereinafter referred to as "Compound group SX1046").

The Compound (L-5), wherein Q represents the group represented by Q28; $R^{1a}$ represents a hydrogen atom; $R^{1b}$ represents any one substituent described in Table 1A or Table 2A; and $R^{3b}$ represents a chlorine atom (hereinafter referred to as "Compound group SX1047").

The Compound (L-5), wherein Q represents the group represented by Q28; $R^{1a}$ represents any one substituent described in Table 1A or Table 2A; $R^{1b}$ represents a hydrogen atom; and $R^{3b}$ represents a chlorine atom (hereinafter referred to as "Compound group SX1048").

The Compound (L-5), wherein Q represents the group represented by Q29; $R^{1b}$ represents any one substituent described in Table 1A or Table 2A; and $R^{3b}$ represents a chlorine atom (hereinafter referred to as "Compound group SX1049").

The Compound (L-5), wherein Q represents the group represented by Q30; $R^{1b}$ represents any one substituent described in Table 1A or Table 2A; and $R^{3b}$ represents a chlorine atom (hereinafter referred to as "Compound group SX1050").

The Compound (L-5), wherein Q represents the group represented by Q11; $R^{1a}$ represents a hydrogen atom; $R^{1b}$ represents any one substituent described in Table 1A or Table 2A; and $R^{3b}$ represents a bromine atom (hereinafter referred to as "Compound group SX1051").

The Compound (L-5), wherein Q represents the group represented by Q11; $R^{1a}$ represents any one substituent described in Table 1A or Table 2A; $R^{1b}$ represents a hydrogen atom; and $R^{3b}$ represents a bromine atom (hereinafter referred to as "Compound group SX1052").

The Compound (L-5), wherein Q represents the group represented by Q12; $R^{1a}$ represents a hydrogen atom; $R^{1b}$ represents any one substituent described in Table 1A or Table 2A; and $R^{3b}$ represents a bromine atom (hereinafter referred to as "Compound group SX1053").

The Compound (L-5), wherein Q represents the group represented by Q12; $R^{1a}$ represents any one substituent described in Table 1A or Table 2A; $R^{1b}$ represents a hydrogen atom; and $R^{3b}$ represents a bromine atom (hereinafter referred to as "Compound group SX1054").

The Compound (L-5), wherein Q represents the group represented by Q13; $R^{1a}$ represents a hydrogen atom; $R^{1b}$ represents any one substituent described in Table 1A or Table 2A; and $R^{3b}$ represents a bromine atom (hereinafter referred to as "Compound group SX1055").

The Compound (L-5), wherein Q represents the group represented by Q13; $R^{1a}$ represents any one substituent described in Table 1A or Table 2A; $R^{1b}$ represents a hydrogen atom; and $R^{3b}$ represents a bromine atom (hereinafter referred to as "Compound group SX1056").

The Compound (L-5), wherein Q represents the group represented by Q14; $R^{1a}$ represents a hydrogen atom; $R^{1b}$ represents any one substituent described in Table 1A or Table 2A; and $R^{3b}$ represents a bromine atom (hereinafter referred to as "Compound group SX1057").

The Compound (L-5), wherein Q represents the group represented by Q14; $R^{1a}$ represents any one substituent described in Table 1A or Table 2A; $R^{1b}$ represents a hydrogen atom; and $R^{3b}$ represents a bromine atom (hereinafter referred to as "Compound group SX1058").

The Compound (L-5), wherein Q represents the group represented by Q15; $R^{1a}$ represents a hydrogen atom; $R^{1b}$ represents any one substituent described in Table 1A or Table 2A; and $R^{3b}$ represents a bromine atom (hereinafter referred to as "Compound group SX1059").

The Compound (L-5), wherein Q represents the group represented by Q15; $R^{1a}$ represents any one substituent described in Table 1A or Table 2A; $R^{1b}$ represents a hydrogen atom; and $R^{3b}$ represents a bromine atom (hereinafter referred to as "Compound group SX1060").

The Compound (L-5), wherein Q represents the group represented by Q16; $R^{1a}$ represents a hydrogen atom; $R^{1b}$ represents any one substituent described in Table 1A or Table 2A; and $R^{3b}$ represents a bromine atom (hereinafter referred to as "Compound group SX1061").

The Compound (L-5), wherein Q represents the group represented by Q16; $R^{1a}$ represents any one substituent described in Table 1A or Table 2A; $R^{1b}$ represents a hydrogen atom; and $R^{3b}$ represents a bromine atom (hereinafter referred to as "Compound group SX1062").

The Compound (L-5), wherein Q represents the group represented by Q17; $R^{1a}$ represents a hydrogen atom; $R^{1b}$ represents any one substituent described in Table 1A or Table 2A; and $R^{3b}$ represents a bromine atom (hereinafter referred to as "Compound group SX1063").

The Compound (L-5), wherein Q represents the group represented by Q17; $R^{1a}$ represents any one substituent described in Table 1A or Table 2A; $R^{1b}$ represents a hydrogen atom; and $R^{3b}$ represents a bromine atom (hereinafter referred to as "Compound group SX1064").

The Compound (L-5), wherein Q represents the group represented by Q18; $R^{1a}$ represents a hydrogen atom; $R^{1b}$ represents any one substituent described in Table 1A or Table 2A; and $R^{3b}$ represents a bromine atom (hereinafter referred to as "Compound group SX1065").

The Compound (L-5), wherein Q represents the group represented by Q18; $R^{1a}$ represents any one substituent described in Table 1A or Table 2A; $R^{1b}$ represents a hydrogen atom; and $R^{3b}$ represents a bromine atom (hereinafter referred to as "Compound group SX1066").

The Compound (L-5), wherein Q represents the group represented by Q19; $R^{1b}$ represents any one substituent described in Table 1A or Table 2A; and $R^{3b}$ represents a bromine atom (hereinafter referred to as "Compound group SX1067").

The Compound (L-5), wherein Q represents the group represented by Q20; $R^{1b}$ represents any one substituent described in Table 1A or Table 2A; and $R^{3b}$ represents a bromine atom (hereinafter referred to as "Compound group SX1068").

The Compound (L-5), wherein Q represents the group represented by Q21; $R^{1b}$ represents any one substituent described in Table 1A or Table 2A; and $R^{3b}$ represents a bromine atom (hereinafter referred to as "Compound group SX1069").

The Compound (L-5), wherein Q represents the group represented by Q22; $R^{1b}$ represents any one substituent described in Table 1A or Table 2A; and $R^{3b}$ represents a bromine atom (hereinafter referred to as "Compound group SX1070").

The Compound (L-5), wherein Q represents the group represented by Q23; $R^{1b}$ represents any one substituent described in Table 1A or Table 2A; and $R^{3b}$ represents a bromine atom (hereinafter referred to as "Compound group SX1071").

The Compound (L-5), wherein Q represents the group represented by Q24; $R^{1b}$ represents any one substituent described in Table 1A or Table 2A; and $R^{3b}$ represents a bromine atom (hereinafter referred to as "Compound group SX1072").

The Compound (L-5), wherein Q represents the group represented by Q25; $R^{1b}$ represents any one substituent described in Table 1A or Table 2A; and $R^{3b}$ represents a bromine atom (hereinafter referred to as "Compound group SX1073").

The Compound (L-5), wherein Q represents the group represented by Q26; $R^{1b}$ represents any one substituent described in Table 1A or Table 2A; and $R^{3b}$ represents a bromine atom (hereinafter referred to as "Compound group SX1074").

The Compound (L-5), wherein Q represents the group represented by Q27; $R^{1a}$ represents a hydrogen atom; $R^{1b}$ represents any one substituent described in Table 1A or Table 2A; and $R^{3b}$ represents a bromine atom (hereinafter referred to as "Compound group SX1075").

The Compound (L-5), wherein Q represents the group represented by Q27; $R^{1a}$ represents any one substituent described in Table 1A or Table 2A; $R^{1b}$ represents a hydrogen atom; and $R^{3b}$ represents a bromine atom (hereinafter referred to as "Compound group SX1076").

The Compound (L-5), wherein Q represents the group represented by Q28; $R^{1a}$ represents a hydrogen atom; $R^{1b}$ represents any one substituent described in Table 1A or Table 2A; and $R^{3b}$ represents a bromine atom (hereinafter referred to as "Compound group SX1077").

The Compound (L-5), wherein Q represents the group represented by Q28; $R^{1a}$ represents any one substituent described in Table 1A or Table 2A; $R^{1b}$ represents a hydrogen atom; and $R^{3b}$ represents a bromine atom (hereinafter referred to as "Compound group SX1078").

The Compound (L-5), wherein Q represents the group represented by Q29; $R^{1b}$ represents any one substituent described in Table 1A or Table 2A; and $R^{3b}$ represents a bromine atom (hereinafter referred to as "Compound group SX1079").

The Compound (L-5), wherein Q represents the group represented by Q30; $R^{1b}$ represents any one substituent described in Table 1A or Table 2A; and $R^{3b}$ represents a bromine atom (hereinafter referred to as "Compound group SX1080").

The Compound (L-5), wherein Q represents the group represented by Q11; $R^{1a}$ represents a hydrogen atom; $R^{1b}$ represents any one substituent described in Table 1A or Table 2A; and $R^{3b}$ represents an iodine atom (hereinafter referred to as "Compound group SX1081").

The Compound (L-5), wherein Q represents the group represented by Q11; $R^{1a}$ represents any one substituent described in Table 1A or Table 2A; $R^{1b}$ represents a hydrogen atom; and $R^{3b}$ represents an iodine atom (hereinafter referred to as "Compound group SX1082").

The Compound (L-5), wherein Q represents the group represented by Q12; $R^{1a}$ represents a hydrogen atom; $R^{1b}$ represents any one substituent described in Table 1A or Table 2A; and $R^{3b}$ represents an iodine atom (hereinafter referred to as "Compound group SX1083").

The Compound (L-5), wherein Q represents the group represented by Q12; $R^{1a}$ represents any one substituent described in Table 1A or Table 2A; $R^{1b}$ represents a hydrogen atom; and $R^{3b}$ represents an iodine atom (hereinafter referred to as "Compound group SX1084").

The Compound (L-5), wherein Q represents the group represented by Q13; $R^{1a}$ represents a hydrogen atom; $R^{1b}$ represents any one substituent described in Table 1A or Table 2A; and $R^{3b}$ represents an iodine atom (hereinafter referred to as "Compound group SX1085").

The Compound (L-5), wherein Q represents the group represented by Q13; $R^{1a}$ represents any one substituent described in Table 1A or Table 2A; $R^{1b}$ represents a hydrogen atom; and $R^{3b}$ represents an iodine atom (hereinafter referred to as "Compound group SX1086").

The Compound (L-5), wherein Q represents the group represented by Q14; $R^{1a}$ represents a hydrogen atom; $R^{1b}$ represents any one substituent described in Table 1A or Table 2A; and $R^{3b}$ represents an iodine atom (hereinafter referred to as "Compound group SX1087").

The Compound (L-5), wherein Q represents the group represented by Q14; $R^{1a}$ represents any one substituent described in Table 1A or Table 2A; $R^{1b}$ represents a hydrogen atom; and $R^{3b}$ represents an iodine atom (hereinafter referred to as "Compound group SX1088").

The Compound (L-5), wherein Q represents the group represented by Q15; $R^{1a}$ represents a hydrogen atom; $R^{1b}$ represents any one substituent described in Table 1A or Table 2A; and $R^{3b}$ represents an iodine atom (hereinafter referred to as "Compound group SX1089").

The Compound (L-5), wherein Q represents the group represented by Q15; $R^{1a}$ represents any one substituent hydrogen atom; and $R^{3b}$ represents an iodine atom (hereinafter referred to as "Compound group SX1090").

The Compound (L-5), wherein Q represents the group represented by Q16; $R^{1a}$ represents a hydrogen atom; $R^{1b}$ represents any one substituent described in Table 1A or Table 2A; and $R^{3b}$ represents an iodine atom (hereinafter referred to as "Compound group SX1091").

The Compound (L-5), wherein Q represents the group represented by Q16; $R^{1a}$ represents any one substituent described in Table 1A or Table 2A; $R^{1b}$ represents a hydrogen atom; and $R^{3b}$ represents an iodine atom (hereinafter referred to as "Compound group SX1092").

The Compound (L-5), wherein Q represents the group represented by Q17; $R^{1a}$ represents a hydrogen atom; $R^{1b}$ represents any one substituent described in Table 1A or Table 2A; and $R^{3b}$ represents an iodine atom (hereinafter referred to as "Compound group SX1093").

The Compound (L-5), wherein Q represents the group represented by Q17; $R^{1a}$ represents any one substituent described in Table 1A or Table 2A; $R^{1b}$ represents a hydrogen atom; and $R^{3b}$ represents an iodine atom (hereinafter referred to as "Compound group SX1094").

The Compound (L-5), wherein Q represents the group represented by Q18; $R^{1a}$ represents a hydrogen atom; $R^{1b}$ represents any one substituent described in Table 1A or Table 2A; and $R^{3b}$ represents an iodine atom (hereinafter referred to as "Compound group SX1095").

The Compound (L-5), wherein Q represents the group represented by Q18; $R^{1a}$ represents any one substituent described in Table 1A or Table 2A; $R^{1b}$ represents a hydrogen atom; and $R^{3b}$ represents an iodine atom (hereinafter referred to as "Compound group SX1096").

The Compound (L-5), wherein Q represents the group represented by Q19; $R^{1b}$ represents any one substituent described in Table 1A or Table 2A; and $R^{3b}$ represents an iodine atom (hereinafter referred to as "Compound group SX1097").

The Compound (L-5), wherein Q represents the group represented by Q20; $R^{1b}$ represents any one substituent described in Table 1A or Table 2A; and $R^{3b}$ represents an iodine atom (hereinafter referred to as "Compound group SX1098").

The Compound (L-5), wherein Q represents the group represented by Q21; $R^{1b}$ represents any one substituent described in Table 1A or Table 2A; and $R^{3b}$ represents an iodine atom (hereinafter referred to as "Compound group SX1099").

The Compound (L-5), wherein Q represents the group represented by Q22; $R^{1b}$ represents any one substituent described in Table 1A or Table 2A; and $R^{3b}$ represents an iodine atom (hereinafter referred to as "Compound group SX1100").

The Compound (L-5), wherein Q represents the group represented by Q23; $R^{1b}$ represents any one substituent described in Table 1A or Table 2A; and $R^{3b}$ represents an iodine atom (hereinafter referred to as "Compound group SX1101").

The Compound (L-5), wherein Q represents the group represented by Q24; $R^{1b}$ represents any one substituent described in Table 1A or Table 2A; and $R^{3b}$ represents an iodine atom (hereinafter referred to as "Compound group SX1102").

The Compound (L-5), wherein Q represents the group represented by Q25; $R^{1b}$ represents any one substituent described in Table 1A or Table 2A; and $R^{3b}$ represents an iodine atom (hereinafter referred to as "Compound group SX1103").

The Compound (L-5), wherein Q represents the group represented by Q26; $R^{1b}$ represents any one substituent described in Table 1A or Table 2A; and $R^{3b}$ represents an iodine atom (hereinafter referred to as "Compound group SX1104").

The Compound (L-5), wherein Q represents the group represented by Q27; $R^{1a}$ represents a hydrogen atom; $R^{1b}$ represents any one substituent described in Table 1A or Table 2A; and $R^{3b}$ represents an iodine atom (hereinafter referred to as "Compound group SX1105").

The Compound (L-5), wherein Q represents the group represented by Q27; $R^{1a}$ represents any one substituent described in Table 1A or Table 2A; $R^{1b}$ represents a hydrogen atom; and $R^{3b}$ represents an iodine atom (hereinafter referred to as "Compound group SX1106").

The Compound (L-5), wherein Q represents the group represented by Q28; $R^{1a}$ represents a hydrogen atom; $R^{1b}$ represents any one substituent described in Table 1A or Table 2A; and $R^{3b}$ represents an iodine atom (hereinafter referred to as "Compound group SX1107").

The Compound (L-5), wherein Q represents the group represented by Q28; $R^{1a}$ represents any one substituent described in Table 1A or Table 2A; $R^{1b}$ represents a hydrogen atom; and $R^{3b}$ represents an iodine atom (hereinafter referred to as "Compound group SX1108").

The Compound (L-5), wherein Q represents the group represented by Q29; $R^{1b}$ represents any one substituent described in Table 1A or Table 2A; and $R^{3b}$ represents an iodine atom (hereinafter referred to as "Compound group SX1109").

The Compound (L-5), wherein Q represents the group represented by Q30; $R^{1b}$ represents any one substituent described in Table 1A or Table 2A; and $R^{3b}$ represents an iodine atom (hereinafter referred to as "Compound group SX1110").

Q31 to Q60 represent the following groups.

| | |
|---|---|
| 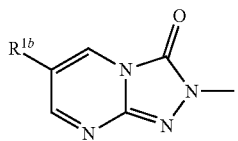 | Q35 |
| 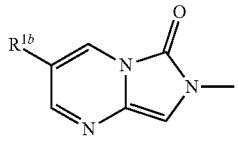 | Q36 |
| 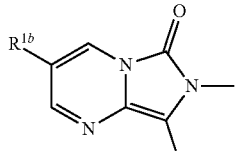 | Q37 |
| 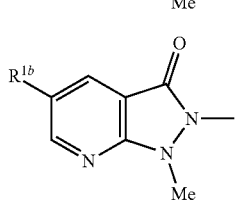 | Q38 |
| 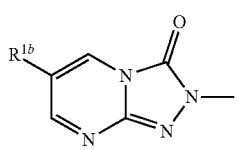 | Q39 |
| 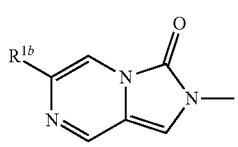 | Q40 |
| 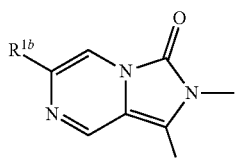 | Q41 |
| 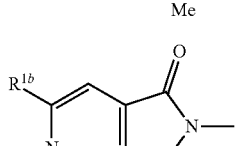 | Q42 |
| 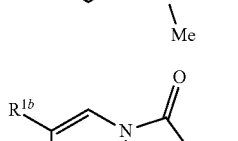 | Q43 |
| 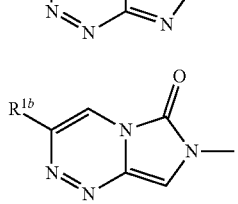 | Q44 |
| 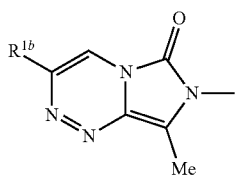 | Q45 |
| 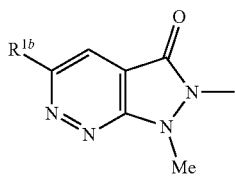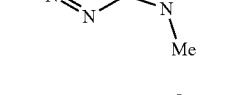 | Q46 |
| 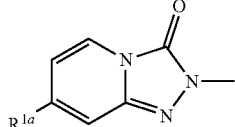 | Q47 |
| 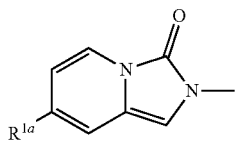 | Q48 |
| 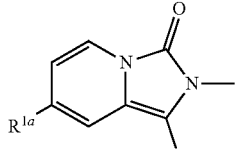 | Q49 |
| 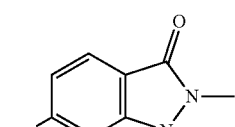 | Q50 |
| 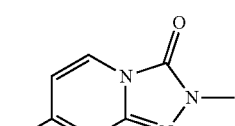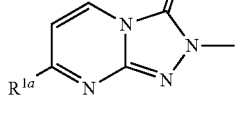 | Q51 |
| 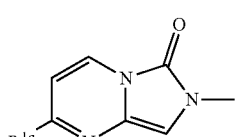 | Q52 |
| 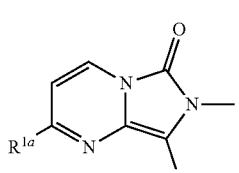 | Q53 |

-continued

Q54 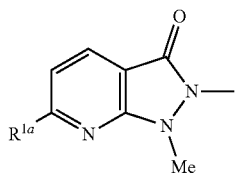

Q55 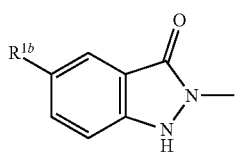

Q56 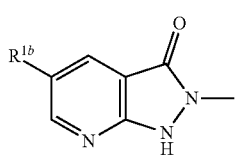

Q57 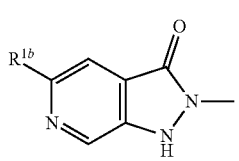

Q58 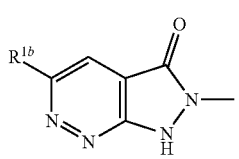

Q59 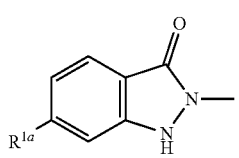

Q60 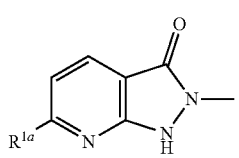

A compound represented by formula (L-6):

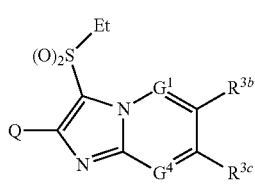

(L-6)

(hereinafter referred to as "Compound (L-6)"), wherein Q represents the group represented by Q31; $R^{1b}$ represents $CF_3$; $G^1$ and $G^4$ each represent CH; $R^{3b}$ represents any one substituent described in Table 3A to Table 11A; and $R^{3c}$ represents a hydrogen atom (hereinafter referred to as "Compound group SX1111").

TABLE 3A

F
Me
Et
Pr
i-Pr
$CHF_2$
$CH=CH_2$
$CMe=CH_2$
c-Pr
c-Bu
c-Pen
c-Hex
1-F—c-Pr
2,2-$F_2$—c-Pr
1-CN—c-Pr
1-CN—c-Bu
1-CN—c-Pen
1-CN—c-Hex
CHO
C(O)Me
C(O)c-Pr
C(O)OEt
C(O)NHc—Pr
CH=N—OH
CH=N—OMe
CH=N—OEt
CH=N—$OCH_2CF_3$
CMe=N—OH
CMe=N—OMe
CMe=N—OEt
CMe=N—$OCH_2CF_3$
$C(NH_2)$=N—$OCH_2CF_3$
SEt
S(O)Et
$S(O)_2Et$

TABLE 4A

Ph
3-F—Ph
4-F—Ph
3-Cl—Ph
4-Cl—Ph
3-$CF_3$—Ph
4-$CF_3$—Ph
3-$NMe_2$—Ph
4-$NMe_2$—Ph
3-CN—Ph
4-CN—Ph
4-C(O)$NMe_2$—Ph
4-NHC(O)Me—Ph
3,4-$F_2$—Ph
3,5-$F_2$—Ph
2,4-$F_2$—Ph
3,4,5-$F_3$—Ph
3,4-$Cl_2$—Ph
3,5-$Cl_2$—Ph
3,5-$Cl_2$-4-F—Ph
OPh
O—2-F—Ph
O—3-$CF_3$—Ph
O—4-$CF_3$—Ph
$NH_2$
$NHCH_2CF_3$
NHc-Pr
NH(1-CN—c-Pr)
NHOMe
$NMe_2$
NHC(O)Me
NHC(O)c-Pr
NMeC(O)c-Pr
$NO_2$
CN

TABLE 5A
Py2
4-F—Py2
5-F—Py2
4-Cl—Py2
5-Cl—Py2
4-CF$_3$—Py2
5-CF$_3$—Py2
6-CF$_3$—Py2
3-Me—Py2
4-Me—Py2
5-Me—Py2
6-Me—Py2
4-CN—Py2
5-CN—Py2
5-OCH$_2$CF$_2$CF$_3$—Py2
3,5-F$_2$—Py2
Py3
6-CF$_3$—Py3
5-CF$_3$—Py3
6-F—Py3
6-Cl—Py3
Py4
OPy2
OPy3
OPy4
O—5-CF$_3$—Py2
O—6-CF$_3$—Py2
OMe
OEt
OPr
Oi-Pr
Oc-Pr
OCMe$_2$CN
CMe$_2$CN
CMeCN$_2$
TABLE 6A
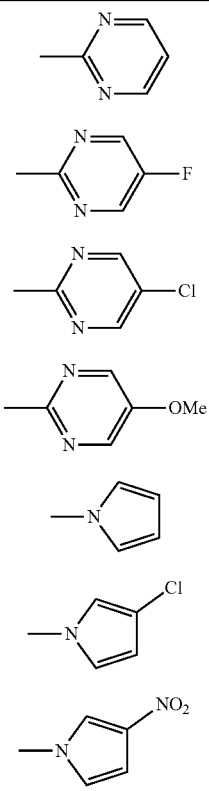
TABLE 6A-continued
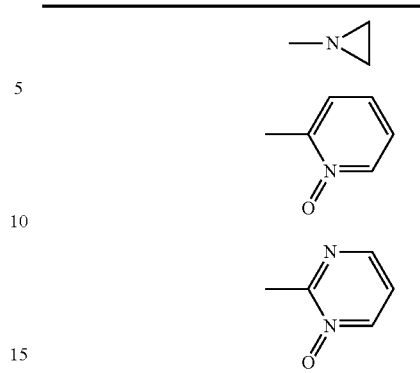
TABLE 7A
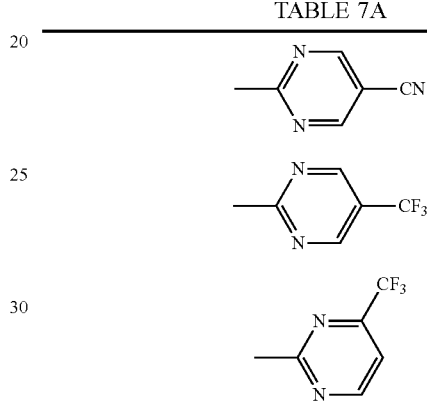
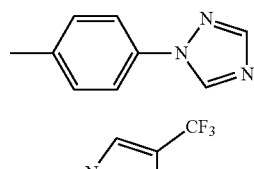
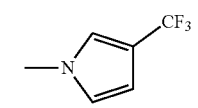
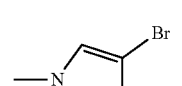
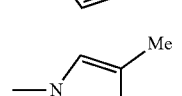
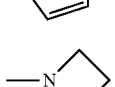
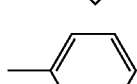
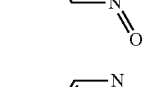

TABLE 8A

TABLE 9A

TABLE 9A-continued

TABLE 10A

TABLE 10A-continued

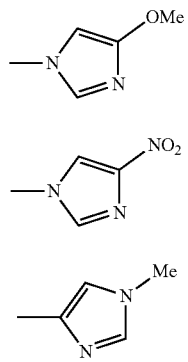

TABLE 11A

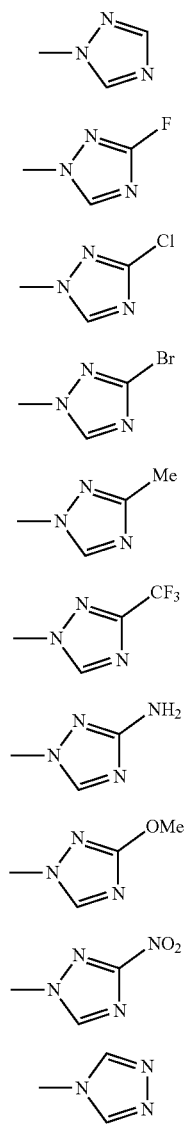

The Compound (L-6), wherein Q represents the group represented by Q32; $R^{1b}$ represents $CF_3$; $G^1$ and $G^4$ each represent CH; $R^{3b}$ represents any one substituent described in Table 3A to Table 11A; and $R^{3c}$ represents a hydrogen atom (hereinafter referred to as "Compound group SX1112").

The Compound (L-6), wherein Q represents the group represented by Q33; $R^{1b}$ represents $CF_3$; $G^1$ and $G^4$ each represent CH; $R^{3b}$ represents any one substituent described in Table 3A to Table 11A; and $R^{3c}$ represents a hydrogen atom (hereinafter referred to as "Compound group SX1113").

The Compound (L-6), wherein Q represents the group represented by Q34; $R^{1b}$ represents $CF_3$; $G^1$ and $G^4$ each represent CH; $R^{3b}$ represents any one substituent described in Table 3A to Table 11A; and $R^{3c}$ represents a hydrogen atom (hereinafter referred to as "Compound group SX1114").

The Compound (L-6), wherein Q represents the group represented by Q35; $R^{1b}$ represents $CF_3$; $G^1$ and $G^4$ each represent CH; $R^{3b}$ represents any one substituent described in Table 3A to Table 11A; and $R^{3c}$ represents a hydrogen atom (hereinafter referred to as "Compound group SX1115").

The Compound (L-6), wherein Q represents the group represented by Q36; $R^{1b}$ represents $CF_3$; $G^1$ and $G^4$ each represent CH; $R^{3b}$ represents any one substituent described in Table 3A to Table 11A; and $R^{3c}$ represents a hydrogen atom (hereinafter referred to as "Compound group SX1116").

The Compound (L-6), wherein Q represents the group represented by Q37; $R^{1b}$ represents $CF_3$; $G^1$ and $G^4$ each represent CH; $R^{3b}$ represents any one substituent described in Table 3A to Table 11A; and $R^{3c}$ represents a hydrogen atom (hereinafter referred to as "Compound group SX1117").

The Compound (L-6), wherein Q represents the group represented by Q38; $R^{1b}$ represents $CF_3$; $G^1$ and $G^4$ each represent CH; $R^{3b}$ represents any one substituent described in Table 3A to Table 11A; and $R^{3c}$ represents a hydrogen atom (hereinafter referred to as "Compound group SX1118").

The Compound (L-6), wherein Q represents the group represented by Q39; $R^{1b}$ represents $CF_3$; $G^1$ and $G^4$ each represent CH; $R^{3b}$ represents any one substituent described in Table 3A to Table 11A; and $R^{3c}$ represents a hydrogen atom (hereinafter referred to as "Compound group SX1119").

The Compound (L-6), wherein Q represents the group represented by Q40; $R^{1b}$ represents $CF_3$; $G^1$ and $G^4$ each represent CH; $R^{3b}$ represents any one substituent described in Table 3A to Table 11A; and $R^{3c}$ represents a hydrogen atom (hereinafter referred to as "Compound group SX1120").

The Compound (L-6), wherein Q represents the group represented by Q41; $R^{1b}$ represents $CF_3$; $G^1$ and $G^4$ each represent CH; $R^{3b}$ represents any one substituent described in Table 3A to Table 11A; and $R^{3c}$ represents a hydrogen atom (hereinafter referred to as "Compound group SX1121").

The Compound (L-6), wherein Q represents the group represented by Q42; $R^{1b}$ represents $CF_3$; $G^1$ and $G^4$ each represent CH; $R^{3b}$ represents any one substituent described in Table 3A to Table 11A; and $R^{3c}$ represents a hydrogen atom (hereinafter referred to as "Compound group SX1122").

The Compound (L-6), wherein Q represents the group represented by Q43; $R^{1b}$ represents $CF_3$; $G^1$ and $G^4$ each represent CH; $R^{3b}$ represents any one substituent described in Table 3A to Table 11A; and $R^{3c}$ represents a hydrogen atom (hereinafter referred to as "Compound group SX1123").

The Compound (L-6), wherein Q represents the group represented by Q44; $R^{1b}$ represents $CF_3$; $G^1$ and $G^4$ each represent CH; $R^{3b}$ represents any one substituent described in Table 3A to Table 11A; and $R^{3c}$ represents a hydrogen atom (hereinafter referred to as "Compound group SX1124").

The Compound (L-6), wherein Q represents the group represented by Q45; $R^{1b}$ represents $CF_3$; $G^1$ and $G^4$ each represent CH; $R^{3b}$ represents any one substituent described in Table 3A to Table 11A; and $R^{3c}$ represents a hydrogen atom (hereinafter referred to as "Compound group SX1125").

The Compound (L-6), wherein Q represents the group represented by Q46; $R^{1b}$ represents $CF_3$; $G^1$ and $G^4$ each represent CH; $R^{3b}$ represents any one substituent described in Table 3A to Table 11A; and $R^{3c}$ represents a hydrogen atom (hereinafter referred to as "Compound group SX1126").

The Compound (L-6), wherein Q represents the group represented by Q47; $R^{1a}$ represents $CF_3$; $G^1$ and $G^4$ each represent CH; $R^{3b}$ represents any one substituent described in Table 3A to Table 11A; and $R^{3c}$ represents a hydrogen atom (hereinafter referred to as "Compound group SX1127").

The Compound (L-6), wherein Q represents the group represented by Q48; $R^{1a}$ represents $CF_3$; $G^1$ and $G^4$ each represent CH; $R^{3b}$ represents any one substituent described in Table 3A to Table 11A; and $R^{3c}$ represents a hydrogen atom (hereinafter referred to as "Compound group SX1128").

The Compound (L-6), wherein Q represents the group represented by Q49; $R^{1a}$ represents $CF_3$; $G^1$ and $G^4$ each represent CH; $R^{3b}$ represents any one substituent described in Table 3A to Table 11A; and $R^{3c}$ represents a hydrogen atom (hereinafter referred to as "Compound group SX1129").

The Compound (L-6), wherein Q represents the group represented by Q50; $R^{1a}$ represents $CF_3$; $G^1$ and $G^4$ each represent CH; $R^{3b}$ represents any one substituent described in Table 3A to Table 11A; and $R^{3c}$ represents a hydrogen atom (hereinafter referred to as "Compound group SX1130").

The Compound (L-6), wherein Q represents the group represented by Q51; $R^{1a}$ represents $CF_3$; $G^1$ and $G^4$ each represent CH; $R^{3b}$ represents any one substituent described in Table 3A to Table 11A; and $R^{3c}$ represents a hydrogen atom (hereinafter referred to as "Compound group SX1131").

The Compound (L-6), wherein Q represents the group represented by Q52; $R^{1a}$ represents $CF_3$; $G^1$ and $G^4$ each represent CH; $R^{3b}$ represents any one substituent described in Table 3A to Table 11A; and $R^{3c}$ represents a hydrogen atom (hereinafter referred to as "Compound group SX1132").

The Compound (L-6), wherein Q represents the group represented by Q53; $R^{1a}$ represents $CF_3$; $G^1$ and $G^4$ each represent CH; $R^{3b}$ represents any one substituent described in Table 3A to Table 11A; and $R^{3c}$ represents a hydrogen atom (hereinafter referred to as "Compound group SX1133").

The Compound (L-6), wherein Q represents the group represented by Q54; $R^{1a}$ represents $CF_3$; $G^1$ and $G^4$ each represent CH; $R^{3b}$ represents any one substituent described in Table 3A to Table 11A; and $R^{3c}$ represents a hydrogen atom (hereinafter referred to as "Compound group SX1134").

The Compound (L-6), wherein Q represents the group represented by Q55; $R^{1b}$ represents $CF_3$; $G^1$ and $G^4$ each represent CH; $R^{3b}$ represents any one substituent described in Table 3A to Table 11A; and $R^{3c}$ represents a hydrogen atom (hereinafter referred to as "Compound group SX1135").

The Compound (L-6), wherein Q represents the group represented by Q56; $R^{1b}$ represents $CF_3$; $G^1$ and $G^4$ each represent CH; $R^{3b}$ represents any one substituent described in Table 3A to Table 11A; and $R^{3c}$ represents a hydrogen atom (hereinafter referred to as "Compound group SX1136").

The Compound (L-6), wherein Q represents the group represented by Q57; $R^{1b}$ represents $CF_3$; $G^1$ and $G^4$ each represent CH; $R^{3b}$ represents any one substituent described in Table 3A to Table 11A; and $R^{3c}$ represents a hydrogen atom (hereinafter referred to as "Compound group SX1137").

The Compound (L-6), wherein Q represents the group represented by Q58; $R^{1b}$ represents $CF_3$; $G^1$ and $G^4$ each represent CH; $R^{3b}$ represents any one substituent described in Table 3A to Table 11A; and $R^{3c}$ represents a hydrogen atom (hereinafter referred to as "Compound group SX1138").

The Compound (L-6), wherein Q represents the group represented by Q59; $R^{1a}$ represents $CF_3$; $G^1$ and $G^4$ each represent CH; $R^{3b}$ represents any one substituent described in Table 3A to Table 11A; and $R^{3c}$ represents a hydrogen atom (hereinafter referred to as "Compound group SX1139").

The Compound (L-6), wherein Q represents the group represented by Q60; $R^{1a}$ represents $CF_3$; $G^1$ and $G^4$ each represent CH; $R^{3b}$ represents any one substituent described in Table 3A to Table 11A; and $R^{3c}$ represents a hydrogen atom (hereinafter referred to as "Compound group SX1140").

The Compound (L-6), wherein Q represents the group represented by Q31; $R^{1b}$ represents $C_3F_5$; $G^1$ and $G^4$ each represent CH; $R^{3b}$ represents any one substituent described in Table 3A to Table 11A; and $R^{3c}$ represents a hydrogen atom (hereinafter referred to as "Compound group SX1141").

The Compound (L-6), wherein Q represents the group represented by Q32; $R^{1b}$ represents $C_3F_5$; $G^1$ and $G^4$ each represent CH; $R^{3b}$ represents any one substituent described in Table 3A to Table 11A; and $R^{3c}$ represents a hydrogen atom (hereinafter referred to as "Compound group SX1142").

The Compound (L-6), wherein Q represents the group represented by Q33; $R^{1b}$ represents $C_3F_5$; $G^1$ and $G^4$ each represent CH; $R^{3b}$ represents any one substituent described in Table 3A to Table 11A; and $R^{3c}$ represents a hydrogen atom (hereinafter referred to as "Compound group SX1143").

The Compound (L-6), wherein Q represents the group represented by Q34; $R^{1b}$ represents $C_2F_5$; $G^1$ and $G^4$ each represent CH; $R^{3b}$ represents any one substituent described in Table 3A to Table 11A; and $R^{3c}$ represents a hydrogen atom (hereinafter referred to as "Compound group SX1144").

The Compound (L-6), wherein Q represents the group represented by Q35; $R^{1b}$ represents $C_2F_5$; $G^1$ and $G^4$ each represent CH; $R^{3b}$ represents any one substituent described The Compound (L-6), wherein Q represents the group represented by Q36; $R^{1b}$ represents $C_2F_5$; $G^1$ and $G^4$ each represent CH; $R^{3b}$ represents any one substituent described in Table 3A to Table 11A; and $R^{3c}$ represents a hydrogen atom (hereinafter referred to as "Compound group SX1146").

The Compound (L-6), wherein Q represents the group represented by Q37; $R^{1b}$ represents $C_2F_5$; $G^1$ and $G^4$ each represent CH; $R^{3b}$ represents any one substituent described in Table 3A to Table 11A; and $R^{3c}$ represents a hydrogen atom (hereinafter referred to as "Compound group SX1147").

The Compound (L-6), wherein Q represents the group represented by Q38; $R^{1b}$ represents $C_2F_5$; $G^1$ and $G^4$ each represent CH; $R^{3b}$ represents any one substituent described in Table 3A to Table 11A; and $R^{3c}$ represents a hydrogen atom (hereinafter referred to as "Compound group SX1148").

The Compound (L-6), wherein Q represents the group represented by Q39; $R^{1b}$ represents $C_2F_5$; $G^1$ and $G^4$ each represent CH; $R^{3b}$ represents any one substituent described in Table 3A to Table 11A; and $R^{3c}$ represents a hydrogen atom (hereinafter referred to as "Compound group SX1149").

The Compound (L-6), wherein Q represents the group represented by Q40; $R^{1b}$ represents $C_2F_5$; $G^1$ and $G^4$ each represent CH; $R^{3b}$ represents any one substituent described in Table 3A to Table 11A; and $R^{3c}$ represents a hydrogen atom (hereinafter referred to as "Compound group SX1150").

The Compound (L-6), wherein Q represents the group represented by Q41; $R^{1b}$ represents $C_2F_5$; $G^1$ and $G^4$ each represent CH; $R^{3b}$ represents any one substituent described in Table 3A to Table 11A; and $R^{3c}$ represents a hydrogen atom (hereinafter referred to as "Compound group SX1151").

The Compound (L-6), wherein Q represents the group represented by Q42; $R^{1b}$ represents $C_2F_5$; $G^1$ and $G^4$ each represent CH; $R^{3b}$ represents any one substituent described in Table 3A to Table 11A; and $R^{3c}$ represents a hydrogen atom (hereinafter referred to as "Compound group SX1152").

The Compound (L-6), wherein Q represents the group represented by Q43; $R^{1b}$ represents $C_2F_5$; $G^1$ and $G^4$ each represent CH; $R^{3b}$ represents any one substituent described in Table 3A to Table 11A; and $R^{3c}$ represents a hydrogen atom (hereinafter referred to as "Compound group SX1153").

The Compound (L-6), wherein Q represents the group represented by Q44; $R^{1b}$ represents $C_2F_5$; $G^1$ and $G^4$ each represent CH; $R^{3b}$ represents any one substituent described in Table 3A to Table 11A; and $R^{3c}$ represents a hydrogen atom (hereinafter referred to as "Compound group SX1154").

The Compound (L-6), wherein Q represents the group represented by Q45; $R^{1b}$ represents $C_2F_5$; $G^1$ and $G^4$ each represent CH; $R^{3b}$ represents any one substituent described in Table 3A to Table 11A; and $R^{3c}$ represents a hydrogen atom (hereinafter referred to as "Compound group SX1155").

The Compound (L-6), wherein Q represents the group represented by Q46; $R^{1b}$ represents $C_2F_5$; $G^1$ and $G^4$ each represent CH; $R^{3b}$ represents any one substituent described in Table 3A to Table 11A; and $R^{3c}$ represents a hydrogen atom (hereinafter referred to as "Compound group SX1156").

The Compound (L-6), wherein Q represents the group represented by Q47; $R^{1a}$ represents $C_2F_5$; $G^1$ and $G^4$ each represent CH; $R^{3b}$ represents any one substituent described in Table 3A to Table 11A; and $R^{3c}$ represents a hydrogen atom (hereinafter referred to as "Compound group SX1157").

The Compound (L-6), wherein Q represents the group represented by Q48; $R^{1a}$ represents $C_2F_5$; $G^1$ and $G^4$ each represent CH; $R^{3b}$ represents any one substituent described in Table 3A to Table 11A; and $R^{3c}$ represents a hydrogen atom (hereinafter referred to as "Compound group SX1158").

The Compound (L-6), wherein Q represents the group represented by Q49; $R^{1a}$ represents $C_2F_5$; $G^1$ and $G^4$ each represent CH; $R^{3b}$ represents any one substituent described in Table 3A to Table 11A; and $R^{3c}$ represents a hydrogen atom (hereinafter referred to as "Compound group SX1159").

The Compound (L-6), wherein Q represents the group represented by Q50; $R^{1a}$ represents $C_2F_5$; $G^1$ and $G^4$ each represent CH; $R^{3b}$ represents any one substituent described in Table 3A to Table 11A; and $R^{3c}$ represents a hydrogen atom (hereinafter referred to as "Compound group SX1160").

The Compound (L-6), wherein Q represents the group represented by Q51; $R^{1a}$ represents $C_2F_5$; $G^1$ and $G^4$ each represent CH; $R^{3b}$ represents any one substituent described in Table 3A to Table 11A; and $R^{3c}$ represents a hydrogen atom (hereinafter referred to as "Compound group SX1161").

The Compound (L-6), wherein Q represents the group represented by Q52; $R^{1a}$ represents $C_2F_5$; $G^1$ and $G^4$ each represent CH; $R^{3b}$ represents any one substituent described in Table 3A to Table 11A; and $R^{3c}$ represents a hydrogen atom (hereinafter referred to as "Compound group SX1162").

The Compound (L-6), wherein Q represents the group represented by Q53; $R^{1a}$ represents $C_2F_5$; $G^1$ and $G^4$ each represent CH; $R^{3b}$ represents any one substituent described in Table 3A to Table 11A; and $R^{3c}$ represents a hydrogen atom (hereinafter referred to as "Compound group SX1163").

The Compound (L-6), wherein Q represents the group represented by Q54; $R^{1a}$ represents $C_2F_5$; $G^1$ and $G^4$ each represent CH; $R^{3b}$ represents any one substituent described in Table 3A to Table 11A; and $R^{3c}$ represents a hydrogen atom (hereinafter referred to as "Compound group SX1164").

The Compound (L-6), wherein Q represents the group represented by Q55; $R^{1b}$ represents $C_2F_5$; $G^1$ and $G^4$ each represent CH; $R^{3b}$ represents any one substituent described in Table 3A to Table 11A; and $R^{3c}$ represents a hydrogen atom (hereinafter referred to as "Compound group SX1165").

The Compound (L-6), wherein Q represents the group represented by Q56; $R^{1b}$ represents $C_2F_5$; $G^1$ and $G^4$ each represent CH; $R^{3b}$ represents any one substituent described in Table 3A to Table 11A; and $R^{3c}$ represents a hydrogen atom (hereinafter referred to as "Compound group SX1166").

The Compound (L-6), wherein Q represents the group represented by Q57; $R^{1b}$ represents $C_2F_5$; $G^1$ and $G^4$ each represent CH; $R^{3b}$ represents any one substituent described in Table 3A to Table 11A; and $R^{3c}$ represents a hydrogen atom (hereinafter referred to as "Compound group SX1167").

The Compound (L-6), wherein Q represents the group represented by Q58; $R^{1b}$ represents $C_2F_5$; $G^1$ and $G^4$ each represent CH; $R^{3b}$ represents any one substituent described in Table 3A to Table 11A; and $R^{3c}$ represents a hydrogen atom (hereinafter referred to as "Compound group SX1168").

The Compound (L-6), wherein Q represents the group represented by Q59; $R^{1a}$ represents $C_2F_5$; $G^1$ and $G^4$ each represent CH; $R^{3b}$ represents any one substituent described in Table 3A to Table 11A; and $R^{3c}$ represents a hydrogen atom (hereinafter referred to as "Compound group SX1169").

The Compound (L-6), wherein Q represents the group represented by Q60; $R^{1a}$ represents $C_2F_5$; $G^1$ and $G^4$ each represent CH; $R^{3b}$ represents any one substituent described in Table 3A to Table 11A; and $R^{3c}$ represents a hydrogen atom (hereinafter referred to as "Compound group SX1170").

The Compound (L-6), wherein Q represents the group represented by Q31; $R^{1b}$ represents $CF_3$; $G^1$ and $G^4$ each represent CH; $R^{3b}$ represents a hydrogen atom; and $R^{3c}$ represents any one substituent described in Table 3A to Table 11A (hereinafter referred to as "Compound group SX1171").

The Compound (L-6), wherein Q represents the group represented by Q32; $R^{1b}$ represents $CF_3$; $G^1$ and $G^4$ each represent CH; $R^{3b}$ represents a hydrogen atom; and $R^{3c}$ represents any one substituent described in Table 3A to Table 11A (hereinafter referred to as "Compound group SX1172").

The Compound (L-6), wherein Q represents the group represented by Q33; $R^{1b}$ represents $CF_3$; $G^1$ and $G^4$ each represent CH; $R^{3b}$ represents a hydrogen atom; and $R^{3c}$ represents any one substituent described in Table 3A to Table 11A (hereinafter referred to as "Compound group SX1173").

The Compound (L-6), wherein Q represents the group represented by Q34; $R^{1b}$ represents $CF_3$; $G^1$ and $G^4$ each represent CH; $R^{3b}$ represents a hydrogen atom; and $R^{3c}$ represents any one substituent described in Table 3A to Table 11A (hereinafter referred to as "Compound group SX1174").

The Compound (L-6), wherein Q represents the group represented by Q35; $R^{1b}$ represents $CF_3$; $G^1$ and $G^4$ each represent CH; $R^{3b}$ represents a hydrogen atom; and $R^{3c}$ represents any one substituent described in Table 3A to Table 11A (hereinafter referred to as "Compound group SX1175").

The Compound (L-6), wherein Q represents the group represented by Q36; $R^{1b}$ represents $CF_3$; $G^1$ and $G^4$ each represent CH; $R^{3b}$ represents a hydrogen atom; and $R^{3c}$ represents any one substituent described in Table 3A to Table 11A (hereinafter referred to as "Compound group SX1176").

The Compound (L-6), wherein Q represents the group represented by Q37; $R^{1b}$ represents $CF_3$; $G^1$ and $G^4$ each represent CH; $R^{3b}$ represents a hydrogen atom; and $R^{3c}$ represents any one substituent described in Table 3A to Table 11A (hereinafter referred to as "Compound group SX1177").

The Compound (L-6), wherein Q represents the group represented by Q38; $R^{1b}$ represents $CF_3$; $G^1$ and $G^4$ each represent CH; $R^{3b}$ represents a hydrogen atom; and $R^{3c}$ represents any one substituent described in Table 3A to Table 11A (hereinafter referred to as "Compound group SX1178").

The Compound (L-6), wherein Q represents the group represented by Q39; $R^{1b}$ represents $CF_3$; $G^1$ and $G^4$ each represent CH; $R^{3b}$ represents a hydrogen atom; and $R^{3c}$ represents any one substituent described in Table 3A to Table 11A (hereinafter referred to as "Compound group SX1179").

The Compound (L-6), wherein Q represents the group represented by Q40; $R^{1b}$ represents $CF_3$; $G^1$ and $G^4$ each represent CH; $R^{3b}$ represents a hydrogen atom; and $R^{3c}$ represents any one substituent described in Table 3A to Table 11A (hereinafter referred to as "Compound group SX1180").

The Compound (L-6), wherein Q represents the group represented by Q41; $R^{1b}$ represents $CF_3$; $G^1$ and $G^4$ each represent CH; $R^{3b}$ represents a hydrogen atom; and $R^{3c}$ represents any one substituent described in Table 3A to Table 11A (hereinafter referred to as "Compound group SX1181").

The Compound (L-6), wherein Q represents the group represented by Q42; $R^{1b}$ represents $CF_3$; $G^1$ and $G^4$ each represent CH; $R^{3b}$ represents a hydrogen atom; and $R^{3c}$ represents any one substituent described in Table 3A to Table 11A (hereinafter referred to as "Compound group SX1182").

The Compound (L-6), wherein Q represents the group represented by Q43; $R^{1b}$ represents $CF_3$; $G^1$ and $G^4$ each represent CH; $R^{3b}$ represents a hydrogen atom; and $R^{3c}$ represents any one substituent described in Table 3A to Table 11A (hereinafter referred to as "Compound group SX1183").

The Compound (L-6), wherein Q represents the group represented by Q44; $R^{1b}$ represents $CF_3$; $G^1$ and $G^4$ each represent CH; $R^{3b}$ represents a hydrogen atom; and $R^{3c}$ represents any one substituent described in Table 3A to Table 11A (hereinafter referred to as "Compound group SX1184").

The Compound (L-6), wherein Q represents the group represented by Q45; $R^{1b}$ represents $CF_3$; $G^1$ and $G^4$ each represent CH; $R^{3b}$ represents a hydrogen atom; and $R^{3c}$ represents any one substituent described in Table 3A to Table 11A (hereinafter referred to as "Compound group SX1185").

The Compound (L-6), wherein Q represents the group represented by Q46; $R^{1b}$ represents $CF_3$; $G^1$ and $G^4$ each represent CH; $R^{3b}$ represents a hydrogen atom; and $R^{3c}$ represents any one substituent described in Table 3A to Table 11A (hereinafter referred to as "Compound group SX1186").

The Compound (L-6), wherein Q represents the group represented by Q47; $R^{1a}$ represents $CF_3$; $G^1$ and $G^4$ each represent CH; $R^{3b}$ represents a hydrogen atom; and $R^{3c}$ represents any one substituent described in Table 3A to Table 11A (hereinafter referred to as "Compound group SX1187").

The Compound (L-6), wherein Q represents the group represented by Q48; $R^{1a}$ represents $CF_3$; $G^1$ and $G^4$ each represent CH; $R^{3b}$ represents a hydrogen atom; and $R^{3c}$ represents any one substituent described in Table 3A to Table 11A (hereinafter referred to as "Compound group SX1188").

The Compound (L-6), wherein Q represents the group represented by Q49; $R^{1a}$ represents $CF_3$; $G^1$ and $G^4$ each represent CH; $R^{3b}$ represents a hydrogen atom; and $R^{3c}$ represents any one substituent described in Table 3A to Table 11A (hereinafter referred to as "Compound group SX1189").

The Compound (L-6), wherein Q represents the group represented by Q50; $R^{1a}$ represents $CF_3$; $G^1$ and $G^4$ each represent CH; $R^{3b}$ represents a hydrogen atom; and $R^{3c}$ represents any one substituent described in Table 3A to Table 11A (hereinafter referred to as "Compound group SX1190").

The Compound (L-6), wherein Q represents the group represented by Q51; $R^{1a}$ represents $CF_3$; $G^1$ and $G^4$ each represent CH; $R^{3b}$ represents a hydrogen atom; and $R^{3c}$ represents any one substituent described in Table 3A to Table 11A (hereinafter referred to as "Compound group SX1191").

The Compound (L-6), wherein Q represents the group represented by Q52; $R^{1a}$ represents $CF_3$; $G^1$ and $G^4$ each represent CH; $R^{3b}$ represents a hydrogen atom; and $R^{3c}$ represents any one substituent described in Table 3A to Table 11A (hereinafter referred to as "Compound group SX1192").

The Compound (L-6), wherein Q represents the group represented by Q53; $R^{1a}$ represents $CF_3$; $G^1$ and $G^4$ each represent CH; $R^{3b}$ represents a hydrogen atom; and $R^{3c}$ represents any one substituent described in Table 3A to Table 11A (hereinafter referred to as "Compound group SX1193").

The Compound (L-6), wherein Q represents the group represented by Q54; $R^{1a}$ represents $CF_3$; $G^1$ and $G^4$ each represent CH; $R^{3b}$ represents a hydrogen atom; and $R^{3c}$ represents any one substituent described in Table 3A to Table 11A (hereinafter referred to as "Compound group SX1194").

The Compound (L-6), wherein Q represents the group represented by Q55; $R^{1b}$ represents $CF_3$; $G^1$ and $G^4$ each represent CH; $R^{3b}$ represents a hydrogen atom; and $R^{3c}$ represents any one substituent described in Table 3A to Table 11A (hereinafter referred to as "Compound group SX1195").

The Compound (L-6), wherein Q represents the group represented by Q56; $R^{1b}$ represents $CF_3$; $G^1$ and $G^4$ each represent CH; $R^{3b}$ represents a hydrogen atom; and $R^{3c}$ represents any one substituent described in Table 3A to Table 11A (hereinafter referred to as "Compound group SX1196").

The Compound (L-6), wherein Q represents the group represented by Q57; $R^{1b}$ represents $CF_3$; $G^1$ and $G^4$ each represent CH; $R^{3b}$ represents a hydrogen atom; and $R^{3c}$ represents any one substituent described in Table 3A to Table 11A (hereinafter referred to as "Compound group SX1197").

The Compound (L-6), wherein Q represents the group represented by Q58; $R^{1b}$ represents $CF_3$; $G^1$ and $G^4$ each represent CH; $R^{3b}$ represents a hydrogen atom; and $R^{3c}$ represents any one substituent described in Table 3A to Table 11A (hereinafter referred to as "Compound group SX1198").

The Compound (L-6), wherein Q represents the group represented by Q59; $R^{1a}$ represents $CF_3$; $G^1$ and $G^4$ each represent CH; $R^{3b}$ represents a hydrogen atom; and $R^{3c}$ represents any one substituent described in Table 3A to Table 11A (hereinafter referred to as "Compound group SX1199").

The Compound (L-6), wherein Q represents the group represented by Q60; $R^{1a}$ represents $CF_3$; $G^1$ and $G^4$ each represent CH; $R^{3b}$ represents a hydrogen atom; and $R^{3c}$ represents any one substituent described in Table 3A to Table 11A (hereinafter referred to as "Compound group SX1200").

The Compound (L-6), wherein Q represents the group represented by Q31; $R^{1b}$ represents $C_2F_5$; $G^1$ and $G^4$ each represent CH; $R^{3b}$ represents a hydrogen atom; and $R^{3c}$ represents any one substituent described in Table 3A to Table 11A (hereinafter referred to as "Compound group SX1201").

The Compound (L-6), wherein Q represents the group represented by Q32; $R^{1b}$ represents $C_2F_5$; $G^1$ and $G^4$ each represent CH; $R^{3b}$ represents a hydrogen atom; and $R^{3c}$ represents any one substituent described in Table 3A to Table 11A (hereinafter referred to as "Compound group SX1202").

The Compound (L-6), wherein Q represents the group represented by Q33; $R^{1b}$ represents $C_2F_5$; $G^1$ and $G^4$ each represent CH; $R^{3b}$ represents a hydrogen atom; and $R^{3c}$ represents any one substituent described in Table 3A to Table 11A (hereinafter referred to as "Compound group SX1203").

The Compound (L-6), wherein Q represents the group represented by Q34; $R^{1b}$ represents $C_2F_5$; $G^1$ and $G^4$ each represent CH; $R^{3b}$ represents a hydrogen atom; and $R^{3c}$ represents any one substituent described in Table 3A to Table 11A (hereinafter referred to as "Compound group SX1204").

The Compound (L-6), wherein Q represents the group represented by Q35; $R^{1b}$ represents $C_2F_5$; $G^1$ and $G^4$ each represent CH; $R^{3b}$ represents a hydrogen atom; and $R^{3c}$ represents any one substituent described in Table 3A to Table 11A (hereinafter referred to as "Compound group SX1205").

The Compound (L-6), wherein Q represents the group represented by Q36; $R^{1b}$ represents $C_2F_5$; $G^1$ and $G^4$ each represent CH; $R^{3b}$ represents a hydrogen atom; and $R^{3c}$ represents any one substituent described in Table 3A to Table 11A (hereinafter referred to as "Compound group SX1206").

The Compound (L-6), wherein Q represents the group represented by Q37; $R^{1b}$ represents $C_2F_5$; $G^1$ and $G^4$ each represent CH; $R^{3b}$ represents a hydrogen atom; and $R^{3c}$ represents any one substituent described in Table 3A to Table 11A (hereinafter referred to as "Compound group SX1207").

The Compound (L-6), wherein Q represents the group represented by Q38; $R^{1b}$ represents $C_2F_5$; $G^1$ and $G^4$ each represent CH; $R^{3b}$ represents a hydrogen atom; and $R^{3c}$ represents any one substituent described in Table 3A to Table 11A (hereinafter referred to as "Compound group SX1208").

The Compound (L-6), wherein Q represents the group represented by Q39; $R^{1b}$ represents $C_2F_5$; $G^1$ and $G^4$ each represent CH; $R^{3b}$ represents a hydrogen atom; and $R^{3c}$ represents any one substituent described in Table 3A to Table 11A (hereinafter referred to as "Compound group SX1209").

The Compound (L-6), wherein Q represents the group represented by Q40; $R^{1b}$ represents $C_2F_5$; $G^1$ and $G^4$ each represent CH; $R^{3b}$ represents a hydrogen atom; and $R^{3c}$ represents any one substituent described in Table 3A to Table 11A (hereinafter referred to as "Compound group SX1210").

The Compound (L-6), wherein Q represents the group represented by Q41; $R^{1b}$ represents $C_2F_5$; $G^1$ and $G^4$ each represent CH; $R^{3b}$ represents a hydrogen atom; and $R^{3c}$ represents any one substituent described in Table 3A to Table 11A (hereinafter referred to as "Compound group SX1211").

The Compound (L-6), wherein Q represents the group represented by Q42; $R^{1b}$ represents $C_2F_5$; $G^1$ and $G^4$ each represent CH; $R^{3b}$ represents a hydrogen atom; and $R^{3c}$ represents any one substituent described in Table 3A to Table 11A (hereinafter referred to as "Compound group SX1212").

The Compound (L-6), wherein Q represents the group represented by Q43; $R^{1b}$ represents $C_2F_5$; $G^1$ and $G^4$ each represent CH; $R^{3b}$ represents a hydrogen atom; and $R^{3c}$ represents any one substituent described in Table 3A to Table 11A (hereinafter referred to as "Compound group SX1213").

The Compound (L-6), wherein Q represents the group represented by Q44; $R^{1b}$ represents $C_2F_5$; $G^1$ and $G^4$ each represent CH; $R^{3b}$ represents a hydrogen atom; and $R^{3c}$ represents any one substituent described in Table 3A to Table 11A (hereinafter referred to as "Compound group SX1214").

The Compound (L-6), wherein Q represents the group represented by Q45; $R^{1b}$ represents $C_2F_5$; $G^1$ and $G^4$ each represent CH; $R^{3b}$ represents a hydrogen atom; and $R^{3c}$ represents any one substituent described in Table 3A to Table 11A (hereinafter referred to as "Compound group SX1215").

The Compound (L-6), wherein Q represents the group represented by Q46; $R^{1b}$ represents $C_2F_5$; $G^1$ and $G^4$ each represent CH; $R^{3b}$ represents a hydrogen atom; and $R^{3c}$ represents any one substituent described in Table 3A to Table 11A (hereinafter referred to as "Compound group SX1216").

The Compound (L-6), wherein Q represents the group represented by Q47; $R^{1a}$ represents $C_2F_5$; $G^1$ and $G^4$ each represent CH; $R^{3b}$ represents a hydrogen atom; and $R^{3c}$ represents any one substituent described in Table 3A to Table 11A (hereinafter referred to as "Compound group SX1217").

The Compound (L-6), wherein Q represents the group represented by Q48; $R^{1a}$ represents $C_2F_5$; $G^1$ and $G^4$ each represent CH; $R^{3b}$ represents a hydrogen atom; and $R^{3c}$ represents any one substituent described in Table 3A to Table 11A (hereinafter referred to as "Compound group SX1218").

The Compound (L-6), wherein Q represents the group represented by Q49; $R^{1a}$ represents $C_2F_5$; $G^1$ and $G^4$ each represent CH; $R^{3b}$ represents a hydrogen atom; and $R^{3c}$ represents any one substituent described in Table 3A to Table 11A (hereinafter referred to as "Compound group SX1219").

The Compound (L-6), wherein Q represents the group represented by Q50; $R^{1a}$ represents $C_2F_5$; $G^1$ and $G^4$ each represent CH; $R^{3b}$ represents a hydrogen atom; and $R^{3c}$ represents any one substituent described in Table 3A to Table 11A (hereinafter referred to as "Compound group SX1220").

The Compound (L-6), wherein Q represents the group represented by Q51; $R^{1a}$ represents $C_2F_5$; $G^1$ and $G^4$ each represent CH; $R^{3b}$ represents a hydrogen atom; and $R^{3c}$ represents any one substituent described in Table 3A to Table 11A (hereinafter referred to as "Compound group SX1221").

The Compound (L-6), wherein Q represents the group represented by Q52; $R^{1a}$ represents $C_2F_5$; $G^1$ and $G^4$ each represent CH; $R^{3b}$ represents a hydrogen atom; and $R^{3c}$ represents any one substituent described in Table 3A to Table 11A (hereinafter referred to as "Compound group SX1222").

The Compound (L-6), wherein Q represents the group represented by Q53; $R^{1a}$ represents $C_2F_5$; $G^1$ and $G^4$ each represent CH; $R^{3b}$ represents a hydrogen atom; and $R^{3c}$ represents any one substituent described in Table 3A to Table 11A (hereinafter referred to as "Compound group SX1223").

The Compound (L-6), wherein Q represents the group represented by Q54; $R^{1a}$ represents $C_2F_5$; $G^1$ and $G^4$ each represent CH; $R^{3b}$ represents a hydrogen atom; and $R^{3c}$ represents any one substituent described in Table 3A to Table 11A (hereinafter referred to as "Compound group SX1224").

The Compound (L-6), wherein Q represents the group represented by Q55; $R^{1b}$ represents $C_2F_5$; $G^1$ and $G^4$ each represent CH; $R^{3b}$ represents a hydrogen atom; and $R^{3c}$ represents any one substituent described in Table 3A to Table 11A (hereinafter referred to as "Compound group SX1225").

The Compound (L-6), wherein Q represents the group represented by Q56; $R^{1b}$ represents $C_2F_5$; $G^1$ and $G^4$ each represent CH; $R^{3b}$ represents a hydrogen atom; and $R^{3c}$ represents any one substituent described in Table 3A to Table 11A (hereinafter referred to as "Compound group SX1226").

The Compound (L-6), wherein Q represents the group represented by Q57; $R^{1b}$ represents $C_2F_5$; $G^1$ and $G^4$ each represent CH; $R^{3b}$ represents a hydrogen atom; and $R^{3c}$ represents any one substituent described in Table 3A to Table 11A (hereinafter referred to as "Compound group SX1227").

The Compound (L-6), wherein Q represents the group represented by Q58; $R^{1b}$ represents $C_2F_5$; $G^1$ and $G^4$ each represent CH; $R^{3b}$ represents a hydrogen atom; and $R^{3c}$ represents any one substituent described in Table 3A to Table 11A (hereinafter referred to as "Compound group SX1228").

The Compound (L-6), wherein Q represents the group represented by Q59; $R^{1a}$ represents $C_2F_5$; $G^1$ and $G^4$ each represent CH; $R^{3b}$ represents a hydrogen atom; and $R^{3c}$ represents any one substituent described in Table 3A to Table 11A (hereinafter referred to as "Compound group SX1229").

The Compound (L-6), wherein Q represents the group represented by Q60; $R^{1a}$ represents $C_2F_5$; $G^1$ and $G^4$ each represent CH; $R^{3b}$ represents a hydrogen atom; and $R^{3c}$ represents any one substituent described in Table 3A to Table 11A (hereinafter referred to as "Compound group SX1230").

The Compound (L-6), wherein Q represents the group represented by Q31; $R^{1b}$ represents $CF_3$; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX1231").

The Compound (L-6), wherein Q represents the group represented by Q32; $R^{1b}$ represents $CF_3$; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX1232").

The Compound (L-6), wherein Q represents the group represented by Q33; $R^{1b}$ represents $CF_3$; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX1233").

The Compound (L-6), wherein Q represents the group represented by Q34; $R^{1b}$ represents $CF_3$; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX1234").

The Compound (L-6), wherein Q represents the group represented by Q35; $R^{1b}$ represents $CF_3$; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX1235").

The Compound (L-6), wherein Q represents the group represented by Q36; $R^{1b}$ represents $CF_3$; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX1236").

The Compound (L-6), wherein Q represents the group represented by Q37; $R^{1b}$ represents $CF_3$; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX1237").

The Compound (L-6), wherein Q represents the group represented by Q38; $R^{1b}$ represents $CF_3$; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX1238").

The Compound (L-6), wherein Q represents the group represented by Q39; $R^{1b}$ represents $CF_3$; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX1239").

The Compound (L-6), wherein Q represents the group represented by Q40; $R^{1b}$ represents $CF_3$; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX1240").

The Compound (L-6), wherein Q represents the group represented by Q41; $R^{1b}$ represents $CF_3$; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX1241").

The Compound (L-6), wherein Q represents the group represented by Q42; $R^{1b}$ represents $CF_3$; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX1242").

The Compound (L-6), wherein Q represents the group represented by Q43; $R^{1b}$ represents $CF_3$; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX1243").

The Compound (L-6), wherein Q represents the group represented by Q44; $R^{1b}$ represents $CF_3$; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX1244").

The Compound (L-6), wherein Q represents the group represented by Q45; $R^{1b}$ represents $CF_3$; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX1245").

The Compound (L-6), wherein Q represents the group represented by Q46; $R^{1b}$ represents $CF_3$; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX1246").

The Compound (L-6), wherein Q represents the group represented by Q47; $R^{1a}$ represents $CF_3$; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX1247").

The Compound (L-6), wherein Q represents the group represented by Q48; $R^{1a}$ represents $CF_3$; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX1248").

The Compound (L-6), wherein Q represents the group represented by Q49; $R^{1a}$ represents $CF_3$; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX1249").

The Compound (L-6), wherein Q represents the group represented by Q50; $R^{1a}$ represents $CF_3$; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX1250").

The Compound (L-6), wherein Q represents the group represented by Q51; $R^{1a}$ represents $CF_3$; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX1251").

The Compound (L-6), wherein Q represents the group represented by Q52; $R^{1a}$ represents $CF_3$; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX1252").

The Compound (L-6), wherein Q represents the group represented by Q53; $R^{1a}$ represents $CF_3$; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX1253").

The Compound (L-6), wherein Q represents the group represented by Q54; $R^{1a}$ represents $CF_3$; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX1254").

The Compound (L-6), wherein Q represents the group represented by Q55; $R^{1b}$ represents $CF_3$; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX1255").

The Compound (L-6), wherein Q represents the group represented by Q56; $R^{1b}$ represents $CF_3$; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX1256").

The Compound (L-6), wherein Q represents the group represented by Q57; $R^{1b}$ represents $CF_3$; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX1257").

The Compound (L-6), wherein Q represents the group represented by Q58; $R^{1b}$ represents $CF_3$; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX1258").

The Compound (L-6), wherein Q represents the group represented by Q59; $R^{1a}$ represents $CF_3$; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX1259").

The Compound (L-6), wherein Q represents the group represented by Q60; $R^{1a}$ represents $CF_3$; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX1260").

The Compound (L-6), wherein Q represents the group represented by Q31; $R^{1b}$ represents $C_2F_5$; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX1261").

The Compound (L-6), wherein Q represents the group represented by Q32; $R^{1b}$ represents $C_2F_5$; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX1262").

The Compound (L-6), wherein Q represents the group represented by Q33; $R^{1b}$ represents $C_2F_5$; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX1263").

The Compound (L-6), wherein Q represents the group represented by Q34; $R^{1b}$ represents $C_2F_5$; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX1264").

The Compound (L-6), wherein Q represents the group represented by Q35; $R^{1b}$ represents $C_2F_5$; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX1265").

The Compound (L-6), wherein Q represents the group represented by Q36; $R^{1b}$ represents $C_2F_5$; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX1266").

The Compound (L-6), wherein Q represents the group represented by Q37; $R^{1b}$ represents $C_2F_5$; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX1267").

The Compound (L-6), wherein Q represents the group represented by Q38; $R^{1b}$ represents $C_2F_5$; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX1268").

The Compound (L-6), wherein Q represents the group represented by Q39; $R^{1b}$ represents $C_2F_5$; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX1269").

The Compound (L-6), wherein Q represents the group represented by Q40; $R^{1b}$ represents $C_2F_5$; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX1270").

The Compound (L-6), wherein Q represents the group represented by Q41; $R^{1b}$ represents $C_2F_5$; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX1271").

The Compound (L-6), wherein Q represents the group represented by Q42; $R^{1b}$ represents $C_2F_5$; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX1272").

The Compound (L-6), wherein Q represents the group represented by Q43; $R^{1b}$ represents $C_2F_5$; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX1273").

The Compound (L-6), wherein Q represents the group represented by Q44; $R^{1b}$ represents $C_2F_5$; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX1274").

The Compound (L-6), wherein Q represents the group represented by Q45; $R^{1b}$ represents $C_2F_5$; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX1275").

The Compound (L-6), wherein Q represents the group represented by Q46; $R^{1b}$ represents $C_2F_5$; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX1276").

The Compound (L-6), wherein Q represents the group represented by Q47; $R^{1a}$ represents $C_2F_5$; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX1277").

The Compound (L-6), wherein Q represents the group represented by Q48; $R^{1a}$ represents $C_2F_5$; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX1278").

The Compound (L-6), wherein Q represents the group represented by Q49; $R^{1a}$ represents $C_2F_5$; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX1279").

The Compound (L-6), wherein Q represents the group represented by Q50; $R^{1a}$ represents $C_2F_5$; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX1280").

The Compound (L-6), wherein Q represents the group represented by Q51; $R^{1a}$ represents $C_2F_5$; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX1281").

The Compound (L-6), wherein Q represents the group represented by Q52; $R^{1a}$ represents $C_2F_5$; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX1282").

The Compound (L-6), wherein Q represents the group represented by Q53; $R^{1a}$ represents $C_2F_5$; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX1283").

The Compound (L-6), wherein Q represents the group represented by Q54; $R^{1a}$ represents $C_2F_5$; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX1284").

The Compound (L-6), wherein Q represents the group represented by Q55; $R^{1b}$ represents $C_2F_5$; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX1285").

The Compound (L-6), wherein Q represents the group represented by Q56; $R^{1b}$ represents $C_2F_5$; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX1286").

The Compound (L-6), wherein Q represents the group represented by Q57; $R^{1b}$ represents $C_2F_5$; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX1287").

The Compound (L-6), wherein Q represents the group represented by Q58; $R^{1b}$ represents $C_2F_5$; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX1288").

The Compound (L-6), wherein Q represents the group represented by Q59; $R^{1a}$ represents $C_2F_5$; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX1289").

The Compound (L-6), wherein Q represents the group represented by Q60; $R^{1a}$ represents $C_2F_5$; $G^1$ represents a nitrogen atom; $G^4$ represents CH; $R^{3b}$ represents any one substituent described in Table 3A to Table 11A; and $R^{3c}$ represents a hydrogen atom (hereinafter referred to as "Compound group SX1290").

The Compound (L-6), wherein Q represents the group represented by Q31; $R^{1b}$ represents $CF_3$; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX1291").

The Compound (L-6), wherein Q represents the group represented by Q32; $R^{1b}$ represents $CF_3$; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX1292").

The Compound (L-6), wherein Q represents the group represented by Q33; $R^{1b}$ represents $CF_3$; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX1293").

The Compound (L-6), wherein Q represents the group represented by Q34; $R^{1b}$ represents $CF_3$; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX1294").

The Compound (L-6), wherein Q represents the group represented by Q35; $R^{1b}$ represents $CF_3$; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX1295").

The Compound (L-6), wherein Q represents the group represented by Q36; $R^{1b}$ represents $CF_3$; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX1296").

The Compound (L-6), wherein Q represents the group represented by Q37; $R^{1b}$ represents $CF_3$; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX1297").

The Compound (L-6), wherein Q represents the group represented by Q38; $R^{1b}$ represents $CF_3$; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX1298").

The Compound (L-6), wherein Q represents the group represented by Q39; $R^{1b}$ represents $CF_3$; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX1299").

The Compound (L-6), wherein Q represents the group represented by Q40; $R^{1b}$ represents $CF_3$; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX1300").

The Compound (L-6), wherein Q represents the group represented by Q41; $R^{1b}$ represents $CF_3$; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX1301").

The Compound (L-6), wherein Q represents the group represented by Q42; $R^{1b}$ represents $CF_3$; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX1302").

The Compound (L-6), wherein Q represents the group represented by Q43; $R^{1b}$ represents $CF_3$; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX1303").

The Compound (L-6), wherein Q represents the group represented by Q44; $R^{1b}$ represents $CF_3$; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX1304").

The Compound (L-6), wherein Q represents the group represented by Q45; $R^{1b}$ represents $CF_3$; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX1305").

The Compound (L-6), wherein Q represents the group represented by Q46; $R^{1b}$ represents $CF_3$; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX1306").

The Compound (L-6), wherein Q represents the group represented by Q47; $R^{1a}$ represents $CF_3$; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX1307").

The Compound (L-6), wherein Q represents the group represented by Q48; $R^{1a}$ represents $CF_3$; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX1308").

The Compound (L-6), wherein Q represents the group represented by Q49; $R^{1a}$ represents $CF_3$; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX1309").

The Compound (L-6), wherein Q represents the group represented by Q50; $R^{1a}$ represents $CF_3$; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX1310").

The Compound (L-6), wherein Q represents the group represented by Q51; $R^{1a}$ represents $CF_3$; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX1311").

The Compound (L-6), wherein Q represents the group represented by Q52; $R^{1a}$ represents $CF_3$; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX1312").

The Compound (L-6), wherein Q represents the group represented by Q53; $R^{1a}$ represents $CF_3$; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX1313").

The Compound (L-6), wherein Q represents the group represented by Q54; $R^{1a}$ represents $CF_3$; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX1314").

The Compound (L-6), wherein Q represents the group represented by Q55; $R^{1b}$ represents $CF_3$; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX1315").

The Compound (L-6), wherein Q represents the group represented by Q56; $R^{1b}$ represents $CF_3$; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX1316").

The Compound (L-6), wherein Q represents the group represented by Q57; $R^{1b}$ represents $CF_3$; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX1317").

The Compound (L-6), wherein Q represents the group represented by Q58; $R^{1b}$ represents $CF_3$; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX1318").

The Compound (L-6), wherein Q represents the group represented by Q59; $R^{1a}$ represents $CF_3$; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX1319").

The Compound (L-6), wherein Q represents the group represented by Q60; $R^{1a}$ represents $CF_3$; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX1320").

The Compound (L-6), wherein Q represents the group represented by Q31; $R^{1b}$ represents $C_3F_5$; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX1321").

The Compound (L-6), wherein Q represents the group represented by Q32; $R^{1b}$ represents $C_2F_5$; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX1322").

The Compound (L-6), wherein Q represents the group represented by Q33; $R^{1b}$ represents $C_2F_5$; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX1323").

The Compound (L-6), wherein Q represents the group represented by Q34; $R^{1b}$ represents $C_2F_5$; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX1324").

The Compound (L-6), wherein Q represents the group represented by Q35; $R^{1b}$ represents $C_2F_5$; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX1325").

The Compound (L-6), wherein Q represents the group represented by Q36; $R^{1b}$ represents $C_2F_5$; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX1326").

The Compound (L-6), wherein Q represents the group represented by Q37; $R^{1b}$ represents $C_2F_5$; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX1327").

The Compound (L-6), wherein Q represents the group represented by Q38; $R^{1b}$ represents $C_2F_5$; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX1328").

The Compound (L-6), wherein Q represents the group represented by Q39; $R^{1b}$ represents $C_2F_5$; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX1329").

The Compound (L-6), wherein Q represents the group represented by Q40; $R^{1b}$ represents $C_2F_5$; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX1330").

The Compound (L-6), wherein Q represents the group represented by Q41; $R^{1b}$ represents $C_2F_5$; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX1331").

The Compound (L-6), wherein Q represents the group represented by Q42; $R^{1b}$ represents $C_2F_5$; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX1332").

The Compound (L-6), wherein Q represents the group represented by Q43; $R^{1b}$ represents $C_2F_5$; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX1333").

The Compound (L-6), wherein Q represents the group represented by Q44; $R^{1b}$ represents $C_2F_5$; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX1334").

The Compound (L-6), wherein Q represents the group represented by Q45; $R^{1b}$ represents $C_2F_5$; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX1335").

The Compound (L-6), wherein Q represents the group represented by Q46; $R^{1b}$ represents $C_2F_5$; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX1336").

The Compound (L-6), wherein Q represents the group represented by Q47; $R^{1a}$ represents $C_2F_5$; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX1337").

The Compound (L-6), wherein Q represents the group represented by Q48; $R^{1a}$ represents $C_2F_5$; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX1338").

The Compound (L-6), wherein Q represents the group represented by Q49; $R^{1a}$ represents $C_2F_5$; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX1339").

The Compound (L-6), wherein Q represents the group represented by Q50; $R^{1a}$ represents $C_2F_5$; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX1340").

The Compound (L-6), wherein Q represents the group represented by Q51; $R^{1a}$ represents $C_2F_5$; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX1341").

The Compound (L-6), wherein Q represents the group represented by Q52; $R^{1a}$ represents $C_2F_5$; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX1342").

The Compound (L-6), wherein Q represents the group represented by Q53; $R^{1a}$ represents $C_2F_5$; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX1343").

The Compound (L-6), wherein Q represents the group represented by Q54; $R^{1a}$ represents $C_2F_5$; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX1344").

The Compound (L-6), wherein Q represents the group represented by Q55; $R^{1b}$ represents $C_2F_5$; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX1345").

The Compound (L-6), wherein Q represents the group represented by Q56; $R^{1b}$ represents $C_2F_5$; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX1346").

The Compound (L-6), wherein Q represents the group represented by Q57; $R^{1b}$ represents $C_2F_5$; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX1347").

The Compound (L-6), wherein Q represents the group represented by Q58; $R^{1b}$ represents $C_2F_5$; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX1348").

The Compound (L-6), wherein Q represents the group represented by Q59; $R^{1a}$ represents $C_2F_5$; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX1349").

The Compound (L-6), wherein Q represents the group represented by Q60; $R^{1a}$ represents $C_2F_5$; $G^1$ represents a nitrogen atom; $G^4$ represents CH; $R^{3b}$ represents a hydrogen atom; and $R^{3c}$ represents any one substituent described in Table 3A to Table 11A (hereinafter referred to as "Compound group SX1350").

The Compound (L-6), wherein Q represents the group represented by Q31; $R^{1b}$ represents $CF_3$; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX1351").

The Compound (L-6), wherein Q represents the group represented by Q32; $R^{1b}$ represents $CF_3$; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX1352").

The Compound (L-6), wherein Q represents the group represented by Q33; $R^{1b}$ represents $CF_3$; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX1353").

The Compound (L-6), wherein Q represents the group represented by Q34; $R^{1b}$ represents $CF_3$; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX1354").

The Compound (L-6), wherein Q represents the group represented by Q35; $R^{1b}$ represents $CF_3$; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX1355").

The Compound (L-6), wherein Q represents the group represented by Q36; $R^{1b}$ represents $CF_3$; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX1356").

The Compound (L-6), wherein Q represents the group represented by Q37; $R^{1b}$ represents $CF_3$; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX1357").

The Compound (L-6), wherein Q represents the group represented by Q38; $R^{1b}$ represents $CF_3$; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX1358").

The Compound (L-6), wherein Q represents the group represented by Q39; $R^{1b}$ represents $CF_3$; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX1359").

The Compound (L-6), wherein Q represents the group represented by Q40; $R^{1b}$ represents $CF_3$; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX1360").

The Compound (L-6), wherein Q represents the group represented by Q41; $R^{1b}$ represents $CF_3$; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX1361").

The Compound (L-6), wherein Q represents the group represented by Q42; $R^{1b}$ represents $CF_3$; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX1362").

The Compound (L-6), wherein Q represents the group represented by Q43; $R^{1b}$ represents $CF_3$; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX1363").

The Compound (L-6), wherein Q represents the group represented by Q44; $R^{1b}$ represents $CF_3$; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX1364").

The Compound (L-6), wherein Q represents the group represented by Q45; $R^{1b}$ represents $CF_3$; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX1365").

The Compound (L-6), wherein Q represents the group represented by Q46; $R^{1b}$ represents $CF_3$; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX1366").

The Compound (L-6), wherein Q represents the group represented by Q47; $R^{1a}$ represents $CF_3$; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX1367").

The Compound (L-6), wherein Q represents the group represented by Q48; $R^{1a}$ represents $CF_3$; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX1368").

The Compound (L-6), wherein Q represents the group represented by Q49; $R^{1a}$ represents $CF_3$; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX1369").

The Compound (L-6), wherein Q represents the group represented by Q50; $R^{1a}$ represents $CF_3$; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX1370").

The Compound (L-6), wherein Q represents the group represented by Q51; $R^{1a}$ represents $CF_3$; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX1371").

The Compound (L-6), wherein Q represents the group represented by Q52; $R^{1a}$ represents $CF_3$; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX1372").

The Compound (L-6), wherein Q represents the group represented by Q53; $R^{1a}$ represents $CF_3$; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX1373").

The Compound (L-6), wherein Q represents the group represented by Q54; $R^{1a}$ represents $CF_3$; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX1374").

The Compound (L-6), wherein Q represents the group represented by Q55; $R^{1b}$ represents $CF_3$; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX1375").

The Compound (L-6), wherein Q represents the group represented by Q56; $R^{1b}$ represents $CF_3$; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX1376").

The Compound (L-6), wherein Q represents the group represented by Q57; $R^{1b}$ represents $CF_3$; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX1377").

The Compound (L-6), wherein Q represents the group represented by Q58; $R^{1b}$ represents $CF_3$; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX1378").

The Compound (L-6), wherein Q represents the group represented by Q59; $R^{1a}$ represents $CF_3$; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX1379").

The Compound (L-6), wherein Q represents the group represented by Q60; $R^{1a}$ represents $CF_3$; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX1380").

The Compound (L-6), wherein Q represents the group represented by Q31; $R^{1b}$ represents $C_2F_5$; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX1381").

The Compound (L-6), wherein Q represents the group represented by Q32; $R^{1b}$ represents $C_2F_5$; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX1382").

The Compound (L-6), wherein Q represents the group represented by Q33; $R^{1b}$ represents $C_2F_5$; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX1383").

The Compound (L-6), wherein Q represents the group represented by Q34; $R^{1b}$ represents $C_2F_5$; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX1384").

The Compound (L-6), wherein Q represents the group represented by Q35; $R^{1b}$ represents $C_2F_5$; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX1385").

The Compound (L-6), wherein Q represents the group represented by Q36; $R^{1b}$ represents $C_2F_5$; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX1386").

The Compound (L-6), wherein Q represents the group represented by Q37; $R^{1b}$ represents $C_2F_5$; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX1387").

The Compound (L-6), wherein Q represents the group represented by Q38; $R^{1b}$ represents $C_2F_5$; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX1388").

The Compound (L-6), wherein Q represents the group represented by Q39; $R^{1b}$ represents $C_2F_5$; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX1389").

The Compound (L-6), wherein Q represents the group represented by Q40; $R^{1b}$ represents $C_2F_5$; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX1390").

The Compound (L-6), wherein Q represents the group represented by Q41; $R^{1b}$ represents $C_2F_5$; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX1391").

The Compound (L-6), wherein Q represents the group represented by Q42; $R^{1b}$ represents $C_2F_5$; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX1392").

The Compound (L-6), wherein Q represents the group represented by Q43; $R^{1b}$ represents $C_2F_5$; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX1393").

The Compound (L-6), wherein Q represents the group represented by Q44; $R^{1b}$ represents $C_2F_5$; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX1394").

The Compound (L-6), wherein Q represents the group represented by Q45; $R^{1b}$ represents $C_2F_5$; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX1395").

The Compound (L-6), wherein Q represents the group represented by Q46; $R^{1b}$ represents $C_2F_5$; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX1396").

The Compound (L-6), wherein Q represents the group represented by Q47; $R^{1a}$ represents $C_2F_5$; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX1397").

The Compound (L-6), wherein Q represents the group represented by Q48; $R^{1a}$ represents $C_2F_5$; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX1398").

The Compound (L-6), wherein Q represents the group represented by Q49; $R^{1a}$ represents $C_2F_5$; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX1399").

The Compound (L-6), wherein Q represents the group represented by Q50; $R^{1a}$ represents $C_2F_5$; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX1400").

The Compound (L-6), wherein Q represents the group represented by Q51; $R^{1a}$ represents $C_2F_5$; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX1401").

The Compound (L-6), wherein Q represents the group represented by Q52; $R^{1a}$ represents $C_2F_5$; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX1402").

The Compound (L-6), wherein Q represents the group represented by Q53; $R^{1a}$ represents $C_2F_5$; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX1403").

The Compound (L-6), wherein Q represents the group represented by Q54; $R^{1a}$ represents $C_2F_5$; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX1404").

The Compound (L-6), wherein Q represents the group represented by Q55; $R^{1b}$ represents $C_2F_5$; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX1405").

The Compound (L-6), wherein Q represents the group represented by Q56; $R^{1b}$ represents $C_2F_5$; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX1406").

The Compound (L-6), wherein Q represents the group represented by Q57; $R^{1b}$ represents $C_2F_5$; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX1407").

The Compound (L-6), wherein Q represents the group represented by Q58; $R^{1b}$ represents $C_2F_5$; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX1408").

The Compound (L-6), wherein Q represents the group represented by Q59; $R^{1a}$ represents $C_2F_5$; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX1409").

The Compound (L-6), wherein Q represents the group represented by Q60; $R^{1a}$ represents $C_2F_5$; $G^1$ represents CH; $G^4$ represents a nitrogen atom; $R^{3b}$ represents any one substituent described in Table 3A to Table 11A; and $R^{3c}$ represents a hydrogen atom (hereinafter referred to as "Compound group SX1410").

The Compound (L-6), wherein Q represents the group represented by Q31; $R^{1b}$ represents $CF_3$; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX1411").

The Compound (L-6), wherein Q represents the group represented by Q32; $R^{1b}$ represents $CF_3$; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX1412").

The Compound (L-6), wherein Q represents the group represented by Q33; $R^{1b}$ represents $CF_3$; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX1413").

The Compound (L-6), wherein Q represents the group represented by Q34; $R^{1b}$ represents $CF_3$; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX1414").

The Compound (L-6), wherein Q represents the group represented by Q35; $R^{1b}$ represents $CF_3$; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX1415").

The Compound (L-6), wherein Q represents the group represented by Q36; $R^{1b}$ represents $CF_3$; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX1416").

The Compound (L-6), wherein Q represents the group represented by Q37; $R^{1b}$ represents $CF_3$; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX1417").

The Compound (L-6), wherein Q represents the group represented by Q38; $R^{1b}$ represents $CF_3$; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX1418").

The Compound (L-6), wherein Q represents the group represented by Q39; $R^{1b}$ represents $CF_3$; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX1419").

The Compound (L-6), wherein Q represents the group represented by Q40; $R^{1b}$ represents $CF_3$; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX1420").

The Compound (L-6), wherein Q represents the group represented by Q41; $R^{1b}$ represents $CF_3$; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX1421").

The Compound (L-6), wherein Q represents the group represented by Q42; $R^{1b}$ represents $CF_3$; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX1422").

The Compound (L-6), wherein Q represents the group represented by Q43; $R^{1b}$ represents $CF_3$; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX1423").

The Compound (L-6), wherein Q represents the group represented by Q44; $R^{1b}$ represents $CF_3$; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX1424").

The Compound (L-6), wherein Q represents the group represented by Q45; $R^{1b}$ represents $CF_3$; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX1425").

The Compound (L-6), wherein Q represents the group represented by Q46; $R^{1b}$ represents $CF_3$; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX1426").

The Compound (L-6), wherein Q represents the group represented by Q47; $R^{1a}$ represents $CF_3$; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX1427").

The Compound (L-6), wherein Q represents the group represented by Q48; $R^{1a}$ represents $CF_3$; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX1428").

The Compound (L-6), wherein Q represents the group represented by Q49; $R^{1a}$ represents $CF_3$; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX1429").

The Compound (L-6), wherein Q represents the group represented by Q50; $R^{1a}$ represents $CF_3$; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX1430").

The Compound (L-6), wherein Q represents the group represented by Q51; $R^{1a}$ represents $CF_3$; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX1431").

The Compound (L-6), wherein Q represents the group represented by Q52; $R^{1a}$ represents $CF_3$; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX1432").

The Compound (L-6), wherein Q represents the group represented by Q53; $R^{1a}$ represents $CF_3$; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX1433").

The Compound (L-6), wherein Q represents the group represented by Q54; $R^{1a}$ represents $CF_3$; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX1434").

The Compound (L-6), wherein Q represents the group represented by Q55; $R^{1b}$ represents $CF_3$; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX1435").

The Compound (L-6), wherein Q represents the group represented by Q56; $R^{1b}$ represents $CF_3$; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX1436").

The Compound (L-6), wherein Q represents the group represented by Q57; $R^{1b}$ represents $CF_3$; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX1437").

The Compound (L-6), wherein Q represents the group represented by Q58; $R^{1b}$ represents $CF_3$; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX1438").

The Compound (L-6), wherein Q represents the group represented by Q59; $R^{1a}$ represents $CF_3$; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX1439").

The Compound (L-6), wherein Q represents the group represented by Q60; $R^{1a}$ represents $CF_3$; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX1440").

The Compound (L-6), wherein Q represents the group represented by Q31; $R^{1b}$ represents $C_2F_5$; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX1441").

The Compound (L-6), wherein Q represents the group represented by Q32; $R^{1b}$ represents $C_2F_5$; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX1442").

The Compound (L-6), wherein Q represents the group represented by Q33; $R^{1b}$ represents $C_2F_5$; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX1443").

The Compound (L-6), wherein Q represents the group represented by Q34; $R^{1b}$ represents $C_2F_5$; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX1444").

The Compound (L-6), wherein Q represents the group represented by Q35; $R^{1b}$ represents $C_2F_5$; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX1445").

The Compound (L-6), wherein Q represents the group represented by Q36; $R^{1b}$ represents $C_2F_5$; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX1446").

The Compound (L-6), wherein Q represents the group represented by Q37; $R^{1b}$ represents $C_2F_5$; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX1447").

The Compound (L-6), wherein Q represents the group represented by Q38; $R^{1b}$ represents $C_2F_5$; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX1448").

The Compound (L-6), wherein Q represents the group represented by Q39; $R^{1b}$ represents $C_2F_5$; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX1449").

The Compound (L-6), wherein Q represents the group represented by Q40; $R^{1b}$ represents $C_2F_5$; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX1450").

The Compound (L-6), wherein Q represents the group represented by Q41; $R^{1b}$ represents $C_2F_5$; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX1451").

The Compound (L-6), wherein Q represents the group represented by Q42; $R^{1b}$ represents $C_2F_5$; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX1452").

The Compound (L-6), wherein Q represents the group represented by Q43; $R^{1b}$ represents $C_2F_5$; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX1453").

The Compound (L-6), wherein Q represents the group represented by Q44; $R^{1b}$ represents $C_2F_5$; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX1454").

The Compound (L-6), wherein Q represents the group represented by Q45; $R^{1b}$ represents $C_2F_5$; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX1455").

The Compound (L-6), wherein Q represents the group represented by Q46; $R^{1b}$ represents $C_2F_5$; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX1456").

The Compound (L-6), wherein Q represents the group represented by Q47; $R^{1a}$ represents $C_2F_5$; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX1457").

The Compound (L-6), wherein Q represents the group represented by Q48; $R^{1a}$ represents $C_2F_5$; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX1458").

The Compound (L-6), wherein Q represents the group represented by Q49; $R^{1a}$ represents $C_2F_5$; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX1459").

The Compound (L-6), wherein Q represents the group represented by Q50; $R^{1a}$ represents $C_2F_5$; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX1460").

The Compound (L-6), wherein Q represents the group represented by Q51; $R^{1a}$ represents $C_2F_5$; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX1461").

The Compound (L-6), wherein Q represents the group represented by Q52; $R^{1a}$ represents $C_2F_5$; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX1462").

The Compound (L-6), wherein Q represents the group represented by Q53; $R^{1a}$ represents $C_2F_5$; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX1463").

The Compound (L-6), wherein Q represents the group represented by Q54; $R^{1a}$ represents $C_2F_5$; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX1464").

The Compound (L-6), wherein Q represents the group represented by Q55; $R^{1b}$ represents $C_2F_5$; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX1465").

The Compound (L-6), wherein Q represents the group represented by Q56; $R^{1b}$ represents $C_2F_5$; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX1466").

The Compound (L-6), wherein Q represents the group represented by Q57; $R^{1b}$ represents $C_2F_5$; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX1467").

The Compound (L-6), wherein Q represents the group represented by Q58; $R^{1b}$ represents $C_2F_5$; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX1468").

The Compound (L-6), wherein Q represents the group represented by Q59; $R^{1a}$ represents $C_2F_5$; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX1469").

The Compound (L-6), wherein Q represents the group represented by Q60; $R^{1a}$ represents $C_2F_5$; $G^1$ represents CH; $G^4$ represents a nitrogen atom; $R^{3b}$ represents a hydrogen atom; and $R^{3c}$ represents any one substituent described in Table 3A to Table 11A (hereinafter referred to as "Compound group SX1470").

A compound represented by formula (L-7):

(L-7)

(hereinafter referred to as "Compound (L-7)"), wherein Q represents the group represented by Q31; $R^{1b}$ represents $CF_3$; and $R^{3c}$ represents any one substituent described in Table 3A to Table 11A (hereinafter referred to as "Compound group SX1471").

The Compound (L-7), wherein Q represents the group represented by Q32; $R^{1b}$ represents $CF_3$; and $R^{3c}$ represents any one substituent described in Table 3A to Table 11A (hereinafter referred to as "Compound group SX1472").

The Compound (L-7), wherein Q represents the group represented by Q33; $R^{1b}$ represents $CF_3$; and $R^{3c}$ represents any one substituent described in Table 3A to Table 11A (hereinafter referred to as "Compound group SX1473").

The Compound (L-7), wherein Q represents the group represented by Q34; $R^{1b}$ represents $CF_3$; and $R^{3c}$ represents any one substituent described in Table 3A to Table 11A (hereinafter referred to as "Compound group SX1474").

The Compound (L-7), wherein Q represents the group represented by Q35; $R^{1b}$ represents $CF_3$; and $R^{3c}$ represents any one substituent described in Table 3A to Table 11A (hereinafter referred to as "Compound group SX1475").

The Compound (L-7), wherein Q represents the group represented by Q36; $R^{1b}$ represents $CF_3$; and $R^{3c}$ represents any one substituent described in Table 3A to Table 11A (hereinafter referred to as "Compound group SX1476").

The Compound (L-7), wherein Q represents the group represented by Q37; $R^{1b}$ represents $CF_3$; and $R^{3c}$ represents any one substituent described in Table 3A to Table 11A (hereinafter referred to as "Compound group SX1477").

The Compound (L-7), wherein Q represents the group represented by Q38; $R^{1b}$ represents $CF_3$; and $R^{3c}$ represents any one substituent described in Table 3A to Table 11A (hereinafter referred to as "Compound group SX1478").

The Compound (L-7), wherein Q represents the group represented by Q39; $R^{1b}$ represents $CF_3$; and $R^{3c}$ represents any one substituent described in Table 3A to Table 11A (hereinafter referred to as "Compound group SX1479").

The Compound (L-7), wherein Q represents the group represented by Q40; $R^{1b}$ represents $CF_3$; and $R^{3c}$ represents any one substituent described in Table 3A to Table 11A (hereinafter referred to as "Compound group SX1480").

The Compound (L-7), wherein Q represents the group represented by Q41; $R^{1b}$ represents $CF_3$; and $R^{3c}$ represents any one substituent described in Table 3A to Table 11A (hereinafter referred to as "Compound group SX1481").

The Compound (L-7), wherein Q represents the group represented by Q42; $R^{1b}$ represents $CF_3$; and $R^{3c}$ represents any one substituent described in Table 3A to Table 11A (hereinafter referred to as "Compound group SX1482").

The Compound (L-7), wherein Q represents the group represented by Q43; $R^{1b}$ represents $CF_3$; and $R^{3c}$ represents any one substituent described in Table 3A to Table 11A (hereinafter referred to as "Compound group SX1483").

The Compound (L-7), wherein Q represents the group represented by Q44; $R^{1b}$ represents $CF_3$; and $R^{3c}$ represents any one substituent described in Table 3A to Table 11A (hereinafter referred to as "Compound group SX1484").

The Compound (L-7), wherein Q represents the group represented by Q45; $R^{1b}$ represents $CF_3$; and $R^{3c}$ represents any one substituent described in Table 3A to Table 11A (hereinafter referred to as "Compound group SX1485").

The Compound (L-7), wherein Q represents the group represented by Q46; $R^{1b}$ represents $CF_3$; and $R^{3c}$ represents any one substituent described in Table 3A to Table 11A (hereinafter referred to as "Compound group SX1486").

The Compound (L-7), wherein Q represents the group represented by Q47; $R^{1a}$ represents $CF_3$; and $R^{3c}$ represents any one substituent described in Table 3A to Table 11A (hereinafter referred to as "Compound group SX1487").

The Compound (L-7), wherein Q represents the group represented by Q48; $R^{1a}$ represents $CF_3$; and $R^{3c}$ represents any one substituent described in Table 3A to Table 11A (hereinafter referred to as "Compound group SX1488").

The Compound (L-7), wherein Q represents the group represented by Q49; $R^{1a}$ represents $CF_3$; and $R^{3c}$ represents any one substituent described in Table 3A to Table 11A (hereinafter referred to as "Compound group SX1489").

The Compound (L-7), wherein Q represents the group represented by Q50; $R^{1a}$ represents $CF_3$; and $R^{3c}$ represents any one substituent described in Table 3A to Table 11A (hereinafter referred to as "Compound group SX1490").

The Compound (L-7), wherein Q represents the group represented by Q51; $R^{1a}$ represents $CF_3$; and $R^{3c}$ represents any one substituent described in Table 3A to Table 11A (hereinafter referred to as "Compound group SX1491").

The Compound (L-7), wherein Q represents the group represented by Q52; $R^{1a}$ represents $CF_3$; and $R^{3c}$ represents any one substituent described in Table 3A to Table 11A (hereinafter referred to as "Compound group SX1492").

The Compound (L-7), wherein Q represents the group represented by Q53; $R^{1a}$ represents $CF_3$; and $R^{3c}$ represents any one substituent described in Table 3A to Table 11A (hereinafter referred to as "Compound group SX1493").

The Compound (L-7), wherein Q represents the group represented by Q54; $R^{1a}$ represents $CF_3$; and $R^{3c}$ represents any one substituent described in Table 3A to Table 11A (hereinafter referred to as "Compound group SX1494").

The Compound (L-7), wherein Q represents the group represented by Q55; $R^{1b}$ represents $CF_3$; and $R^{3c}$ represents any one substituent described in Table 3A to Table 11A (hereinafter referred to as "Compound group SX1495").

The Compound (L-7), wherein Q represents the group represented by Q56; $R^{1b}$ represents $CF_3$; and $R^{3c}$ represents any one substituent described in Table 3A to Table 11A (hereinafter referred to as "Compound group SX1496").

The Compound (L-7), wherein Q represents the group represented by Q57; $R^{1b}$ represents $CF_3$; and $R^{3c}$ represents any one substituent described in Table 3A to Table 11A (hereinafter referred to as "Compound group SX1497").

The Compound (L-7), wherein Q represents the group represented by Q58; $R^{1b}$ represents $CF_3$; and $R^{3c}$ represents any one substituent described in Table 3A to Table 11A (hereinafter referred to as "Compound group SX1498").

The Compound (L-7), wherein Q represents the group represented by Q59; $R^{1a}$ represents $CF_3$; and $R^{3c}$ represents any one substituent described in Table 3A to Table 11A (hereinafter referred to as "Compound group SX1499").

The Compound (L-7), wherein Q represents the group represented by Q60; $R^{1a}$ represents $CF_3$; and $R^{3c}$ represents any one substituent described in Table 3A to Table 11A (hereinafter referred to as "Compound group SX1500").

The Compound (L-7), wherein Q represents the group represented by Q31; $R^{1b}$ represents $C_2F_5$; and $R^{3c}$ represents any one substituent described in Table 3A to Table 11A (hereinafter referred to as "Compound group SX1501").

The Compound (L-7), wherein Q represents the group represented by Q32; $R^{1b}$ represents $C_2F_5$; and $R^{3c}$ represents any one substituent described in Table 3A to Table 11A (hereinafter referred to as "Compound group SX1502").

The Compound (L-7), wherein Q represents the group represented by Q33; $R^{1b}$ represents $C_2F_5$; and $R^{3c}$ represents any one substituent described in Table 3A to Table 11A (hereinafter referred to as "Compound group SX1503").

The Compound (L-7), wherein Q represents the group represented by Q34; $R^{1b}$ represents $C_2F_5$; and $R^{3c}$ represents any one substituent described in Table 3A to Table 11A (hereinafter referred to as "Compound group SX1504").

The Compound (L-7), wherein Q represents the group represented by Q35; $R^{1b}$ represents $C_2F_5$; and $R^{3c}$ represents any one substituent described in Table 3A to Table 11A (hereinafter referred to as "Compound group SX1505").

The Compound (L-7), wherein Q represents the group represented by Q36; $R^{1b}$ represents $C_2F_5$; and $R^{3c}$ represents any one substituent described in Table 3A to Table 11A (hereinafter referred to as "Compound group SX1506").

The Compound (L-7), wherein Q represents the group represented by Q37; $R^{1b}$ represents $C_2F_5$; and $R^{3c}$ represents any one substituent described in Table 3A to Table 11A (hereinafter referred to as "Compound group SX1507").

The Compound (L-7), wherein Q represents the group represented by Q38; $R^{1b}$ represents $C_2F_5$; and $R^{3c}$ represents any one substituent described in Table 3A to Table 11A (hereinafter referred to as "Compound group SX1508").

The Compound (L-7), wherein Q represents the group represented by Q39; $R^{1b}$ represents $C_2F_5$; and $R^{3c}$ represents any one substituent described in Table 3A to Table 11A (hereinafter referred to as "Compound group SX1509").

The Compound (L-7), wherein Q represents the group represented by Q40; $R^{1b}$ represents $C_2F_5$; and $R^{3c}$ represents any one substituent described in Table 3A to Table 11A (hereinafter referred to as "Compound group SX1510").

The Compound (L-7), wherein Q represents the group represented by Q41; $R^{1b}$ represents $C_2F_5$; and $R^{3c}$ represents any one substituent described in Table 3A to Table 11A (hereinafter referred to as "Compound group SX1511").

The Compound (L-7), wherein Q represents the group represented by Q42; $R^{1b}$ represents $C_2F_5$; and $R^{3c}$ represents any one substituent described in Table 3A to Table 11A (hereinafter referred to as "Compound group SX1512").

The Compound (L-7), wherein Q represents the group represented by Q43; $R^{1b}$ represents $C_2F_5$; and $R^{3c}$ represents any one substituent described in Table 3A to Table 11A (hereinafter referred to as "Compound group SX1513").

The Compound (L-7), wherein Q represents the group represented by Q44; $R^{1b}$ represents $C_2F_5$; and $R^{3c}$ represents any one substituent described in Table 3A to Table 11A (hereinafter referred to as "Compound group SX1514").

The Compound (L-7), wherein Q represents the group represented by Q45; $R^{1b}$ represents $C_2F_5$; and $R^{3c}$ represents any one substituent described in Table 3A to Table 11A (hereinafter referred to as "Compound group SX1515").

The Compound (L-7), wherein Q represents the group represented by Q46; $R^{1b}$ represents $C_2F_5$; and $R^{3c}$ represents any one substituent described in Table 3A to Table 11A (hereinafter referred to as "Compound group SX1516").

The Compound (L-7), wherein Q represents the group represented by Q47; $R^{1a}$ represents $C_2F_5$; and $R^{3c}$ represents any one substituent described in Table 3A to Table 11A (hereinafter referred to as "Compound group SX1517").

The Compound (L-7), wherein Q represents the group represented by Q48; $R^{1a}$ represents $C_2F_5$; and $R^{3c}$ represents any one substituent described in Table 3A to Table 11A (hereinafter referred to as "Compound group SX1518").

The Compound (L-7), wherein Q represents the group represented by Q49; $R^{1a}$ represents $C_2F_5$; and $R^{3c}$ represents any one substituent described in Table 3A to Table 11A (hereinafter referred to as "Compound group SX1519").

The Compound (L-7), wherein Q represents the group represented by Q50; $R^{1a}$ represents $C_2F_5$; and $R^{3c}$ represents any one substituent described in Table 3A to Table 11A (hereinafter referred to as "Compound group SX1520").

The Compound (L-7), wherein Q represents the group represented by Q51; $R^{1a}$ represents $C_2F_5$; and $R^{3c}$ represents any one substituent described in Table 3A to Table 11A (hereinafter referred to as "Compound group SX1521").

The Compound (L-7), wherein Q represents the group represented by Q52; $R^{1a}$ represents $C_2F_5$; and $R^{3c}$ represents any one substituent described in Table 3A to Table 11A (hereinafter referred to as "Compound group SX1522").

The Compound (L-7), wherein Q represents the group represented by Q53; $R^{1a}$ represents $C_2F_5$; and $R^{3c}$ represents any one substituent described in Table 3A to Table 11A (hereinafter referred to as "Compound group SX1523").

The Compound (L-7), wherein Q represents the group represented by Q54; $R^{1a}$ represents $C_2F_5$; and $R^{3c}$ represents any one substituent described in Table 3A to Table 11A (hereinafter referred to as "Compound group SX1524").

The Compound (L-7), wherein Q represents the group represented by Q55; $R^{1b}$ represents $C_2F_5$; and $R^{3c}$ represents any one substituent described in Table 3A to Table 11A (hereinafter referred to as "Compound group SX1525").

The Compound (L-7), wherein Q represents the group represented by Q56; $R^{1b}$ represents $C_2F_5$; and $R^{3c}$ represents any one substituent described in Table 3A to Table 11A (hereinafter referred to as "Compound group SX1526").

The Compound (L-7), wherein Q represents the group represented by Q57; $R^{1b}$ represents $C_2F_5$; and $R^{3c}$ represents any one substituent described in Table 3A to Table 11A (hereinafter referred to as "Compound group SX1527").

The Compound (L-7), wherein Q represents the group represented by Q58; $R^{1b}$ represents $C_2F_5$; and $R^{3c}$ represents any one substituent described in Table 3A to Table 11A (hereinafter referred to as "Compound group SX1528").

The Compound (L-7), wherein Q represents the group represented by Q59; $R^{1a}$ represents $C_2F_5$; and $R^{3c}$ represents any one substituent described in Table 3A to Table 11A (hereinafter referred to as "Compound group SX1529").

The Compound (L-7), wherein Q represents the group represented by Q60; $R^{1a}$ represents $C_2F_5$; and $R^{3c}$ represents any one substituent described in Table 3A to Table 11A (hereinafter referred to as "Compound group SX1530").

A compound represented by formula (L-8):

(L-8)

(hereinafter referred to as "Compound (L-8)"), wherein Q represents the group represented by Q31; $R^{1b}$ represents $CF_3$; and $R^{3b}$ represents any one substituent described in Table 3A to Table 11A (hereinafter referred to as "Compound group SX1531").

The Compound (L-8), wherein Q represents the group represented by Q32; $R^{1b}$ represents $CF_3$; and $R^{3b}$ represents any one substituent described in Table 3A to Table 11A (hereinafter referred to as "Compound group SX1532").

The Compound (L-8), wherein Q represents the group represented by Q33; $R^{1b}$ represents $CF_3$; and $R^{3b}$ represents any one substituent described in Table 3A to Table 11A (hereinafter referred to as "Compound group SX1533").

The Compound (L-8), wherein Q represents the group represented by Q34; $R^{1b}$ represents $CF_3$; and $R^{3b}$ represents any one substituent described in Table 3A to Table 11A (hereinafter referred to as "Compound group SX1534").

The Compound (L-8), wherein Q represents the group represented by Q35; $R^{1b}$ represents $CF_3$; and $R^{3b}$ represents any one substituent described in Table 3A to Table 11A (hereinafter referred to as "Compound group SX1535").

The Compound (L-8), wherein Q represents the group represented by Q36; $R^{1b}$ represents $CF_3$; and $R^{3b}$ represents any one substituent described in Table 3A to Table 11A (hereinafter referred to as "Compound group SX1536").

The Compound (L-8), wherein Q represents the group represented by Q37; $R^{1b}$ represents $CF_3$; and $R^{3b}$ represents any one substituent described in Table 3A to Table 11A (hereinafter referred to as "Compound group SX1537").

The Compound (L-8), wherein Q represents the group represented by Q38; $R^{1b}$ represents $CF_3$; and $R^{3b}$ represents any one substituent described in Table 3A to Table 11A (hereinafter referred to as "Compound group SX1538").

The Compound (L-8), wherein Q represents the group represented by Q39; $R^{1b}$ represents $CF_3$; and $R^{3b}$ represents any one substituent described in Table 3A to Table 11A (hereinafter referred to as "Compound group SX1539").

The Compound (L-8), wherein Q represents the group represented by Q40; $R^{1b}$ represents $CF_3$; and $R^{3b}$ represents any one substituent described in Table 3A to Table 11A (hereinafter referred to as "Compound group SX1540").

The Compound (L-8), wherein Q represents the group represented by Q41; $R^{1b}$ represents $CF_3$; and $R^{3b}$ represents any one substituent described in Table 3A to Table 11A (hereinafter referred to as "Compound group SX1541").

The Compound (L-8), wherein Q represents the group represented by Q42; $R^{1b}$ represents $CF_3$; and $R^{3b}$ represents any one substituent described in Table 3A to Table 11A (hereinafter referred to as "Compound group SX1542").

The Compound (L-8), wherein Q represents the group represented by Q43; $R^{1b}$ represents $CF_3$; and $R^{3b}$ represents any one substituent described in Table 3A to Table 11A (hereinafter referred to as "Compound group SX1543").

The Compound (L-8), wherein Q represents the group represented by Q44; $R^{1b}$ represents $CF_3$; and $R^{3b}$ represents any one substituent described in Table 3A to Table 11A (hereinafter referred to as "Compound group SX1544").

The Compound (L-8), wherein Q represents the group represented by Q45; $R^{1b}$ represents $CF_3$; and $R^{3b}$ represents any one substituent described in Table 3A to Table 11A (hereinafter referred to as "Compound group SX1545").

The Compound (L-8), wherein Q represents the group represented by Q46; $R^{1b}$ represents $CF_3$; and $R^{3b}$ represents any one substituent described in Table 3A to Table 11A (hereinafter referred to as "Compound group SX1546").

The Compound (L-8), wherein Q represents the group represented by Q47; $R^{1a}$ represents $CF_3$; and $R^{3b}$ represents any one substituent described in Table 3A to Table 11A (hereinafter referred to as "Compound group SX1547").

The Compound (L-8), wherein Q represents the group represented by Q48; $R^{1a}$ represents $CF_3$; and $R^{3b}$ represents any one substituent described in Table 3A to Table 11A (hereinafter referred to as "Compound group SX1548").

The Compound (L-8), wherein Q represents the group represented by Q49; $R^{1a}$ represents $CF_3$; and $R^{3b}$ represents any one substituent described in Table 3A to Table 11A (hereinafter referred to as "Compound group SX1549").

The Compound (L-8), wherein Q represents the group represented by Q50; $R^{1a}$ represents $CF_3$; and $R^{3b}$ represents any one substituent described in Table 3A to Table 11A (hereinafter referred to as "Compound group SX1550").

The Compound (L-8), wherein Q represents the group represented by Q51; $R^{1a}$ represents $CF_3$; and $R^{3b}$ represents any one substituent described in Table 3A to Table 11A (hereinafter referred to as "Compound group SX1551").

The Compound (L-8), wherein Q represents the group represented by Q52; $R^{1a}$ represents $CF_3$; and $R^{3b}$ represents any one substituent described in Table 3A to Table 11A (hereinafter referred to as "Compound group SX1552").

The Compound (L-8), wherein Q represents the group represented by Q53; $R^{1a}$ represents $CF_3$; and $R^{3b}$ represents any one substituent described in Table 3A to Table 11A (hereinafter referred to as "Compound group SX1553").

The Compound (L-8), wherein Q represents the group represented by Q54; $R^{1a}$ represents $CF_3$; and $R^{3b}$ represents any one substituent described in Table 3A to Table 11A (hereinafter referred to as "Compound group SX1554").

The Compound (L-8), wherein Q represents the group represented by Q55; $R^{1b}$ represents $CF_3$; and $R^{3b}$ represents any one substituent described in Table 3A to Table 11A (hereinafter referred to as "Compound group SX1555").

The Compound (L-8), wherein Q represents the group represented by Q56; $R^{1b}$ represents $CF_3$; and $R^{3b}$ represents any one substituent described in Table 3A to Table 11A (hereinafter referred to as "Compound group SX1556").

The Compound (L-8), wherein Q represents the group represented by Q57; $R^{1b}$ represents $CF_3$; and $R^{3b}$ represents any one substituent described in Table 3A to Table 11A (hereinafter referred to as "Compound group SX1557").

The Compound (L-8), wherein Q represents the group represented by Q58; $R^{1b}$ represents $CF_3$; and $R^{3b}$ represents any one substituent described in Table 3A to Table 11A (hereinafter referred to as "Compound group SX1558").

The Compound (L-8), wherein Q represents the group represented by Q59; $R^{1a}$ represents $CF_3$; and $R^{3b}$ represents any one substituent described in Table 3A to Table 11A (hereinafter referred to as "Compound group SX1559").

The Compound (L-8), wherein Q represents the group represented by Q60; $R^{1a}$ represents $CF_3$; and $R^{3b}$ represents any one substituent described in Table 3A to Table 11A (hereinafter referred to as "Compound group SX1560").

The Compound (L-8), wherein Q represents the group represented by Q31; $R^{1b}$ represents $C_2F_5$; and $R^{3b}$ represents any one substituent described in Table 3A to Table 11A (hereinafter referred to as "Compound group SX1561").

The Compound (L-8), wherein Q represents the group represented by Q32; $R^{1b}$ represents $C_2F_5$; and $R^{3b}$ represents any one substituent described in Table 3A to Table 11A (hereinafter referred to as "Compound group SX1562").

The Compound (L-8), wherein Q represents the group represented by Q33; $R^{1b}$ represents $C_2F_5$; and $R^{3b}$ represents any one substituent described in Table 3A to Table 11A (hereinafter referred to as "Compound group SX1563").

The Compound (L-8), wherein Q represents the group represented by Q34; $R^{1b}$ represents $C_2F_5$; and $R^{3b}$ represents any one substituent described in Table 3A to Table 11A (hereinafter referred to as "Compound group SX1564").

The Compound (L-8), wherein Q represents the group represented by Q35; $R^{1b}$ represents $C_2F_5$; and $R^{3b}$ represents any one substituent described in Table 3A to Table 11A (hereinafter referred to as "Compound group SX1565").

The Compound (L-8), wherein Q represents the group represented by Q36; $R^{1b}$ represents $C_2F_5$; and $R^{3b}$ represents any one substituent described in Table 3A to Table 11A (hereinafter referred to as "Compound group SX1566").

The Compound (L-8), wherein Q represents the group represented by Q37; $R^{1b}$ represents $C_2F_5$; and $R^{3b}$ represents any one substituent described in Table 3A to Table 11A (hereinafter referred to as "Compound group SX1567").

The Compound (L-8), wherein Q represents the group represented by Q38; $R^{1b}$ represents $C_2F_5$; and $R^{3b}$ represents any one substituent described in Table 3A to Table 11A (hereinafter referred to as "Compound group SX1568").

The Compound (L-8), wherein Q represents the group represented by Q39; $R^{1b}$ represents $C_2F_5$; and $R^{3b}$ represents any one substituent described in Table 3A to Table 11A (hereinafter referred to as "Compound group SX1569").

The Compound (L-8), wherein Q represents the group represented by Q40; $R^{1b}$ represents $C_2F_5$; and $R^{3b}$ represents any one substituent described in Table 3A to Table 11A (hereinafter referred to as "Compound group SX1570").

The Compound (L-8), wherein Q represents the group represented by Q41; $R^{1b}$ represents $C_2F_5$; and $R^{3b}$ represents any one substituent described in Table 3A to Table 11A (hereinafter referred to as "Compound group SX1571").

The Compound (L-8), wherein Q represents the group represented by Q42; $R^{1b}$ represents $C_2F_5$; and $R^{3b}$ represents any one substituent described in Table 3A to Table 11A (hereinafter referred to as "Compound group SX1572").

The Compound (L-8), wherein Q represents the group represented by Q43; $R^{1b}$ represents $C_2F_5$; and $R^{3b}$ represents any one substituent described in Table 3A to Table 11A (hereinafter referred to as "Compound group SX1573").

The Compound (L-8), wherein Q represents the group represented by Q44; $R^{1b}$ represents $C_2F_5$; and $R^{3b}$ represents any one substituent described in Table 3A to Table 11A (hereinafter referred to as "Compound group SX1574").

The Compound (L-8), wherein Q represents the group represented by Q45; $R^{1b}$ represents $C_2F_5$; and $R^{3b}$ represents any one substituent described in Table 3A to Table 11A (hereinafter referred to as "Compound group SX1575").

The Compound (L-8), wherein Q represents the group represented by Q46; $R^{1b}$ represents $C_2F_5$; and $R^{3b}$ represents any one substituent described in Table 3A to Table 11A (hereinafter referred to as "Compound group SX1576").

The Compound (L-8), wherein Q represents the group represented by Q47; $R^{1a}$ represents $C_2F_5$; and $R^{3b}$ represents any one substituent described in Table 3A to Table 11A (hereinafter referred to as "Compound group SX1577").

The Compound (L-8), wherein Q represents the group represented by Q48; $R^{1a}$ represents $C_2F_5$; and $R^{3b}$ represents any one substituent described in Table 3A to Table 11A (hereinafter referred to as "Compound group SX1578").

The Compound (L-8), wherein Q represents the group represented by Q49; $R^{1a}$ represents $C_2F_5$; and $R^{3b}$ represents any one substituent described in Table 3A to Table 11A (hereinafter referred to as "Compound group SX1579").

The Compound (L-8), wherein Q represents the group represented by Q50; $R^{1a}$ represents $C_2F_5$; and $R^{3b}$ represents any one substituent described in Table 3A to Table 11A (hereinafter referred to as "Compound group SX1580").

The Compound (L-8), wherein Q represents the group represented by Q51; $R^{1a}$ represents $C_2F_5$; and $R^{3b}$ represents any one substituent described in Table 3A to Table 11A (hereinafter referred to as "Compound group SX1581").

The Compound (L-8), wherein Q represents the group represented by Q52; $R^{1a}$ represents $C_2F_5$; and $R^{3b}$ represents any one substituent described in Table 3A to Table 11A (hereinafter referred to as "Compound group SX1582").

The Compound (L-8), wherein Q represents the group represented by Q53; $R^{1a}$ represents $C_2F_5$; and $R^{3b}$ represents any one substituent described in Table 3A to Table 11A (hereinafter referred to as "Compound group SX1583").

The Compound (L-8), wherein Q represents the group represented by Q54; $R^{1a}$ represents $C_2F_5$; and $R^{3b}$ represents any one substituent described in Table 3A to Table 11A (hereinafter referred to as "Compound group SX1584").

The Compound (L-8), wherein Q represents the group represented by Q55; $R^{1b}$ represents $C_2F_5$; and $R^{3b}$ represents any one substituent described in Table 3A to Table 11A (hereinafter referred to as "Compound group SX1585").

The Compound (L-8), wherein Q represents the group represented by Q56; $R^{1b}$ represents $C_2F_5$; and $R^{3b}$ represents any one substituent described in Table 3A to Table 11A (hereinafter referred to as "Compound group SX1586").

The Compound (L-8), wherein Q represents the group represented by Q57; $R^{1b}$ represents $C_2F_5$; and $R^{3b}$ represents any one substituent described in Table 3A to Table 11A (hereinafter referred to as "Compound group SX1587").

The Compound (L-8), wherein Q represents the group represented by Q58; $R^{1b}$ represents $C_2F_5$; and $R^{3b}$ represents any one substituent described in Table 3A to Table 11A (hereinafter referred to as "Compound group SX1588").

The Compound (L-8), wherein Q represents the group represented by Q59; $R^{1a}$ represents $C_2F_5$; and $R^{3b}$ represents any one substituent described in Table 3A to Table 11A (hereinafter referred to as "Compound group SX1589").

The Compound (L-8), wherein Q represents the group represented by Q60; $R^{1a}$ represents $C_2F_5$; and $R^{3b}$ represents any one substituent described in Table 3A to Table 11A (hereinafter referred to as "Compound group SX1590").

A compound represented by formula (L-9):

(L-9)

(hereinafter referred to as "Compound (L-9)"), wherein n represents 1; $R^2$ represents an ethyl group; $R^{3c}$ represents a hydrogen atom; and $R^{3b}$ represents any one substituent of a hydrogen atom, a chlorine atom, a bromine atom, an iodine atom, $CF_3$, and substituents described in Table 3A to Table 11A (hereinafter referred to as "Compound group SX1591").

The Compound (L-9), wherein n represents 0; $R^2$ represents an ethyl group; $R^{3c}$ represents a hydrogen atom; and $R^{3b}$ represents any one substituent of a hydrogen atom, a chlorine atom, a bromine atom, an iodine atom, $CF_3$, and substituents described in Table 3A to Table 11A (hereinafter referred to as "Compound group SX1592").

The Compound (L-9), wherein n represents 2; $R^2$ represents a methyl group; $R^{3c}$ represents a hydrogen atom; and $R^{3b}$ represents any one substituent of a hydrogen atom, a chlorine atom, a bromine atom, an iodine atom, $CF_3$, and substituents described in Table 3A to Table 11A (hereinafter referred to as "Compound group SX1593").

The Compound (L-9), wherein n represents 1; $R^2$ represents a methyl group; $R^{3c}$ represents a hydrogen atom; and $R^{3b}$ represents any one substituent of a hydrogen atom, a chlorine atom, a bromine atom, an iodine atom, $CF_3$, and substituents described in Table 3A to Table 11A (hereinafter referred to as "Compound group SX1594").

The Compound (L-9), wherein n represents 0; $R^2$ represents a methyl group; $R^{3c}$ represents a hydrogen atom; and $R^{3b}$ represents any one substituent of a hydrogen atom, a chlorine atom, a bromine atom, an iodine atom, $CF_3$, and substituents described in Table 3A to Table 11A (hereinafter referred to as "Compound group SX1595").

The Compound (L-9), wherein n represents 1; $R^2$ represents an ethyl group; $R^{3b}$ represents a hydrogen atom; and $R^{3c}$ represents any one substituent of a chlorine atom, a bromine atom, an iodine atom, $CF_3$, and substituents described in Table 3A to Table 11A (hereinafter referred to as "Compound group SX1596").

The Compound (L-9), wherein n represents 0; $R^2$ represents an ethyl group; $R^{3b}$ represents a hydrogen atom; and $R^{3c}$ represents any one substituent of a chlorine atom, a bromine atom, an iodine atom, $CF_3$, and substituents described in Table 3A to Table 11A (hereinafter referred to as "Compound group SX1597").

The Compound (L-9), wherein n represents 2; $R^2$ represents a methyl group; $R^{3b}$ represents a hydrogen atom; and $R^{3c}$ represents any one substituent of a chlorine atom, a bromine atom, an iodine atom, $CF_3$, and substituents described in Table 3A to Table 11A (hereinafter referred to as "Compound group SX1598").

The Compound (L-9), wherein n represents 1; $R^2$ represents a methyl group; $R^{3b}$ represents a hydrogen atom; and $R^{3c}$ represents any one substituent of a chlorine atom, a bromine atom, an iodine atom, $CF_3$, and substituents described in Table 3A to Table 11A (hereinafter referred to as "Compound group SX1599").

The Compound (L-9), wherein n represents 0; $R^2$ represents a methyl group; $R^{3b}$ represents a hydrogen atom; and $R^{3c}$ represents any one substituent of a chlorine atom, a bromine atom, an iodine atom, CFs, and substituents described in Table 3A to Table 11A (hereinafter referred to as "Compound group SX1600").

A compound represented by formula (L-10):

(L-10)

(hereinafter referred to as "Compound (L-10)"), wherein n represents 1; $R^2$ represents an ethyl group; $R^{3c}$ represents a hydrogen atom; and $R^{3b}$ represents any one substituent of a hydrogen atom, a chlorine atom, a bromine atom, an iodine atom, $CF_3$, and substituents described in Table 3A to Table 11A (hereinafter referred to as "Compound group SX1601").

The Compound (L-10), wherein n represents 0; $R^2$ represents an ethyl group; $R^{3c}$ represents a hydrogen atom; and $R^{3b}$ represents any one substituent of a hydrogen atom, a chlorine atom, a bromine atom, an iodine atom, $CF_3$, and substituents described in Table 3A to Table 11A (hereinafter referred to as "Compound group SX1602").

The Compound (L-10), wherein n represents 2; $R^2$ represents a methyl group; $R^{3c}$ represents a hydrogen atom; and $R^{3b}$ represents any one substituent of a hydrogen atom, a chlorine atom, a bromine atom, an iodine atom, $CF_3$, and substituents described in Table 3A to Table 11A (hereinafter referred to as "Compound group SX1603").

The Compound (L-10), wherein n represents 1; $R^2$ represents a methyl group; $R^{3c}$ represents a hydrogen atom; and $R^{3b}$ represents any one substituent of a hydrogen atom, a chlorine atom, a bromine atom, an iodine atom, $CF_3$, and substituents described in Table 3A to Table 11A (hereinafter referred to as "Compound group SX1604").

The Compound (L-10), wherein n represents 0; $R^2$ represents a methyl group; $R^{3c}$ represents a hydrogen atom; and $R^{3b}$ represents any one substituent of a hydrogen atom, a chlorine atom, a bromine atom, an iodine atom, $CF_3$, and substituents described in Table 3A to Table 11A (hereinafter referred to as "Compound group SX1605").

The Compound (L-10), wherein n represents 1; $R^2$ represents an ethyl group; $R^{3b}$ represents a hydrogen atom; and $R^{3c}$ represents any one substituent of a chlorine atom, a bromine atom, an iodine atom, $CF_3$, and substituents described in Table 3A to Table 11A (hereinafter referred to as "Compound group SX1606").

The Compound (L-10), wherein n represents 0; $R^2$ represents an ethyl group; $R^{3b}$ represents a hydrogen atom; and $R^{3c}$ represents any one substituent of a chlorine atom, a bromine atom, an iodine atom, $CF_3$, and substituents described in Table 3A to Table 11A (hereinafter referred to as "Compound group SX1607").

The Compound (L-10), wherein n represents 2; $R^2$ represents a methyl group; $R^{3b}$ represents a hydrogen atom; and $R^{3c}$ represents any one substituent of a chlorine atom, a bromine atom, an iodine atom, CFs, and substituents described in Table 3A to Table 11A (hereinafter referred to as "Compound group SX1608").

The Compound (L-10), wherein n represents 1; $R^2$ represents a methyl group; $R^{3b}$ represents a hydrogen atom; and $R^{3c}$ represents any one substituent of a chlorine atom, a bromine atom, an iodine atom, $CF_3$, and substituents described in Table 3A to Table 11A (hereinafter referred to as "Compound group SX1609").

The Compound (L-10), wherein n represents 0; $R^2$ represents a methyl group; $R^{3b}$ represents a hydrogen atom; and $R^{3c}$ represents any one substituent of a chlorine atom, a bromine atom, an iodine atom, $CF_3$, and substituents described in Table 3A to Table 11A (hereinafter referred to as "Compound group SX1610").

A compound represented by formula (L-11):

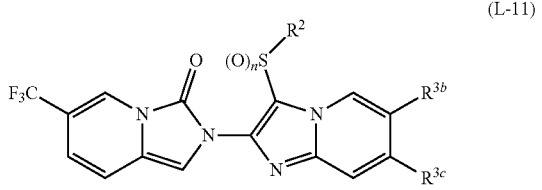

(L-11)

(hereinafter referred to as "Compound (L-11)"), wherein n represents 1; $R^2$ represents an ethyl group; $R^{3c}$ represents a hydrogen atom; and $R^{3b}$ represents any one substituent of a hydrogen atom, a chlorine atom, a bromine atom, an iodine atom, CFs, and substituents described in Table 3A to Table 11A (hereinafter referred to as "Compound group SX1611").

The Compound (L-11), wherein n represents 0; $R^2$ represents an ethyl group; $R^{3c}$ represents a hydrogen atom; and $R^{3b}$ represents any one substituent of a hydrogen atom, a chlorine atom, a bromine atom, an iodine atom, $CF_3$, and substituents described in Table 3A to Table 11A (hereinafter referred to as "Compound group SX1612").

The Compound (L-11), wherein n represents 2; $R^2$ represents a methyl group; $R^{3c}$ represents a hydrogen atom; and $R^{3b}$ represents any one substituent of a hydrogen atom, a chlorine atom, a bromine atom, an iodine atom, $CF_3$, and substituents described in Table 3A to Table 11A (hereinafter referred to as "Compound group SX1613").

The Compound (L-11), wherein n represents 1; $R^2$ represents a methyl group; $R^{3c}$ represents a hydrogen atom; and $R^{3b}$ represents any one substituent of a hydrogen atom, a chlorine atom, a bromine atom, an iodine atom, $CF_3$, and substituents described in Table 3A to Table 11A (hereinafter referred to as "Compound group SX1614").

The Compound (L-11), wherein n represents 0; $R^2$ represents a methyl group; $R^{3c}$ represents a hydrogen atom; and $R^{3b}$ represents any one substituent of a hydrogen atom, a chlorine atom, a bromine atom, an iodine atom, $CF_3$, and substituents described in Table 3A to Table 11A (hereinafter referred to as "Compound group SX1615").

The Compound (L-11), wherein n represents 1; $R^2$ represents an ethyl group; $R^{3b}$ represents a hydrogen atom; and $R^{3c}$ represents any one substituent of a chlorine atom, a bromine atom, an iodine atom, $CF_3$, and substituents described in Table 3A to Table 11A (hereinafter referred to as "Compound group SX1616").

The Compound (L-11), wherein n represents 0; $R^2$ represents an ethyl group; $R^{3b}$ represents a hydrogen atom; and $R^{3c}$ represents any one substituent of a chlorine atom, a bromine atom, an iodine atom, $CF_3$, and substituents described in Table 3A to Table 11A (hereinafter referred to as "Compound group SX1617").

The Compound (L-11), wherein n represents 2; $R^2$ represents a methyl group; $R^{3b}$ represents a hydrogen atom; and $R^{3c}$ represents any one substituent of a chlorine atom, a bromine atom, an iodine atom, $CF_3$, and substituents described in Table 3A to Table 11A (hereinafter referred to as "Compound group SX1618").

The Compound (L-11), wherein n represents 1; $R^2$ represents a methyl group; $R^{3b}$ represents a hydrogen atom; and $R^{3c}$ represents any one substituent of a chlorine atom, a bromine atom, an iodine atom, CFs, and substituents described in Table 3A to Table 11A (hereinafter referred to as "Compound group SX16119").

The Compound (L-11), wherein n represents 0; $R^2$ represents a methyl group; $R^{3b}$ represents a hydrogen atom; and $R^{3c}$ represents any one substituent of a chlorine atom, a bromine atom, an iodine atom, $CF_3$, and substituents described in Table 3A to Table 11A (hereinafter referred to as "Compound group SX1620").

A compound represented by formula (L-12):

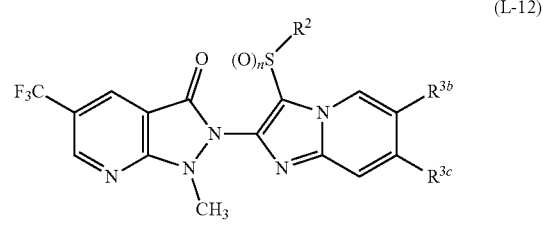

(L-12)

(hereinafter referred to as "Compound (L-12)"), wherein n represents 1; $R^2$ represents an ethyl group; $R^{3c}$ represents a hydrogen atom; and $R^{3b}$ represents any one substituent of a hydrogen atom, a chlorine atom, a bromine atom, an iodine atom, $CF_3$, and substituents described in Table 3A to Table 11A (hereinafter referred to as "Compound group SX1621").

The Compound (L-12), wherein n represents 0; $R^2$ represents an ethyl group; $R^{3c}$ represents a hydrogen atom; and $R^{3b}$ represents any one substituent of a hydrogen atom, a chlorine atom, a bromine atom, an iodine atom, $CF_3$, and substituents described in Table 3A to Table 11A (hereinafter referred to as "Compound group SX1622").

The Compound (L-12), wherein n represents 2; $R^2$ represents a methyl group; $R^{3c}$ represents a hydrogen atom; and $R^{3b}$ represents any one substituent of a hydrogen atom, a chlorine atom, a bromine atom, an iodine atom, $CF_3$, and substituents described in Table 3A to Table 11A (hereinafter referred to as "Compound group SX1623").

The Compound (L-12), wherein n represents 1; $R^2$ represents a methyl group; $R^{3c}$ represents a hydrogen atom; and $R^{3b}$ represents any one substituent of a hydrogen atom, a chlorine atom, a bromine atom, an iodine atom, $CF_3$, and substituents described in Table 3A to Table 11A (hereinafter referred to as "Compound group SX1624").

The Compound (L-12), wherein n represents 0; $R^2$ represents a methyl group; $R^{3c}$ represents a hydrogen atom; and $R^{3b}$ represents any one substituent of a hydrogen atom, a chlorine atom, a bromine atom, an iodine atom, $CF_3$, and substituents described in Table 3A to Table 11A (hereinafter referred to as "Compound group SX1625").

The Compound (L-12), wherein n represents 1; $R^2$ represents an ethyl group; $R^{3b}$ represents a hydrogen atom; and $R^{3c}$ represents any one substituent of a chlorine atom, a bromine atom, an iodine atom, $CF_3$, and substituents described in Table 3A to Table 11A (hereinafter referred to as "Compound group SX1626").

The Compound (L-12), wherein n represents 0; $R^2$ represents an ethyl group; $R^{3b}$ represents a hydrogen atom; and $R^{3c}$ represents any one substituent of a chlorine atom, a bromine atom, an iodine atom, $CF_3$, and substituents described in Table 3A to Table 11A (hereinafter referred to as "Compound group SX1627").

The Compound (L-12), wherein n represents 2; $R^2$ represents a methyl group; $R^{3b}$ represents a hydrogen atom; and $R^{3c}$ represents any one substituent of a chlorine atom, a bromine atom, an iodine atom, $CF_3$, and substituents described in Table 3A to Table 11A (hereinafter referred to as "Compound group SX1628").

The Compound (L-12), wherein n represents 1; $R^2$ represents a methyl group; $R^{3b}$ represents a hydrogen atom; and $R^{3c}$ represents any one substituent of a chlorine atom, a bromine atom, an iodine atom, $CF_3$, and substituents described in Table 3A to Table 11A (hereinafter referred to as "Compound group SX1629").

The Compound (L-12), wherein n represents 0; $R^2$ represents a methyl group; $R^{3b}$ represents a hydrogen atom; and $R^{3c}$ represents any one substituent of a chlorine atom, a bromine atom, an iodine atom, $CF_3$, and substituents described in Table 3A to Table 11A (hereinafter referred to as "Compound group SX1630").

Next, Formulation Examples of the Present compound are shown below. The "part (s)" represents "part (s) by weight".

Also, the expression of "Present compound S" represents the compounds described in the Compound groups SX1 to SX1630.

Formulation Example 1

Any one of the Present compound S (10 parts) is mixed with a mixture of xylene (35 parts) and DMF (35 parts), then polyoxyethylene styryl phenyl ether (14 parts) and calcium dodecylbenzene sulfonate (6 parts) are added thereto, and the resulting mixture is mixed to obtain each formulation.

Formulation Example 2

Sodium lauryl sulfate (4 parts), calcium lignin sulfonate (2 parts), wet silica (20 parts), and diatomaceous earth (54 parts) are mixed, any one of the Present compound S (20 parts) is added thereto, and the resulting mixture is mixed to obtain each formulation.

Formulation Example 3

To any one of the Present compound S (2 parts) are added wet silica (1 part), calcium lignin sulfonate (2 parts), bentonite (30 parts), and kaolin clay (65 parts), and the resulting mixture is mixed. To the mixture is then added an appropriate amount of water, the resulting mixture is additionally stirred, and subjected to granulation with a granulator and forced-air drying to obtain each formulation.

Formulation Example 4

Any one of the Present compound S (1 part) is mixed with an appropriate amount of acetone, then wet silica (5 parts), acidic isopropyl phosphate (0.3 part), and kaolin clay (93.7 parts) are added thereto, the resulting mixture is mixed with stirring thoroughly, and acetone is removed from the mixture by evaporation to obtain each formulation.

Formulation Example 5

A mixture of polyoxyethylene alkyl ether sulfate ammonium salt and wet silica (weight ratio of 1:1) (35 parts), any one of the Present compound S (20 parts), and water (45 parts) are thoroughly mixed to obtain each formulation.

Formulation Example 6

Any one of the Present compound S (10 parts), and a mixture of benzyl alcohol (18 parts) and DMSO (9 parts) are mixed, GERONOL (registered trademark) TE250 (6.3 parts), Ethylan (trademark) NS-500LQ (2.7 parts), and solvent naphtha (54 parts) are added thereto, and the resulting mixture is mixed to obtain each formulation.

Formulation Example 7

Any one of the Present compound S (0.1 part) is mixed with a mixture of xylene (5 parts) and trichloroethane (5 parts), and the resulting mixture is then mixed with kerosene (89.9 parts) to obtain each formulation.

Formulation Example 8

Any one of the Present compound S (10 mg) is mixed with acetone (0.5 ml), the resulting solution is added dropwise to a solid feed powder for an animal (solid feed powder for rearing and breeding CE-2, manufactured by CLEA Japan, Inc.) (5 g), the resulting mixture is uniformly mixed, and then acetone is dried by evaporation to obtain each poison bait.

Formulation Example 9

Any one of the Present compound S (0.1 part) and Neothiozole (manufactured by Chuo Kasei Co., Ltd.) (49.9 parts) are placed into an aerosol can. After mounting an aerosol valve, dimethyl ether (25 parts) and LPG (25 parts) are filled, then the aerosol can is shaken, and further an actuator is mounted thereto to obtain each oily aerosol.

Formulation Example 10

A mixture of any one of the Present compound S (0.6 part), 2,6-di-tert-butyl-4-methylphenol (0.01 part), xylene (5 part), kerosene (3.39 parts), and Rheodol (registered trademark) MO-60 (1 part), and distilled water (50 parts) are filled into an aerosol container, and a valve part is attached. Then, LPG (40 parts) is filled therein through the valve to obtain each aqueous aerosol.

Formulation Example 11

Any one of the Present compound S (0.1 g) is mixed with propylene glycol (2 mL), and the resulting solution is impregnated into a ceramic plate having a size of 4.0 cm×4.0 cm and a thickness of 1.2 cm to obtain each thermal smoking agent.

Formulation Example 12

Any one of the Present compound S (5 parts) and ethylene-methyl methacrylate copolymer (the ratio of the methyl methacrylate relative to the total weight of the copolymer: 10% by weight) (95 parts) are melted and kneaded, and the resulting kneaded product is extruded from an extrusion molding machine to obtain each rod-shaped molded product having a length of 15 cm and a diameter of 3 mm.

Formulation Example 13

Any one of the Present compound S (5 parts) and a flexible vinyl chloride resin (95 parts) are melted and kneaded, and the resulting kneaded product is extruded from an extrusion molding machine to obtain each rod-shaped molded product having a length of 15 cm and a diameter of 3 mm.

Formulation Example 14

Any one of the Present compound S (100 mg), lactose (68.75 mg), corn starch (237.5 mg), microcrystalline cellulose (43.75 mg), polyvinylpyrrolidone (18.75 mg), sodium carboxymethyl starch (28.75 mg), and magnesium stearate (2.5 mg) are mixed, and the resulting mixture is compressed to an appropriate size to obtain each tablet.

Formulation Example 15

Any one of the Present compound S (25 mg), lactose (60 mg), corn starch (25 mg), carmellose calcium (6 mg), and an appropriate amount of 5% hydroxypropyl methylcellulose are mixed, and the resulting mixture is filled into a hard shell gelatin capsule or a hydroxypropyl methylcellulose capsule to obtain each capsule.

Formulation Example 16

To any one of the Present compound S (100 mg), fumaric acid (500 mg), sodium chloride (2,000 mg), methylparaben (150 mg), propylparaben (50 mg), granulated sugar (25,000 mg), sorbitol (70% solution) (13,000 mg), Veegum (registered trademark) K (100 mg), perfume (35 mg), and colorant (500 mg) is added distilled water so that the final volume is set to be 100 ml, and the resulting mixture is mixed to obtain each suspension for oral administration.

Formulation Example 17

Any one of the Present compound S (5 parts) is mixed with an emulsifier (5 parts), benzyl alcohol (3 parts), and propylene glycol (30 parts), phosphate buffer is added thereto so that the pH of the solution is set to be 6.0 to 6.5, and then water is added thereto as the rest parts to obtain each solution for oral administration.

Formulation Example 18

Aluminum distearate (5 parts) is added to fractional distilled coconut oil (57 parts) and polysorbate 85 (3 parts), and dispersed by heating. The resulting mixture is cooled to room temperature, and saccharin (25 parts) is dispersed in the oil vehicle. Any one of the Present compound S (10 parts) is distributed thereto to obtain each paste-like formulation for oral administration.

Formulation Example 19

Any one of the Present compound S (5 parts) is mixed with a limestone filler (95 parts), and the resulting mixture is subjected to a wet granulation to obtain each granule for oral administration.

Formulation Example 20

Any one of the Present compound S (5 parts) is mixed with diethylene glycol monoethyl ether (80 parts), propylene carbonate (15 parts) is added thereto, and the resulting mixture is mixed to obtain each spot-on solution.

Formulation Example 21

Any one of the Present compound S (10 parts) is mixed with diethylene glycol monoethyl ether (70 parts), 2-octyldodecanol (20 parts) is added thereto, and the resulting mixture is mixed to obtain each pour-on solution.

Formulation Example 22

Any one of the Present compound S (0.1 part), sodium polyoxyethylene lauryl ether sulfate (25% aqueous solution) (40 parts), lauramidopropyl betaine (5 parts), coconut oil fatty acid ethanolamide (5 parts), carboxyvinyl polymer (0.5 part), and purified water (49.4 parts) are thoroughly mixed to obtain each shampoo formulation.

Formulation Example 23

Any one of the Present compound S (0.15 part), an animal feed (95 parts), and a mixture (4.85 parts) consisting of calcium hydrogen phosphate, diatomaceous earth, Aerosil (registered trademark), and carbonate (or chalk) are mixed with stirring thoroughly to obtain each premix for an animal feed.

Formulation Example 24

Any one of the Present compound S (7.2 g) and Hosco (registered trademark) S-55 (92.8 g) are mixed at 100° C., the resulting mixture is poured into a suppository mold, and subjected to cooling solidification to obtain each suppository.

Next, Test Examples are used to show effects of the Present compounds on harmful arthropods. In the following Test Examples, the tests were carried out at 25° C.
Test Method 1

Each test compound is formulated according to the method described in the Formulation Example 6 to obtain each formulation, and water containing Sindaine (registered trademark) (0.03% by volume) is added thereto to prepare a diluted solution containing a prescribed concentration of each test compound.

Cucumber (*Cucumis sativus*) seedlings (on the developmental stage of the second true leaf) are planted in a container and approximately 30 cotton aphids (*Aphis gossypii*) (all stages of life) are released onto the cucumber seedlings. After 1 day, each of said diluted solutions is sprayed into the seedlings in a ratio of 10 mL/seedling. After additional 5 days, the number of the surviving insects is examined and the controlling value is calculated by the following equation.

Controlling value (%)={1−(Cb×Tai)/(Cai×Tb)}×100 wherein the symbols in the equation represent the following meanings.
Cb: Number of the test insects in non-treated area;
Cai: Number of the surviving insects at the time of the investigation in non-treated area;
Tb: Number of the test insects in treated area;
Tai: Number of the surviving insects at the time of the investigation in treated area;
Here, the "non-treated area" represents an area where the same treatment procedure as that of the treated area is done except for not using each test compound.

Test Example 1-1

When the prescribed concentration was 200 ppm and the following Present compound was used as a test compound to carry out a test according to the Test method 1, the following Present compound showed 90% or greater as the controlling value.
Present Compound: 2

Test Example 1-2

When the prescribed concentration was 50 ppm and each of the following Present compounds was used as a test compound to carry out a test according to the Test method 1, each of the following Present compounds showed 90% or greater as the controlling value.
Present Compounds: 2, 4, 5, 7, 8, 9, 10, 11, 14, 15, 16, 17, 18, 19

Test Method 2

Each test compound is formulated according to the method described in the Formulation Example 5 to obtain each formulation, and water is added thereto to prepare a diluted solution containing a prescribed concentration of each test compound.

Cucumber seedlings (on the developmental stage of the second true leaf) are planted in a container, and each of said diluted solutions is irrigated into the plant foot in a ratio of 5 mL/seedlings. After 7 days, approximately 30 cotton aphids (*Aphis gossypii*) (all stages of life) are released onto the surfaces of leaves of the cucumber seedlings. After additional 6 days, the number of the surviving insects is examined and the controlling value is calculated by the following equation.

Controlling value (%)={1−(Cb×Tai)/(Cai×Tb)}×100 wherein the symbols in the equation represent the following meanings.
Cb: Number of the test insects in non-treated area;
Cai: Number of the surviving insects at the time of the investigation in non-treated area;
Tb: Number of the test insects in treated area;
Tai: Number of the surviving insects at the time of the investigation in treated area;
Here, the "non-treated area" represents an area where the same treatment procedure as that of the treated area is done except for not using each test compound.

Test Example 2

When the prescribed concentration was 250 ppm and each of the following Present compounds was used as a test compound to carry out a test according to the Test method 2, each of the following Present compounds showed 90% or greater as the controlling value.
Present Compounds: 2, 4, 5, 8, 19

Test Method 3

Each test compound is formulated according to the method described in the Formulation Example 6 to obtain each formulation, and water containing Sindaine (registered trademark) (0.03% by volume) is added thereto to prepare a diluted solution containing a prescribed concentration of each test compound.

Cabbage (*Brassicae oleracea*) seedlings (on the developmental stage of the second to third true leaf) are planted in a container, and each of said diluted solutions is sprayed into the seedlings in a ratio of 20 mL/seedlings. Thereafter, the stem and leaf of the seedlings are cut out, and placed into a container lined with a filter paper. Five (5) the 3rd instar larvae of cotton worm (*Spodoptera litura*) are released into the container. After 5 days, the number of the surviving insects is counted, and the mortality of insects is calculated by the following equation.

Mortality (%)=(1−Number of surviving insects/5)×100

Test Example 3-1

When the prescribed concentration was 200 ppm and the following Present compound was used as a test compound to carry out a test according to the Test method 3, the following Present compound showed 80% or greater as the mortality.
Present Compound: 2

Test Example 3-2

When the prescribed concentration was 50 ppm and each of the following Present compounds was used as a test compound to carry out a test according to the Test method 3, each of the following Present compounds showed 80% or greater as the mortality.
Present Compounds: 2, 4, 5, 6, 8, 10, 11, 17, 19

Test Method 4

Each test compound is formulated according to the method described in the Formulation Example 6 to obtain each formulation, and water containing Sindaine (registered trademark) (0.03% by volume) is added thereto to prepare a diluted solution containing a prescribed concentration of each test compound.

Cabbage seedlings (on the developmental stage of the second to third true leaf) are planted in a container, and each of said diluted solutions is sprayed into the seedlings in a ratio of 20 mL/seedlings. Thereafter, the stem and leaf of the seedlings are cut out, and placed into a container lined with a filter paper. Five (5) the 3rd instar larvae of diamondback moth (*Plutella xylostella*) are released into the container. After 5 days, the number of the surviving insects is counted, and the mortality of insects is calculated by the following equation.

Mortality (%)=(1−Number of surviving insects/5)×100

Test Example 4-1

When the prescribed concentration was 200 ppm and the following Present compound was used as a test compound to carry out a test according to the Test method 4, the following Present compound showed 80% or greater as the mortality.
Present Compound: 2

Test Example 4-2

When the prescribed concentration was 50 ppm and each of the following Present compounds was used as a test compound to carry out a test according to the Test method 4, each of the following Present compounds showed 80% or greater as the mortality.
Present Compounds: 2, 4, 5, 6, 7, 8, 9, 10, 11, 16, 17, 18, 19

Test Method 5

Each test compound is dissolved into a mixed solution (50 µL) of polyoxyethylene sorbitan mono-cocoate and acetone (at a volume ratio of polyoxyethylene sorbitan mono-cocoate:acetone=5:95) per 1 mg of the test compound. Water containing Sindaine (registered trademark) (0.03% by volume) is added thereto to prepare a diluted solution containing a prescribed concentration of each test compound.

Young seedlings of corns (*Zea mays*) are immersed into each of said diluted solutions for 30 seconds. Thereafter, two of the resulting seedlings are placed into a petri dish (diameter: 90 mm), and 10 the 2nd instar larvae of western corn rootworm (*Dabrotica virgifera virgifera*) are released into the dish. After 5 days, the number of the dead insects is counted, and the mortality of insects is calculated by the following equation.

Mortality (%)=(Number of dead insects/10)×100

Test Example 5

When the prescribed concentration was 50 ppm and each of the following Present compounds was used as a test compound to carry out a test according to the Test Example 5, each of the following Present compounds showed 80% or greater as the mortality.
Present Compounds: 2, 4, 5, 6, 8

Test Method 6

The Present compound (1 mg) is dissolved into a mixed solution (10 µL) of xylene, DMF, and surfactant (at a volume ratio of xylene:DMF:surfactant=4:4:1), and the resulting solution is diluted with water containing a spreader (0.02% by volume) to prepare a diluted solution A containing a prescribed concentration of the Present compound.

The Present ingredient (1 mg) is dissolved into a mixed solution (10 µL) of xylene, DMF, and surfactant (at a volume ratio of xylene:DMF:surfactant=4:4:1), and the resulting solution is diluted with water containing a spreader (0.02% by volume) to prepare a diluted solution B containing a prescribed concentration of the Present ingredient.

The diluted solution A and the diluted solution B are mixed to prepare a diluted solution C.

A lamina (length: 1.5 cm) of cucumber cotyledon is placed into each well of a 24 well microplate, then two (2) wingless adults and eight (8) larvae of cotton aphids (*Aphis gossypii*) are released into each well, and 20 µL of the diluted solution C is sprayed into each well. Said well is defined as "treated area".

A well into which 20 µL of water containing a spreader (0.02% by volume) instead of the diluted solution C is sprayed is defined as "non-treated area".

After the diluted solution C is dried, the upper part of the microplate is covered by a film sheet. After 5 days, the number of the surviving insects in each well is examined.

The controlling value is calculated by the following equation.

Controlling value (%)={1−(*Tai*)/(*Cai*)}×100 wherein the symbols in the equation represent the following meanings.
Cai: Number of the surviving insects at the time of the investigation in non-treated area;
Tai: Number of the surviving insects at the time of the investigation in treated area.

Specific examples of the diluted solution C of which the effects can be confirmed in the Test method 6 include the following 1) to 5).

1) A diluted solution C of any one combination described in the List A, wherein the concentration of the Present compound is 200 ppm and the concentration of the Present ingredient is 2,000 ppm. In the List A, Comp X represents any one compound selected from the Present compounds 1 to 19.

List A:
Comp X+clothianidin; Comp X+thiamethoxam; Comp X+imidacloprid; Comp X+thiacloprid; Comp X+flupyradifurone; Comp X+sulfoxaflor; Comp X+triflumezopyrim; Comp X+dicloromezotiaz; Comp X+beta-cyfluthrin; Comp X+tefluthrin; Comp X+fipronil; Comp X+chlorantraniliprole; Comp X+cyantraniliprole; Comp X+tetraniliprole; Comp X+thiodicarb; Comp X+carbofuran; Comp X+fluxametamide; Comp X+afoxolaner; Comp X+fluralaner; Comp X+broflanilide; Comp X+abamectin; Comp X+fluopyram; Comp X+fluensulfone; Comp X+fluazaindolizine; Comp X+tioxazafen; Comp X+flupyrimin; Comp X+mycorrhizal fungi; Comp X+*Bradyrhizobium japonicum* TA-11; Comp X+*Bacillus firmus*; Comp X+*Bacillus firmus* 1-1582; Comp X+*Bacillus amyloliquefaciens*; Comp X+*Bacillus amyloliquefaciens* FZB42; Comp X+*Pasteuria nishizawae*; Comp X+*Pasteuria nishizawae* Pn1; Comp X+*Pasteuria penetrans*; Comp X+tebuconazole; Comp X+prothioconazole; Comp X+metconazole; Comp X+ipconazole; Comp X+triticonazole; Comp X+difenoconazole; Comp X+imazalil; Comp X+triadimenol; Comp X+tetraconazole; Comp X+flutriafol; Comp X+mandestrobin; Comp X+azoxystrobin; Comp X+pyraclostrobin; Comp X+trifloxystrobin; Comp X+fluoxastrobin; Comp X+picoxystrobin; Comp X+fenamidone; Comp X+metalaxyl; Comp X+metalaxyl-M; Comp X+fludioxonil; Comp X+sedaxane; Comp X+penflufen; CompX+fluxapyroxad; Comp X+benzovindiflupyr; Comp X+boscalid; Comp X+carboxin; Comp X+penthiopyrad; CompX+flutolanil; Comp X+captan; Comp X+thiram; Comp X+tolclofosmethyl; Comp X+thiabendazole; Comp X+ethaboxam; Comp X+mancozeb; Comp X+picarbutrazox; Comp X+oxathiapiprolin; Comp X+silthiofam; Comp X+inpyrfluxam.

2) A diluted solution C of any one combination described in the List A, wherein the concentration of the Present compound is 200 ppm and the concentration of the Present ingredient is 200 ppm.

3) A diluted solution C of any one combination described in the List A, wherein the concentration of the Present compound is 500 ppm and the concentration of the Present ingredient is 50 ppm.

4) A diluted solution C of any one combination described in the List A, wherein the concentration of the Present compound is 500 ppm and the concentration of the Present ingredient is 5 ppm.
5) A diluted solution C of any one combination described in the List A, wherein the concentration of the Present compound is 500 ppm and the concentration of the Present ingredient is 0.5 ppm.

INDUSTRIAL APPLICABILITY

The Present compounds have excellent control effects on harmful arthropods.

The invention claimed is:
1. A compound represented by the following formula (I):

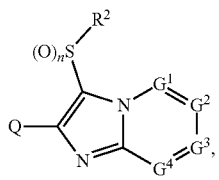

wherein:
R$^2$ represents a C1-C6 alkyl group optionally substituted with at least one halogen atom, a cyclopropyl group, or a cyclopropylmethyl group;
n represents 0, 1, or 2;
G$^1$ represents a nitrogen atom or CR$^{3a}$;
G$^2$ represents a nitrogen atom or CR$^{3b}$;
G$^3$ represents a nitrogen atom or CR$^{3c}$;
G$^4$ represents a nitrogen atom or CR$^{3d}$;
R$^{3a}$, R$^{3b}$, R$^{3c}$, and R$^{3d}$ are identical to or different from each other, and each represent a C1-C6 chain hydrocarbon group optionally substituted with at least one substituent selected from Group B, a C3-C7 cycloalkyl group optionally substituted with at least one substituent selected from Group E, a phenyl group optionally substituted with at least one substituent selected from Group H, a 5 or 6 membered aromatic heterocyclic group optionally substituted with at least one or more substituent(s) substituent selected from Group H, OR$^{12}$, NR$^{11}$R$^{12}$, NR$^{11a}$R$^{12a}$, NR$^{24}$NR$^{11}$R$^{12}$, NR$^{24}$OR$^{11}$, NR$^{11}$C(O)R$^{13}$, NR$^{24}$NR$^{11}$C(O)R$^{13}$, NR$^{11}$C(O)OR$^{14}$, NR$^{24}$NR$^{11}$C(O)OR$^{14}$, NR$^{11}$C(O)NR$^{31}$R$^{32}$, NR$^{24}$NR$^{11}$C(O)NR$^{31}$R$^{32}$, N=CHNR$^{31}$R$^{32}$, N=S(O)$_p$R$^{15}$R$^{16}$, C(O)R$^{13}$, C(O)OR$^{17}$, C(O)NR$^{31}$R$^{32}$, C(O)NR$^{11}$S(O)$_2$R$^{23}$, CR$^{30}$=NOR$^{17}$, NR$^{11}$CR$^{24}$=NOR$^{17}$, S(O)$_m$R$^{23}$, a cyano group, a nitro group, a hydrogen atom, or a halogen atom;
p represents 0 or 1;
m represents 0, 1, or 2;
R$^{30}$ represents a C1-C6 chain hydrocarbon group optionally substituted with at least one halogen atom, a halogen atom, OR$^{35}$, NR$^{36}$R$^{37}$, or a hydrogen atom;
R$^{35}$ represents a C1-C6 chain hydrocarbon group optionally substituted with at least one halogen atom;
R$^{17}$ represents a C1-C6 chain hydrocarbon group optionally substituted with at least one halogen atom, a phenyl group optionally substituted with at least one substituent selected from Group D, or a hydrogen atom;
R$^{11}$, R$^{24}$, R$^{36}$, and R$^{37}$ are identical to or different from each other, and each represent a C1-C6 chain hydrocarbon group optionally substituted with at least one halogen atom, or a hydrogen atom;
R$^{12}$ represents a C1-C6 chain hydrocarbon group optionally substituted at least one substituent selected from Group F, a C3-C7 cycloalkyl group optionally substituted with at least one substituent selected from Group J, a C3-C7 cycloalkenyl group optionally substituted with at least one substituent selected from Group J, a phenyl group optionally substituted with at least one substituent selected from Group D, a 6 membered aromatic heterocyclic group optionally substituted with at least one substituent selected from Group D, a hydrogen atom, or S(O)$_2$R$^{23}$;
R$^{23}$ represents a C1-C6 chain hydrocarbon group optionally substituted with at least one halogen atom, or a phenyl group optionally substituted with at least one substituent selected from Group D;
R$^{11a}$ and R$^{12a}$ are combined with the nitrogen atom to which they are attached to form a 3-7 membered nonaromatic heterocyclic group optionally substituted with at least one substituent selected from Group E;
R$^{13}$ represents a C1-C6 chain hydrocarbon group optionally substituted with at least one halogen atom, a C3-C7 cycloalkyl group optionally substituted with at least one halogen atom, a (C3-C6 cycloalkyl) C1-C3 alkyl group optionally substituted with at least one halogen atom, a phenyl group optionally substituted with at least one substituent selected from Group D, a 5 or 6 membered aromatic heterocyclic group optionally substituted with at least one substituent selected from Group D, or a hydrogen atom;
R$^{14}$ represents a C1-C6 chain hydrocarbon group optionally substituted with at least one halogen atom, a C3-C7 cycloalkyl group optionally substituted with at least one halogen atom, a (C3-C6 cycloalkyl) C1-C3 alkyl group optionally substituted with at least one halogen atom, or a phenyl C1-C3 alkyl group, wherein the phenyl moiety in the phenyl C$_1$-C$_3$ alkyl group is optionally substituted with at least one substituent selected from Group D;
R$^{15}$ and R$^{16}$ are identical to or different from each other, and each represent a C1-C6 alkyl group optionally substituted with one or more halogen atom(s);
R$^{31}$ represents a C1-C6 alkyl group optionally substituted with at least one halogen atom, or a hydrogen atom;
R$^{32}$ represents a C1-C6 chain hydrocarbon group optionally substituted with at least one substituent substituent(s) selected from Group F, a C3-C7 cycloalkyl group optionally substituted with at least one substituent selected from Group J, S(O)$_2$R$^{23}$, or a hydrogen atom;
Q represents a group represented by Q1 or a group represented by Q2;

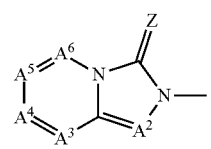

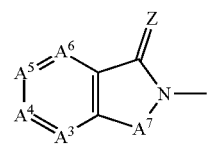

Z represents an oxygen atom or a sulfur atom;

$A^2$ represents a nitrogen atom or $CR^{6b}$;

$A^3$ represents a nitrogen atom or $CR^{6c}$;

$A^6$ represents a nitrogen atom or $CR^{6f}$;

$A^7$ represents $NR^{6g}$, $CR^{6h}R^{6i}$, or an oxygen atom;

the combination of $A^4$ and $A^5$ represents:

a combination wherein $A^4$ represents $CR^{1a}$, and $A^5$ represents a nitrogen atom or $CR^{6e}$; or a combination wherein $A^4$ represents a nitrogen atom or $CR^{6d}$, and $A^5$ represents $CR^{1b}$;

$R^{1a}$ and $R^{1b}$ are identical to or different from each other, and each represent a $C_1$-$C_6$ chain hydrocarbon group substituted with at least one substituent selected from the group consisting of a cyano group and a halogen atom, a C3-C4 cycloalkyl group optionally substituted with at least one substituent selected from the group consisting of a cyano group and a halogen atom, $SR^8$, $S(O)R^8$, $S(O)_2R^8$, $OR^8$, or $OS(O)_2R^8$;

$R^8$ represents a C1-C6 chain hydrocarbon group substituted with at least one substituent selected from the group consisting of a cyano group and a halogen atom, or a C3-C4 cycloalkyl group optionally substituted with at least one substituent selected from the group consisting of a cyano group and a halogen atom;

$R^{6b}$, $R^{6h}$, and $R^{6i}$ are identical to or different from each other, and each represent a C1-C6 chain hydrocarbon group optionally substituted with at least one halogen atom, a C3-C7 cycloalkyl group optionally substituted with at least one halogen atom, a halogen atom, or a hydrogen atom;

$R^{6c}$, $R^{6d}$, $R^{6e}$, and $R^{6f}$ are identical to or different from each other, and each represent a C1-C6 chain hydrocarbon group optionally substituted with at least one halogen atom, a C3-C7 cycloalkyl group optionally substituted with at least one halogen atom, a C1-C6 alkoxy group optionally substituted with at least one halogen atom, $NR^{25}R^{26}$, $C(O)R^7$, $C(O)OR^7$, $C(O)NR^{19}R^{20}$, $NR^{25}C(O)R^{18}$, $NR^{25}C(O)OR^{18}$, $NR^{25}C(O)NR^{19}R^{20}$, a cyano group, a halogen atom, or a hydrogen atom;

$R^{6g}$ represents a C1-C6 chain hydrocarbon group optionally substituted with at least one halogen atom, or a hydrogen atom;

$R^{19}$ and $R^{25}$ are identical to or different from each other, and each represent a C1-C6 chain hydrocarbon group optionally substituted with at least one halogen atom, or a hydrogen atom;

$R^{26}$ represents a C1-C6 chain hydrocarbon group optionally substituted with at least one substituent selected from Group L, a C3-C7 cycloalkyl group optionally substituted with at least one substituent selected from Group M, a C3-C7 cycloalkenyl group optionally substituted with at least one substituent selected from Group M, a phenyl group optionally substituted with at least one substituent selected from Group K, a 6 membered aromatic heterocyclic group optionally substituted with at least one substituent selected from Group K, a hydrogen atom, or $S(O)_2R^{27}$;

$R^{27}$ represents a C1-C6 chain hydrocarbon group optionally substituted with at least one halogen atom, a C3-C7 cycloalkyl group optionally substituted with at least one halogen atom, or a phenyl group optionally substituted with at least one substituent selected from Group K; and $R^7$, $R^{18}$, and $R^{20}$ are identical to or different from each other, and each represent a C1-C6 chain hydrocarbon group optionally substituted with at least one substituent selected from Group L, a C3-C7 cycloalkyl group optionally substituted with at least one substituent selected from Group M, or a hydrogen atom;

Group B: a group consisting of a C1-C6 alkoxy group optionally substituted with at least one halogen atom, a C3-C6 alkenyloxy group optionally substituted with at least one halogen atom, a C3-C6 alkynyloxy group optionally substituted with at least one halogen atom, a C1-C6 alkylsulfanyl group optionally substituted with at least one halogen atom, a C1-C6 alkylsulfinyl group optionally substituted with at least one halogen atom, a C1-C6 alkylsulfonyl group optionally substituted with at least one halogen atom, a C3-C6 cycloalkyl group optionally substituted with at least one halogen atom, a cyano group, a hydroxy group, and a halogen atom;

Group C: a group consisting of a C1-C6 chain hydrocarbon group optionally substituted with at least one halogen atom, a C1-C6 alkoxy group optionally substituted with at least one halogen atom, a C3-C6 alkenyloxy group optionally substituted with at least one halogen atom, a C3-C6 alkynyloxy group optionally substituted with at least one halogen atom, and a halogen atom;

Group D: a group consisting of a C1-C6 chain hydrocarbon group optionally substituted with at least one halogen atom, a hydroxy group, a C1-C6 alkoxy group optionally substituted with at least one halogen atom, a C3-C6 alkenyloxy group optionally substituted with at least one halogen atom, a C3-C6 alkynyloxy group optionally substituted with at least one halogen atom, a sulfanyl group, a C1-C6 alkylsulfanyl group optionally substituted with at least one halogen atom, a C1-C6 alkylsulfinyl group optionally substituted with at least one halogen atom, a C1-C6 alkylsulfonyl group optionally substituted with at least one halogen atom, an amino group, $NHR^{21}$, $NR^{21}R^{22}$, $C(O)R^{21}$, $OC(O)R^{21}$, $C(O)OR^{21}$, a cyano group, a nitro group, and a halogen atom;

$R^{21}$ and $R^{22}$ are identical to or different from each other, and each represent a C1-C6 alkyl group optionally substituted with at least one halogen atom;

Group E: a group consisting of a C1-C6 chain hydrocarbon group optionally substituted with at least one halogen atom, a C1-C6 alkoxy group optionally substituted with at least one halogen atom, a C3-C6 alkenyloxy group optionally substituted with at least one halogen atom, a C3-C6 alkynyloxy group optionally substituted with at least one halogen atom, a halogen atom, an oxo group, a hydroxy group, a cyano group, and a nitro group;

Group F: a group consisting of a C1-C6 alkoxy group optionally substituted with at least one or more halogen atom, a phenyl group optionally substituted with at least one substituent selected from Group D, a 5 or 6 membered aromatic heterocyclic group optionally substituted with at least one substituent selected from Group D, a C3-C7 cycloalkyl group optionally substituted with at least one halogen atom, a 3-7 membered nonaromatic heterocyclic group optionally substituted with at least one substituent selected from Group C, an amino group, $NHR^{21}$, $NR^{21}R^{22}$, a halogen atom, and a cyano group;

Group H: a group consisting of a C1-C6 alkyl group optionally substituted with at least one halogen atom, a 5 or 6 membered aromatic heterocyclic group optionally substituted with at least one substituent selected from Group D, $OR^{10}$, $NR^9R^{10}$, $C(O)R^{10}$, $C(O)NR^9R^{10}$, OC(O)R$^9$, OC(O)OR$^9$, NR$^{10}$C(O)R$^9$, NR$^{10}$C(O)OR$^9$, C(O)OR$^{10}$, a halogen atom, a nitro group, a cyano group, and an amino group;

R$^9$ represents a C1-C6 alkyl group optionally substituted with at least one halogen atom, or a C3-C6 cycloalkyl group optionally substituted with at least one halogen atom;

R$^{10}$ represents a C1-C6 alkyl group optionally substituted with at least one halogen atom, a C3-C6 cycloalkyl group optionally substituted with at least one halogen atom, or a hydrogen atom;

Group J: a group consisting of a C1-C6 alkyl group optionally substituted with at least one halogen atom, a halogen atom, and a cyano group;

Group K: a group consisting of a C1-C6 chain hydrocarbon group optionally substituted with at least one halogen atom, a C1-C6 alkoxy group optionally substituted with at least one halogen atom, a C3-C6 alkenyloxy group optionally substituted with at least one halogen atom, a C3-C6 alkynyloxy group optionally substituted with at least one halogen atom, a C1-C6 alkylsulfanyl group optionally substituted with at least one halogen atom, a C1-C6 alkylsulfinyl group optionally substituted with at least one halogen atom, a C1-C6 alkylsulfonyl group optionally substituted with at least one halogen atom, a C3-C6 cycloalkyl group optionally substituted with at least one halogen atom, a C1-C6 alkyl optionally substituted with at least one halogen atom amino group, a di(C1-C4 alkyl) amino group optionally substituted with at least one halogen atom, a C$_2$-C$_6$ alkylcarbonyl group optionally substituted with at least one halogen atom, a C2-C6 alkoxycarbonyl group optionally substituted with at least one halogen atom, a C2-C6 alkoxycarbonyloxy group optionally substituted with at least one halogen atom, an aminocarbonyl group, a C1-C6 alkyl optionally substituted with at least one halogen atom aminocarbonyl group, a [di(C1-C4 alkyl) amino optionally substituted with at least one halogen atom carbonyl group, a C2-C6 alkoxycarbonyl optionally substituted with at least one halogen atom amino group, a (C2-C6 alkoxycarbonyl)(C1-C6 alkyl) amino group optionally substituted with at least one halogen atom, a cyano group, an amino group, a nitro group, a hydroxy group, and a halogen atom;

Group L: a group consisting of a C3-C6 cycloalkyl group optionally substituted with at least one halogen atom, a phenyl group optionally substituted with at least one substituent selected from Group K, a 5 or 6 membered aromatic heterocyclic group optionally substituted with at least one substituent selected from Group K, a C1-C6 alkoxy group optionally substituted with at least one halogen atom, a C1-C6 alkyl optionally substituted with at least one halogen atom amino group, a di(C1-C4 alkyl)amino group optionally substituted with at least one halogen atom, a cyano group, an amino group, a nitro group, a hydroxy group, and a halogen atom;

Group M: a group consisting of a C1-C6 alkyl group optionally substituted with at least one halogen atom, a C1-C6 alkoxy group optionally substituted with at least one halogen atom, a C2-C6 alkoxycarbonyl group optionally substituted with at least one halogen atom, an amino group, a cyano group, and a halogen atom;

or an N-oxide thereof.

2. The compound or an N-oxide thereof according to claim 1, wherein Q represents the group represented by Q1.

3. The compound or an N-oxide thereof according to claim 1, wherein Q represents the group represented by Q2.

4. The compound or an N-oxide thereof according to claim 1, wherein

R$^{3a}$, R$^{3b}$, R$^{3c}$, and R$^{3d}$ are identical to or different from each other, and each represent a C1-C6 alkyl group, a C2-C6 alkenyl group, a C3-C7 cycloalkyl group, wherein the C1-C6 alkyl group, the C2-C6 alkenyl group, and the C3-C7 cycloalkyl group are optionally substituted with at least one substituent selected from the group consisting of a halogen atom and a cyano group; a phenyl group, a pyridyl group, a pyrimidinyl group, wherein the phenyl group, the pyridyl group, and the pyrimidinyl group are optionally substituted with at least one substituent selected from Group J; OR$^{12}$, CR$^{30}$=NOR$^{17}$, a hydrogen atom, or a halogen atom.

5. The compound or an N-oxide thereof according to claim 1, wherein

G$^1$ represents a nitrogen atom or CH;
G$^2$ represents CR$^{3b}$;
G$^3$ represents CR$^{3c}$;
G$^4$ represents a nitrogen atom or CH; and
R$^{3b}$ and R$^{3c}$ are identical to or different from each other, and each represent a C1-C6 alkyl group, a C2-C6 alkenyl group, a C3-C7 cycloalkyl group, wherein the C1-C6 alkyl group, the C2-C6 alkenyl group, and the C3-C7 cycloalkyl group are optionally substituted with at least one substituent selected from the group consisting of a halogen atom and a cyano group; OR$^{12}$, a hydrogen atom, or a halogen atom.

6. The compound or an N-oxide thereof according to claim 1 wherein

G$^1$ represents CH;
G$^2$ represents CR$^{3b}$;
G$^3$ represents CR$^{3c}$;
G$^4$ represents CH; and
R$^{3b}$ and R$^{3c}$ are identical to or different from each other, and each represent a C1-C6 alkyl group optionally substituted with at least one halogen atom, or a hydrogen atom.

7. The compound or an N-oxide thereof according to claim 1, wherein

R$^{1a}$ and R$^{1b}$ are identical to or different from each other, and each represent a C1-C6 alkyl group substituted with at least one substituent selected from the group consisting of a cyano group and a halogen atom; or a cyclopropyl group optionally substituted with at least one substituent selected from the group consisting of a cyano group and a halogen atom.

8. The compound or an N-oxide thereof according to claim 1, wherein R$^2$ represents an ethyl group.

9. The compound or an N-oxide thereof according to claim 1, wherein Z represents an oxygen atom.

10. A composition for controlling a harmful arthropod comprising the compound or an N-oxide thereof of claim 1.

11. A composition comprising at least one ingredient selected from the group consisting of Group (a), Group (b), Group (c), and Group (d), and the compound or an N-oxide thereof of claim 1:

Group (a): a group consisting of insecticidal active ingredients, miticidal active ingredients, and nematicidal active ingredients;
Group (b): fungicidal active ingredients;
Group (c): plant growth regulatory ingredients;
Group (d): repellent ingredients.

12. A method for controlling a harmful arthropod, the method comprising:
   applying an effective amount of the compound or an N-oxide thereof of claim 1 to a harmful arthropod or a habitat where a harmful arthropod lives.

13. A seed or a vegetative reproduction organ holding an effective amount of the compound or an N-oxide thereof of claim 1 for controlling a harmful arthropod.

14. A method for controlling a harmful arthropod, the method comprising:
   applying an effective amount of the composition of claim 11 to a harmful arthropod or a habitat where a harmful arthropod lives.

15. A seed or a vegetative reproduction organ holding an effective amount of the composition of claim 11 for controlling a harmful arthropod.

* * * * *